United States Patent
Jiang et al.

(10) Patent No.: US 10,604,520 B2
(45) Date of Patent: Mar. 31, 2020

(54) N-ACYL AMINO ACID COMPOUNDS AND METHODS OF USE

(71) Applicant: Pliant Therapeutics, Inc., Redwood City, CA (US)

(72) Inventors: Lan Jiang, Foster City, CA (US); David John Morgans, Jr., Los Altos, CA (US); Gustave Bergnes, Pacifica, CA (US); Chun Chen, Albany, CA (US); Hui Li, Santa Clara, CA (US); Patrick Andre, Short Hills, NJ (US); Randall L. Halcomb, Foster City, CA (US); Jacob Cha, Burlingame, CA (US); Timothy Hom, Sunnyvale, CA (US)

(73) Assignee: Pliant Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 15/698,435

(22) Filed: Sep. 7, 2017

(65) Prior Publication Data

US 2018/0093984 A1 Apr. 5, 2018

Related U.S. Application Data

(60) Provisional application No. 62/384,682, filed on Sep. 7, 2016.

(51) Int. Cl.
| | |
|---|---|
| *C07D 471/04* | (2006.01) |
| *C07D 213/74* | (2006.01) |
| *C07D 233/70* | (2006.01) |
| *C07D 233/88* | (2006.01) |
| *C07D 241/06* | (2006.01) |
| *C07D 241/08* | (2006.01) |
| *C07D 263/28* | (2006.01) |
| *C07D 265/08* | (2006.01) |
| *C07D 277/18* | (2006.01) |
| *C07D 279/06* | (2006.01) |
| *A61P 9/00* | (2006.01) |
| *A61P 17/00* | (2006.01) |
| *A61P 13/12* | (2006.01) |
| *A61P 1/00* | (2006.01) |
| *A61P 11/00* | (2006.01) |
| *A61P 1/16* | (2006.01) |

(52) U.S. Cl.
CPC .............. *C07D 471/04* (2013.01); *A61P 1/00* (2018.01); *A61P 1/16* (2018.01); *A61P 9/00* (2018.01); *A61P 11/00* (2018.01); *A61P 13/12* (2018.01); *A61P 17/00* (2018.01); *C07D 213/74* (2013.01); *C07D 233/70* (2013.01); *C07D 233/88* (2013.01); *C07D 241/06* (2013.01); *C07D 241/08* (2013.01); *C07D 263/28* (2013.01); *C07D 265/08* (2013.01); *C07D 277/18* (2013.01); *C07D 279/06* (2013.01)

(58) Field of Classification Search
CPC .. C07D 471/04; C07D 233/70; C07D 213/74; C07D 233/88; C07D 241/06; C07D 241/08; C07D 263/28; C07D 265/08; C07D 277/18; C07D 279/06; A61P 9/00; A61P 17/00; A61P 13/12; A61P 1/00; A61P 11/00; A61P 1/16
See application file for complete search history.

(56) References Cited

U.S. PATENT DOCUMENTS

| | | | |
|---|---|---|---|
| 5,741,796 A | 4/1998 | Hartman et al. | |
| 6,005,117 A | 12/1999 | Wehner et al. | |
| 6,020,366 A | 2/2000 | Picard et al. | |
| 6,218,415 B1 | 4/2001 | Wehner et al. | |
| 6,399,620 B1 | 6/2002 | Wehner et al. | |
| 6,413,955 B1 | 7/2002 | Askew et al. | |
| 9,085,606 B2 * | 7/2015 | Ruminski | ................ C07K 5/06 |
| 10,131,658 B2 | 11/2018 | DeGrado et al. | |
| 10,214,522 B2 | 2/2019 | DeGrado et al. | |
| 2002/0010176 A1 | 1/2002 | Askew et al. | |
| 2003/0087910 A1 * | 5/2003 | Makovec | ............. C07D 215/14 514/249 |
| 2005/0026973 A1 * | 2/2005 | Leclerc | ................ C07D 277/68 514/367 |

(Continued)

FOREIGN PATENT DOCUMENTS

| | | | |
|---|---|---|---|
| CN | 105732480 A | * | 7/2016 |
| WO | WO-1995/32710 A1 | | 12/1995 |

(Continued)

OTHER PUBLICATIONS

CN-105732480-A (2016); ProQuest English machine translation p. 1-20.*

(Continued)

*Primary Examiner* — John M Mauro
(74) *Attorney, Agent, or Firm* — Morrison & Foerster LLP

(57) ABSTRACT

The invention relates to compounds of formula (I):

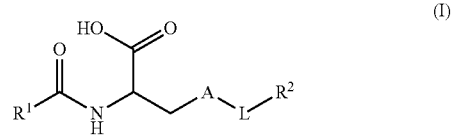

or a salt thereof, wherein $R^1$, A, L, and $R^2$ and n are as described herein. Compounds of formula (I) and pharmaceutical compositions thereof are αvβ1 integrin inhibitors that are useful for treating tissue specific fibrosis.

52 Claims, No Drawings

(56) References Cited

U.S. PATENT DOCUMENTS

| | | | |
|---|---|---|---|
| 2007/0039624 A1* | 2/2007 | Roberts | A61J 7/04 |
| | | | 128/898 |
| 2008/0045521 A1 | 2/2008 | Arnould et al. | |
| 2015/0087690 A1* | 3/2015 | Accili | C12N 15/1138 |
| | | | 514/44 A |
| 2016/0264566 A1 | 9/2016 | DeGrado et al. | |
| 2016/0376266 A1 | 12/2016 | DeGrado et al. | |
| 2018/0244648 A1 | 8/2018 | Harrison et al. | |
| 2019/0276449 A1 | 9/2019 | Cha | |

FOREIGN PATENT DOCUMENTS

| | | | | |
|---|---|---|---|---|
| WO | WO-9800137 A1 * | 1/1998 | | C07C 279/22 |
| WO | WO-1998/31359 A1 | 7/1998 | | |
| WO | WO-1999/31061 A1 | 6/1999 | | |
| WO | WO-2000/72801 A2 | 12/2000 | | |
| WO | WO-2001/12183 A1 | 2/2001 | | |
| WO | WO-2002/060438 A1 | 8/2002 | | |
| WO | WO-2002/098849 A2 | 12/2002 | | |
| WO | WO-2002/098849 A3 | 12/2002 | | |
| WO | WO-2004/024675 A1 | 3/2004 | | |
| WO | WO-2007091046 A1 * | 8/2007 | | C07C 233/87 |
| WO | WO-2007/141473 A1 | 12/2007 | | |
| WO | WO-2007141473 A1 * | 12/2007 | | C07D 213/73 |
| WO | WO-2008093065 A1 * | 8/2008 | | C07D 213/81 |
| WO | WO-2008/157162 A1 | 12/2008 | | |
| WO | WO-2010/114726 A1 | 10/2010 | | |
| WO | WO-2016/134223 A2 | 8/2016 | | |
| WO | WO-2017155857 A1 * | 9/2017 | | |
| WO | WO-2017/181062 A1 | 10/2017 | | |
| WO | WO-2018/009501 A1 | 1/2018 | | |
| WO | WO-2018/089353 A1 | 5/2018 | | |
| WO | WO-2018/089355 A1 | 5/2018 | | |
| WO | WO-2018/089357 A1 | 5/2018 | | |
| WO | WO-2018/089358 A1 | 5/2018 | | |
| WO | WO-2018/089360 A1 | 5/2018 | | |
| WO | WO-2018/119087 A1 | 6/2018 | | |
| WO | WO-2018/160522 A1 | 9/2018 | | |

OTHER PUBLICATIONS

Xie, Z., "Design, synthesis of novel tryptophan derivatives for antiplatelet aggregation activity based on tripeptide pENW ( pGlu-Asn-Trp)." European journal of medicinal chemistry 102 (2015): 363-374.*

Delouvrié, B., "Structure-activity relationship of a series of non peptidic RGD integrin antagonists targeting α 5 β 1: Part 1." Bioorganic & medicinal chemistry letters 22.12 (2012): 4111-4116.*

Heckmann, D., "Rational design of highly active and selective ligands for the α5β1 integrin receptor." ChemBioChem 9.9 (2008): 1397-1407.*

Patsenker, E., "Role of integrins in fibrosing liver diseases." American journal of physiology—gastrointestinal and liver physiology 301.3 (2011): G425-G434.*

Reed, N.I. et al. (May 20, 2015). "The $\alpha_v\beta_1$ Integrin Plays a Critical in vivo Role in Tissue Fibrosis," *Science Translational Medicine* 7(288):288ra79, pp. 1-9.

Whitman, D.B. et al. (2004). "Nonpeptide $\alpha_v\beta_3$ Antagonists. Part 9: Improved Pharmacokinetic Profile Through the Use of an Aliphatic, Des-Amide Backbone," *Bioorganic & Medicinal Chemistry Letters* 14:4411-4415.

International Search Report and Written Opinion dated Nov. 3, 2017, for PCT Application No. PCT/US2017/50543 filed on Sep. 7, 2017, eleven pages.

International Preliminary Report on Patentability dated Mar. 21, 2019, for PCT Application No. PCT/US2017/50543 filed Sep. 7, 2017, nine pages.

* cited by examiner

N-ACYL AMINO ACID COMPOUNDS AND METHODS OF USE

CROSS-REFERENCE TO RELATED APPLICATIONS

This application claims priority benefit of U.S. Provisional Patent Application No. 62/384,682, filed Sep. 7, 2016. The entire contents of that application are hereby incorporated by reference herein.

BACKGROUND OF THE INVENTION

Fibrosis, a pathologic feature of many diseases, is caused by a dysfunction in the body's natural ability to repair damaged tissues. If left untreated, fibrosis can result in scarring of vital organs causing irreparable damage and eventual organ failure.

Patients with nonalcoholic fatty liver disease (NAFLD) may progress from simple steatosis to nonalcoholic steatohepatitis (NASH) and then fibrosis. While liver fibrosis is reversible in its initial stages, progressive liver fibrosis can lead to cirrhosis.

Fibrosis in the kidney, characterized by glomerulosclerosis and tubulointerstitial fibrosis, is the final common manifestation of a wide variety of chronic kidney diseases (CKD). Irrespective of the initial causes, progressive CKD often results in widespread tissue scarring that leads to destruction of kidney parenchyma and end-stage renal failure, a devastating condition that requires dialysis or kidney replacement.

Scleroderma encompasses a spectrum of complex and variable conditions primarily characterized by fibrosis, vascular alterations, and autoimmunity. The scleroderma spectrum of disorders share the common feature of fibrosis, resulting in hardening or thickening of the skin. For some patients, this hardening occurs only in limited areas, but for others, it can spread to other major organs.

Following myocardial infarction, cardiac structural remodeling is associated with an inflammatory reaction, resulting in scar formation at the site of the infarction. This scar formation is a result of fibrotic tissue deposition which may lead to reduced cardiac function and disruption of electrical activity within the heart.

Crohn's Disease is a chronic disease of unknown etiology tending to progress even in the setting of medical or surgical treatment. Intestinal fibrosis is among the most common complications of Crohn's disease, resulting in stricture formation in the small intestine and colon.

Idiopathic pulmonary fibrosis (IPF) is a chronic, progressive, fibrosing disease of unknown etiology, occurring in adults and limited to the lungs. In IPF, the lung tissue becomes thickened, stiff, and scarred. As lung fibrosis progresses, it becomes more difficult for the lungs to transfer oxygen into the bloodstream and the organs do not receive the oxygen needed to function properly. IPF currently affects approximately 200,000 people in the U.S., resulting in 40,000 deaths per year. Patients diagnosed with IPF experience progressive breathlessness and eventually, complete respiratory failure.

Available courses of treatment are scarce, as there are currently no options on the market proven to have an effect on long-term patient survival or symptomatology. There remains a need for treatment of fibrotic diseases.

The $\alpha v \beta 1$ integrin, which is highly expressed on activated fibroblasts, directly binds to the latency-associated peptide of transforming growth factor-$\beta 1$ (TGF$\beta 1$) and mediates TGF$\beta 1$ activation; it plays a critical in vivo role in tissue fibrosis. The present disclosure provides for $\alpha v \beta 1$ integrin inhibitors that may be useful for tissue-specific treatment of fibrosis.

BRIEF SUMMARY OF THE INVENTION

Disclosed are N-acyl amino acid compounds that are $\alpha v \beta 1$ integrin inhibitors, compositions containing these compounds and methods for treating diseases mediated by $\alpha v \beta 1$ integrin such as a fibrotic disease.

In one aspect, provided is a compound of formula (I), or any variation thereof, or a salt thereof (e.g., a pharmaceutically acceptable salt thereof), as detailed herein.

Further provided is a pharmaceutical composition comprising a compound of formula (I), or any variation thereof detailed herein, or a salt thereof (e.g., a pharmaceutically acceptable salt thereof), and a pharmaceutically acceptable carrier or excipient.

In another aspect, provided is a method of treating a fibrotic disease in an individual (such as a human) in need thereof comprising administering to the individual a therapeutically effective amount of a compound of formula (I), or any variation thereof detailed herein, or a pharmaceutically acceptable salt thereof. In some embodiments, the fibrotic disease is pulmonary fibrosis, liver fibrosis, skin fibrosis, cardiac fibrosis, kidney fibrosis, or gastrointestinal fibrosis.

In another aspect, provided is a method of delaying the onset and/or development of a fibrotic disease in an individual (such as a human) who is at risk for developing a fibrotic disease.

Also provided is a compound of formula (I), or any variation thereof detailed herein, or a pharmaceutical composition thereof, for the treatment of a fibrotic disease.

Also provided is use of a compound of formula (I), or any variation thereof detailed herein, or a pharmaceutically acceptable salt thereof, in the manufacture of a medicament for the treatment of a fibrotic disease.

Further provided is a kit comprising a compound of formula (I), or any variation thereof detailed herein, or a pharmaceutically acceptable salt thereof. In some embodiments, the kit comprises instructions for use according to a method described herein, such as a method of treating a fibrotic disease in an individual.

In another aspect, provided is a method of making a compound of formula (I) or any variation thereof. Also provided are compound intermediates useful in synthesis of a compound of formula (I), or any variation thereof.

DETAILED DESCRIPTION OF THE INVENTION

The invention provides, inter alia, compounds of formula (I), and variations thereof, pharmaceutical compositions comprising compounds of formula (I), and methods of using such compounds and compositions in treating fibrotic diseases.

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, n-nonyl, n-decyl, and the like.

"Alkylene" as used herein refers to the same residues as alkyl, but having bivalency. Particular alkylene groups are those having 1 to 20 carbon atoms (a "$C_1$-$C_{20}$ alkylene"), having 1 to 10 carbon atoms (a "$C_1$-$C_{10}$ alkylene"), having 6 to 10 carbon atoms (a "$C_6$-$C_{10}$ alkylene"), having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), isopropylene (—$CH_2CH(CH_3)$—), butylene (—$CH_2(CH_2)_2CH_2$—), isobutylene (—$CH_2CH(CH_3)CH_2$—), pentylene (—$CH_2(CH_2)_3CH_2$—), hexylene (—$CH_2(CH_2)_4CH_2$—), heptylene (—$CH_2(CH_2)_5CH_2$—), octylene (—$CH_2(CH_2)_6CH_2$—), and the like.

"Alkenyl" as used herein refers to and includes, unless otherwise stated, an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). An alkenyl group may have "cis" or "trans" configurations, or alternatively have "E" or "Z" configurations. Particular alkenyl groups are those having 2 to 20 carbon atoms (a "$C_2$-$C_{20}$ alkenyl"), having 6 to 10 carbon atoms (a "$C_6$-$C_{10}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, for example, pent-1-enyl, pent-2-enyl, hex-1-enyl, hex-2-enyl, hex-3-enyl, and the like.

"Alkenylene" as used herein refers to the same residues as alkenyl, but having bivalency. Particular alkylene groups are those having 2 to 20 carbon atoms (a "$C_2$-$C_{20}$ alkenylene"), having 2 to 10 carbon atoms (a "$C_2$-$C_{10}$ alkenylene"), having 6 to 10 carbon atoms (a "$C_6$-$C_{10}$ alkenylene"), having 2 to 6 carbon atoms (a "$C_2$-$C_6$ alkenylene"), 2 to 4 carbon atoms (a "$C_2$-$C_4$ alkenylene") or 2 to 3 carbon atoms (a "$C_2$-$C_3$ alkenylene"). Examples of alkenylene include, but are not limited to, groups such as ethenylene (or vinylene) (—CH=CH—), propenylene (—CH=CHCH$_2$—), 1,4-but-1-enylene (—CH=CH—CH$_2$CH$_2$—), 1,4-but-2-enylene (—CH$_2$CH=CHCH$_2$—), 1,6-hex-1-enylene (—CH=CH—(CH$_2$)$_3$CH$_2$—), and the like.

"Alkynyl" as used herein refers to and includes, unless otherwise stated, an unsaturated linear (i.e., unbranched) or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 6 to 10 carbon atoms (a "$C_6$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Alkynylene" as used herein refers to the same residues as alkynyl, but having bivalency. Particular alkylene groups are those having 2 to 20 carbon atoms (a "$C_2$-$C_{20}$ alkynylene"), having 2 to 10 carbon atoms (a "$C_2$-$C_{10}$ alkynylene"), having 6 to 10 carbon atoms (a "$C_6$-$C_{10}$ alkynylene"), having 2 to 6 carbon atoms (a "$C_2$-$C_6$ alkynylene"), 2 to 4 carbon atoms (a "$C_2$-$C_4$ alkynylene") or 2 to 3 carbon atoms (a "$C_2$-$C_3$ alkynylene"). Examples of alkynylene include, but are not limited to, groups such as ethynylene (or acetylenylene) (—C≡C—), propynylene (—C≡CCH$_2$—), and the like.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Cycloalkylene" as used herein refers to the same residues as cycloalkyl, but having bivalency. Cycloalkylene can consist of one ring or multiple rings which may be fused, spiro or bridged, or combinations thereof. Particular cycloalkylene groups are those having from 3 to 12 annular carbon atoms. A preferred cycloalkylene is a cyclic hydrocarbon having from 3 to 8 annular carbon atoms (a "$C_3$-$C_8$ cycloalkylene"), having 3 to 6 carbon atoms (a "$C_3$-$C_6$ cycloalkylene"), or having from 3 to 4 annular carbon atoms (a "$C_3$-$C_4$ cycloalkylene"). Examples of cycloalkylene include, but are not limited to, cyclopropylene, cyclobutylene, cyclopentylene, cyclohexylene, cycloheptylene, norbornylene, and the like. A cycloalkylene may attach to the remaining structures via the same ring carbon atom or different ring carbon atoms. When a cycloalkylene attaches to the remaining structures via two different ring carbon atoms, the connecting bonds may be cis- or trans- to each other. For example, cyclopropylene may include 1,1-cyclopropylene and 1,2-cyclopropylene (e.g., cis-1,2-cyclopropylene or trans-1,2-cyclopropylene), or a mixture thereof.

"Cycloalkenyl" refers to and includes, unless otherwise stated, an unsaturated cyclic non-aromatic univalent hydrocarbon structure, having at least one site of olefinic unsaturation (i.e., having at least one moiety of the formula C=C) and having the number of carbon atoms designated (i.e., $C_2$-$C_{10}$ means two to ten carbon atoms). Cycloalkenyl can consist of one ring, such as cyclohexyl, or multiple rings, such as norbornenyl. A preferred cycloalkenyl is an unsaturated cyclic hydrocarbon having from 3 to 8 annular carbon atoms (a "$C_3$-$C_8$ cycloalkenyl"). Examples of cycloalkenyl groups include, but are not limited to, cyclopropenyl, cyclobutenyl, cyclopentenyl, cyclohexenyl, norbornenyl, and the like.

"Cycloalkenylene" as used herein refers to the same residues as cycloalkenyl, but having bivalency.

"Aryl" or "Ar" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Arylene" as used herein refers to the same residues as aryl, but having bivalency. Particular arylene groups are those having from 6 to 14 annular carbon atoms (a "$C_6$-$C_{14}$ arylene").

"Heteroaryl" as used herein refers to an unsaturated aromatic cyclic group having from 1 to 14 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5 to 14-membered rings having 1 to 12 annular carbon atoms and 1 to 6 annular heteroatoms independently selected from nitrogen, oxygen and sulfur, 5 to 10-membered rings having 1 to 8 annular carbon atoms and 1 to 4 annular heteroatoms independently selected from nitrogen, oxygen and sulfur, or 5, 6 or 7-membered rings having 1 to 5 annular carbon atoms and 1 to 4 annular heteroatoms independently selected from nitrogen, oxygen and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. A heteroaryl group may be connected to the parent structure at a ring carbon atom or a ring heteroatom.

"Heteroarylene" as used herein refers to the same residues as heteroaryl, but having bivalency.

"Heterocycle", "heterocyclic", or "heterocyclyl" as used herein refers to a saturated or an unsaturated non-aromatic cyclic group having a single ring or multiple condensed rings, and having from 1 to 14 annular carbon atoms and from 1 to 6 annular heteroatoms, such as nitrogen, sulfur or oxygen, and the like. A heterocycle comprising more than one ring may be fused, bridged or spiro, or any combination thereof. In fused ring systems, one or more of the fused rings can be cycloalkyl, aryl or heteroaryl. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

"Heterocyclylene" as used herein refers to the same residues as heterocyclyl, but having bivalency.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C═O.

"Thiocarbonyl" refers to the group C═S.

"Oxo" refers to the moiety ═O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents.

Unless clearly indicated otherwise, "an individual" as used herein intends a mammal, including but not limited to a primate, human, bovine, horse, feline, canine, or rodent. In one variation, the individual is a human.

As used herein, "treatment" or "treating" is an approach for obtaining beneficial or desired results including clinical results. For purposes of this invention, beneficial or desired results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, delaying the occurrence or recurrence of the disease, delay or slowing the progression of the disease, ameliorating the disease state, providing a remission (whether partial or total) of the disease, decreasing the dose of one or more other medications required to treat the disease, enhancing effect of another medication, delaying the progression of the disease, increasing the quality of life, and/or prolonging survival. Also encompassed by "treatment" is a reduction of pathological consequence of fibrosis. The methods of the invention contemplate any one or more of these aspects of treatment.

As used herein, the term "effective amount" intends such amount of a compound of the invention which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents (e.g., a compound, or pharmaceutically acceptable salt thereof), and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

A "therapeutically effective amount" refers to an amount of a compound or salt thereof sufficient to produce a desired therapeutic outcome.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Compounds

In one aspect, provided is a compound of formula (I):

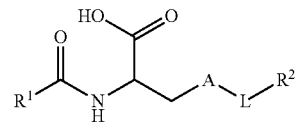

or a salt thereof, wherein:
$R^1$ is $C_6$-$C_{14}$ aryl or 5- to 10-membered heteroaryl, wherein the $C_6$-$C_{14}$ aryl and 5- to 10-membered heteroaryl of $R^1$ are independently optionally substituted by $R^{10}$;
$R^2$ is
  5- to 10-membered heteroaryl containing at least 2 ring nitrogen atoms,
  3- to 12-membered heterocyclyl containing at least 2 ring nitrogen atoms,
  —NH—$R^3$,
  —$R^3$—$R^{10}$, or
  —$R^3$—N$R^{3a}R^{3b}$,
  wherein the 5- to 10-membered heteroaryl and 3- to 12-membered heterocyclyl of $R^2$ are independently optionally substituted by $R^{10}$;

R³ is 5- to 10-membered heteroaryl containing at least 1 ring nitrogen atom, or 3- to 12-membered heterocyclyl containing at least 1 ring nitrogen atom, wherein the 5- to 10-membered heteroaryl and 3- to 12-membered heterocyclyl of R³ are independently optionally substituted by R¹⁰;

-A-L- is -A¹-L¹-, -A²-L²-, or A³;

A¹ is $C_3$-$C_8$ cycloalkylene, $C_3$-$C_8$ cycloalkenylene, $C_6$-$C_{14}$ arylene, 5- to 10-membered heteroarylene or 3- to 12-membered heterocyclylene, wherein the $C_3$-$C_8$ cycloalkylene, $C_3$-$C_8$ cycloalkenylene, $C_6$-$C_{14}$ arylene, 5- to 10-membered heteroarylene and 3- to 12-membered heterocyclylene of A¹ are independently optionally substituted by R¹⁰;

A² is $C_3$-$C_8$ alkylene or $C_3$-$C_8$ alkenylene, wherein the $C_3$-$C_8$ alkylene and $C_3$-$C_8$ alkenylene of A² are independently optionally substituted by R⁹;

A³ is $C_5$-$C_{10}$ alkylene or $C_5$-$C_{10}$ alkenylene, wherein the $C_5$-$C_{10}$ alkylene and $C_5$-$C_{10}$ alkenylene of A³ are independently optionally substituted by R⁹;

L¹ is —O—Z—, —O—Z—X¹—, —O—Y¹—, —O—Y¹—X¹—, —O—Z—Y¹—, —O—Z—Y¹—X¹—, —O—Z—X¹—Y¹—, —O—Z—X¹—Y¹—X¹—, —Z—O—Z—, —X¹—Z—O—Z—, —Z—O—Z—X¹—, —X¹—Z—O—Z—X¹—, —Z—O—Y¹—, —Z—O—Y¹—X¹—, —X¹—Z—O—Y¹—, —X¹—Z—O—Y¹—X¹—, —N(R⁴)—Z—, —N(R⁴)—Z—X¹—, X², —X²—Y¹—, Y², or —Y²—X²—;

L² is $C_3$-$C_6$ cycloalkylene optionally substituted by R¹⁰;

each X¹ is independently $C_1$-$C_6$ alkylene or $C_2$-$C_6$ alkenylene, wherein the $C_1$-$C_6$ alkylene and $C_2$-$C_6$ alkenylene of X¹ are independently optionally substituted by R¹⁰;

each X² is independently $C_1$-$C_6$ alkylene or $C_2$-$C_6$ alkenylene, wherein the $C_1$-$C_6$ alkylene and $C_2$-$C_6$ alkenylene of X² are independently optionally substituted by R⁹;

each Y¹ is independently $C_3$-$C_6$ cycloalkylene optionally substituted by R¹⁰;

each Y² is independently saturated 3- to 4-membered heterocyclylene optionally substituted by R¹⁰;

each Z is independently —CR⁵ᵃR⁵ᵇ—;

each R³ᵃ, R³ᵇ, R⁴, R⁵ᵃ and R⁵ᵇ is independently H or $C_1$-$C_6$ alkyl;

each R⁹ is independently $C_1$-$C_6$ alkyl, $C_2$-$C_6$ alkenyl, $C_2$-$C_6$ alkynyl, halogen, —CN, —OR¹¹, —SR¹¹, —NR¹²R¹³, —NO₂, —C=NH(OR¹¹), —C(O)R¹¹, —OC(O)R¹¹, —C(O)OR¹¹, —C(O)NR¹²R¹³, —NR¹¹C(O)R¹², —NR¹¹C(O)OR¹², —NR¹¹C(O)NR¹²R¹³, —S(O)R¹¹, —S(O)₂R¹¹, —NR¹¹S(O)R¹², —NR¹¹S(O)₂R¹², —S(O)NR¹²R¹³, —S(O)₂NR¹²R¹³, —P(O)(OR¹²)(OR¹³), $C_3$-$C_8$ cycloalkyl, 3- to 12-membered heterocyclyl, 5- to 10-membered heteroaryl, $C_6$-$C_{14}$ aryl, wherein each R⁹ is independently optionally substituted by halogen, oxo, —OR¹⁴, —NR¹⁴R¹⁵, —C(O)R¹⁴, —CN, —S(O)R¹⁴, —S(O)₂R¹⁴, —P(O)(OR¹⁴)(OR¹⁵), $C_3$-$C_8$ cycloalkyl, 3- to 12-membered heterocyclyl, 5- to 10-membered heteroaryl, $C_6$-$C_{14}$ aryl, or $C_1$-$C_6$ alkyl optionally substituted by oxo, —OH or halogen;

each R¹⁰ is independently oxo or R⁹;

R¹¹ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —OR¹⁶, —NR¹⁶R¹⁷, —P(O)(OR¹⁶)(OR¹⁷), or $C_1$-$C_6$ alkyl optionally substituted by halogen, —OH or oxo;

R¹² and R¹³ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —OR¹⁶, —NR¹⁶R¹⁷ or $C_1$-$C_6$ alkyl optionally substituted by halogen, —OH or oxo;

or R¹² and R¹¹ are taken together with the atom to which they attached to form a 3- to 6-membered heterocyclyl optionally substituted by halogen, oxo, —OR¹⁶, —NR¹⁶R¹⁷ or $C_1$-$C_6$ alkyl optionally substituted by halogen, oxo or —OH;

R¹⁴ and R¹⁵ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or R¹⁴ and R¹⁵ are taken together with the atom to which they attached to form a 3- to 6-membered heterocyclyl optionally substituted by halogen, oxo or $C_1$-$C_6$ alkyl optionally substituted by halogen or oxo; and R¹⁶ and R¹⁷ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or R¹⁶ and R¹⁷ are taken together with the atom to which they attached to form a 3-6 membered heterocyclyl optionally substituted by halogen, oxo or $C_1$-$C_6$ alkyl optionally substituted by oxo or halogen.

In another embodiment, R² is —NR³ᵃ-pyridyl, wherein pyridyl is optionally substituted by R¹⁰. In another embodiment, R² is —NH-pyridyl, wherein pyridyl is optionally substituted by R¹⁰. In another embodiment, R² is

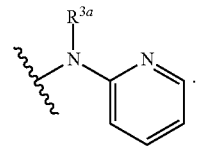

In another embodiment, R² is

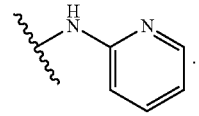 [SMILES: *Nc1ccccn1]

In another embodiment, R² is —R³—NR³ᵃR³ᵇ. In another embodiment, R² is —R³—NHR³ᵃ. In another embodiment, R² is -(pyridyl)-NR³ᵃR³ᵇ, where pyridyl is optionally substituted by R¹⁰. In another embodiment, R² is

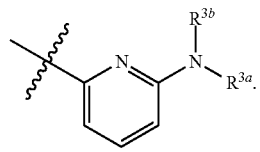

In another embodiment, $R^2$ is

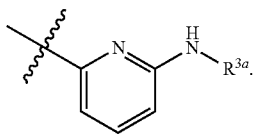

In some embodiments, the compound is other than a compound in Table IX and salts thereof. In some embodiments, the compound herein, such as a compound of formula (I), is other than a compound selected from one or more of Compound Nos. 1x-164x in Table 1X. In some embodiments, the compounds of the disclosure, and methods of using the compounds detailed herein, encompass any of the compounds of formula (I), including those listed Table 1X and salts thereof.

TABLE IX

| No. | Chemical Name [1] |
|---|---|
| 1x | L-Tyrosine, N-[(2-methyl-1-naphthalenyl)carbonyl]-O-[4-(2-pyridinylamino)butyl]- |
| 2x | L-Tyrosine, N-[(5-chloro-1,3-benzodioxol-4-yl)carbonyl]-O-[3-(2-pyridinylamino)propyl]- |
| 3x | L-Tyrosine, N-[(5-chloro-1,3-benzodioxol-4-yl)carbonyl]-O-[2-(5,6,7,8-tetrahydro-1,8-naphthyridin-2-yl)ethyl]- |
| 4x | L-Tyrosine, N-[(3-chloro-1-methyl-1H-indol-2-yl)carbonyl]-O-[2-(5,6,7,8-tetrahydro-1,8-naphthyridin-2-yl)ethyl]- |
| 5x | L-Tyrosine, N-[[1-cyclohexyl-2-(3-furanyl)-1H-benzimidazol-5-yl]carbonyl]-O-(1H-tetrazol-5-ylmethyl)- |
| 6x | L-Tyrosine, N-(2,6-dichlorobenzoyl)-O-[(5,6,7,8-tetrahydro-1,8-naphthyridin-2-yl)methyl]- |
| 7x | L-Tyrosine, N-(2-chloro-4-methoxybenzoyl)-O-[2-(3,4-dihydro-2H-pyrido[3,2-b]-1,4-oxazin-6-yl)ethyl]- |
| 8x | L-Tyrosine, N-(2-chloro-6-methylbenzoyl)-O-[2-(3,4-dihydro-2H-pyrido[3,2-b]-1,4-oxazin-6-yl)ethyl]- |
| 9x | L-Tyrosine, N-(2-fluoro-6-methylbenzoyl)-O-[2-(5,6,7,8-tetrahydro-1,8-naphthyridin-2-yl)ethyl]- |
| 10x | L-Tyrosine, N-[(2-ethyl-3-thienyl)carbonyl]-O-[2-(5,6,7,8-tetrahydro-1,8-naphthyridin-2-yl)ethyl]- |
| 11x | L-Tryptophan, N-benzoyl-5-[4-(1-piperazinyl)butoxy]- |
| 12x | L-Tyrosine, N-(2-chlorobenzoyl)-O-[2-(5,6,7,8-tetrahydro-1,8-naphthyridin-2-yl)ethyl]- |
| 13x | L-Tyrosine, N-[(3-chloro-2-thienyl)carbonyl]-O-[2-(5,6,7,8-tetrahydro-1,8-naphthyridin-2-yl)ethyl]- |
| 14x | 2-Pyridinepropanoic acid, a-[(2,6-dichlorobenzoyl)amino]-5-[2-(5,6,7,8-tetrahydro-1,8-naphthyridin-2-yl)ethoxy]-, (αS)- |
| 15x | L-Tyrosine, N-(2-chloro-6-fluorobenzoyl)-O-[2-(5,6,7,8-tetrahydro-1,8-naphthyridin-2-yl)ethyl]- |
| 16x | L-Tyrosine, N-[(3-chloro-4-pyridinyl)carbonyl]-O-[2-(3,4-dihydro-2H-pyrido[3,2-b]-1,4-oxazin-6-yl)ethyl]- |
| 17x | L-Tyrosine, O-[2-(5,6,7,8-tetrahydro-1,8-naphthyridin-2-yl)ethyl]-N-(2,4,6-trimethylbenzoyl)- |
| 18x | L-Tyrosine, N-[(3,5-dichloro-4-pyridinyl)carbonyl]-O-[2-(3,4-dihydro-2H-pyrido[3,2-b]-1,4-oxazin-6-yl)ethyl]- |
| 19x | L-Tyrosine, N-(2,4-dichlorobenzoyl)-O-[2-(5,6,7,8-tetrahydro-1,8-naphthyridin-2-yl)ethyl]- |
| 20x | 2-Pyridinepropanoic acid, α-[(2-chloro-4-methoxybenzoyl)amino]-5-[2-(5,6,7,8-tetrahydro-1,8-naphthyridin-2-yl)ethoxy]-, (αS)- |
| 21x | 2-Pyridinepropanoic acid, α-[(2-chlorobenzoyl)amino]-5-[2-(5,6,7,8-tetrahydro-1,8-naphthyridin-2-yl)ethoxy]-, (αS)- |
| 22x | L-Tyrosine, N-(2-chloro-6-fluoro-3-methylbenzoyl)-O-[2-(3,4-dihydro-2H-pyrido[3,2-b]-1,4-oxazin-6-yl)ethyl]- |
| 23x | 3-Pyridinepropanoic acid, α-[(2-chlorobenzoyl)amino]-6-[2-(5,6,7,8-tetrahydro-1,8-naphthyridin-2-yl)ethoxy]-, (αS)- |
| 24x | L-Tyrosine, N-(2,6-dichlorobenzoyl)-O-[2-(5,6,7,8-tetrahydro-1,8-naphthyridin-2-yl)ethyl]- |
| 25x | L-Tyrosine, N-(2-chloro-6-fluorobenzoyl)-O-[2-(3,4-dihydro-2H-pyrido[3,2-b]-1,4-oxazin-6-yl)ethyl]- |
| 26x | L-Tyrosine, N-(2-chloro-5-fluorobenzoyl)-O-[2-(3,4-dihydro-2H-pyrido[3,2-b]-1,4-oxazin-6-yl)ethyl]- |
| 27x | 2-Naphthalenepropanoic acid, α-(benzoylamino)-6-[2-(1-piperazinyl)ethoxy]- |
| 28x | L-Tyrosine, O-[2-(3,4-dihydro-2H-pyrido[3,2-b]-1,4-oxazin-6-yl)ethyl]-N-(2-ethyl-4-fluorobenzoyl)- |
| 29x | L-Tyrosine, N-(2,6-dichlorobenzoyl)-O-[2-(5,6,7,8-tetrahydro-5-methyl-1,8-naphthyridin-2-yl)ethyl]- |
| 30x | 2-Pyridinepropanoic acid, α-[[(3-chloro-2-thienyl)carbonyl]amino]-5-[2-(5,6,7,8-tetrahydro-1,8-naphthyridin-2-yl)ethoxy]-, (αS)- |
| 31x | L-Tyrosine, N-(2,6-dichlorobenzoyl)-O-[2-(1,2,3,4-tetrahydro-1-methylpyrido[2,3-b]pyrazin-6-yl)ethyl]- |
| 32x | L-Tryptophan, N-benzoyl-5-[3-[4-[(1,1-dimethylethoxy)carbonyl]-1-piperazinyl]propoxy]- |
| 33x | L-Tyrosine, N-(2,6-dimethylbenzoyl)-O-[2-(5,6,7,8-tetrahydro-1,8-naphthyridin-2-yl)ethyl]- |

TABLE IX-continued

| No. | Chemical Name [1] |
|---|---|
| 34x | L-Tyrosine, O-[2-(3,4-dihydro-2H-pyrido[3,2-b]-1,4-oxazin-6-yl)ethyl]-N-[(3-methyl-4-pyridinyl)carbonyl]- |
| 35x | L-Tyrosine, N-(2-chloro-6-methylbenzoyl)-O-[2-(5,6,7,8-tetrahydro-1,8-naphthyridin-2-yl)ethyl]- |
| 36x | L-Tyrosine, N-[(3-chloro-2-thienyl)carbonyl]-O-[2-(3,4-dihydro-2H-pyrido[3,2-b]-1,4-oxazin-6-yl)ethyl]- |
| 37x | 2-Thiophenepropanoic acid, α-[[(3,5-dichloro-4-pyridinyl)carbonyl]amino]-5-[2-(5,6,7,8-tetrahydro-1,8-naphthyridin-2-yl)ethoxy]-, (αS)- |
| 38x | L-Tyrosine, N-(2-chloro-3,6-difluorobenzoyl)-O-[2-(5,6,7,8-tetrahydro-1,8-naphthyridin-2-yl)ethyl]- |
| 39x | 2-Pyridinepropanoic acid, α-[(2-fluoro-4-methylbenzoyl)amino]-5-[2-(5,6,7,8-tetrahydro-1,8-naphthyridin-2-yl)ethoxy]-, (αS)- |
| 40x | L-Tyrosine, N-(2,6-dichlorobenzoyl)-O-[2-(5,6,7,8-tetrahydro-4-methyl-1,8-naphthyridin-2-yl)ethyl]- |
| 41x | 2-Pyridinepropanoic acid, α-[(2-chloro-4-fluorobenzoyl)amino]-5-[2-(5,6,7,8-tetrahydro-1,8-naphthyridin-2-yl)ethoxy]-, (αS)- |
| 42x | L-Tyrosine, N-(2,6-dichlorobenzoyl)-O-[2-(3,4-dihydro-2H-pyrido[3,2-b]-1,4-oxazin-6-yl)ethyl]- |
| 43x | 3-Pyridinepropanoic acid, α-[(2-chloro-4-fluorobenzoyl)amino]-6-[2-(5,6,7,8-tetrahydro-1,8-naphthyridin-2-yl)ethoxy]-, (αS)- |
| 44x | L-Tyrosine, N-(2-chlorobenzoyl)-O-[2-(3,4-dihydro-2H-pyrido[3,2-b]-1,4-oxazin-6-yl)ethyl]- |
| 45x | L-Tyrosine, O-[2-(3,4-dihydro-2H-pyrido[3,2-b]-1,4-oxazin-6-yl)ethyl]-N-(2-ethyl-5-fluorobenzoyl)- |
| 46x | 1-Piperazinecarboxylic acid, 4-[2-[[6-[2-(benzoylamino)-2-carboxyethyl]-2-naphthalenyl]oxy]ethyl]-, 1-(1,1-dimethylethyl) ester |
| 47x | L-Tyrosine, O-[2-(3,4-dihydro-2H-pyrido[3,2-b]-1,4-oxazin-6-yl)ethyl]-N-(2,4,6-trimethylbenzoyl)- |
| 48x | L-Tyrosine, O-[2-(3,4-dihydro-2H-pyrido[3,2-b]-1,4-oxazin-6-yl)ethyl]-N-(2,6-dimethylbenzoyl)- |
| 49x | 3-Pyridinepropanoic acid, α-[[(3-chloro-2-thienyl)carbonyl]amino]-6-[2-(5,6,7,8-tetrahydro-1,8-naphthyridin-2-yl)ethoxy]-, (αS)- |
| 50x | L-Tryptophan, N-benzoyl-5-[4-[4-[(1,1-dimethylethoxy)carbonyl]-1-piperazinyl]butoxy]- |
| 51x | L-Tyrosine, N-(2-methylbenzoyl)-O-[2-(5,6,7,8-tetrahydro-1,8-naphthyridin-2-yl)ethyl]- |
| 52x | L-Tyrosine, N-[(3,5-dichloro-4-pyridinyl)carbonyl]-O-[2-(5,6,7,8-tetrahydro-1,8-naphthyridin-2-yl)ethyl]- |
| 53x | L-Tryptophan, N-benzoyl-5-[3-(1-piperazinyl)propoxy]- |
| 54x | L-Tyrosine, N-(6-chloro-2-fluoro-3-methylbenzoyl)-O-[2-(5,6,7,8-tetrahydro-1,8-naphthyridin-2-yl)ethyl]- |
| 55x | L-Tyrosine, N-[(4-methoxy-3-thienyl)carbonyl]-O-[2-(5,6,7,8-tetrahydro-1,8-naphthyridin-2-yl)ethyl]- |
| 56x | L-Tyrosine, N-(2-chloro-4-fluorobenzoyl)-O-[2-(5,6,7,8-tetrahydro-1,8-naphthyridin-2-yl)ethyl]- |
| 57x | L-Tyrosine, O-[2-(3,4-dihydro-2H-pyrido[3,2-b]-1,4-oxazin-6-yl)ethyl]-N-[(3,5-dimethyl-4-isoxazolyl)carbonyl]- |
| 58x | L-Tyrosine, N-(2-chloro-5-methylbenzoyl)-O-[2-(5,6,7,8-tetrahydro-1,8-naphthyridin-2-yl)ethyl]- |
| 59x | 2-Pyridinepropanoic acid, α-[(2-ethyl-4-fluorobenzoyl)amino]-5-[2-(5,6,7,8-tetrahydro-1,8-naphthyridin-2-yl)ethoxy]-, αS)- |
| 60x | L-Tyrosine, N-(2,6-dichlorobenzoyl)-O-[2-(5,6,7,8-tetrahydro-7-methyl-1,8-naphthyridin-2-yl)ethyl]- |
| 61x | 2-Pyridinepropanoic acid, α-[(2-chloro-6-fluorobenzoyl)amino]-5-[2-(5,6,7,8-tetrahydro-1,8-naphthyridin-2-yl)ethoxy]-, (αS)- |
| 62x | 3-Pyridinepropanoic acid, α-[(2-chloro-6-fluorobenzoyl)amino]-6-[2-(5,6,7,8-tetrahydro-1,8-naphthyridin-2-yl)ethoxy]-, (αS)- |
| 63x | L-Tyrosine, N-(2-chloro-4-fluorobenzoyl)-O-[2-(3,4-dihydro-2H-pyrido[3,2-b]-1,4-oxazin-6-yl)ethyl]- |
| 64x | 3-Pyridinepropanoic acid, α-[(2,6-dichlorobenzoyl)amino]-6-[2-(5,6,7,8-tetrahydro-1,8-naphthyridin-2-yl)ethoxy]-, (αS)- |
| 65x | L-Tyrosine, N-(2,6-dichlorobenzoyl)-O-[2-(5,6,7,8-tetrahydro-1,8-naphthyridin-2-yl)propyl]- |
| 66x | L-Tyrosine, N-(2,6-dichlorobenzoyl)-O-[2-methyl-2-(5,6,7,8-tetrahydro-1,8-naphthyridin-2-yl)propyl]- |
| 67x | L-Tyrosine, N-(2,6-dichlorobenzoyl)-O-[2-(2-pyridinylamino)ethyl]- |
| 68x | D-Tyrosine, N-benzoyl-O-[3-(2-pyridinylamino)propyl]- |
| 69x | L-Tyrosine, N-(2,6-dichlorobenzoyl)-O-[3-[(4,6-dimethyl-2-pyridinyl)amino]propyl]- |
| 70x | L-Tyrosine, N-(2,6-dimethylbenzoyl)-O-[3-(2-pyridinylamino)propyl]- |
| 71x | L-Tyrosine, N-(3,5-dimethylbenzoyl)-O-[3-(2-pyridinylamino)propyl]- |
| 72x | L-Tyrosine, N-(2,6-dichlorobenzoyl)-O-[3-[(4-methyl-2-pyridinyl)amino]propyl]- |
| 73x | L-Phenylalanine, N-(2,6-dichlorobenzoyl)-3-[4-(2-pyridinylamino)butoxy]- |
| 74x | L-Tyrosine, N-(2-chloro-3,6-difluorobenzoyl)-O-[3-(2-pyridinylamino)propyl]- |
| 75x | L-Tyrosine, O-[3-[(1,4,5,6-tetrahydro-2-pyridinyl)amino]propyl]-N-(2,4,6-trimethylbenzoyl)- |
| 76x | L-Tyrosine, N-(2-chloro-6-fluoro-3-methylbenzoyl)-O-[3-(2-pyridinylamino)propyl]- |

TABLE IX-continued

| No. | Chemical Name [1] |
|---|---|
| 77x | L-Tyrosine, O-[3-(4-pyrimidinylamino)propyl]-N-(2,4,6-trimethylbenzoyl)- |
| 78x | L-Tyrosine, N-(2,6-dichlorobenzoyl)-O-[3-[(4-methoxy-2-pyridinyl)amino]propyl]- |
| 79x | L-Tyrosine, N-(2,4-dichlorobenzoyl)-O-[3-(2-pyridinylamino)propyl]- |
| 80x | L-Tyrosine, O-[4-(2-pyridinylamino)butyl]-N-(2,4,6-trimethylbenzoyl)- |
| 81x | L-Tyrosine, N-benzoyl-O-[4-[(1,4,5,6-tetrahydro-2-pyrimidinyl)amino]butyl]- |
| 82x | L-Tyrosine, N-(2,6-dichlorobenzoyl)-O-[3-(2-pyridinylamino)propyl]- |
| 83x | L-Tyrosine, N-(4-methoxy-2,6-dimethylbenzoyl)-O-[3-(2-pyridinylamino)propyl]- |
| 84x | L-Tyrosine, N-(2,6-dichlorobenzoyl)-O-[3-[(4-ethyl-2-pyridinyl)amino]propyl]- |
| 85x | L-Tyrosine, N-(4-methylbenzoyl)-O-[3-(2-pyridinylamino)propyl]- |
| 86x | D-Tyrosine, O-[3-(2-pyridinylamino)propyl]-N-(2,4,6-trimethylbenzoyl)- |
| 87x | L-Tyrosine, N-(2,6-dichlorobenzoyl)-O-[3-[(6-methyl-2-pyridinyl)amino]propyl]- |
| 88x | L-Phenylalanine, N-(2,6-dichlorobenzoyl)-3-[2-(2-pyridinylamino)ethoxy]- |
| 89x | L-Tyrosine, O-[2-(2-benzothiazolylamino)ethyl]-N-(2,6-dichlorobenzoyl)- |
| 90x | L-Tyrosine, N-(2-chloro-4-fluorobenzoyl)-O-[3-(2-pyridinylamino)propyl]- |
| 91x | L-Tyrosine, N-(2-methylbenzoyl)-O-[3-(2-pyridinylamino)propyl]- |
| 92x | L-Tyrosine, N-(6-chloro-2-fluoro-3-methylbenzoyl)-O-[3-(2-pyridinylamino)propyl]- |
| 93x | L-Tyrosine, O-[3-[(1,4,5,6-tetrahydro-2-pyrimidinyl)amino]propyl]-N-(2,4,6-trimethylbenzoyl)- |
| 94x | L-Tyrosine, N-(2-chloro-5-methylbenzoyl)-O-[3-(2-pyridinylamino)propyl]- |
| 95x | L-Tyrosine, O-[3-(2-pyrimidinylamino)propyl]-N-(2,4,6-trimethylbenzoyl)- |
| 96x | L-Tyrosine, O-[2-(1H-benzimidazol-2-ylamino)ethyl]-N-(2,6-dichlorobenzoyl)- |
| 97x | L-Tyrosine, N-[2,6-dimethyl-4-(1-methylethoxy)benzoyl]-O-[4-(2-pyridinylamino)butyl]- |
| 98x | L-Tyrosine, N-benzoyl-O-[4-(2-pyrimidinylamino)butyl]- |
| 99x | L-Tyrosine, N-(2,6-dichlorobenzoyl)-O-[4-(2-pyridinylamino)butyl]- |
| 100x | L-Tyrosine, O-[3-(2-pyridinylamino)propyl]-N-(2,4,6-trichlorobenzoyl)- |
| 101x | L-Tyrosine, N-[2,6-dimethyl-4-(1-methylethoxy)benzoyl]-O-[3-(2-pyridinylamino)propyl]- |
| 102x | L-Tyrosine, O-[3-(2-pyridinylamino)propyl]-N-[(2,4,6-trimethyl-3-pyridinyl)carbonyl]- |
| 103x | L-Tyrosine, N-(2,6-dichlorobenzoyl)-O-[3-[(3-methyl-2-pyridinyl)amino]propyl]- |
| 104x | L-Tyrosine, N-(2,6-dichlorobenzoyl)-O-[3-[(5-methyl-2-pyridinyl)amino]propyl]- |
| 105x | L-Tyrosine, N-(2-bromo-6-chlorobenzoyl)-O-[3-(2-pyridinylamino)propyl]- |
| 106x | L-Tyrosine, N-(2,6-dichloro-3-methylbenzoyl)-O-[3-(2-pyridinylamino)propyl]- |
| 107x | L-Tyrosine, N-[4-(1-methylethoxy)benzoyl]-O-[3-(2-pyridinylamino)propyl]- |
| 108x | L-Tyrosine, N-(3-chloro-2-methylbenzoyl)-O-[3-(2-pyridinylamino)propyl]- |
| 109x | L-Tyrosine, O-[3-[(1,4,5,6-tetrahydro-2-pyrazinyl)amino]propyl]-N-(2,4,6-trimethylbenzoyl)- |
| 110x | L-Tyrosine, N-(2-chloro-6-fluorobenzoyl)-O-[3-(2-pyridinylamino)propyl]- |
| 111x | L-Tyrosine, O-[3-(2-pyrazinylamino)propyl]-N-(2,4,6-trimethylbenzoyl)- |
| 112x | L-Tyrosine, N-(2,6-dichlorobenzoyl)-O-[3-[(5-methoxy-2-pyridinyl)amino]propyl]- |
| 113x | L-Tyrosine, N-(2-chlorobenzoyl)-O-[3-(2-pyridinylamino)propyl]- |
| 114x | L-Tyrosine, N-(2,6-diethylbenzoyl)-O-[4-(2-pyridinylamino)butyl]- |
| 115x | L-Tyrosine, N-benzoyl-O-[4-(2-pyridinylamino)butyl]- |
| 116x | 2-(2,6-dichlorobenzamido)-3-(3-(3-(pyridin-2-ylamino)propoxy)phenyl)propanoic acid |
| 117x | 2-(4-isopropoxybenzamido)-3-(4-(3-(pyridin-2-ylamino)propoxy)phenyl)propanoic acid |
| 118x | Phenylalanine, 4-[3-[(2-pyridinylamino)methyl]-1-azetidinyl]-N-(2,4,6-trimethylbenzoyl)- |
| 119x | Phenylalanine, N-(4-chloro-2-ethyl-6-methylbenzoyl)-4-[3-[(2-pyridinylamino)methyl]-1-azetidinyl]- |
| 120x | Phenylalanine, N-[2-ethyl-4-(1H-imidazol-1-yl)-6-methylbenzoyl]-4-[3-[(2-pyridinylamino)methyl]-1-azetidinyl]- |
| 121x | Phenylalanine, N-(4-acetyl-2-ethyl-6-methylbenzoyl)-4-[3-[(2-pyridinylamino)methyl]-1-azetidinyl]- |
| 122x | Phenylalanine, N-(2-ethyl-4-fluoro-6-methylbenzoyl)-4-[3-[(2-pyridinylamino)methyl]-1-azetidinyl]- |
| 123x | Phenylalanine, N-[2-ethyl-6-methyl-4-(trifluoromethyl)benzoyl]-4-[3-[(2-pyridinylamino)methyl]-1-azetidinyl]- |
| 124x | Phenylalanine, N-(4-cyano-2-ethyl-6-methylbenzoyl)-4-[3-[(2-pyridinylamino)methyl]-1-azetidinyl]- |
| 125x | Phenylalanine, N-(2-ethyl-6-methylbenzoyl)-4-[3-[(2-pyridinylamino)methyl]-1-azetidinyl]- |
| 126x | 2-Thiophenepropanoic acid, a-[(2-chloro-4-fluorobenzoyl)amino]-5-[3-(5,6,7,8-tetrahydro-1,8-naphthyridin-2-yl)propyl]-, (αS)- |
| 127x | 2-Pyridinepropanoic acid, a-[(2-chlorobenzoyl)amino]-5-[3-(5,6,7,8-tetrahydro-1,8-naphthyridin-2-yl)propyl]-, (αS)- |
| 128x | 3-Pyridinepropanoic acid, a-[(2-chloro-4-fluorobenzoyl)amino]-6-[3-(5,6,7,8-tetrahydro-1,8-naphthyridin-2-yl)propyl]-, (αS)- |
| 129x | 2-Thiophenepropanoic acid, α-[[(3,5-dichloro-4-pyridinyl)carbonyl]amino]-5-[3-(5,6,7,8-tetrahydro-1,8-naphthyridin-2-yl)propyl]-, (αS)- |
| 130x | L-Phenylalanine, N-(2-chloro-4-fluorobenzoyl)-4-[3-(3,4-dihydro-2H-pyrido[3,2-b]-1,4-oxazin-6-yl)propyl]- |

TABLE IX-continued

| No. | Chemical Name [1] |
|---|---|
| 131x | 2-Thiophenepropanoic acid, α-[(2-chloro-6-fluorobenzoyl)amino]-5-[3-(5,6,7,8-tetrahydro-1,8-naphthyridin-2-yl)propyl]-, (αS)- |
| 132x | 2-Pyridinepropanoic acid, α-[(2-fluoro-6-methylbenzoyl)amino]-5-[3-(5,6,7,8-tetrahydro-1,8-naphthyridin-2-yl)propyl]-, (αS)- |
| 133x | 3-Pyridinepropanoic acid, α-[(2-chloro-6-fluorobenzoyl)amino]-6-[3-(5,6,7,8-tetrahydro-1,8-naphthyridin-2-yl)propyl]-, (αS)- |
| 134x | L-Phenylalanine, N-(2,6-dichlorobenzoyl)-4-[3-(3,4-dihydro-2H-pyrido[3,2-b]-1,4-oxazin-6-yl)propyl]- |
| 135x | 2-Thiophenepropanoic acid, α-[(2,6-dichlorobenzoyl)amino]-5-[3-(5,6,7,8-tetrahydro-1,8-naphthyridin-2-yl)propyl]-, (αS)- |
| 136x | 2-Pyridinepropanoic acid, α-[(2-chloro-4-fluorobenzoyl)amino]-5-[3-(5,6,7,8-tetrahydro-1,8-naphthyridin-2-yl)propyl]-, (αS)- |
| 137x | 2-Pyridinepropanoic acid, α-[[(3-chloro-2-thienyl)carbonyl]amino]-5-[3-(5,6,7,8-tetrahydro-1,8-naphthyridin-2-yl)propyl]-, (αS)- |
| 138x | L-Phenylalanine, N-(2-chlorobenzoyl)-4-[3-(5,6,7,8-tetrahydro-1,8-naphthyridin-2-yl)propyl]- |
| 139x | L-Phenylalanine, N-(2-chloro-6-fluorobenzoyl)-4-[3-(5,6,7,8-tetrahydro-1,8-naphthyridin-2-yl)propyl]- |
| 140x | 2-Pyridinepropanoic acid, α-[(2-chloro-6-fluorobenzoyl)amino]-5-[3-(5,6,7,8-tetrahydro-1,8-naphthyridin-2-yl)propyl]-, (αS)- |
| 141x | 2-Pyridinepropanoic acid, α-[(2,6-dichlorobenzoyl)amino]-5-[3-(5,6,7,8-tetrahydro-1,8-naphthyridin-2-yl)propyl]-, (αS)- |
| 142x | L-Phenylalanine, N-(2,6-dichlorobenzoyl)-4-[3-(5,6,7,8-tetrahydro-1,8-naphthyridin-2-yl)propyl]- |
| 143x | 3-Pyridinepropanoic acid, α-[(2,6-dichlorobenzoyl)amino]-6-[3-(5,6,7,8-tetrahydro-1,8-naphthyridin-2-yl)propyl]-, (αS)- |
| 144x | L-Phenylalanine, N-[(3,5-dimethyl-4-isoxazolyl)carbonyl]-4-[3-(5,6,7,8-tetrahydro-1,8-naphthyridin-2-yl)propyl]- |
| 145x | L-Phenylalanine, N-(2-chlorobenzoyl)-4-[3-(3,4-dihydro-2H-pyrido[3,2-b]-1,4-oxazin-6-yl)propyl]- |
| 146x | 2-Thiophenepropanoic acid, α-[[3-[(dimethylamino)methyl]benzoyl]amino]-5-[(8-methyl-6,10-dioxo-7,9-diazaspiro[4.5]dec-7-en-9-yl)methyl]- |
| 147x | 2-Thiophenepropanoic acid, α-[(2-chlorobenzoyl)amino]-5-[3-(5,6,7,8-tetrahydro-1,8-naphthyridin-2-yl)propyl]-, (αS)- |
| 148x | L-Phenylalanine, N-(2-chloro-4-fluorobenzoyl)-4-[3-(5,6,7,8-tetrahydro-1,8-naphthyridin-2-yl)propyl]- |
| 149x | 3-Pyridinepropanoic acid, α-[(2-chlorobenzoyl)amino]-6-[3-(5,6,7,8-tetrahydro-1,8-naphthyridin-2-yl)propyl]-, (αS)- |
| 150x | 2-Thiophenepropanoic acid, α-[[(3,5-dimethyl-4-isoxazolyl)carbonyl]amino]-5-[3-(5,6,7,8-tetrahydro-1,8-naphthyridin-2-yl)propyl]-, (αS)- |
| 151x | L-Phenylalanine, N-(2-chloro-6-fluorobenzoyl)-4-[3-(3,4-dihydro-2H-pyrido[3,2-b]-1,4-oxazin-6-yl)propyl]- |
| 152x | 3-Pyridinepropanoic acid, α-[[(3-chloro-2-thienyl)carbonyl]amino]-6-[3-(5,6,7,8-tetrahydro-1,8-naphthyridin-2-yl)propyl]-, (αS)- |
| 153x | L-Phenylalanine, N-(2,6-dichlorobenzoyl)-4-[3-(2-pyridinylamino)propyl]- |
| 154x | L-Phenylalanine, N-(2,6-dichlorobenzoyl)-4-[4-(2-pyridinylamino)butyl]- |
| 155x | 5-Benzofuranpropanoic acid, α-[(2,6-dichlorobenzoyl)amino]-2-[2-(2-pyridinylamino)ethyl]-, (αS)- |
| 156x | 2-(2,6-dichlorobenzamido)-3-(4-(4-(pyridin-2-ylamino)butyl)-1H-imidazol-1-yl)propanoic acid |
| 157x | 2-(2,6-dichlorobenzamido)-3-(5-(4-(pyridin-2-ylamino)butyl)oxazol-2-yl)propanoic acid |
| 158x | 2-(2,6-dichlorobenzamido)-3-(4-(5-(pyridin-2-ylamino)pentyl)phenyl)propanoic acid |
| 159x | 2-(2,6-dichlorobenzamido)-3-(4-(2-(pyridin-2-ylamino)ethyl)-1H-1,2,3-triazol-1-yl)propanoic acid |
| 160x | 2-(2,6-dichlorobenzamido)-3-(4-(3-(pyridin-2-ylamino)propyl)-1H-1,2,3-triazol-1-yl)propanoic acid |
| 161x | 2-(2,6-dichlorobenzamido)-3-(4-(4-(pyridin-2-ylamino)butyl)-1H-1,2,3-triazol-1-yl)propanoic acid |
| 162x | 2-(2,6-dichlorobenzamido)-3-(4-(5-(pyridin-2-ylamino)pentyl)-1H-1,2,3-triazol-1-yl)propanoic acid |
| 163x | 2-(2,6-dichlorobenzamido)-3-(2-((4-(pyridin-2-ylamino)butyl)amino)pyrimidin-5-yl)propanoic acid |
| 164x | 1,8-Naphthyridine-2-nonanoic acid, α-(benzoylamino)-5,6,7,8-tetrahydro-, (αS)- |

[1] Chemical names are either index names for the compound as in CAS Registry ® database or generated using the ChemBioDraw ® Ultra version 14.0.0.117 software.

In some embodiments, the compound of the formula (I) is a derivative of (S)-2-acylaminopropionic acid, having the formula (I-A):

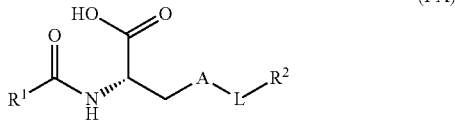

(I-A)

or a salt thereof, wherein $R^1$, A, L and $R^2$ are as defined for formula (I).

In some embodiments, the compound of the formula (I) is a derivative of (R)-2-acylaminopropionic acid, having the formula (I-B):

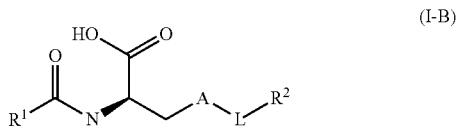

(I-B)

or a salt thereof, wherein $R^1$, A, L and $R^2$ are as defined for formula (I).

In some embodiments of the compound of formula (I), (I-A) or (I-B), or a salt thereof, $R^1$ is $C_6$-$C_{14}$ aryl or 5- to 10-membered heteroaryl, wherein the $C_6$-$C_{14}$ aryl and 5- to 10-membered heteroaryl of $R^1$ are independently optionally substituted by $R^{10}$. In one variation, $R^1$ is a monocyclic aryl or heteroaryl. In another variation, $R^1$ is bicyclic aryl or heteroaryl.

In some embodiments, $R^1$ is a fused bicyclic $C_9$-$C_{14}$ aryl optionally substituted by $R^{10}$ or a fused bicyclic 7- to 10-membered heteroaryl optionally substituted by $R^{10}$. In one variation, the compound is other than any applicable compounds in Table 1X, e.g., Compound Nos. 1x-5x in Table 1X, and salts thereof.

In some embodiments, $R^1$ is a fused bicyclic 7- to 10-membered heteroaryl optionally substituted by $R^{10}$. In some embodiments, $R^1$ is indazolyl (e.g., 1H-indazolyl or 2H-indazolyl, more specifically 1H-indazol-5-yl, 1H-indazol-6-yl, 2H-indazol-5-yl or 2H-indazol-6-yl) optionally substituted by $R^{10}$. In some embodiments, $R^1$ is benzimidazolyl (e.g., 1H-benzo[d]imidazolyl, more specifically 1H-benzo[d]imidazol-5-yl or 1H-benzo[d]imidazol-6-yl) optionally substituted by $R^{10}$. In some embodiments, $R^1$ is a benzoxazolyl (e.g., benzo[d]oxazol-5-yl) optionally substituted by $R^{10}$. In one variation, $R^1$ is a fused bicyclic 7- to 10-membered heteroaryl optionally substituted by $R^{10}$, provided that the fused bicyclic 7- to 10-membered heteroaryl $R^1$ is not an indolyl (e.g., indol-2-yl) or 1,3-benzodioxolyl (e.g., 1,3-benzodioxol-4-yl). In another variation, $R^1$ is other than a 1H-benzimidazolyl (e.g., 1H-benzo[d]imidazol-5-yl).

In some embodiments, $R^1$ is a fused bicyclic $C_9$-$C_{14}$ aryl optionally substituted by $R^{10}$. In some embodiments, $R^1$ is a naphthalenyl optionally substituted by $R^{10}$.

In some embodiments, $R^1$ is phenyl optionally substituted by $R^{10}$. In some embodiments, $R^1$ is phenyl. In some embodiments, $R^1$ is phenyl substituted by 1 to 5 substituents independently selected from the group consisting of F, Cl, —CN, methyl, —$CHF_2$, —$CF_3$, cyclopropylmethyl, tert-butyl, cyclopropyl and phenyl.

In some embodiments, $R^1$ is a monocyclic 5- or 6-membered heteroaryl optionally substituted by $R^{10}$. In some embodiments, $R^1$ is a monocyclic 5- or 6-membered heteroaryl optionally substituted by $R^{10}$. In some embodiments, $R^1$ is a monocyclic 5-membered heteroaryl optionally substituted by $R^{10}$. In some embodiments, $R^1$ is a monocyclic 6-membered heteroaryl (e.g., pyridinyl, pyrimidinyl and pyrazinyl) optionally substituted by 1 to 3 substituents independently selected from the group consisting of F, Cl, —CN, methyl, —$CHF_2$, —$CF_3$, cyclopropylmethyl, tert-butyl, cyclopropyl and phenyl.

In some of these embodiments, $R^1$ is selected from the group consisting of phenyl, 2,6-dichlorophenyl, 2,6-dichloro-4-cyanophenyl, 2,6-difluorophenyl, 2-trifluoromethyl-6-fluorophenyl, 3-amino-4-hydroxylphenyl, 3-formamido-4-hydroxyphenyl, 6-1H-indazolyl, 1-methyl-1H-6-indazolyl, 5-1H-indazolyl, 1-methyl-1H-5-indazolyl, 2-methyl-2H-6-indazolyl, 2-methyl-2H-5-indazolyl, 3-pyridinyl, 4-pyridinyl, 3,5-dichloro-4-pyridinyl, 2-methyl-4-pyrimidinyl, 5-phenyl-2-pyrazinyl, 4-difluoromethyl-2-pyrazinyl, 2-chloro-5-fluorophenyl, 3,5-dichlorophenyl, 5-benzo[d]oxazolyl, 1-methyl-1H-5-benzo[d]imidazolyl, and 1-methyl-1H-6-benzo[d]imidazolyl.

In some embodiments of the compound of formula (I), (I-A) or (I-B), or a salt thereof, the -A-L- moiety is -$A^1$-$L^1$-, -$A^2$-$L^2$-, or $A^3$. In some embodiments, the -A-L-moiety is -$A^1$-$L^1$-, wherein $A^1$ is a cyclic moiety and $L^1$ is a linker moiety linking $A^1$ and $R^2$. In some embodiments, the -A-L-moiety is -$A^2$-$L^2$-, wherein $A^2$ is an acyclic moiety and $L^2$ is a cyclic moiety linking $A^2$ and $R^2$. In some embodiments, the -A-L- moiety is $A^3$, which is directly attached to the $R^2$ group. In one variation, the compound is other than any applicable compounds in Table 1X, and salts thereof.

In some embodiments, $A^1$ is $C_3$-$C_8$ cycloalkylene, $C_3$-$C_8$ cycloalkenylene, $C_6$-$C_{14}$ arylene, 5- to 10-membered heteroarylene or 3- to 12-membered heterocyclylene, wherein the $C_3$-$C_8$ cycloalkylene, $C_3$-$C_8$ cycloalkenylene, $C_6$-$C_{14}$ arylene, 5- to 10-membered heteroarylene and 3- to 12-membered heterocyclylene of $A^1$ are independently optionally substituted by $R^{10}$.

In some of these embodiments, $A^1$ is $C_6$-$C_{14}$ arylene optionally substituted by $R^9$. In one variation, $A^1$ is phenylene (e.g., 1,4-phenylene or 1,3-phenylene) optionally substituted by $R^9$. In one particular variation, $A^1$ is 1,4-phenylene. In another particular variation, $A^1$ is 1,3-phenylene.

In some of these embodiments, $A^1$ is $C_3$-$C_8$ cycloalkylene optionally substituted by $R^{10}$. In one variation, $A^1$ is $C_3$-$C_6$ cycloalkylene optionally substituted by $R^{10}$. In one variation, $A^1$ is $C_3$-$C_8$ cycloalkylene optionally substituted by $R^{10}$. In another variation, $A^1$ is $C_3$-$C_4$ cycloalkylene optionally substituted by $R^{10}$. In another variation, $A^1$ is $C_3$-$C_4$ cycloalkylene optionally substituted by $R^9$. In one particular variation, $A^1$ is 1,2-cyclopropylene or 1,1-cyclopropylene. In another particular variation, $A^1$ is 1,3-cyclobutylene, 1,2-cyclobutylene or 1,1-cyclobutylene. In one particular variation, $A^1$ is 1,4-cyclohexylene.

In some of these embodiments, $A^1$ is 5- to 10-membered heteroarylene optionally substituted by $R^{10}$. In one variation, $A^1$ is 5- to 10-membered heteroarylene optionally substituted by $R^9$. In one variation, $A^1$ is 5- to 6-membered heteroarylene optionally substituted by $R^9$. In one variation, $A^1$ is 7- to 10-membered bicyclic heteroarylene optionally substituted by $R^9$. In one particular variation, $A^1$ is 2,5-benzo[d]oxazolylene.

In some of these embodiments, $A^1$ is 3- to 12-membered heterocyclylene optionally substituted by $R^{10}$. In some of these embodiments, $A^1$ is 3- to 12-membered heterocyclylene optionally substituted by $R^9$. In some of these embodiments, $A^1$ is 3- to 6-membered heterocyclylene optionally substituted by $R^{10}$. In one particular variation, $A^1$ is 1,3-azetidinylene. In another particular variation, $A^1$ is 1,3-pyrrolidinylene.

In some of these embodiments, $A^1$ is selected from the group consisting of 1,4-phenylene, 1,3-phenylene, 1,1-cyclopropylene, 1,2-cyclopropylene, 1,3-cyclobutylene, 1,4-cyclohexylene, 1,3-azetidinylene, 1,3-pyrrolidinylene, and 2,5-benzo[d]oxazolylene.

In some embodiments, $L^1$ is a linker moiety defined as —O—Z—, —O—Z—$X^1$—, —O—$Y^1$—, —O—$Y^1$—$X^1$—, —O—Z—$Y^1$—, —O—Z—$Y^1$—$X^1$—, —O—Z—$X^1$—$Y^1$—, —O—Z—$X^1$—$Y^1$—$X^1$—, —Z—O—Z—, —$X^1$—Z—O—Z—, —Z—O—Z—$X^1$—, —$X^1$—Z—O—Z—$X^1$—, —Z—O—$Y^1$—, —Z—O—$Y^1$—$X^1$—, —$X^1$—Z—O—$Y^1$—$X^1$—, —N($R^4$)—Z—, —N($R^4$)—Z—$X^1$—, $X^2$—, —$X^2$—$Y^1$—, —$Y^2$—, or —$Y^2$—$X^2$—.

In some embodiments, $L^1$ is a linker moiety comprising an ether group, which is further defined as —O—Z—, —O—Z—$X^1$—, —O—$Y^1$—, —O—$Y^1$—$X^1$—, —O—Z—$Y^1$—, —O—Z—$Y^1$—$X^1$—, —O—Z—$X^1$—$Y^1$—, —O—Z—$X^1$—$Y^1$—$X^1$—, —Z—O—Z—, —$X^1$—Z—O—Z—, —Z—O—Z—$X^1$—, —$X^1$—Z—O—, —Z—$X^1$—, —Z—O—$Y^1$—, —Z—O—$Y^1$—$X^1$—, —$X^1$—Z—O—$Y^1$—, or —$X^1$—Z—O—$Y^1$—$X^1$—. In some embodiments, $L^1$ is —O—Z—, —O—Z—$X^1$—, —O—$Y^1$—, —O—Z—$Y^1$—, —O—Z—$X^1$—$Y^1$—, —Z—O—Z—, —$X^1$—Z—O—Z—, —Z—O—Z—$X^1$—, —$X^1$—Z—O—Z—$X^1$—, —Z—O—$Y^1$—, or —$X^1$—Z—O—$Y^1$—. In some embodiments, $L^1$ is —O—$Y^1$—$X^1$—, —O—Z—$Y^1$—$X^1$—, —O—Z—$X^1$—$Y^1$—$X^1$—, —Z—O—$Y^1$—$X^1$—, or —$X^1$—Z—O—$Y^1$—$X^1$—. In some of these embodiments, $X^1$ is $C_1$-$C_6$ alkylene optionally substituted by $R^{10}$. In one variation, $X^1$ is $C_1$-$C_6$ alkylene optionally substituted by $R^9$. In one variation, $X^1$ is $C_1$-$C_6$ alkylene. In some of these embodiments, $X^1$ is $C_2$-$C_6$ alkenylene optionally substituted by $R^{10}$. In one variation, $X^1$ is $C_2$-$C_6$ alkenylene optionally substituted by $R^9$. In one variation, $X^1$ is $C_2$-$C_6$ alkenylene. In some of these embodiments, $Y^1$ is $C_3$-$C_6$ cycloalkylene optionally substituted by $R^{10}$. In one variation, $Y^1$ is $C_3$-$C_6$ cycloalkylene optionally substituted by $R^9$. In one variation, $Y^1$ is $C_3$-$C_6$ cycloalkylene. In some of these embodiments, Z is —$CR^{5a}R^{5b}$— where each $R^{5a}$ and $R^{5b}$ is independently H or $C_1$-$C_6$ alkyl. In one variation, each of $R^{5a}$ and $R^{5b}$ is H.

In some embodiments, $L^1$ is selected from the group consisting of —O—(CH$_2$)$_3$—, —O—(CH$_2$)$_4$—, —CH$_2$—O—(CH$_2$)$_3$—, —CH$_2$—O—(CH$_2$)$_2$—, —CH(CH$_3$)—O—(CH$_2$)$_2$—, —CH$_2$—O—(CH$_2$)$_3$—,

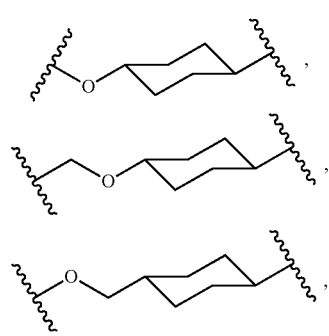

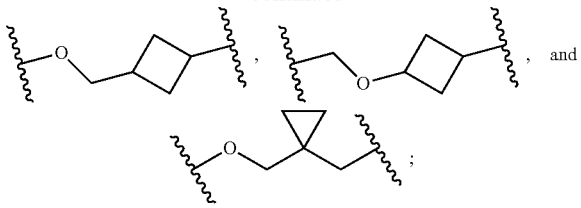

and; wherein the wavy lines denote attachment points to the parent molecule.

Unless indicated otherwise, when the structure or formula of a bivalent group is shown, the orientation of the bivalent group is intended to be in alignment with the orientation of the parent structure. For example, when an $L^1$ group which is part of an -$A^1$-$L^1$- moiety is shown as the formula —O—(CH$_2$)$_3$—, it is intended that the oxygen atom on the left side of —O—(CH$_2$)$_3$— is attached to the $A^1$ moiety, the terminal carbon atom on the right side of —O—(CH$_2$)$_3$— is attached to the parent structure to the right of the -$A^1$-$L^1$- moiety.

In some embodiments, $L^1$ is a linker moiety comprising an amino group, which is further defined as —N($R^4$)—Z— or —N($R^4$)—Z—$X^1$—. In some of these embodiments, Z is —$CR^{5a}R^{5b}$—. In some of these embodiments, each $R^{3a}$, $R^{3b}$, $R^4$, $R^{5a}$ and $R^{5b}$ is independently H or $C_1$-$C_6$ alkyl. In one variation, $R^4$ is H. In one variation, each of $R^{5a}$ and $R^{5b}$ is H. In some of these embodiments, $X^1$ is $C_1$-$C_6$ alkylene optionally substituted by $R^{10}$. In one variation, $X^1$ is $C_1$-$C_6$ alkylene optionally substituted by $R^9$. In one variation, $X^1$ is $C_1$-$C_6$ alkylene. In some embodiments, $L^1$ is —N($R^4$)—Z—$X^1$— where $R^4$ is H, Z is —$CR^{5a}R^{5b}$— where each of $R^{5a}$ and $R^{5b}$ is H, and $X^1$ is $C_1$-$C_6$ alkylene.

In some embodiments, $L^1$ is —NH—C(CH$_3$)$_2$—(CH$_2$)$_2$—.

In some embodiments, $X^1$ is $C_1$-$C_6$ alkylene, i.e., —(CH$_2$)$_n$—, where n is 1 to 6. In some embodiments, $X^1$ is —(CH$_2$)$_n$—, where n is 1 to 5, 1 to 4, 1 to 3, 1 to 2, 2 to 6, 2 to 5, 2 to 4, 2 to 3, 3 to 6, 3 to 5, 3 to 4, 4 to 6, 4 to 5, or 5 to 6. In some embodiments, $X^1$ is —(CH$_2$)$_n$—, where n is 1, 2, 3, 4, 5 or 6. In some embodiments, Z is —CH$_2$—. In some embodiments, the —Z—$X^1$— moiety is —(CH$_2$)$_m$—, where m is 2 to 7. In some embodiments, $L^1$ is —O—Z—$X^1$—, which is further defined as —O—(CH$_2$)$_m$—, where m is 2 to 7. In some embodiments, $L^1$ is —Z—O—Z—$X^1$—, which is further defined as —$CR^{5a}R^{5b}$—O—(CH$_2$)$_m$—, where m is 2 to 6. In one variation, $L^1$ is —CH$_2$—O—(CH$_2$)$^m$—. In another variation, $L^1$ is —CH(CH$_3$)—O—(CH$_2$)$_m$—. In some embodiments, $L^1$ is —N($R^4$)—Z—$X^1$—, which is further defined as —N($R^4$)—(CH$_2$)$_m$—, where m is 2 to 7. In some embodiments, $R^4$ is H. In some embodiments, m is 2, 3, 4, 5, 6 or 7. In some embodiments, m is 2, 3 or 4.

In some embodiments, $L^1$ is —O—Z—, —O—Z—$X^1$—, —Z—O—Z—, —$X^1$—Z—O—Z—, —Z—O—Z—$X^1$—, or —$X^1$—Z—O—Z—$X^1$—, which is further defined as —(CH$_2$)$_n$—O—(CH$_2$)$_m$—, where n is 0, 1, 2, 3, 4, 5 or 6 and m is 1, 2, 3, 4, 5 or 6. In some embodiments, one or more of the methylene groups of $L^1$ is independently optionally substituted by $R^9$. In one variation, n is 0 or 1 and m is 2, 3 or 4. In one variation, n is 0 and m is 2, 3 or 4. In another variation, n is 1 and m is 2, 3 or 4.

In some embodiments, $L^1$ is —O—$Y^1$—, —O—$Y^1$—$X^1$—, —O—Z—$Y^1$—, —O—Z—$Y^1$—$X^1$—, —O—Z—$X^1$—$Y^1$—, —O—Z—

$X^1-Y^1-X^1-$, $-Z-O-Y^1-$, $-Z-O-Y^1-X^1-$, $-X^1-Z-O-Y^1-$, or $-X^1-Z-O-Y^1-X^1-$, which is further defined as $-(CH_2)_r-O-(CH_2)_s-Y^1-(CH_2)_t-$, where r, s and t are independently 0, 1, 2, 3, 4, 5 or 6, and $Y^1$ is $C_3$-$C_6$ cycloalkylene optionally substituted by $R^{10}$. In some embodiments, one or more of the methylene groups of $L^1$ is independently optionally substituted by $R^9$. In one variation, $Y^1$ is $C_3$-$C_6$ cycloalkylene optionally substituted by $R^9$. In one variation, $Y^1$ is cyclopropylene (e.g., 1,2-cyclopropylene and 1,1-cyclopropylene), cyclobutylene (e.g., 1,3-cyclobutylene) or cyclohexylene (e.g., 1,4-cyclohexylene). In one variation, r, s and t are independently 0 or 1. In one variation, each r, s and t is 0. In another variation, r is 0, s is 1 and t is 1. In another variation, r is 1, s is 0 and t is 0. In another variation, r is 0, s is 1 and t is 0. In one particular variation, r, s and t are independently 0 or 1 and $Y^1$ is cyclopropylene (e.g., 1,2-cyclopropylene and 1,1-cyclopropylene), cyclobutylene (e.g., 1,3-cyclobutylene) or cyclohexylene (e.g., 1,4-cyclohexylene).

In some embodiments, $L^1$ comprising a hydrocarbon group, which is further defined as $X^2$ or $-X^2-Y^1-$. In some of these embodiments, $X^2$ is $C_1$-$C_6$ alkylene optionally substituted by $R^9$. In one variation, $X^2$ is $C_1$-$C_6$ alkylene. In another variation, $X^2$ is $C_1$-$C_6$ alkylene optionally substituted by fluoro. In some of these embodiments, $X^2$ is $C_2$-$C_6$ alkenylene optionally substituted by $R^9$. In one variation, $X^2$ is $C_2$-$C_6$ alkenylene. In some of these embodiments, $Y^1$ is $C_3$-$C_6$ cycloalkylene optionally substituted by $R^{10}$. In one variation, $Y^1$ is $C_3$-$C_6$ cycloalkylene optionally substituted by $R^9$. In one variation, $Y^1$ is $C_3$-$C_6$ cycloalkylene. In some embodiments, $L^1$ is $-X^2-Y^1-$ where $X^2$ is $C_1$-$C_6$ alkenylene and $Y^1$ is $C_3$-$C_6$ cycloalkylene.

In some embodiments, $L^1$ is selected from the group consisting of $-(CH_2)_2-$, $-(CH_2)_4-$, $-(CH_2)_5-$, $-CF_2-(CH_2)_3-$ and

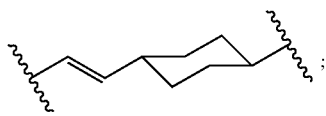 [SMILES: */C=C/C1CCC(*)CC1]

wherein the wavy lines denote attachment points to the parent molecule.

In some embodiments, $L^1$ is a linker moiety comprising a heterocyclyl group, which is further defined as $Y^2$ or $-Y^2-X^2-$. In some of these embodiments, $Y^2$ is a saturated 3- to 4-membered heterocyclylene optionally substituted by $R^{10}$. In some embodiments, $Y^2$ is a saturated 4-membered heterocyclylene optionally substituted by $R^{10}$. In one variation, $Y^2$ is a saturated 3- to 4-membered heterocyclylene optionally substituted by $R^9$. In one variation, $Y^2$ is a saturated 3- to 4-membered heterocyclylene. In one variation, $Y^2$ is a saturated 4-membered heterocyclylene (e.g., 1,3-azetidinylene). In some embodiments, $L^1$ is $-Y^2-X^2-$ where $Y^2$ is a saturated 3- to 4-membered heterocyclylene (e.g., 1,3-azetidinylene) and $X^2$ is $C_1$-$C_6$ alkylene (e.g., methylene).

In some embodiments, $L^1$ is selected from the group consisting of

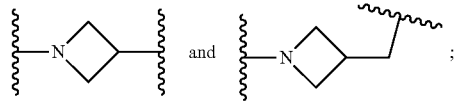

wherein the wavy lines denote attachment points to the parent molecule.

In some embodiments, the -A-L- moiety is $-A^1-L^1-$, wherein $A^1$ and $L^1$ are as detailed herein. It is intended and understood that each and every variation of $A^1$ described herein, where applicable, may be combined with each and every variation of $L^1$ described herein, the same as if each and every combination is individually and specifically described. For example, in some embodiments of the compound of formula (I), (I-A) or (I-B), or a salt thereof, $A^1$ is phenylene (e.g., 1,4-phenylene) and $L^1$ is $-O-(CH_2)_m-$, where m is 2, 3 or 4.

In some embodiments, $A^2$ is $C_3$-$C_8$ alkylene optionally substituted by $R^9$ or $C_3$-$C_8$ alkenylene optionally substituted by $R^9$. In some embodiments, $A^2$ is $C_3$-$C_8$ alkylene optionally substituted by $R^9$. In some embodiments, $A^2$ is $C_4$-$C_8$ alkylene optionally substituted by $R^9$. In some embodiments, $A^2$ is $C_3$-$C_6$ alkylene optionally substituted by $R^9$. In some embodiments, $A^2$ is $C_3$, $C_4$, $C_5$, or $C_6$, $C_7$, $C_8$ alkylene optionally substituted by $R^9$. In some embodiments, $A^2$ is $C_3$-$C_8$ alkylene, $C_4$-$C_8$ alkylene or $C_4$-$C_6$ alkylene. In one variation, $A^2$ is $C_3$, $C_4$, $C_5$, $C_6$, $C_7$, or $C_8$ alkylene. In some embodiments, $A^2$ is $C_3$-$C_8$ alkenylene optionally substituted by $R^9$. In some embodiments, $A^2$ is $C_4$-$C_8$ alkenylene optionally substituted by $R^9$. In some embodiments, $A^2$ is $C_4$-$C_4$ alkenylene optionally substituted by $R^9$. In some embodiments, $A^2$ is $C_3$, $C_4$, $C_5$, $C_6$, $C_7$, or $C_8$ alkenylene optionally substituted by $R^9$. In some embodiments, $A^2$ is $C_3$-$C_8$ alkenylene, $C_4$-$C_8$ alkenylene or $C_4$-$C_6$ alkenylene. In one variation, $A^2$ is $C_3$, $C_4$, $C_5$, $C_6$, $C_7$, or $C_8$ alkenylene.

In some embodiments, $L^2$ is $C_3$-$C_6$ cycloalkylene optionally substituted by $R^{10}$. In some embodiments, $L^2$ is $C_3$-$C_6$ cycloalkylene optionally substituted by $R^9$. In some embodiments, $L^2$ is $C_3$-$C_6$ cycloalkylene. In some embodiments, $L^2$ is $C_3$, $C_4$, $C_5$ or $C_6$ cycloalkylene optionally substituted by $R^{10}$. In some embodiments, $L^2$ is $C_3$, $C_4$, $C_5$ or $C_6$ cycloalkylene optionally substituted by $R^9$. In one variation, $L^2$ is $C_3$, $C_4$, $C_8$ or $C_6$ cycloalkylene.

In some embodiments, the -A-L- moiety is $-A^2-L^2-$, wherein $A^2$ and $L^2$ are as detailed herein. It is intended and understood that each and every variation of $A^2$ described herein, where applicable, may be combined with each and every variation of $L^2$ described herein, the same as if each and every combination is individually and specifically described. For example, in some embodiments, $A^2$ is $C_4$-$C_6$ alkenylene (e.g., $-(CH_2)_4-$) and $L^2$ is $C_3$-$C_6$ cycloalkylene (e.g., 1,2-cyclopropylene).

In some embodiments, $A^1$ is $C_5$-$C_{10}$ alkylene optionally substituted by $R^9$ or $C_5$-$C_{10}$ alkenylene optionally substituted by $R^9$. In some embodiments, $A^1$ is $C_5$-$C_{10}$ alkylene optionally substituted by $R^9$. In some embodiments, $A^1$ is $C_6$-$C_{10}$ alkylene optionally substituted by $R^9$. In some embodiments, $A^1$ is $C_6$-$C_8$ alkylene optionally substituted by $R^9$. In some embodiments, $A^3$ is $C_5$, $C_6$, $C_7$, $C_8$, $C_9$, or $C_{10}$ alkylene optionally substituted by $R^9$. In some embodiments, $A^3$ is $C_5$-$C_{10}$ alkylene, $C_6$-$C_{10}$ alkylene or $C_6$-$C_8$ alkylene. In one variation, $A^1$ is $C_5$, $C_6$, $C_7$, $C_8$, $C_9$, or $C_{10}$ alkylene. In some embodiments, $A^3$ is $C_5$-$C_{10}$ alkenylene optionally substituted by $R^9$. In some embodiments, $A^1$ is $C_6$-$C_{10}$ alkenylene optionally substituted by $R^9$. In some embodiments, $A^1$ is $C_6$-$C_8$ alkenylene optionally substituted by $R^9$. In some embodiments, $A^1$ is $C_5$, $C_6$, $C_7$, $C_8$, $C_9$, or $C_{10}$ alkenylene optionally substituted by $R^9$. In some embodiments, $A^3$ is $C_5$-$C_{10}$ alkenylene, $C_6$-$C_{10}$ alkenylene or $C_6$-$C_8$ alkenylene. In one variation, $A^3$ is $C_5$, $C_6$, $C_7$, $C_8$, $C_9$, or $C_{10}$ alkenylene.

In some embodiments, the -A-L- moiety is selected from the group consisting of —CH$_2$(CH$_2$)CH$_2$—, —CH$_2$(CH$_2$)$_4$CH$_2$—, —CH=CH—(CH$_2$)$_3$CH$_2$—, and

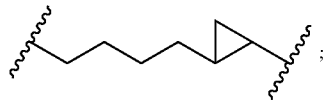 [SMILES: *CCCCC1CC1*]

wherein the wavy lines denote attachment points to the parent molecule.

It is intended and understood that each and every variation of R$^1$ described herein, may be combined with each and every variation of the -A-L- moiety described herein, the same as if each and every combination is individually and specifically described. For example, in some embodiments of the compound of formula (I), (I-A) or (I-B), or a salt thereof, R$^1$ is fused bicyclic 7- to 10-membered heteroaryl optionally substituted by R$^{10}$ and the -A-L- moiety is -A$^1$-L$^1$- where A$^1$ is 1,4-phenylene and L$^1$ is —O—(CH$_2$)$_m$—, where m is 2, 3 or 4. In some embodiments, R$^1$ is monocyclic 5- to 6-membered heteroaryl optionally substituted by R$^9$ and the -A-L- moiety is -A$^1$-L$^1$- where A$^1$ is 1,4-phenylene and L$^1$ is —O—(CH$_2$)$_m$—, where m is 2, 3 or 4. In some embodiments, R$^1$ is phenyl optionally substituted by R$^9$ and the -A-L- moiety is -A$^1$-L$^1$- where A$^1$ is 1,4-phenylene and L$^1$ is —O—(CH$_2$)$_m$—, where m is 2, 3 or 4. In some embodiments, R$^1$ is phenyl optionally substituted by R$^9$ or monocyclic 5- to 6-membered heteroaryl optionally substituted by R$^9$ and the -A-L- moiety is -A$^1$-L$^1$- where A$^1$ is 1,4-phenylene and L$^1$ is —O—(CH$_2$)$_m$—, where m is 2, 3 or 4. In some embodiments, R$^1$ is phenyl optionally substituted by R$^9$ and the -A-L- moiety is -A$^1$-L$^1$- where A$^1$ is 3- to 6-membered heterocyclylene (e.g., 1,3-azetidinylene or 1,3-pyrrolidinylene) optionally substituted by R$^{10}$ and L$^1$ is —O—(CH$_2$)$_m$—, where m is 2, 3 or 4. In some embodiments, R$^1$ is phenyl optionally substituted by R$^9$ and the -A-L- moiety is -A$^1$-L$^1$- where A$^1$ is C$_3$-C$_6$ cycloalkylene (e.g., 1,4-cyclohexylene or 1,3-cyclobutylene) optionally substituted by R$^{10}$ and L$^1$ is —O—(CH$_2$)$_m$—, where m is 2, 3 or 4.

In some embodiments, R$^1$ is phenyl optionally substituted by R$^9$ and the -A-L- moiety is -A$^1$-L$^1$- where A$^1$ is 1,4-phenylene and L$^1$ is —(CH$_2$)$_n$—O—(CH$_2$)$_m$— where n is 0 or 1 and m is 2, 3 or 4. In some embodiments, R$^1$ is phenyl optionally substituted by R$^9$ and the -A-L- moiety is -A$^1$-L$^1$- where A$^1$ is 1,4-phenylene and L$^1$ is —(CH$_2$)$_r$—O—(CH$_2$)$_s$—Y$^1$—(CH$_2$)$_t$—, where r, s and t are independently 0 or 1 and Y$^1$ is cyclopropylene (e.g., 1,2-cyclopropylene and 1,1-cyclopropylene), cyclobutylene (e.g., 1,3-cyclobutylene) or cyclohexylene (e.g., 1,4-cyclohexylene).

In some embodiments, R$^1$ is phenyl optionally substituted by R$^9$ and the -A-L- moiety is -A$^1$-L$^1$- where A$^1$ is 1,4-phenylene and L$^1$ is —N(R$^4$)—(CH$_2$)$_m$— where m is 2, 3 or 4. In one variation, R$^4$ is H.

In some embodiments, R$^1$ is phenyl optionally substituted by R$^9$ and the -A-L- moiety is -A$^1$-L$^1$- where A$^1$ is 1,4-phenylene and L$^1$ is C$_1$-C$_6$ alkylene optionally substituted by fluoro. In some embodiments, R$^1$ is phenyl optionally substituted by R$^9$ and the -A-L- moiety is -A$^1$-L$^1$- where A$^1$ is 1,4-phenylene and L$^1$ is —X$^2$—Y$^1$— where X$^2$ is C$_1$-C$_6$ alkenylene and Y$^1$ is C$_3$-C$_6$ cycloalkylene.

In some embodiments, R$^1$ is phenyl optionally substituted by R$^9$ and the -A-L- moiety is -A$^1$-L$^1$- where A$^1$ is C$_3$-C$_4$ cycloalkylene (e.g., cyclopropylene) optionally substituted by R$^{10}$ and L$^1$ is C$_1$-C$_6$ alkylene (e.g., C$_2$-C$_4$ alkylene). In some embodiments, R$^1$ is phenyl optionally substituted by R$^9$ and the -A-L- moiety is -A$^1$-L$^1$- where A$^1$ is 5- to 10-membered heteroarylene (e.g., 2,5-benzo[d]oxazolylene) optionally substituted by R$^9$ and L$^1$ is C$_1$-C$_6$ alkylene (e.g., C$_2$-C$_4$ alkylene).

In some embodiments, R$^1$ is phenyl optionally substituted by R$^9$ and the -A-L- moiety is -A$^1$-L$^1$- where A$^1$ is C$_3$-C$_4$ cycloalkylene optionally substituted by R$^{10}$ and L$^1$ is C$_1$-C$_6$ alkylene.

In some embodiments, R$^1$ is phenyl optionally substituted by R$^9$ and the -A-L- moiety is -A$^1$-L$^1$- where A$^1$ is C$_3$-C$_4$ cycloalkylene optionally substituted by R$^{10}$ and L$^1$ is C$_1$-C$_6$ alkylene.

In some embodiments, R$^1$ is phenyl optionally substituted by R$^9$ and the -A-L- moiety is -A$^2$-L$^2$- where A$^2$ is C$_4$-C$_6$ alkenylene (e.g., —(CH$_2$)$_4$—) and L$^2$ is C$_3$-C$_6$ cycloalkylene (e.g., 1,2-cyclopropylene).

In some embodiments, R$^1$ is a fused bicyclic 7- to 10-membered heteroaryl (e.g., indazolyl) optionally substituted by R$^{10}$ and the -A-L- moiety is C$_6$-C$_8$ alkylene or C$_6$-C$_8$ alkenylene.

In one variation of any of the preceding embodiments or any other embodiment or variation detailed herein, the compound is other than any applicable compounds in Table 1X and salts thereof.

In some embodiments of the compound of formula (I), (I-A) or (I-B), or a salt thereof, R$^2$ is 5- to 10-membered heteroaryl containing at least 2 ring nitrogen atoms, 3- to 12-membered heterocyclyl containing at least 2 ring nitrogen atoms, or —NH—R$^3$, wherein the 5- to 10-membered heteroaryl and 3- to 12-membered heterocyclyl of R$^2$ are independently optionally substituted by R$^{10}$.

In some embodiments, R$^2$ is 5- to 10-membered heteroaryl containing at least 2 ring nitrogen atoms optionally substituted by R$^{10}$, or 3- to 12-membered heterocyclyl containing at least 2 ring nitrogen atoms optionally substituted by R$^{10}$.

In some embodiments, R$^2$ is selected from the group consisting of 5,6,7,8-tetrahydro-naphthyridinyl, 1,2,3,4-tetrahydro-1,8-naphthyridinyl, 3,4-dihydro-2H-pyrido[3,2-b][1,4]oxazinyl, and 2,3-dihydro-1H-pyrrolo[2,3-b]pyridinyl.

In some embodiments, R$^2$ is —NH—R$^3$, where R$^3$ is 5- to 10-membered heteroaryl containing at least 1 ring nitrogen atom, or 3- to 12-membered heterocyclyl containing at least 1 ring nitrogen atom, wherein the 5- to 10-membered heteroaryl and 3- to 12-membered heterocyclyl of R$^3$ are independently optionally substituted by R$^L$.

In some embodiments, R$^3$ is 5- to 10-membered heteroaryl containing at least 1 ring nitrogen atom optionally substituted by R$^{10}$.

In some embodiments, R$^3$ is a pyridinyl.

In some embodiments, R$^3$ is a 3- to 12-membered heterocyclyl containing at least 1 ring nitrogen atom optionally substituted by R$^{10}$.

In some embodiments, R$^3$ is selected from the group consisting of 4,5-dihydro-1H-imidazolyl, 5,6-dihydro-4H-1,3-oxazinyl, 4,5-dihydrothiazolyl, 3,4,5,6-tetrahydropyrazinyl, and 5,6-dihydro-4H-1,3-thiazinyl.

In some embodiments, R$^2$ is —NR$^{3a}$-pyridyl, wherein pyridyl is optionally substituted by R$^{10}$.

In some embodiments, R$^2$ is —NH-pyridyl, wherein pyridyl is optionally substituted by R$^{10}$.

In some embodiments, $R^2$ is

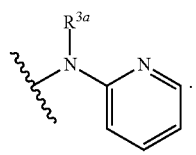

In some embodiments, $R^2$ is.

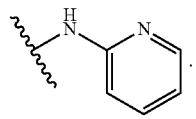 [SMILES: *Nc1ccccn1]

In some embodiments, $R^2$ is —$R^3$—$NR^{3a}R^{3b}$.
In some embodiments, $R^2$ is —$R^3$—$NHR^{3a}$.
In some embodiments, $R^3$ is pyridyl optionally substituted by $R^{10}$.
In some embodiments, $R^2$ is

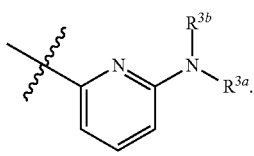

In some embodiments, $R^2$ is

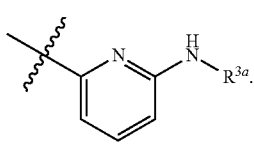

It is intended and understood that each and every variation of $R^1$ and/or -A-L- described herein, may be combined with each and every variation of $R^2$ described herein, the same as if each and every combination is individually and specifically described. For example, in some embodiments, $R^1$ is a fused bicyclic 7- to 10-membered heteroaryl optionally substituted by $R^{10}$, the -A-L- moiety is -$A^1$-$L^1$- where $A^1$ is 1,4-phenylene and $L^1$ is —O—$(CH_2)_m$— where m is 2, 3 or 4, and $R^2$ is 10-membered heteroaryl containing 2 ring nitrogen atoms (e.g., 5,6,7,8-tetrahydro-1,8-naphthyridin-2-yl).

In some embodiments, the compound of formula (I) is of the formula (II):

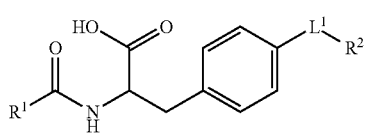

or a salt thereof, wherein $R^1$, $L^1$ and $R^2$ are as defined for formula (I) or any embodiment or variation thereof.

In some embodiments of the compound of formula (II), or a salt thereof, $R^2$ is 5- to 10-membered heteroaryl containing at least 2 ring nitrogen atoms, or 3- to 12-membered heterocyclyl containing at least 2 ring nitrogen atoms, wherein the 5- to 10-membered heteroaryl and 3- to 12-membered heterocyclyl of $R^2$ are independently optionally substituted by $R^{10}$. In another embodiment, $R^2$ is —$NR^{3a}$-pyridyl, wherein pyridyl is optionally substituted by $R^{10}$. In another embodiment, $R^2$ is —NH-pyridyl, wherein pyridyl is optionally substituted by $R^{10}$. In another embodiment, $R^2$ is

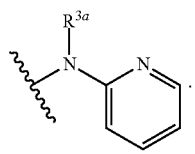

In another embodiment, $R^2$ is

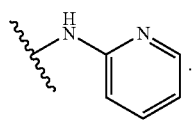

In another embodiment, $R^2$ is —$R^3$—$NR^{3a}R^{3b}$. In another embodiment, $R^2$ is —$R^3$—$NHR^{3a}$. In another embodiment, $R^2$ is -(pyridyl)-$NR^{3a}R^{3b}$, where pyridyl is optionally substituted by $R^{10}$. In another embodiment, $R^2$ is

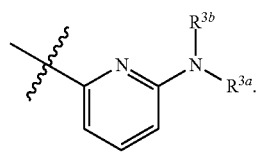

In another embodiment, $R^2$ is

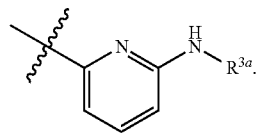

In some embodiments, the compound of formula (II) is of the formula (II-1):

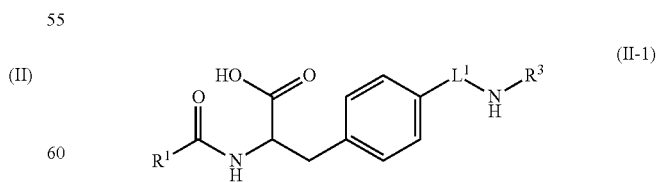

or a salt thereof, wherein $R^1$, $L^1$ and $R^2$ are as defined for formula (I) or any embodiment or variation thereof.

In some embodiments, the compound of formula (I) is of the formula (III):

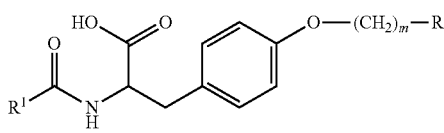

(III)

or a salt thereof, wherein $R^1$ and $R^2$ are as defined for formula (I) or any embodiment or variation thereof, and m is 1, 2, 3, 4, 5 or 6. In one variation, m is 2, 3 or 4. In another embodiment, $R^2$ is —$NR^{3a}$-pyridyl, wherein pyridyl is optionally substituted by $R^{10}$. In another embodiment, $R^2$ is —NH-pyridyl, wherein pyridyl is optionally substituted by $R^{10}$. In another embodiment, $R^2$ is

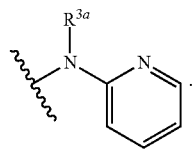

In another embodiment, $R^2$ is

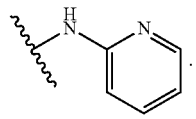 [SMILES: *Nc1ccccn1]

In another embodiment, $R^2$ is —$R^3$—$NR^{3a}R^{3b}$. In another embodiment, $R^2$ is —$R^3$—$NHR^{3a}$. In another embodiment, $R^2$ is -(pyridyl)-$NR^{3a}R^{3b}$, where pyridyl is optionally substituted by $R^{10}$. In another embodiment, $R^2$ is

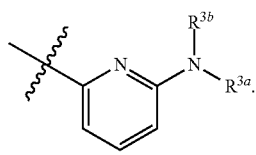

In another embodiment, $R^2$ is

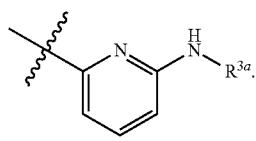

In some embodiments, the compound of formula (III) is of the formula (III-1):

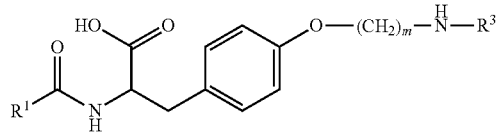

(III-1)

or a salt thereof, wherein $R^1$ and $R^3$ are as defined for formula (I) or any embodiment or variation thereof, and m is 1, 2, 3, 4, 5 or 6. In one variation, m is 3, 4 or 5.

In some embodiments, the compound of formula (III) is of the formula (III-2):

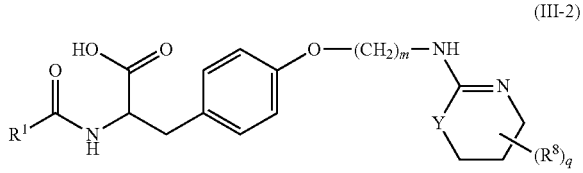

(III-2)

or a salt thereof, wherein $R^1$ is as defined for formula (I) or any embodiment or variation thereof; $R^8$ is as defined for $R^{10}$ of formula (I) or any embodiment or variation thereof; Y is O, S, or $NR^6$; $R^6$ is H or $C_1$-$C_6$ alkyl; m is 1, 2, 3, 4, 5 or 6; and q is 0, 1, 2 or 3. In one variation, m is 3, 4 or 5. In one variation, q is 0.

In some embodiments, the compound of formula (I) is of the formula (IV):

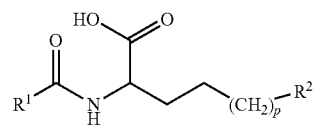

(IV)

or a salt thereof, wherein $R^1$ and $R^2$ are as defined for formula (I) or any embodiment or variation thereof, and p is 4, 5, 6, 7, 8 or 9. In one variation, p is 5, 6 or 7. In another embodiment, $R^2$ is —$NR^{3a}$-pyridyl, wherein pyridyl is optionally substituted by $R^{10}$. In another embodiment, $R^2$ is —NH-pyridyl, wherein pyridyl is optionally substituted by $R^{10}$. In another embodiment, $R^2$ is

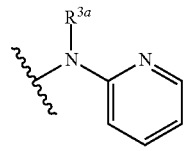

In another embodiment, $R^2$ is

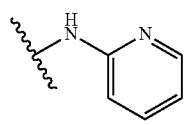

In another embodiment, $R^2$ is —$R^3$—$NR^{3a}R^{3b}$. In another embodiment, $R^2$ is —$R^3$—$NHR^{3a}$. In another embodiment, $R^2$ is -(pyridyl)-$NR^{3a}R^{3b}$, where pyridyl is optionally substituted by $R^{10}$. In another embodiment, $R^2$ is In another embodiment, $R^2$ is

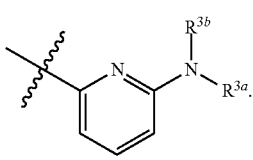

In some embodiments, the compound of formula (IV) is of the formula (IV-1):

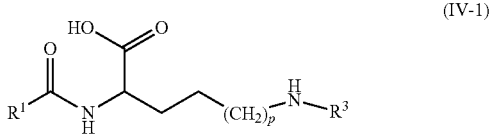

(IV-1)

or a salt thereof, wherein $R^1$ and $R^3$ are as defined for formula (I) or any embodiment or variation thereof, and p is 4, 5, 6, 7, 8 or 9. In one variation, p is 5, 6, 7 or 8.

In some embodiments, the compound of formula (IV) is of the formula (IV-2):

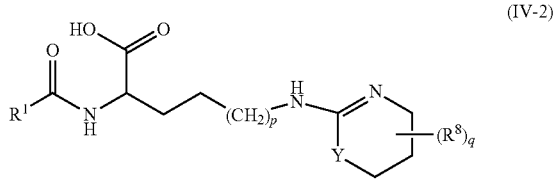

(IV-2)

or a salt thereof, wherein $R^1$ is as defined for formula (I) or any embodiment or variation thereof; $R^8$ is as defined for $R^{10}$ of formula (I) or any embodiment or variation thereof; Y is O, S, or $NR^6$; $R^6$ is H or $C_1$-$C_6$ alkyl; p is 4, 5, 6, 7, 8 or 9; and q is 0, 1, 2 or 3. In one variation, p is 5, 6, 7 or 8. In one variation, q is 0.

In some embodiments, each optional substituent $R^9$ is independently $C_1$-$C_6$ alkyl, $C_2$-$C_6$ alkenyl, $C_2$-$C_6$ alkynyl, halogen, —CN, —$OR^{11}$, —$SR^{11}$, —$NR^{12}R^{13}$, —$NO_2$, —C=$NH(OR^{11})$, —$C(O)R^{11}$, —$OC(O)R^{11}$, —$C(O)OR^{11}$, —$C(O)NR^{12}R^{13}$, —$NR^{11}C(O)R^{12}$, —$NR^{11}C(O)OR^{12}$, —$NR^{11}C(O)NR^{12}R^{13}$, —$S(O)R^{11}$, —$S(O)_2R^{11}$, —$NR^{11}S(O)R^{12}$, —$NR^{11}S(O)_2R^{12}$, —$S(O)NR^{12}R^{13}$, —$S(O)_2NR^{12}R^{13}$, —$P(O)(OR^{12})(OR^{13})$, $C_3$-$C_8$ cycloalkyl, 3- to 12-membered heterocyclyl, 5- to 10-membered heteroaryl or $C_6$-$C_{14}$ aryl, wherein each $R^9$ is independently optionally substituted by halogen, oxo, —$OR^{14}$, —$NR^{14}R^{15}$, —$C(O)R^{14}$, —CN, —$S(O)R^{14}$, —$S(O)_2R^{14}$, —$P(O)(OR^{14})(OR^{15})$, $C_3$-$C_8$ cycloalkyl, 3- to 12-membered heterocyclyl, 5- to 10-membered heteroaryl, $C_6$-$C_{14}$ aryl, or $C_1$-$C_6$ alkyl optionally substituted by oxo, —OH or halogen.

In some embodiments, $R^9$ is independently $C_1$-$C_6$ alkyl, halogen, —CN, —$OR^{11}$, —$NR^{12}R^{13}$, —$C(O)R^{11}$, $C_3$-$C_8$ cycloalkyl, 3- to 12-membered heterocyclyl, 5- to 10-membered heteroaryl or $C_6$-$C_{14}$ aryl, wherein each $R^9$ is independently optionally substituted by halogen, oxo, —$OR^{14}$, —$NR^{14}R^{15}$, —$C(O)R^{14}$, —CN, $C_3$-$C_8$ cycloalkyl, 3- to 12-membered heterocyclyl, 5- to 10-membered heteroaryl, $C_6$-$C_{14}$ aryl, or $C_1$-$C_6$ alkyl optionally substituted by oxo, —OH or halogen. In some embodiments, $R^9$ is independently selected from F, Cl, —CN, methyl, —$CHF_2$, —$CF_3$, cyclopropylmethyl, tert-butyl, cyclopropyl and phenyl.

In some embodiments, $R^{10}$ is independently oxo or any variation detailed herein for $R^9$. In some embodiments, $R^{10}$ is independently oxo, $C_1$-$C_6$ alkyl, halogen, —CN, —$OR^{11}$, —$NR^{12}R^{13}$, —$C(O)R^{11}$, $C_3$-$C_8$ cycloalkyl, 3- to 12-membered heterocyclyl, 5- to 10-membered heteroaryl or $C_6$-$C_{14}$ aryl, wherein each $R^9$ is independently optionally substituted by halogen, oxo, —$OR^{14}$, —$NR^{14}R^{15}$, —$C(O)R^{14}$, —CN, $C_3$-$C_8$ cycloalkyl, 3- to 12-membered heterocyclyl, 5- to 10-membered heteroaryl, $C_6$-$C_{14}$ aryl, or $C_1$-$C_6$ alkyl optionally substituted by oxo, —OH or halogen. In some embodiments, $R^{10}$ is independently selected from oxo, F, Cl, —CN, methyl, —$CHF_2$, —$CF_3$, cyclopropylmethyl, tert-butyl, cyclopropyl and phenyl.

In some embodiments, $R^{11}$, $R^{12}$ and $R^{13}$ are each independently hydrogen or $C_1$-$C_6$ alkyl. In some embodiments, $R^1$ is hydrogen. In some embodiments, $R^{12}$ and $R^{11}$ are each hydrogen.

In some embodiments, $R^{14}$ and $R^{15}$ are each independently hydrogen or $C_1$-$C_6$ alkyl.

In some embodiments, the compound of formula (I) is of the formula (V):

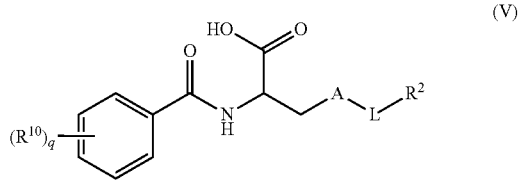

(V)

or a salt thereof, wherein $R^2$, A, and L are as defined for formula (I) or any embodiment or variation thereof, each $R^{10}$ is independently $R^9$ and q is 0, 1, 2, 3, 4, or 5. In one variation, q is 0, 1, 2, or 3. In another embodiment, $R^2$ is —$NR^{3a}$-pyridyl, wherein pyridyl is optionally substituted by $R^3$. In another embodiment, $R^2$ is —NH-pyridyl, wherein pyridyl is optionally substituted by $R^{10}$. In another embodiment, $R^2$ is

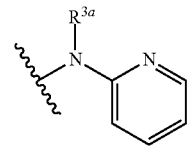

In another embodiment, $R^2$ is

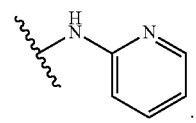

In another embodiment, R² is —R³—NR³ᵃR³ᵇ. In another embodiment, R² is —R³—NHR³ᵃ. In another embodiment, R² is -(pyridyl)-NR³ᵃR³ᵇ, where pyridyl is optionally substituted by R¹⁰. In another embodiment, R² is

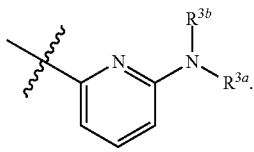

In another embodiment, R² is

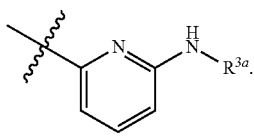

In one variation of formula (V), each R¹⁰ is independently F, Cl, —CN, —OR¹¹, —NH₂, —NH(CO)H, —CF₃, cyclopropyl, pyridinyl, thiazolyl, imidazolyl, or substituted pyrazolyl. In one variation, q is 1, 2, or 3 and each R¹⁰ is independently F, Cl, —CN, —OR, —NH2, —NH(CO)H, —CF₃, cyclopropyl, pyridinyl, thiazolyl, imidazolyl, or substituted pyrazolyl. It is understood that the embodiments of formula (V) may employ any of the A-L-R² embodiments or variations provided herein the same as if each and every combination were specifically and individually listed. For example, in one embodiment, -A-L- is -phenylene-O—(CH2)3-:

In another embodiment, -A-L- is C₆ alkylene:

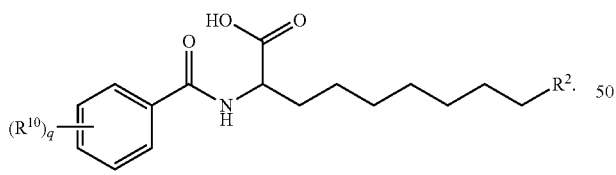

In another embodiment, -A-L- is -phenylene-(CH₂)—O—(CH₂)₃—:

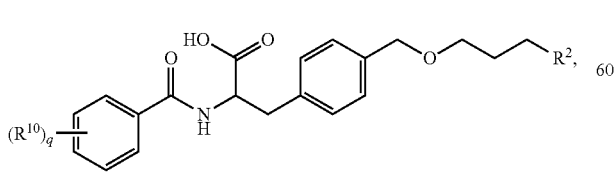

for example, where R² is —NH-pyridyl such as the following:

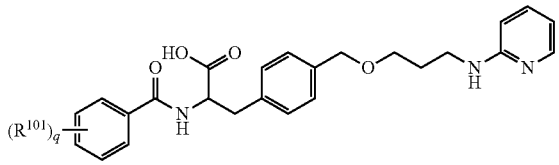

In another embodiment, -A-L- is -phenylene-(CH₂)—O—(CH₂)₂—:

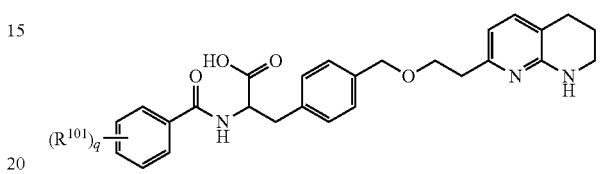

In some embodiments, the compound of formula (I) is of the formula (VI):

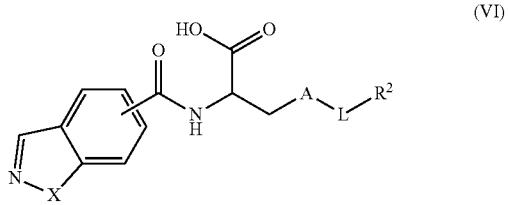

or a salt thereof, wherein R², A, and L are as defined for formula (I) or any embodiment or variation thereof; X is —O—, —S—, or —N(R¹⁰)—; and R¹⁰ is H or C₁-C₆ alkyl optionally substituted by halogen or C₃-C₆ cycloalkyl. In another embodiment, R² is —NR³ᵃ-pyridyl, wherein pyridyl is optionally substituted by R¹⁰. In another embodiment, R² is —NH-pyridyl, wherein pyridyl is optionally substituted by R¹⁰. In another embodiment, R² is

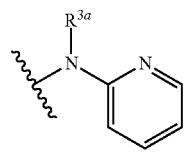

In another embodiment, R² is

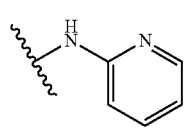

In another embodiment, R² is —R³—NR³ᵃR³ᵇ. In another embodiment, R² is —R³—NHR³ᵃ. In another embodiment, R² is -(pyridyl)-NR³ᵃR³ᵇ, where pyridyl is optionally substituted by R¹⁰. In another embodiment, R² is

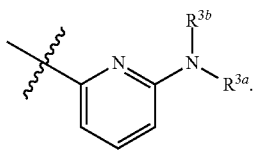

In another embodiment, $R^2$ is

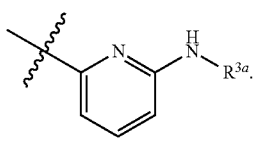

In some embodiments, the compound of formula (VI) is of the formula (VI-1):

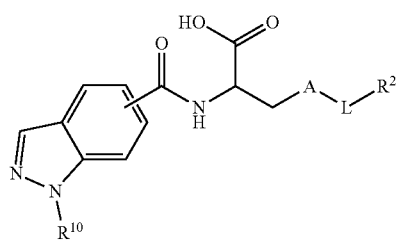

(VI-1)

or a salt thereof, wherein $R^2$, A, and L are as defined for formula (I) or any embodiment or variation thereof and $R^{10}$ is H or $C_1$-$C_6$ alkyl optionally substituted by halogen or $C_3$-$C_6$ cycloalkyl. In some embodiments, the compound of formula (VI-1) is of the formula (VI-1-A):

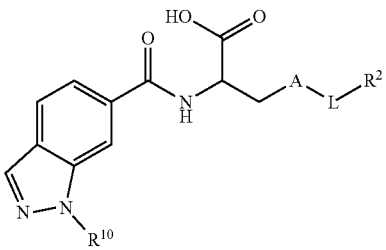

(VI-1-A)

or a salt thereof, wherein $R^2$, A, L, and $R^{10}$ are as defined for formula (I) or any embodiment or variation thereof.

In some embodiments, the compound of formula (VI-1) is of the formula (VI-1-B):

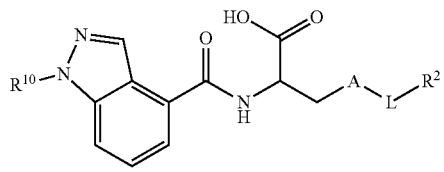

(VI-1-B)

or a salt thereof, wherein $R^2$, A, L, and $R^{10}$ are as defined for formula (I) or any embodiment or variation thereof.

In some embodiments, the compound of formula (VI-1) is of the formula (VI-1-C):

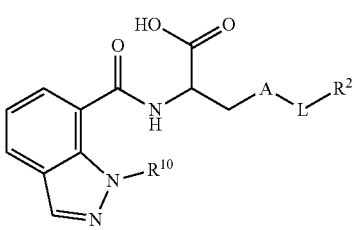

(VI-1-C)

or a salt thereof, wherein $R^2$, A, L, and $R^{10}$ are as defined for formula (I) or any embodiment or variation thereof.

In some embodiments, the compound of formula (VI-1) is of the formula (VI-1-D):

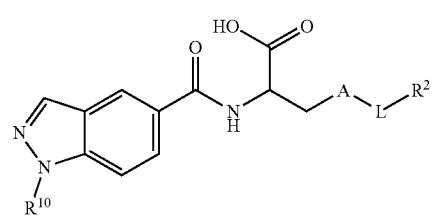

(VI-1-D)

or a salt thereof, wherein $R^2$, A, L, and $R^{10}$ are as defined for formula (I) or any embodiment or variation thereof.

It is understood that the embodiments of formula (VI), (VI-1), (VI-1-A), (VI-1-B), (VI-1-C) and (VI-1-D) may employ any of the A-L-$R^2$ embodiments or variations provided herein the same as if each and every combination were specifically and individually listed.

In some embodiments, the compound of formula (I) is of the formula (VII):

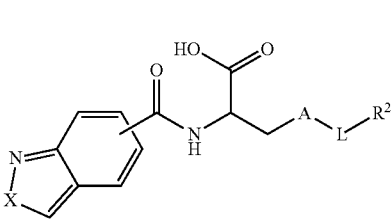

(VII)

or a salt thereof, wherein $R^2$, A, and L are as defined for formula (I) or any embodiment or variation thereof; X is —O—, —S—, or —N($R^{10}$)—; and $R^{10}$ is $C_1$-$C_6$ alkyl optionally substituted by halogen. In another embodiment, $R^2$ is —N$R^{3a}$-pyridyl, wherein pyridyl is optionally substituted by $R^{10}$. In another embodiment, $R^2$ is —NH-pyridyl, wherein pyridyl is optionally substituted by $R^{10}$. In another embodiment, $R^2$ is

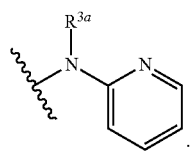

In another embodiment, R² is

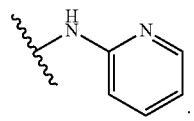

In another embodiment, R² is —R³—NR³ᵃR³ᵇ. In another embodiment, R² is —R³—NHR³ᵃ. In another embodiment, R² is -(pyridyl)-NR³ᵃR³ᵇ, where pyrid is optionally substituted by R¹⁰. In another embodiment, R² is

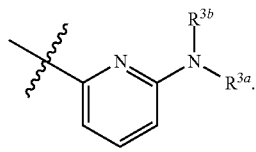

In another embodiment, R² is

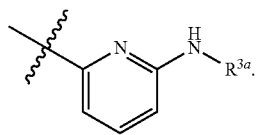

In some embodiments, the compound of formula (VII) is of the formula (VII-1):

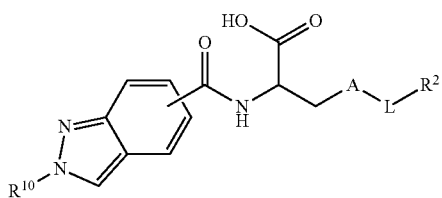

(VII-1)

or a salt thereof, wherein R², A, L, and R¹⁰ are as defined for formula (I) or any embodiment or variation thereof.

In some embodiments, the compound of formula (VII-1) is of the formula (VII-1-A):

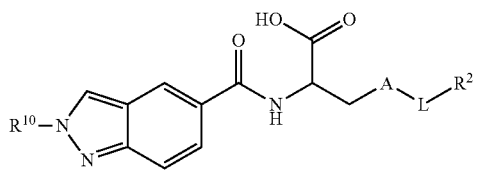

(VII-1-A)

or a salt thereof, wherein R², A, L, and R¹⁰ are as defined for formula (I) or any embodiment or variation thereof.

In some embodiments, the compound of formula (VII-1) is of the formula (VII-1-B):

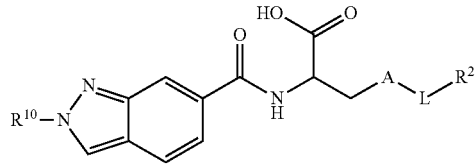

(VII-1-B)

or a salt thereof, wherein R², A, L, and R¹⁰ are as defined for formula (I) or any embodiment or variation thereof.

It is understood that the embodiments of formula (VII), (VII-1), (VII-1-A) and (VII-1-B) may employ any of the A-L-R² embodiments or variations provided herein the same as if each and every combination were specifically and individually listed.

In some embodiments, the compound of formula (I) is of the formula (VIII):

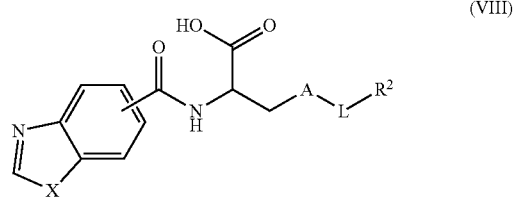

(VIII)

or a salt thereof, wherein R², A, and L are as defined for formula (I) or any embodiment or variation thereof; X is —O—, —S—, or —N(R¹⁰)—; and R¹⁰ is C₁-C₆ alkyl. In another embodiment, R² is —NR³ᵃ-pyridyl, wherein pyridyl is optionally substituted by R¹⁰. In another embodiment, R² is —NH-pyridyl, wherein pyridyl is optionally substituted by R¹⁰. In another embodiment, R² is

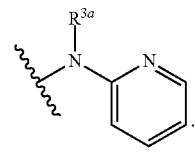

In another embodiment, R² is

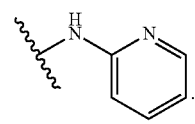

In another embodiment, R² is —R³—NR³ᵃR³ᵇ. In another embodiment, R² is —R³—NHR³ᵃ. In another embodiment, R² is -(pyridyl)-NR³ᵃR³ᵇ, where pyridyl is optionally substituted by R¹⁰. In another embodiment, R² is In another embodiment, $R^2$ is

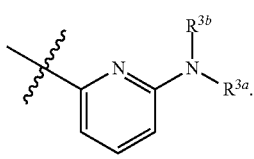

In another embodiment, $R^2$ is

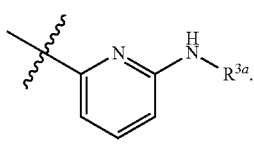

In some embodiments, the compound of formula (VIII) is of the formula (VIII-1):

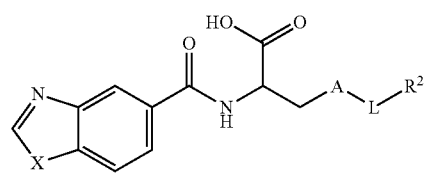
(VIII-1)

or a salt thereof, wherein $R^2$, A, and L are as defined for formula (I) or any embodiment or variation thereof; X is —O—, —S—, or —N($R^{10}$)—; and $R^{10}$ is $C_1$-$C_6$ alkyl.

In some embodiments, the compound of formula (VIII) is of the formula (VIII-2):

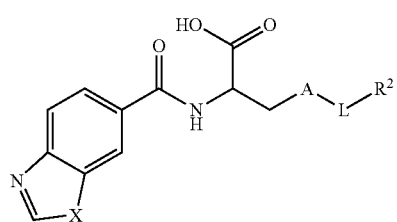
(VIII-2)

or a salt thereof, wherein $R^2$, A, and L are as defined for formula (I) or any embodiment or variation thereof; X is —O—, —S—, or —N($R^{10}$)—; and $R^{1i}$ is $C_1$-$C_6$ alkyl.

It is understood that the embodiments of formula (VIII) and (VIII-1) may employ any of the A-L-$R^2$ embodiments or variations provided herein the same as if each and every combination were specifically and individually listed.

In some embodiments, the compound of formula (I) is of the formula (IX):

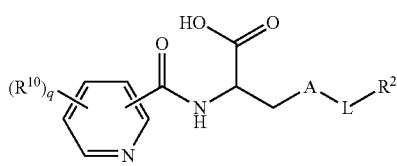
(IX)

or a salt thereof, wherein $R^2$, A, and L are as defined for formula (I) or any embodiment or variation thereof, each $R^{10}$ is independently $R^9$ and q is 0, 1, 2, 3, or 4. In one variation, q is 0, 1, or 2. In one variation, each $R^{10}$ is Cl. In one variation, q is 1, or 2 and each $R^{10}$ is Cl. It is understood that the embodiments of formula (IX) may employ any of the A-L-$R^2$ embodiments or variations provided herein the same as if each and every combination were specifically and individually listed. In another embodiment, $R^2$ is —N$R^{3a}$-pyridyl, wherein pyridyl is optionally substituted by $R^{10}$. In another embodiment, $R^2$ is —NH-pyridyl, wherein pyridyl is optionally substituted by $R^{10}$. In another embodiment, $R^2$ is

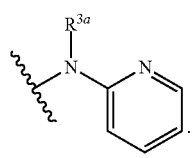

In another embodiment, $R^2$ is

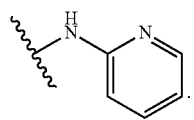

In another embodiment, $R^2$ is —$R^3$—N$R^{3a}R^{3b}$. In another embodiment, $R^2$ is —$R^3$—NH$R^{3a}$. In another embodiment, $R^2$ is -(pyridyl)-N$R^{3a}R^{3b}$, where pyridyl is optionally substituted by $R^{10}$. In another embodiment, $R^2$ is

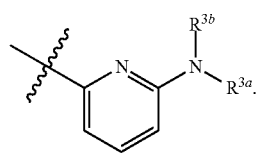

In another embodiment, $R^2$ is

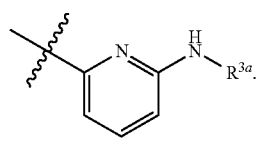

In some embodiments, the compound of formula (I) is of the formula (X):

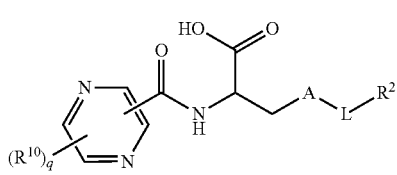
(X)

or a salt thereof, wherein $R^2$, A and L are as defined for formula (I) or any embodiment or variation thereof, each $R^{10}$ is independently $R^9$ and q is 0, 1, 2, or 3. In one variation, q is 0, or 1. In one variation, each $R^{10}$ is independently $C_1$-$C_6$ alkyl or phenyl, wherein the $C_1$-$C_6$ alkyl of $R^{10}$ is optionally substituted by halogen. In one variation, q is 1, or 2 and each $R^{10}$ is independently $C_1$-$C_6$ alkyl or phenyl, wherein the $C_1$-$C_6$ alkyl of $R^{10}$ is optionally substituted by halogen. It is understood that the embodiments of formula (X) may employ any of the A-L-$R^2$ embodiments or variations provided herein the same as if each and every combination were specifically and individually listed. In another embodiment, $R^2$ is —$NR^{3a}$-pyridyl, wherein pyridyl is optionally substituted by $R^{10}$. In another embodiment, $R^2$ is —NH-pyridyl, wherein pyridyl is optionally substituted by $R^{10}$. In another embodiment, $R^2$ is

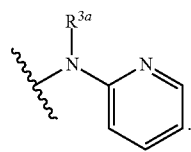

In another embodiment, $R^2$ is

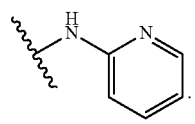

In another embodiment, $R^2$ is —R—$NR^{3a}R^{3b}$. In another embodiment, $R^2$ is —$R^3$—$NHR^{3a}$. In another embodiment, $R^2$ is -(pyridyl)-$NR^{3a}R^{3b}$, where pyridyl is optionally substituted by $R^{10}$. In another embodiment, $R^2$ is

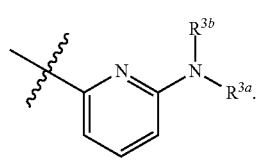

In another embodiment, $R^2$ is

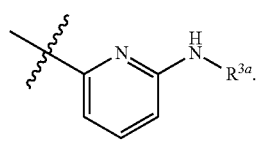

In some embodiments, the compound of formula (I) is of the formula (XI):

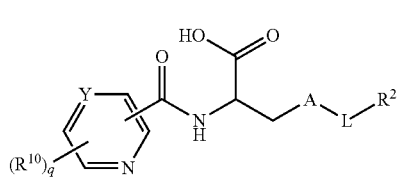

(XI)

or a salt thereof, wherein $R^2$, A, and L are as defined for formula (I) or any embodiment or variation thereof; Y is —N—, —CH—, or C($R^{10}$), each $R^{10}$ is independently $R^9$ and q is 0, 1, 2, or 3. In one variation, q is 0, 1, or 2. In one variation, each $R^{10}$ is independently halogen, $C_1$-$C_6$ alkyl or phenyl, wherein the $C_1$-$C_6$ alkyl is optionally substituted by one to eight halogen atoms. In one variation, q is 1, or 2 and each $R^{10}$ is independently halogen, $C_1$-$C_6$ alkyl or phenyl, wherein the $C_1$-$C_6$ alkyl of $R^{10}$ is optionally substituted by one to eight halogen atoms. In one variation, Y is —N—, q is 1, and each $R^{10}$ is independently $C_1$-$C_6$ alkyl optionally substituted by one to eight halogen atoms or phenyl. It is understood that the embodiments of formula (XI) may employ any of the A-L-$R^2$ embodiments or variations provided herein the same as if each and every combination were specifically and individually listed. In another embodiment, $R^2$ is —$NR^{3a}$-pyridyl, wherein pyridyl is optionally substituted by $R^{10}$. In another embodiment, $R^2$ is —NH-pyridyl, wherein pyridyl is optionally substituted by $R^{10}$. In another embodiment, $R^2$ is

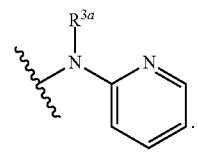

In another embodiment, $R^2$ is

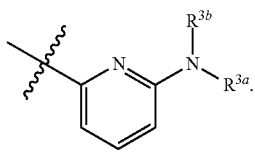

In another embodiment, $R^2$ is —$R^3$—$NR^{3a}R^{3b}$. In another embodiment, $R^2$ is —$R^3$—$NHR^{3a}$. In another embodiment, $R^2$ is -(pyridyl)-$NR^{3a}R^{3b}$, where pyridyl is optionally substituted by $R^{10}$. In another embodiment, $R^2$ is

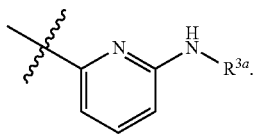

In another embodiment, $R^2$ is

In some embodiments, the compound of formula (I) is of the formula (III-4)

(III-4)

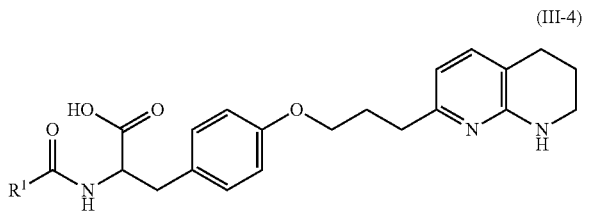

or a salt thereof, wherein $R^1$ is as defined for formula (I) or any embodiment or variation thereof.

In some embodiments, the compound of formula (I) is of the formula (III-5)

(III-5)

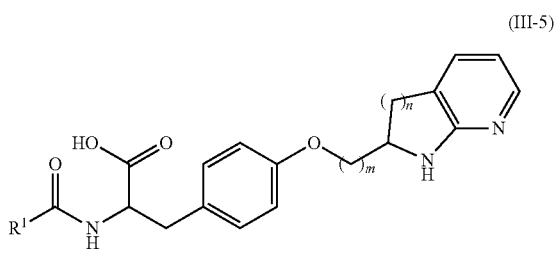

or a salt thereof, wherein $R^1$ is as defined for formula (I) or any embodiment or variation thereof; m is 1, 2, 3, 4, 5, or 6; and n is 1 or 2. In one variation, m is 2, 3, or 4.

In some embodiments, the compound of formula (I) is of the formula (III-1-A)

(III-1-A)

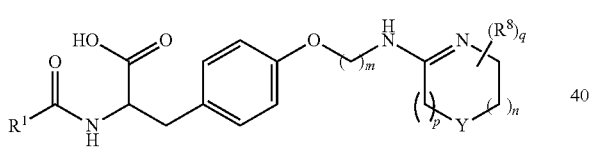

or a salt thereof, wherein $R^1$ is as defined for formula (I) or any embodiment or variation thereof; $R^8$ is as defined for $R^{10}$ of formula (I) or any embodiment or variation thereof; Y is —O—, —S—, or —N($R^6$)—; $R^6$ is H, $C_1$-$C_6$ alkyl, or —C(=O)CH$_3$; m is 1, 2, 3, 4, 5, or 6; n is an integer from 0-8; p is 0 or 1; and q is 0, 1, 2 or 3. In one variation, m is 3, 4 or 5. In one variation, q is 0. In one variation, n is 1 or 2.

In some embodiments, the compound of formula (I) is of the formula (XII):

(XII)

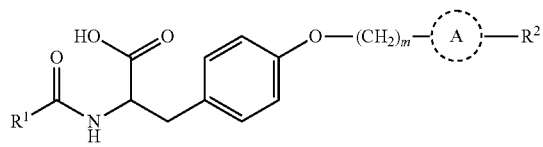

or a salt thereof, wherein $R^1$ and $R^2$ are as defined for formula (I) or any embodiment or variation thereof; m is an integer from 0-7; and

is $C_3$-$C_5$ cycloalkylene optionally substituted by one to six $R^9$ groups where $R^9$ is as defined for formula (I). In one variation, m is 1 and

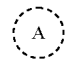

is cyclobutylene. In one variation, m is 1 and

is cyclohexylene. In another embodiment, $R^2$ is —NR$^{3a}$-pyridyl, wherein pyridyl is optionally substituted by $R^{10}$. In another embodiment, $R^2$ is —NH-pyridyl, wherein pyridyl is optionally substituted by $R^{10}$. In another embodiment, $R^2$ is

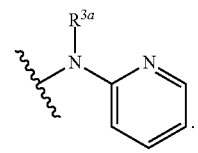

In another embodiment, $R^2$ is

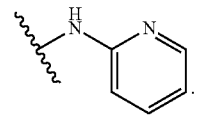

In another embodiment, $R^2$ is —R$^3$—NR$^{3a}$R$^{3b}$. In another embodiment, $R^2$ is —R$^3$—NHR$^{3a}$. In another embodiment, $R^2$ is -(pyridyl)-NR$^{3a}$R$^{3b}$, where pyridyl is optionally substituted by $R^{10}$. In another embodiment, $R^2$ is

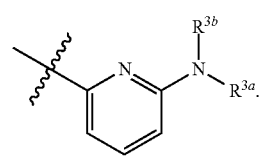

In another embodiment, $R^2$ is

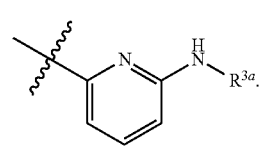

In some embodiments, the compound of formula (I) is of the formula (XIII):

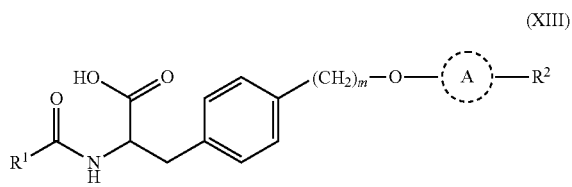
(XIII)

or a salt thereof, wherein R¹ and R² are as defined for formula (I) or any embodiment or variation thereof; m is 0 or 1; and

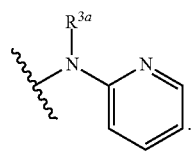

is $C_3$-$C_8$ cycloalkylene optionally substituted by one to six $R^9$ groups where $R^9$ is as defined for formula (I). In another embodiment, $R^2$ is —$NR^{3a}$-pyridyl, wherein pyridyl is optionally substituted by $R^{10}$. In another embodiment, $R^2$ is —NH-pyridyl, wherein pyridyl is optionally substituted by $R^{10}$. In another embodiment, $R^2$ is

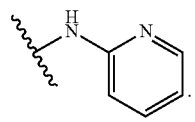

In another embodiment, $R^2$ is

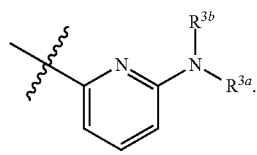

In another embodiment, $R^2$ is —$R^3$—$NR^{3a}R^{3b}$. In another embodiment, $R^2$ is —$R^3$—$NHR^{3a}$. In another embodiment, $R^2$ is -(pyridyl)-$NR^{3a}R^{3b}$, where pyridyl is optionally substituted by $R^{10}$. In another embodiment, $R^2$ is

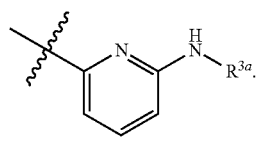

In another embodiment, $R^2$ is

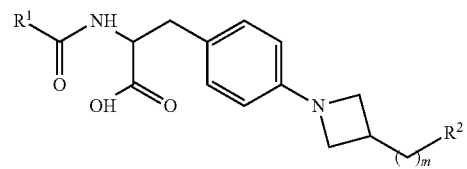

In some embodiments, the compound of formula (I) is of the formula (XIV):

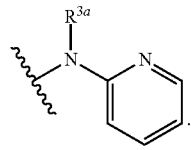
(XIV)

or a salt thereof, wherein R¹ and R² are as defined for formula (I) or any embodiment or variation thereof, and m is 0, 1, 2, 3, 4, 5, or 6. In one variation, m is 0 or 1. In another embodiment, $R^2$ is —$NR^{3a}$-pyridyl, wherein pyridyl is optionally substituted by $R^{10}$. In another embodiment, $R^2$ is —NH-pyridyl, wherein pyridyl substituted by $R^{10}$. In another embodiment, $R^2$ is

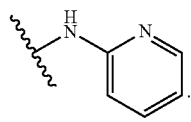

In another embodiment, $R^2$ is

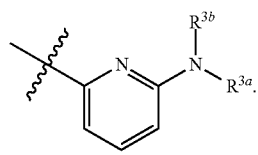

In another embodiment, $R^2$ is —$R^3$—$NR^{3a}R^{3b}$. In another embodiment, $R^2$ is —$R^3$—$NHR^{3a}$. In another embodiment, $R^2$ is -(pyridyl)-$NR^{3a}R^{3b}$, where pyridyl is optionally substituted by $R^{10}$. In another embodiment, $R^2$ is

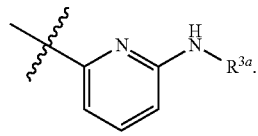

In another embodiment, $R^2$ is

In some embodiments, the compound of formula (III-1) is of the formula (III-1-B):

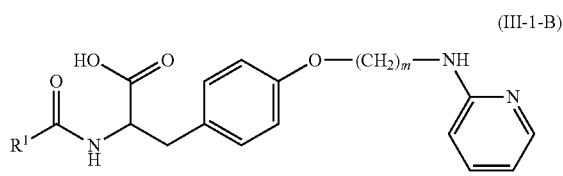
(III-1-B)

or a salt thereof, wherein $R^1$ is as defined for formula (I) or any embodiment or variation thereof, and m is 1, 2, 3, 4, 5, or 6. In one variation, m is 3, 4, or 5. In another embodiment, $R^2$ is —$NR^{3a}$-pyridyl, wherein pyridyl is optionally substituted by $R^{10}$. In another embodiment, $R^2$ is —NH-pyridyl, wherein pyridyl is optionally substituted by $R^{10}$. In another embodiment, $R^2$ is

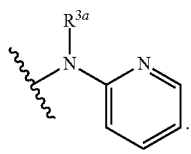

In another embodiment, $R^2$ is

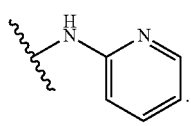

In another embodiment, $R^2$ is —$R^3$—$NR^{3a}R^{3b}$. In another embodiment, $R^2$ is —$R^3$—$NHR^{3a}$. In another embodiment, $R^2$ is -(pyridyl)-$NR^{3a}R^{3b}$, where pyridyl is optionally substituted by $R^{10}$. In another embodiment, $R^2$ is

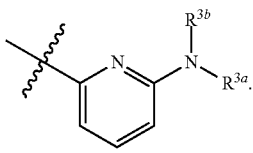

In another embodiment, $R^2$ is

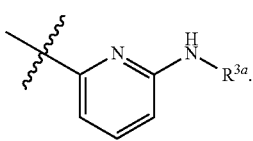

In some embodiments, the compound of formula (I) is of the formula (XV):

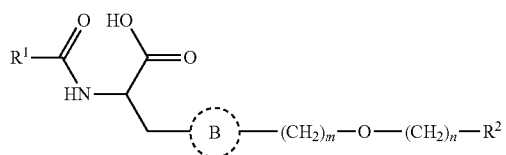
(XV)

or a salt thereof, wherein $R^1$ and $R^2$ are as defined for formula (I) or any embodiment or variation thereof;


is $C_3$-$C_8$ cycloalkylene or $C_3$-$C_8$ cycloalkenylene optionally substituted by one to six $R^{10}$ groups where $R^{10}$ is as defined for formula (I); m is 0, 1, 2, 3, 4, 5, 6, or 7; and n is 1, 2, 3, 4, 5, 6, or 7. In one variation, m is 0 or 1. In one variation, n is 3, 4, or 5. In one variation,

is 1,3-cyclobutylene or 1,4-cyclohexylene. In one particular variation, m is 1, n is 3, and

is 1,3-cyclobutylene:

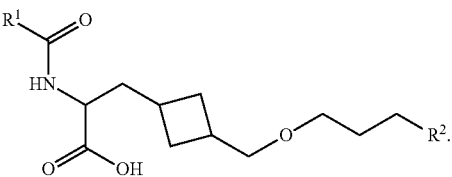

In another embodiment, $R^2$ is —$NR^{3a}$-pyridyl, wherein pyridyl is optionally substituted by $R^{10}$. In another embodiment, $R^2$ is —NH-pyridyl, wherein pyridyl is optionally substituted by $R^{10}$. In another embodiment, $R^2$ is

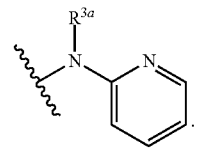

In another embodiment, $R^2$ is

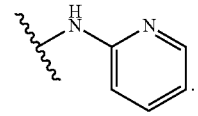

In another embodiment, $R^2$ is —$R^3$—$NR^{3a}R^{3b}$ In another embodiment, $R^2$ is —$R^3$—$NHR^{3a}$. In another embodiment, $R^2$ is -(pyridyl)-$NR^{3a}R^{3b}$ where pyridyl is optionally substituted by $R^{10}$. In another embodiment, $R^2$ is

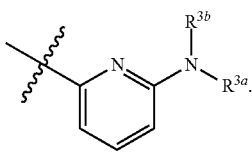

In another embodiment, $R^2$ is

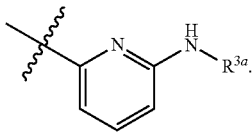

In another particular variation, m is 0, n is 3, and (B)

is 1,3-cyclobutylene:

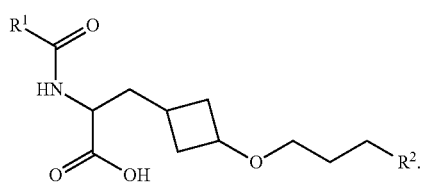

In another embodiment, $R^2$ is —$NR^{3a}$-pyridyl, wherein pyridyl is optionally substituted by $R^{10}$. In another embodiment, $R^2$ is —NH-pyridyl, wherein pyridyl is optionally substituted by $R^{10}$. In another embodiment, $R^2$ is

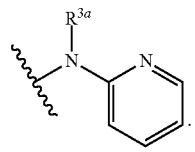

In another embodiment, $R^2$ is

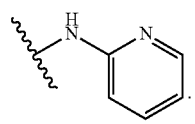

In another embodiment, $R^2$ is —$R^3$—$NR^{3a}R^{3b}$. In another embodiment, $R^2$ is —$R^3$—$NHR^{3a}$. In another embodiment, $R^2$ is -(pyridyl)-$NR^{3a}R^{3b}$, where pyridyl is optionally substituted by $R^{10}$. In another embodiment, $R^2$ is

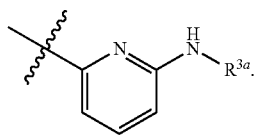

In another embodiment, $R^2$ is

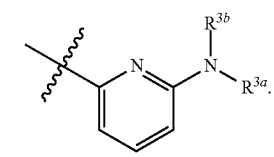

In yet another particular variation, m is 0, n is 3, and (B)

is 1,4-cyclohexylene:

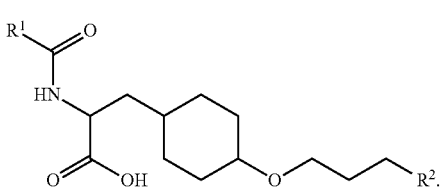

In another embodiment, $R^2$ is —$NR^{3a}$-pyridyl, wherein pyridyl is optionally substituted by $R^{10}$. In another embodiment, $R^2$ is —NH-pyridyl, wherein pyridyl is optionally substituted by $R^{10}$. In another embodiment, $R^2$ is

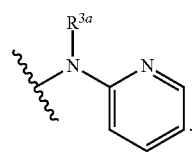

In another embodiment, $R^2$ is

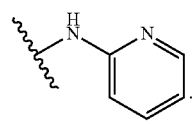

In another embodiment, $R^2$ is —$R^3$—$NR^{3a}R^{3b}$. In another embodiment, $R^2$ is —$R^3$—$NHR^{3a}$. In another embodiment, $R^2$ is -(pyridyl)-$NR^{3a}R^{3b}$, where pyridyl is optionally substituted by $R^{10}$. In another embodiment, $R^2$ is

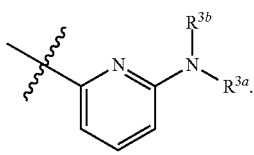

In another embodiment, $R^2$ is

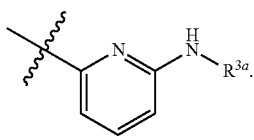

In some embodiments, the compound of formula I is of the formula (XVI):

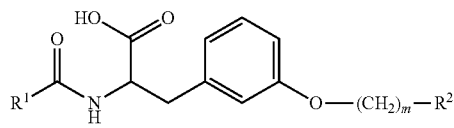

(XVI)

or a salt thereof, wherein $R^1$ and $R^2$ are as defined for formula (I) or any embodiment or variation thereof, and m is 1, 2, 3, 4, 5 or 6. In one variation, m is 2, 3 or 4. In another embodiment, $R^2$ is —$NR^{3a}$-pyridyl, wherein pyridyl is optionally substituted by $R^{10}$. In another embodiment, $R^2$ is —NH-pyridyl, wherein pyridyl is optionally substituted by $R^{10}$. In another embodiment, $R^2$ is

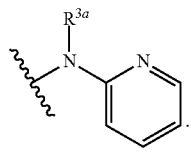

In another embodiment, $R^2$ is

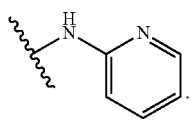 [SMILES: *Nc1ccccn1]

In another embodiment, $R^2$ is —$R^3$—$NR^{3a}R^{3b}$. In another embodiment, $R^2$ is —$R^3$—$NHR^{3a}$. In another embodiment, $R^2$ is -(pyridyl)-$NR^{3a}R^{3b}$, where pyridyl is optionally substituted by $R^{10}$. In another embodiment, $R^2$ is

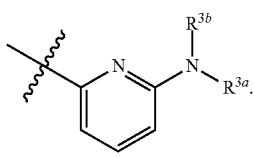

In another embodiment, $R^2$ is

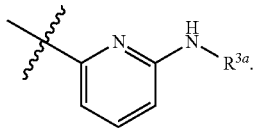

In some embodiments, the compound of formula (III) is of the formula (III-1):

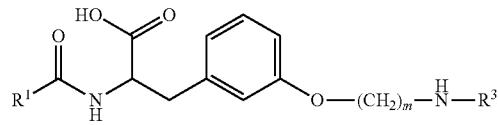

(XVI-1)

or a salt thereof, wherein $R^1$ and $R^3$ are as defined for formula (I) or any embodiment or variation thereof, and m is 1, 2, 3, 4, 5 or 6. In one variation, m is 3, 4 or 5. In another embodiment, $R^2$ is —$NR^{3a}$-pyridyl, wherein pyridyl is optionally substituted by $R^{10}$. In another embodiment, $R^2$ is —NH-pyridyl, wherein pyridyl is optionally substituted by $R^{10}$. In another embodiment, $R^2$ is

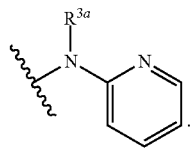

In another embodiment, $R^2$ is

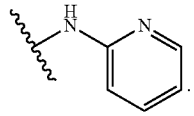

In another embodiment, $R^2$ is —$R^3$—$NR^{3a}R^{3b}$. In another embodiment, $R^2$ is —$R^3$—$NHR^{3a}$. In another embodiment, $R^2$ is -(pyridyl)-$NR^{3a}R^{3b}$, where pyridyl is optionally substituted by $R^{10}$. In another embodiment, $R^2$ is

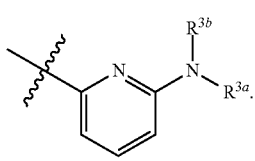

In another embodiment, $R^2$ is

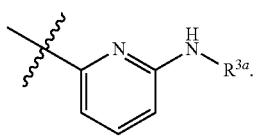

In some embodiments, the compound of formula (III) is of the formula (III-2):

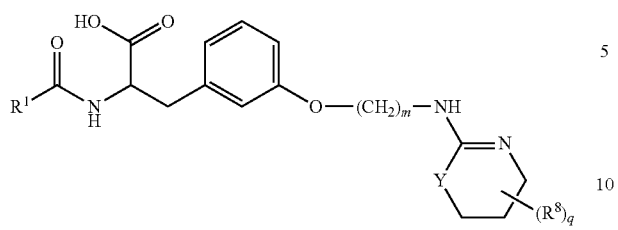

or a salt thereof, wherein $R^1$ is as defined for formula (I) or any embodiment or variation thereof; $R^8$ is as defined for $R^{10}$ of formula (I) or any embodiment or variation thereof; Y is O, S, or $NR^6$; $R^6$ is H or $C_1$-$C_6$ alkyl; m is 1, 2, 3, 4, 5 or 6; and q is 0, 1, 2 or 3. In one variation, m is 3, 4 or 5. In one variation, q is 0.

Also provided is a compound of formula (I), or a salt thereof, or any embodiment or variation thereof, wherein $R^1$ is selected from the group consisting of:

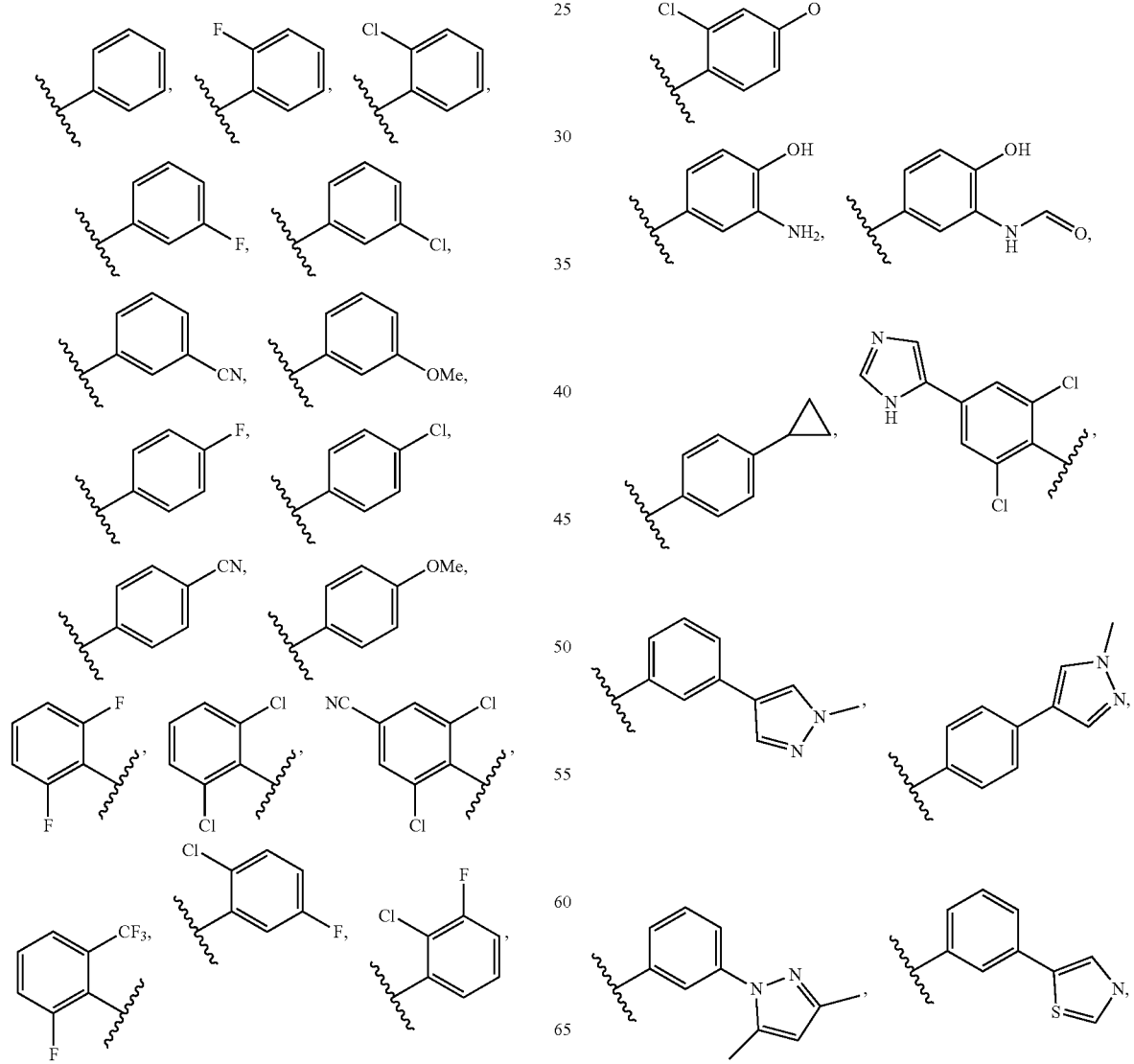

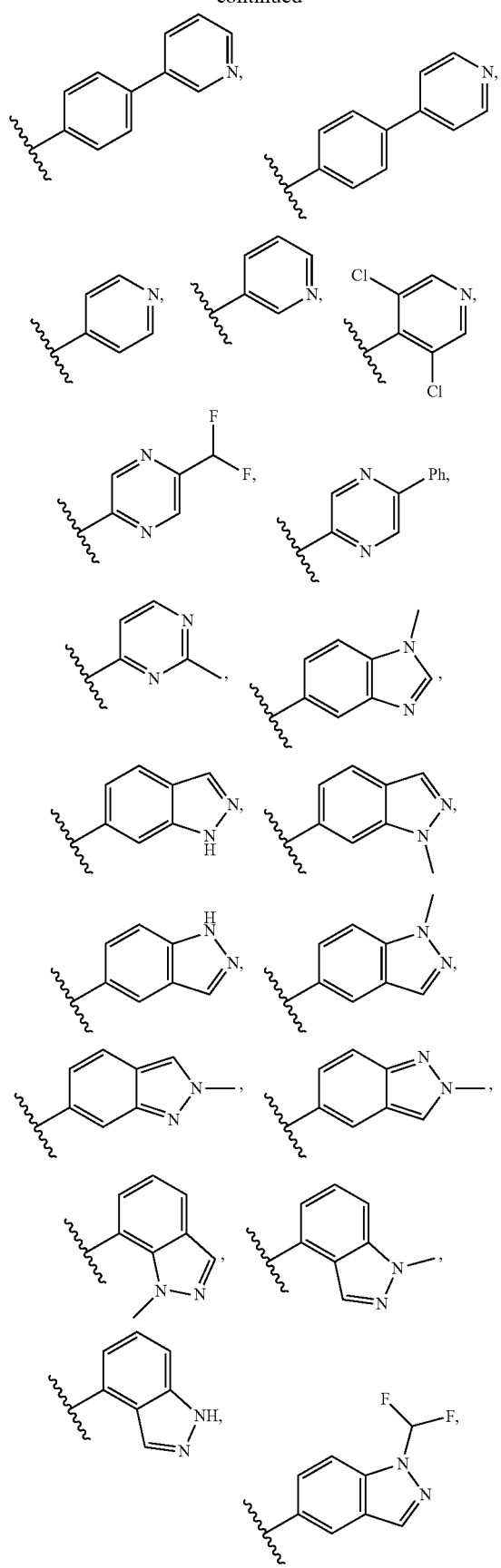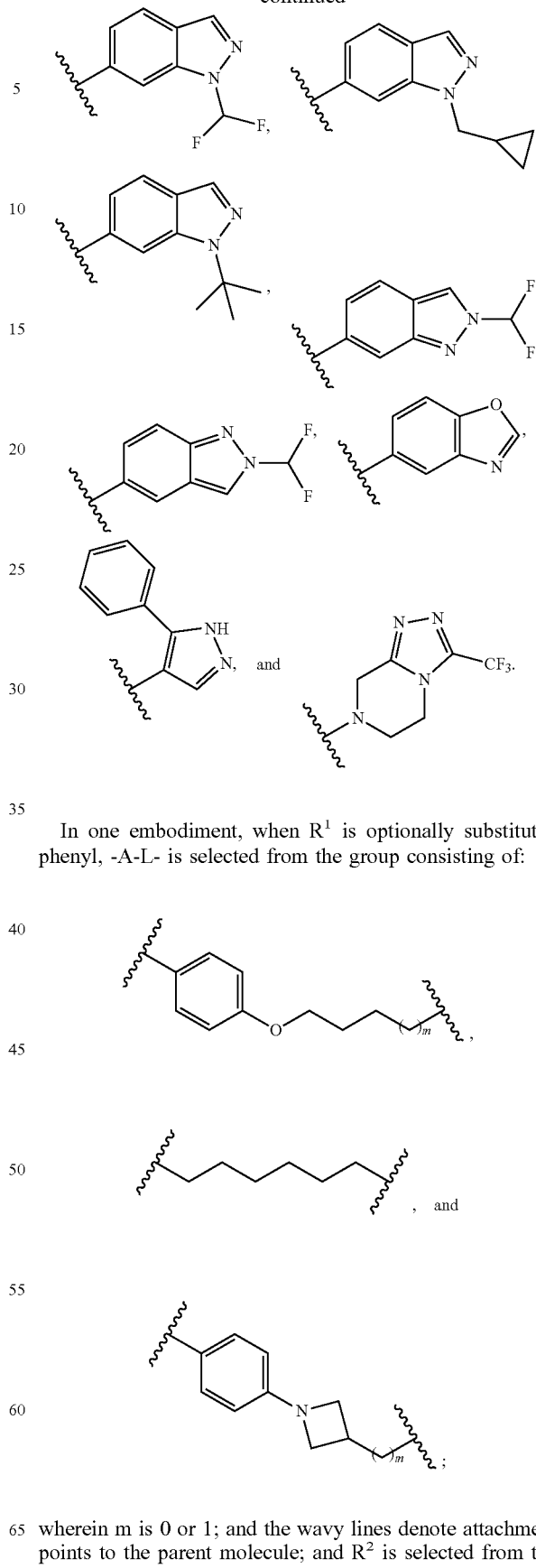
In one embodiment, when $R^1$ is optionally substituted phenyl, -A-L- is selected from the group consisting of:
wherein m is 0 or 1; and the wavy lines denote attachment points to the parent molecule; and $R^2$ is selected from the group consisting of:

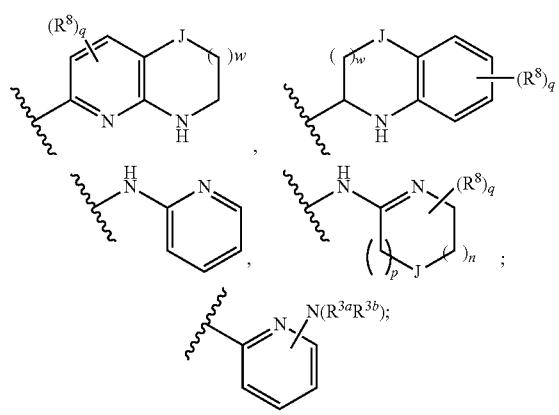

wherein $R^8$ is as defined for $R^{10}$ of formula (I) or any embodiment or variation thereof; J is —O—, —S—, —N($R^6$)—, or —CH$_2$—; $R^6$ is H, $C_1$-$C_6$ alkyl, or —C(=O)CH$_3$; w is 0 or 1; n is 0, 1, 2, 3, 4, 5, 6, or 7; p is 0 or 1; q is 0, 1, 2 or 3; and the wavy lines denote attachment points to the parent molecule. In one variation n is 1 or 2.

In one variation of the preceding embodiment, p is 0 and n is 1:

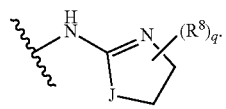

In another variation of the preceding embodiment, p is 0 and n is 2:

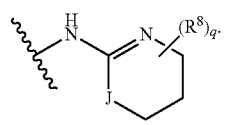

In another variation of the preceding embodiment, p is 1 and n is 1:

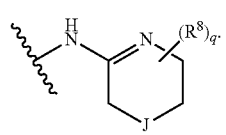

In another variation of the preceding embodiment, -A-L-$R^2$ is selected from the group consisting of:

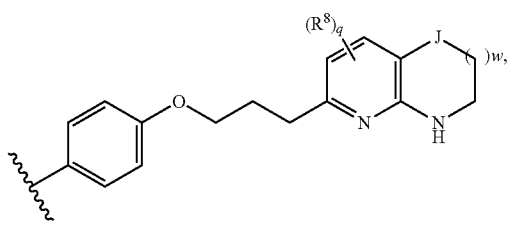

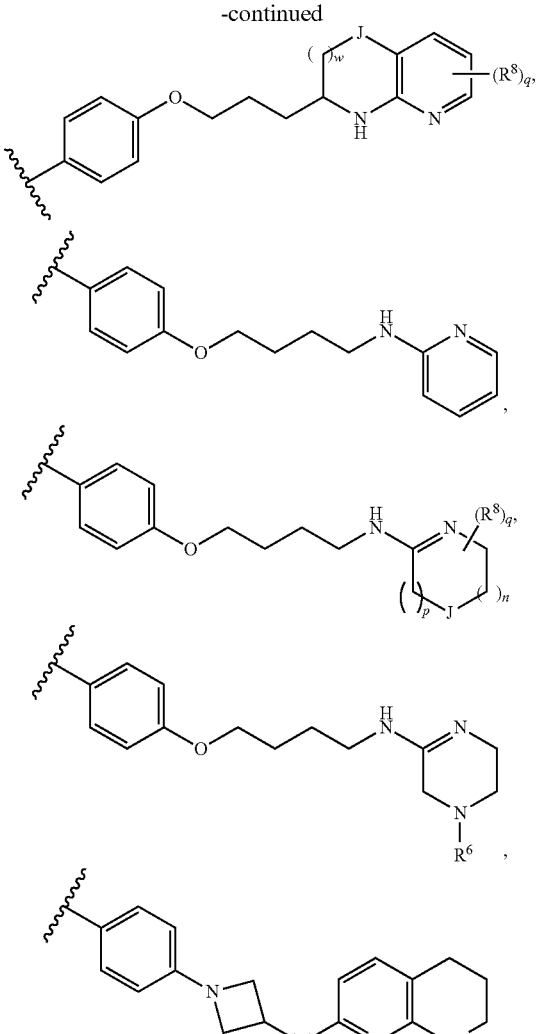

wherein $R^8$ is as defined for $R^{10}$ of formula (I) or any embodiment or variation thereof; J is —O—, —S—, —N($R^6$)—, or —CH$_2$—; $R^6$ is H, $C_1$-$C_6$ alkyl, or —C(=O)CH$_3$; w is 0 or 1; n is 0, 1, 2, 3, 4, 5, 6, or 7; p is 0 or 1; q is 0, 1, 2 or 3; and the wavy lines denote attachment points to the parent molecule. In one variation, A-L-$R^2$ is selected from the group consisting of:

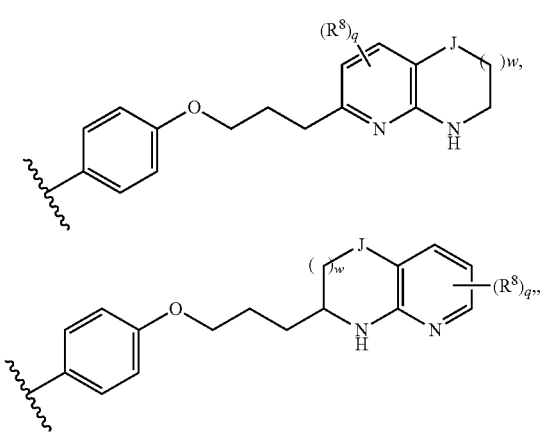

-continued

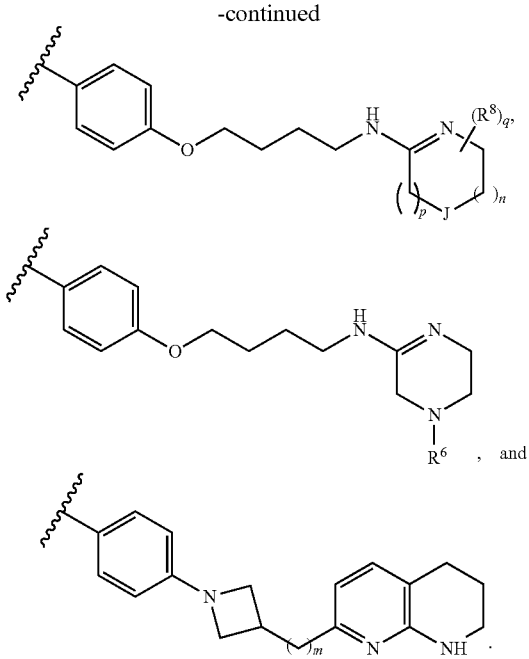

In one variation, -A-L- is

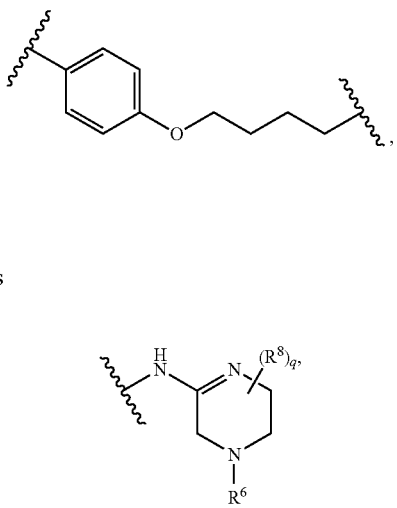

and $R^2$ is

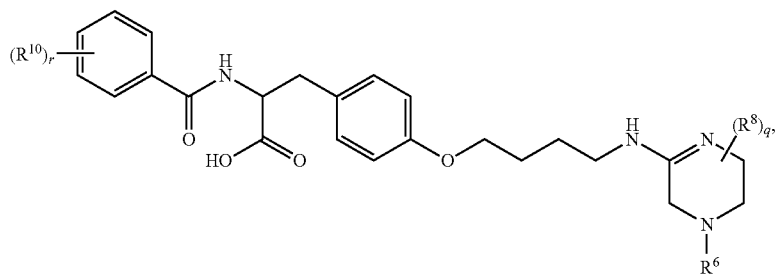

wherein J is —N($R^6$)—, p is 1, and n is 1:

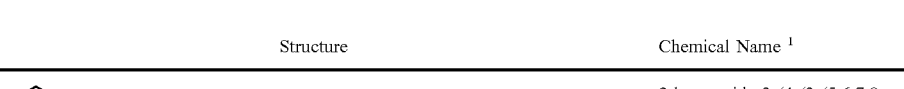

wherein $R^{10}$ is as defined for formula (I) or any embodiment or variation thereof; $R^8$ is as defined for $R^{10}$ of formula (I) or any embodiment or variation thereof; $R^6$ is H, $C_1$-$C_6$ alkyl, or —C(=O)$CH_3$; q is 0, 1, 2, or 3; and r is 0, 1, 2, 3, 4, or 5.

Representative compounds are listed in Table 1 and Table 2.

TABLE 1

| Compound No. | Structure | Chemical Name [1] |
|---|---|---|
| 1 | 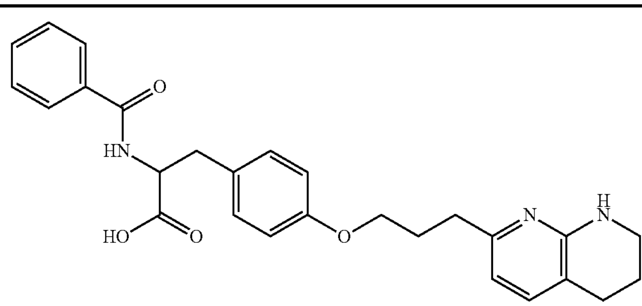 | 2-benzamido-3-(4-(3-(5,6,7,8-tetrahydro-1,8-naphthyridin-2-yl)propoxy)phenyl)propanoic acid |

TABLE 1-continued

| Compound No. | Structure | Chemical Name [1] |
|---|---|---|
| 1a | | (S)-2-benzamido-3-(4-(3-(5,6,7,8-tetrahydro-1,8-naphthyridin-2-yl)propoxy)phenyl)propanoic acid |
| 1b | | (R)-2-benzamido-3-(4-(3-(5,6,7,8-tetrahydro-1,8-naphthyridin-2-yl)propoxy)phenyl)propanoic acid |
| 2 | (structure) | 2-(1-methyl-1H-benzo[d]imidazole-6-carboxamido)-3-(4-(3-(5,6,7,8-tetrahydro-1,8-naphthyridin-2-yl)propoxy)phenyl)propanoic acid |
| 2a | | (S)-2-(1-methyl-1H-benzo[d]imidazole-6-carboxamido)-3-(4-(3-(5,6,7,8-tetrahydro-1,8-naphthyridin-2-yl)propoxy)phenyl)propanoic acid |
| 2b | | (R)-2-(1-methyl-1H-benzo[d]imidazole-6-carboxamido)-3-(4-(3-(5,6,7,8-tetrahydro-1,8-naphthyridin-2-yl)propoxy)phenyl)propanoic acid |
| 3 | (structure) | 2-(5-(difluoromethyl)pyrazine-2-carboxamido)-3-(4-(3-(5,6,7,8-tetrahydro-1,8-naphthyridin-2-yl)propoxy)phenyl)propanoic acid |
| 3a | | (S)-2-(5-(difluoromethyl)pyrazine-2-carboxamido)-3-(4-(3-(5,6,7,8-tetrahydro-1,8-naphthyridin-2-yl)propoxy)phenyl)propanoic acid |
| 3b | | (R)-2-(5-(difluoromethyl)pyrazine-2-carboxamido)-3-(4-(3-(5,6,7,8-tetrahydro-1,8-naphthyridin-2-yl)propoxy)phenyl)propanoic acid |

TABLE 1-continued

| Compound No. | Structure | Chemical Name [1] |
|---|---|---|
| 4 | 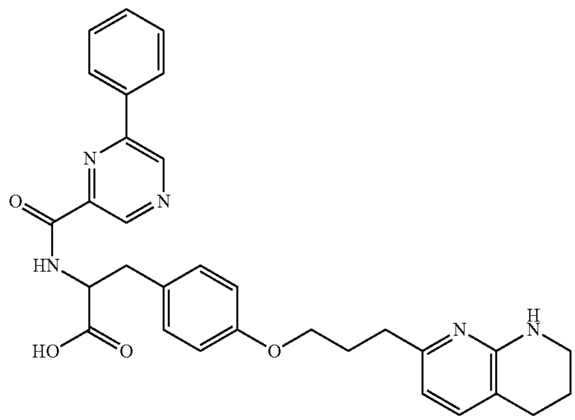 [SMILES: O=C(NC(Cc1ccc(OCCCc2ccc3c(n2)NCCC3)cc1)C(=O)O)c1cncc(-c2ccccc2)n1] | 2-(6-phenylpyrazine-2-carboxamido)-3-(4-(3-(5,6,7,8-tetrahydro-1,8-naphthyridin-2-yl)propoxy)phenyl)propanoic acid |
| 4a | | (S)-2-(6-phenylpyrazine-2-carboxamido)-3-(4-(3-(5,6,7,8-tetrahydro-1,8-naphthyridin-2-yl)propoxy)phenyl)propanoic acid |
| 4b | | (R)-2-(6-phenylpyrazine-2-carboxamido)-3-(4-(3-(5,6,7,8-tetrahydro-1,8-naphthyridin-2-yl)propoxy)phenyl)propanoic acid |
| 5 | 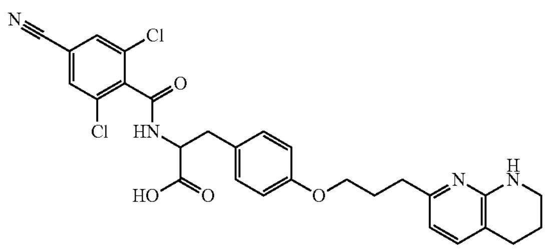 [SMILES: N#Cc1cc(Cl)c(C(=O)NC(Cc2ccc(OCCCc3ccc4c(n3)NCCC4)cc2)C(=O)O)c(Cl)c1] | 2-(2,6-dichloro-4-cyanobenzamido)-3-(4-(3-(5,6,7,8-tetrahydro-1,8-naphthyridin-2-yl)propoxy)phenyl)propanoic acid |
| 5a | | (S)-2-(2,6-dichloro-4-cyanobenzamido)-3-(4-(3-(5,6,7,8-tetrahydro-1,8-naphthyridin-2-yl)propoxy)phenyl)propanoic acid |
| 5b | | (R)-2-(2,6-dichloro-4-cyanobenzamido)-3-(4-(3-(5,6,7,8-tetrahydro-1,8-naphthyridin-2-yl)propoxy)phenyl)propanoic acid |
| 6 | 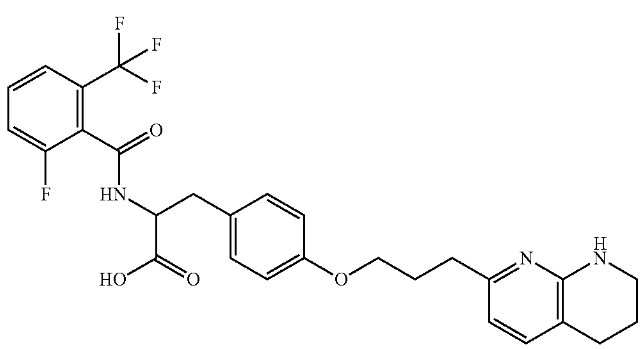 [SMILES: O=C(NC(Cc1ccc(OCCCc2ccc3c(n2)NCCC3)cc1)C(=O)O)c1c(F)cccc1C(F)(F)F] | 2-(2-fluoro-6-(trifluoromethyl)benzamido)-3-(4-(3-(5,6,7,8-tetrahydro-1,8-naphthyridin-2-yl)propoxy)phenyl)propanoic acid |
| 6a | | (S)-2-(2-fluoro-6-(trifluoromethyl)benzamido)-3-(4-(3-(5,6,7,8-tetrahydro-1,8-naphthyridin-2-yl)propoxy)phenyl)propanoic acid |
| 6b | | (R)-2-(2-fluoro-6-(trifluoromethyl)benzamido)-3-(4-(3-(5,6,7,8-tetrahydro-1,8- |

TABLE 1-continued

| Compound No. | Structure | Chemical Name [1] |
|---|---|---|
| | | naphthyridin-2-yl)propoxy) phenyl)propanoic acid |
| 7 | 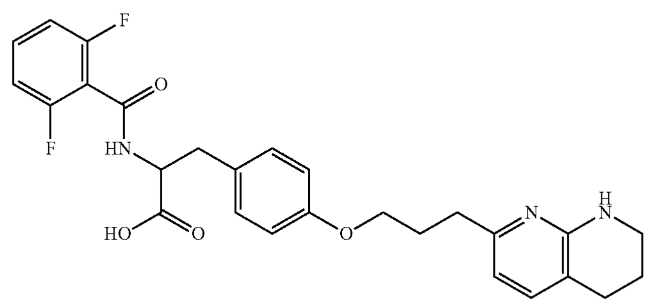 [SMILES: O=C(NC(Cc1ccc(OCCCc2ccc3c(n2)NCCC3)cc1)C(=O)O)c1c(F)cccc1F] | 2-(2,6-difluorobenzamido)-3-(4-(3-(5,6,7,8-tetrahydro-1,8-naphthyridin-2-yl)propoxy) phenyl)propanoic acid |
| 7a | | (S)-2-(2,6-difluorobenzamido)-3-(4-(3-(5,6,7,8-tetrahydro-1,8-naphthyridin-2-yl)propoxy) phenyl)propanoic acid |
| 7b | | (R)-2-(2,6-difluorobenzamido)-3-(4-(3-(5,6,7,8-tetrahydro-1,8-naphthyridin-2-yl)propoxy) phenyl)propanoic acid |
| 8 | 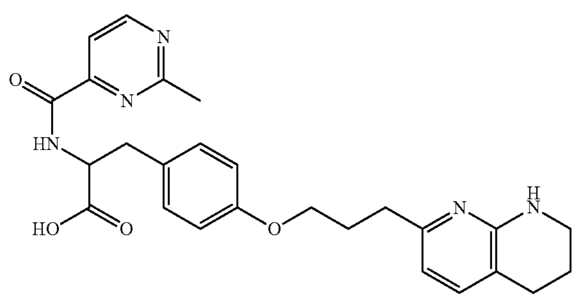 [SMILES: Cc1nccc(C(=O)NC(Cc2ccc(OCCCc3ccc4c(n3)NCCC4)cc2)C(=O)O)n1] | 2-(2-methylpyrimidine-4-carboxamido)-3-(4-(3-(5,6,7,8-tetrahydro-1,8-naphthyridin-2-yl)propoxy)phenyl)propanoic acid |
| 8a | | (S)-2-(2-methylpyrimidine-4-carboxamido)-3-(4-(3-(5,6,7,8-tetrahydro-1,8-naphthyridin-2-yl)propoxy)phenyl)propanoic acid |
| 8b | | (R)-2-(2-methylpyrimidine-4-carboxamido)-3-(4-(3-(5,6,7,8-tetrahydro-1,8-naphthyridin-2-yl)propoxy)phenyl)propanoic acid |
| 9 | 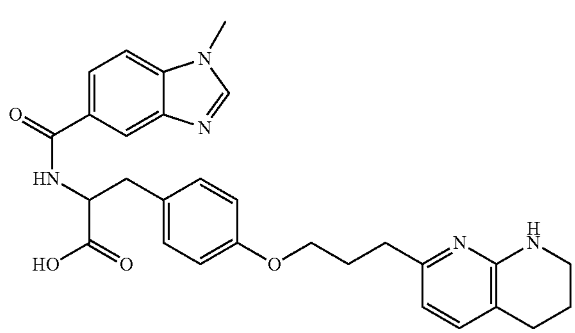 [SMILES: Cn1cnc2cc(C(=O)NC(Cc3ccc(OCCCc4ccc5c(n4)NCCC5)cc3)C(=O)O)ccc21] | 2-(1-methyl-1H-benzo[d]imidazole-5-carboxamido)-3-(4-(3-(5,6,7,8-tetrahydro-1,8-naphthyridin-2-yl)propoxy) phenyl)propanoic acid |
| 9a | | (S)-2-(1-methyl-1H-benzo[d]imidazole-5-carboxamido)-3-(4-(3-(5,6,7,8-tetrahydro-1,8-naphthyridin-2-yl)propoxy) phenyl)propanoic acid |
| 9b | | (R)-2-(1-methyl-1H-benzo[d]imidazole-5-carboxamido)-3-(4-(3-(5,6,7,8-tetrahydro-1,8-naphthyridin-2-yl)propoxy) phenyl)propanoic acid |

TABLE 1-continued

| Compound No. | Structure | Chemical Name [1] |
|---|---|---|
| 10 | 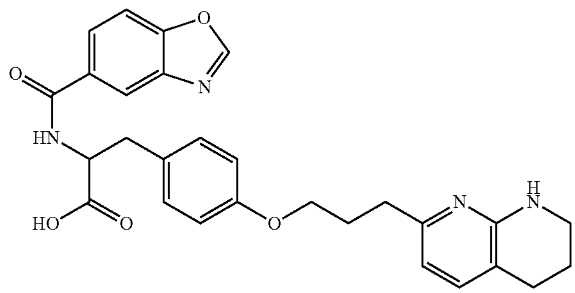 [SMILES: O=C(NC(Cc1ccc(OCCCc2ccc3c(n2)NCCC3)cc1)C(=O)O)c1ccc2ocnc2c1] | 2-(benzo[d]oxazole-5-carboxamido)-3-(4-(3-(5,6,7,8-tetrahydro-1,8-naphthyridin-2-yl)propoxy)phenyl)propanoic acid |
| 10a | | (S)-2-(benzo[d]oxazole-5-carboxamido)-3-(4-(3-(5,6,7,8-tetrahydro-1,8-naphthyridin-2-yl)propoxy)phenyl)propanoic acid |
| 10b | | (R)-2-(benzo[d]oxazole-5-carboxamido)-3-(4-(3-(5,6,7,8-tetrahydro-1,8-naphthyridin-2-yl)propoxy)phenyl)propanoic acid |
| 11 | 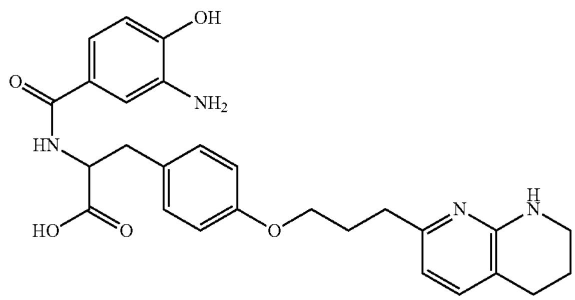 [SMILES: Nc1cc(C(=O)NC(Cc2ccc(OCCCc3ccc4c(n3)NCCC4)cc2)C(=O)O)ccc1O] | 2-(3-amino-4-hydroxybenzamido)-3-(4-(3-(5,6,7,8-tetrahydro-1,8-naphthyridin-2-yl)propoxy)phenyl)propanoic acid |
| 11a | | (S)-2-(3-amino-4-hydroxybenzamido)-3-(4-(3-(5,6,7,8-tetrahydro-1,8-naphthyridin-2-yl)propoxy)phenyl)propanoic acid |
| 11b | | (R)-2-(3-amino-4-hydroxybenzamido)-3-(4-(3-(5,6,7,8-tetrahydro-1,8-naphthyridin-2-yl)propoxy)phenyl)propanoic acid |
| 12 | 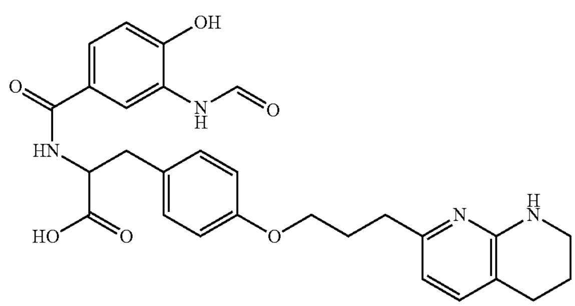 [SMILES: O=CNc1cc(C(=O)NC(Cc2ccc(OCCCc3ccc4c(n3)NCCC4)cc2)C(=O)O)ccc1O] | 2-(3-formamido-4-hydroxybenzamido)-3-(4-(3-(5,6,7,8-tetrahydro-1,8-naphthyridin-2-yl)propoxy)phenyl)propanoic acid |
| 12a | | (S)-2-(3-formamido-4-hydroxybenzamido)-3-(4-(3-(5,6,7,8-tetrahydro-1,8-naphthyridin-2-yl)propoxy)phenyl)propanoic acid |
| 12b | | (R)-2-(3-formamido-4-hydroxybenzamido)-3-(4-(3-(5,6,7,8-tetrahydro-1,8-naphthyridin-2-yl)propoxy)phenyl)propanoic acid |

TABLE 1-continued

| Compound No. | Structure | Chemical Name [1] |
|---|---|---|
| 13 | 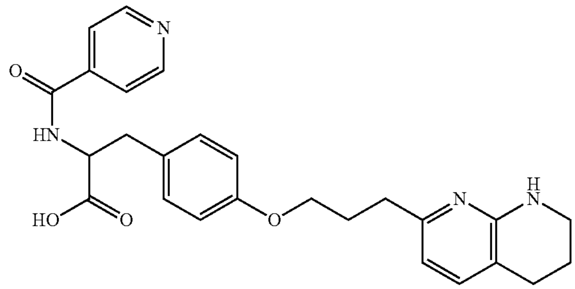 [SMILES: O=C(NC(Cc1ccc(OCCCc2ccc3c(n2)NCCC3)cc1)C(=O)O)c1ccncc1] | 2-(isonicotinamido)-3-(4-(3-(5,6,7,8-tetrahydro-1,8-naphthyridin-2-yl)propoxy) phenyl)propanoic acid |
| 13a | | (S)-2-(isonicotinamido)-3-(4-(3-(5,6,7,8-tetrahydro-1,8-naphthyridin-2-yl)propoxy) phenyl)propanoic acid |
| 13b | | (R)-2-(isonicotinamido)-3-(4-(3-(5,6,7,8-tetrahydro-1,8-naphthyridin-2-yl)propoxy) phenyl)propanoic acid |
| 14 | 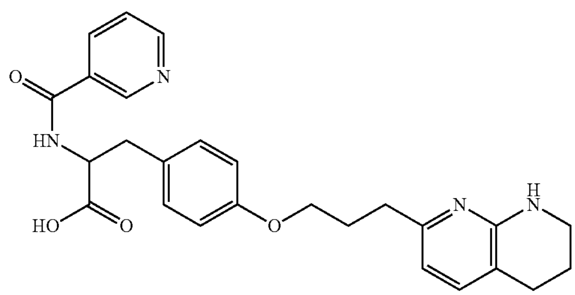 [SMILES: O=C(NC(Cc1ccc(OCCCc2ccc3c(n2)NCCC3)cc1)C(=O)O)c1cccnc1] | 2-(nicotinamido)-3-(4-(3-(5,6,7,8-tetrahydro-1,8-naphthyridin-2-yl)propoxy)phenyl)propanoic acid |
| 14a | | (S)-2-(nicotinamido)-3-(4-(3-(5,6,7,8-tetrahydro-1,8-naphthyridin-2-yl)propoxy) phenyl)propanoic acid |
| 14b | | (R)-2-(nicotinamido)-3-(4-(3-(5,6,7,8-tetrahydro-1,8-naphthyridin-2-yl)propoxy) phenyl)propanoic acid |
| 15 | 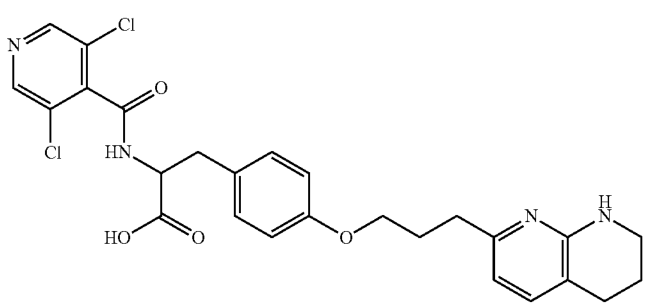 [SMILES: O=C(NC(Cc1ccc(OCCCc2ccc3c(n2)NCCC3)cc1)C(=O)O)c1c(Cl)cncc1Cl] | 2-(3,5-dichloroisonicotinamido)-3-(4-(3-(5,6,7,8-tetrahydro-1,8-naphthyridin-2-yl) propoxy)phenyl)propanoic acid |
| 15a | | (S)-2-(3,5-dichloroisonicotinamido)-3-(4-(3-(5,6,7,8-tetrahydro-1,8-naphthyridin-2-yl)propoxy)phenyl)propanoic acid |
| 15b | | (R)-2-(3,5-dichloroisonicotinamido)-3-(4-(3-(5,6,7,8-tetrahydro-1,8-naphthyridin-2-yl)propoxy)phenyl)propanoic acid |

TABLE 1-continued

| Compound No. | Structure | Chemical Name |
|---|---|---|
| 16 | 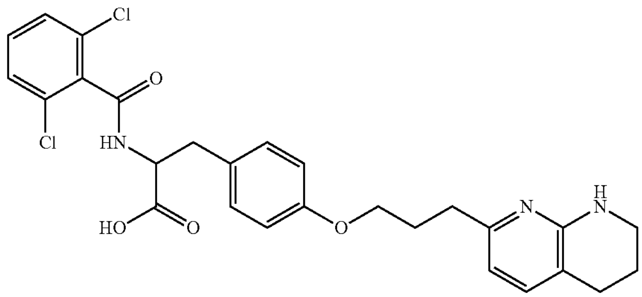 | 2-(2,6-dichlorobenzamido)-3-(4-(3-(5,6,7,8-tetrahydro-1,8-naphthyridin-2-yl)propoxy)phenyl)propanoic acid |
| 16a | | (S)-2-(2,6-dichlorobenzamido)-3-(4-(3-(5,6,7,8-tetrahydro-1,8-naphthyridin-2-yl)propoxy)phenyl)propanoic acid |
| 16b | | (R)-2-(2,6-dichlorobenzamido)-3-(4-(3-(5,6,7,8-tetrahydro-1,8-naphthyridin-2-yl)propoxy)phenyl)propanoic acid |
| 17 | 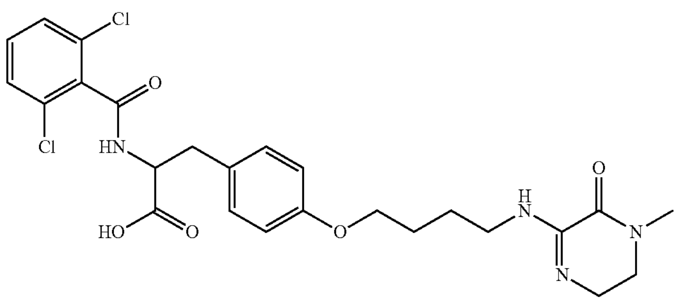 [SMILES: CN1CCN=C(NCCCCOc2ccc(CC(NC(=O)c3c(Cl)cccc3Cl)C(=O)O)cc2)C1=O] | 2-(2,6-dichlorobenzamido)-3-(4-(4-((4-methyl-3-oxo-3,4,5,6-tetrahydropyrazin-2-yl)amino)butoxy)phenyl)propanoic acid |
| 17a | | (S)-2-(2,6-dichlorobenzamido)-3-(4-(4-((4-methyl-3-oxo-3,4,5,6-tetrahydropyrazin-2-yl)amino)butoxy)phenyl)propanoic acid |
| 17b | | (R)-2-(2,6-dichlorobenzamido)-3-(4-(4-((4-methyl-3-oxo-3,4,5,6-tetrahydropyrazin-2-yl)amino)butoxy)phenyl)propanoic acid |
| 18 | 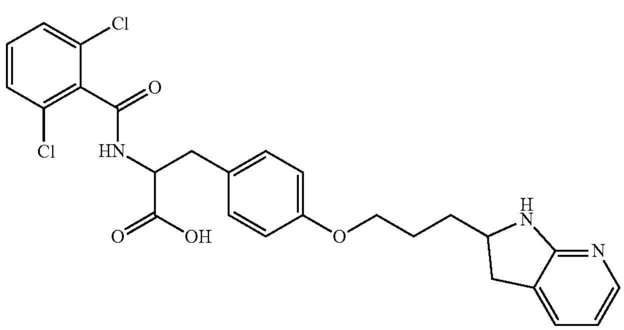 [SMILES: O=C(NC(Cc1ccc(OCCCC2Cc3cccnc3N2)cc1)C(=O)O)c1c(Cl)cccc1Cl] | 2-(2,6-dichlorobenzamido)-3-(4-(3-(2,3-dihydro-1H-pyrrolo[2,3-b]pyridin-2-yl)propoxy)phenyl)propanoic acid |
| 18a | | (S)-2-(2,6-dichlorobenzamido)-3-(4-(3-((S)-2,3-dihydro-1H-pyrrolo[2,3-b]pyridin-2-yl)propoxy)phenyl)propanoic acid |
| 18b | | (R)-2-(2,6-dichlorobenzamido)-3-(4-(3-((R)-2,3-dihydro-1H-pyrrolo[2,3-b]pyridin-2-yl)propoxy)phenyl)propanoic acid |
| 18c | | (S)-2-(2,6-dichlorobenzamido)-3-(4-(3-((R)-2,3-dihydro-1H-pyrrolo[2,3-b]pyridin-2-yl)propoxy)phenyl)propanoic acid |

TABLE 1-continued

| Compound No. | Structure | Chemical Name [1] |
|---|---|---|
| 18d | | (R)-2-(2,6-dichlorobenzamido)-3-(4-(3-((S)-2,3-dihydro-1H-pyrrolo[2,3-b]pyridin-2-yl)propoxy)phenyl)propanoic acid |
| 19 | *structure of 2,6-dichlorobenzamide linked via amide to α-carbon bearing COOH and long alkyl chain to 5,6,7,8-tetrahydro-1,8-naphthyridin-2-yl* | 2-(2,6-dichlorobenzamido)-9-(5,6,7,8-tetrahydro-1,8-naphthyridin-2-yl)nonanoic acid |
| 19a | | (S)-2-(2,6-dichlorobenzamido)-9-(5,6,7,8-tetrahydro-1,8-naphthyridin-2-yl)nonanoic acid |
| 19b | | (R)-2-(2,6-dichlorobenzamido)-9-(5,6,7,8-tetrahydro-1,8-naphthyridin-2-yl)nonanoic acid |
| 20 | *structure with E-alkene in the chain connecting α-amino acid to tetrahydronaphthyridine* | (E)-2-(2,6-dichlorobenzamido)-9-(5,6,7,8-tetrahydro-1,8-naphthyridin-2-yl)non-4-enoic acid |
| 20a | | (S, E)-2-(2,6-dichlorobenzamido)-9-(5,6,7,8-tetrahydro-1,8-naphthyridin-2-yl)non-4-enoic acid |
| 20b | | (R, E)-2-(2,6-dichlorobenzamido)-9-(5,6,7,8-tetrahydro-1,8-naphthyridin-2-yl)non-4-enoic acid |
| 21 | *structure of 2,6-dichlorobenzamido phenylalanine with para-azetidine linked via methylene to tetrahydronaphthyridine* | 2-(2,6-dichlorobenzamido)-3-(4-(3-((5,6,7,8-tetrahydro-1,8-naphthyridin-2-yl)methyl)azetidin-1-yl)phenyl)propanoic acid |
| 21a | | (S)-2-(2,6-dichlorobenzamido)-3-(4-(3-((5,6,7,8-tetrahydro-1,8-naphthyridin-2-yl)methyl)azetidin-1-yl)phenyl)propanoic acid |
| 21b | | (R)-2-(2,6-dichlorobenzamido)-3-(4-(3-((5,6,7,8-tetrahydro-1,8-naphthyridin-2-yl)methyl)azetidin-1-yl)phenyl)propanoic acid |

TABLE 1-continued

| Compound No. | Structure | Chemical Name [1] |
|---|---|---|
| 22 | 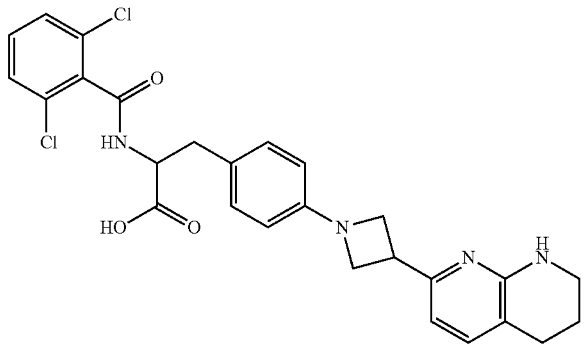 [SMILES: O=C(NC(Cc1ccc(N2CC(c3ccc4c(n3)NCCC4)C2)cc1)C(=O)O)c1c(Cl)cccc1Cl] | 2-(2,6-dichlorobenzamido)-3-(4-(3-(5,6,7,8-tetrahydro-1,8-naphthyridin-2-yl)azetidin-1-yl)phenyl)propanoic acid |
| 22a | | (S)-2-(2,6-dichlorobenzamido)-3-(4-(3-(5,6,7,8-tetrahydro-1,8-naphthyridin-2-yl)azetidin-1-yl)phenyl)propanoic acid |
| 22b | | (R)-2-(2,6-dichlorobenzamido)-3-(4-(3-(5,6,7,8-tetrahydro-1,8-naphthyridin-2-yl)azetidin-1-yl)phenyl)propanoic acid |
| 23 | 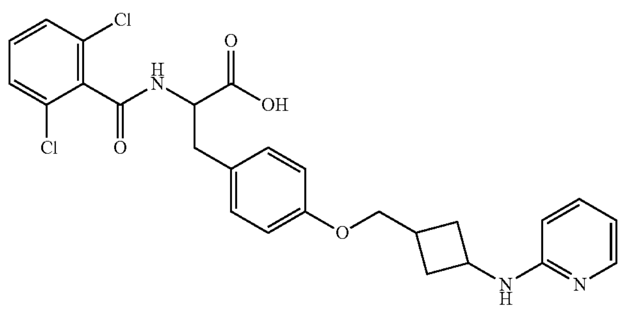 [SMILES: O=C(NC(Cc1ccc(OCC2CC(Nc3ccccn3)C2)cc1)C(=O)O)c1c(Cl)cccc1Cl] | 2-(2,6-dichlorobenzamido)-3-(4-((3-(pyridin-2-ylamino)cyclobutyl)methoxy)phenyl)propanoic acid |
| 23a | | (S)-2-(2,6-dichlorobenzamido)-3-(4-((3-(pyridin-2-ylamino)cyclobutyl)methoxy)phenyl)propanoic acid |
| 23b | | (R)-2-(2,6-dichlorobenzamido)-3-(4-((3-(pyridin-2-ylamino)cyclobutyl)methoxy)phenyl)propanoic acid |
| 24 | 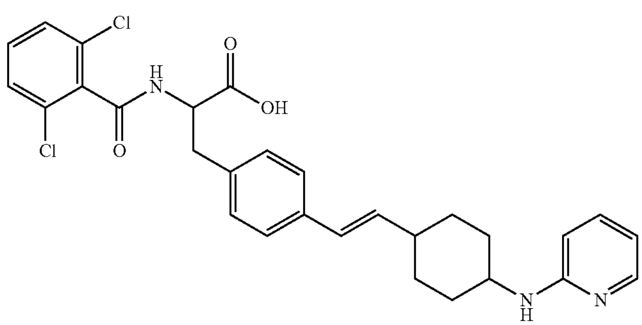 [SMILES: O=C(NC(Cc1ccc(/C=C/C2CCC(Nc3ccccn3)CC2)cc1)C(=O)O)c1c(Cl)cccc1Cl] | (E)-2-(2,6-dichlorobenzamido)-3-(4-(2-(4-(pyridin-3-ylamino)cyclohexyl)vinyl)phenyl)propanoic acid |
| 24a | | (S, E)-2-(2,6-dichlorobenzamido)-3-(4-(2-(4-(pyridin-3-ylamino)cyclohexyl)vinyl)phenyl)propanoic acid |
| 24b | | (R, E)-2-(2,6-dichlorobenzamido)-3-(4-(2-(4-(pyridin-3-ylamino)cyclohexyl)vinyl)phenyl)propanoic acid |

TABLE 1-continued

| Compound No. | Structure | Chemical Name [1] |
|---|---|---|
| 25 | 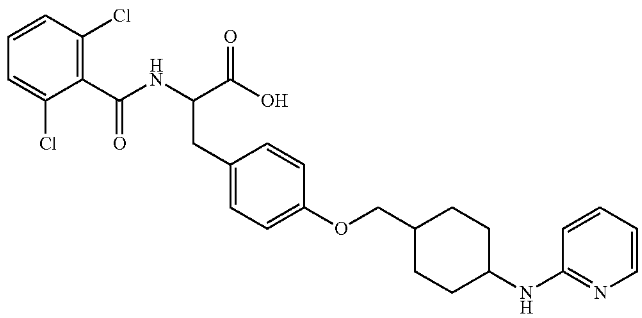 [SMILES: O=C(NC(Cc1ccc(OCC2CCC(Nc3ccccn3)CC2)cc1)C(=O)O)c1c(Cl)cccc1Cl] | 2-(2,6-dichlorobenzamido)-3-(4-((4-(pyridin-2-ylamino)cyclohexyl)methoxy)phenyl)propanoic acid |
| 25a | | (S)-2-(2,6-dichlorobenzamido)-3-(4-((4-(pyridin-2-ylamino)cyclohexyl)methoxy)phenyl)propanoic acid |
| 25b | | (R)-2-(2,6-dichlorobenzamido)-3-(4-((4-(pyridin-2-ylamino)cyclohexyl)methoxy)phenyl)propanoic acid |
| 26 | 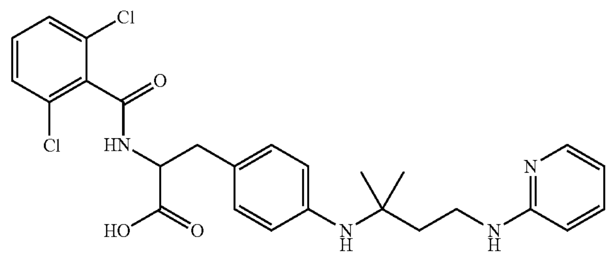 [SMILES: CC(C)(CCNc1ccccn1)Nc1ccc(CC(NC(=O)c2c(Cl)cccc2Cl)C(=O)O)cc1] | 2-(2,6-dichlorobenzamido)-3-(4-((2-methyl-4-(pyridin-2-ylamino)butan-2-yl)amino)phenyl)propanoic acid |
| 26a | | (S)-2-(2,6-dichlorobenzamido)-3-(4-((2-methyl-4-(pyridin-2-ylamino)butan-2-yl)amino)phenyl)propanoic acid |
| 26b | | (R)-2-(2,6-dichlorobenzamido)-3-(4-((2-methyl-4-(pyridin-2-ylamino)butan-2-yl)amino)phenyl)propanoic acid |
| 27 | 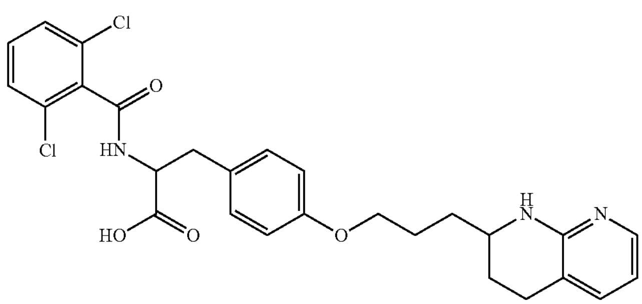 [SMILES: O=C(NC(Cc1ccc(OCCCC2CCc3cccnc3N2)cc1)C(=O)O)c1c(Cl)cccc1Cl] | 2-(2,6-dichlorobenzamido)-3-(4-(3-(1,2,3,4-tetrahydro-1,8-naphthyridin-2-yl)propoxy)phenyl)propanoic acid |
| 27a | | (2S)-2-(2,6-dichlorobenzamido)-3-(4-(3-(1,2,3,4-tetrahydro-1,8-naphthyridin-2-yl)propoxy)phenyl)propanoic acid |
| 27b | | (2R)-2-(2,6-dichlorobenzamido)-3-(4-(3-(1,2,3,4-tetrahydro-1,8-naphthyridin-2-yl)propoxy)phenyl)propanoic acid |

TABLE 1-continued

| Compound No. | Structure | Chemical Name [1] |
|---|---|---|
| 28 | 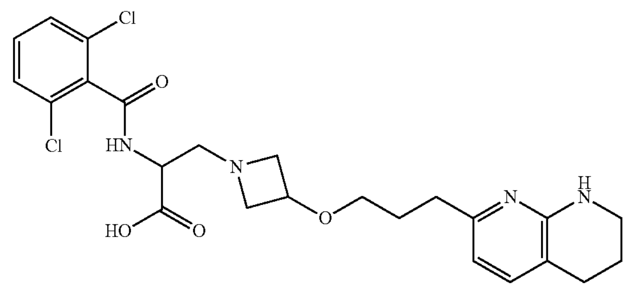 [SMILES: O=C(NC(CN1CC(OCCCc2ccc3c(n2)NCCC3)C1)C(=O)O)c1c(Cl)cccc1Cl] | (+/−)-2-(2,6-dichlorobenzamido)-3-(3-(3-(5,6,7,8-tetrahydro-1,8-naphthyridin-2-yl)propoxy)azetidin-1-yl)propanoic acid |
| 28a | | (S)-2-(2,6-dichlorobenzamido)-3-(3-(3-(5,6,7,8-tetrahydro-1,8-naphthyridin-2-yl)propoxy)azetidin-1-yl)propanoic acid |
| 28b | | (R)-2-(2,6-dichlorobenzamido)-3-(3-(3-(5,6,7,8-tetrahydro-1,8-naphthyridin-2-yl)propoxy)azetidin-1-yl)propanoic acid |
| 29 | 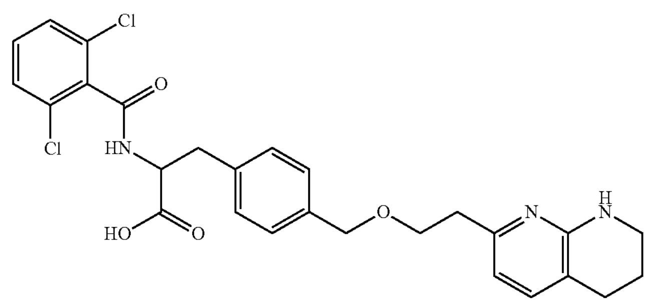 [SMILES: O=C(NC(Cc1ccc(COCCc2ccc3c(n2)NCCC3)cc1)C(=O)O)c1c(Cl)cccc1Cl] | 2-(2,6-dichlorobenzamido)-3-(4-((2-(5,6,7,8-tetrahydro-1,8-naphthyridin-2-yl)ethoxy)methyl)phenyl)propanoic acid |
| 29a | | (S)-2-(2,6-dichlorobenzamido)-3-(4-((2-(5,6,7,8-tetrahydro-1,8-naphthyridin-2-yl)ethoxy)methyl)phenyl)propanoic acid |
| 29b | | (R)-2-(2,6-dichlorobenzamido)-3-(4-((2-(5,6,7,8-tetrahydro-1,8-naphthyridin-2-yl)ethoxy)methyl)phenyl)propanoic acid |
| 30 | 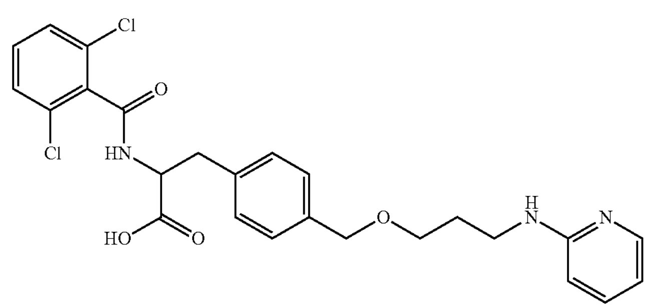 [SMILES: O=C(NC(Cc1ccc(COCCCNc2ccccn2)cc1)C(=O)O)c1c(Cl)cccc1Cl] | 2-(2,6-dichlorobenzamido)-3-(4-((3-(pyridin-2-ylamino)propoxy)methyl)phenyl)propanoic acid |
| 30a | | (S)-2-(2,6-dichlorobenzamido)-3-(4-((3-(pyridin-2-ylamino)propoxy)methyl)phenyl)propanoic acid |
| 30b | | (R)-2-(2,6-dichlorobenzamido)-3-(4-((3-(pyridin-2-ylamino)propoxy)methyl)phenyl)propanoic acid |

TABLE 1-continued

| Compound No. | Structure | Chemical Name [1] |
|---|---|---|
| 31 | 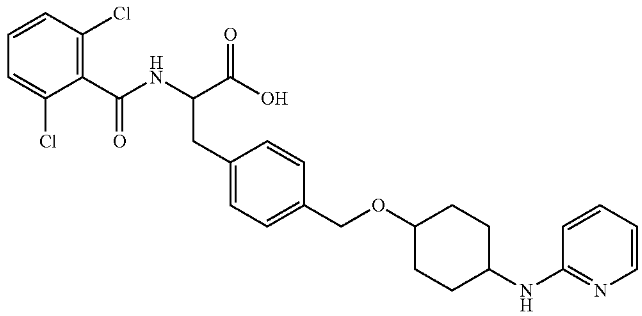 [SMILES: O=C(NC(Cc1ccc(COC2CCC(Nc3ccccn3)CC2)cc1)C(=O)O)c1c(Cl)cccc1Cl] | 2-(2,6-dichlorobenzamido)-3-(4-(((4-(pyridin-2-ylamino)cyclohexyl)oxy)methyl)phenyl)propanoic acid (substituents in cis orientation on cyclohexyl ring) |
| 31a | | (S)-2-(2,6-dichlorobenzamido)-3-(4-(((4-(pyridin-2-ylamino)cyclohexyl)oxy)methyl)phenyl)propanoic acid (substituents in cis orientation on cyclohexyl ring) |
| 31b | | (R)-2-(2,6-dichlorobenzamido)-3-(4-(((4-(pyridin-2-ylamino)cyclohexyl)oxy)methyl)phenyl)propanoic acid (substituents in cis orientation on cyclohexyl ring) |
| 32 | 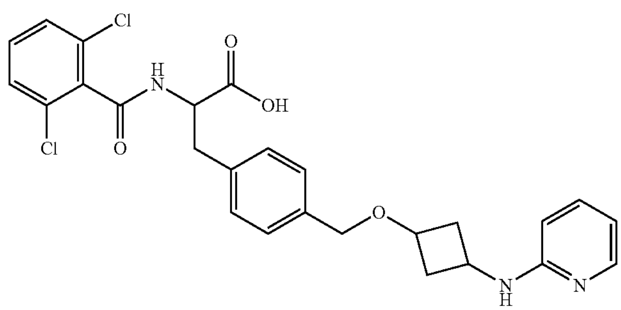 [SMILES: O=C(NC(Cc1ccc(COC2CC(Nc3ccccn3)C2)cc1)C(=O)O)c1c(Cl)cccc1Cl] | 2-(2,6-dichlorobenzamido)-3-(4-((3-(pyridin-2-ylamino)cyclobutoxy)methyl)phenyl)propanoic acid (substituents in cis orientation on cyclobutyl ring) |
| 32a | | (S)-2-(2,6-dichlorobenzamido)-3-(4-((3-(pyridin-2-ylamino)cyclobutoxy)methyl)phenyl)propanoic acid (substituents in cis orientation on cyclobutyl ring) |
| 32b | | (R)-2-(2,6-dichlorobenzamido)-3-(4-((3-(pyridin-2-ylamino)cyclobutoxy)methyl)phenyl)propanoic acid (substituents in cis orientation on cyclobutyl ring) |
| 33 | 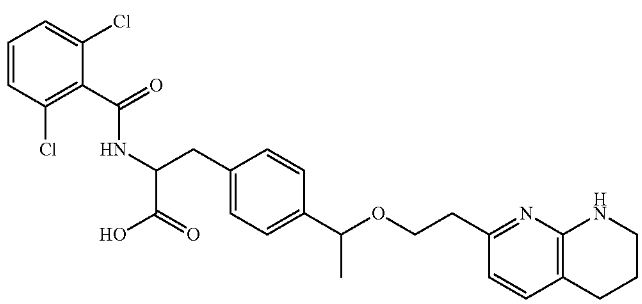 [SMILES: CC(OCCc1ccc2c(n1)NCCC2)c1ccc(CC(NC(=O)c2c(Cl)cccc2Cl)C(=O)O)cc1] | 2-(2,6-dichlorobenzamido)-3-(4-(1-(2-(5,6,7,8-tetrahydro-1,8-naphthyridin-2-yl)ethoxy)ethyl)phenyl)propanoic acid |
| 33a | | (2S)-2-(2,6-dichlorobenzamido)-3-(4-(1-(2-(5,6,7,8-tetrahydro-1,8-naphthyridin-2-yl)ethoxy)ethyl)phenyl)propanoic acid |

TABLE 1-continued

| Compound No. | Structure | Chemical Name[1] |
|---|---|---|
| 33b | | (2R)-2-(2,6-dichlorobenzamido)-3-(4-(1-(2-(5,6,7,8-tetrahydro-1,8-naphthyridin-2-yl)ethoxy)ethyl)phenyl)propanoic acid |
| 34 | (structure) | 2-(4-cyclopropylbenzamido)-3-(4-(3-(5,6,7,8-tetrahydro-1,8-naphthyridin-2-yl)propoxy)phenyl)propanoic acid |
| 34a | | (2S)-2-(4-cyclopropylbenzamido)-3-(4-(3-(5,6,7,8-tetrahydro-1,8-naphthyridin-2-yl)propoxy)phenyl)propanoic acid |
| 34b | | (2R)-2-(4-cyclopropylbenzamido)-3-(4-(3-(5,6,7,8-tetrahydro-1,8-naphthyridin-2-yl)propoxy)phenyl)propanoic acid |
| 35 | (structure) | 2-(3,5-dichlorobenzamido)-3-(4-(3-(5,6,7,8-tetrahydro-1,8-naphthyridin-2-yl)propoxy)phenyl)propanoic acid |
| 35a | | (2S)-2-(3,5-dichlorobenzamido)-3-(4-(3-(5,6,7,8-tetrahydro-1,8-naphthyridin-2-yl)propoxy)phenyl)propanoic acid |
| 35b | | (2R)-2-(3,5-dichlorobenzamido)-3-(4-(3-(5,6,7,8-tetrahydro-1,8-naphthyridin-2-yl)propoxy)phenyl)propanoic acid |
| 36 | (structure) | 2-(2-chloro-5-fluorobenzamido)-3-(4-(3-(5,6,7,8-tetrahydro-1,8-naphthyridin-2-yl)propoxy)phenyl)propanoic acid |
| 36a | | (2S)-2-(2-chloro-5-fluorobenzamido)-3-(4-(3-(5,6,7,8-tetrahydro-1,8-naphthyridin-2-yl)propoxy)phenyl)propanoic acid |

TABLE 1-continued

| Compound No. | Structure | Chemical Name |
|---|---|---|
| 36b | | (2R)-2-(2-chloro-5-fluorobenzamido)-3-(4-(3-(5,6,7,8-tetrahydro-1,8-naphthyridin-2-yl)propoxy)phenyl)propanoic acid |
| 37 | 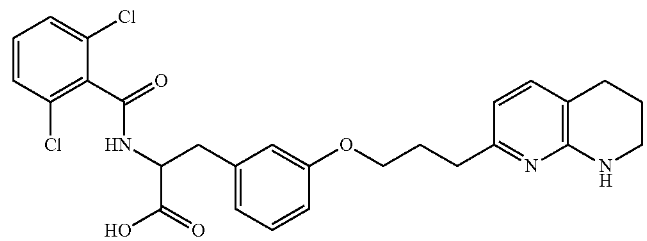 [SMILES: O=C(NC(Cc1cccc(OCCCc2ccc3c(n2)NCCC3)c1)C(=O)O)c1c(Cl)cccc1Cl] | 2-(2,6-dichlorobenzamido)-3-(3-(3-(5,6,7,8-tetrahydro-1,8-naphthyridin-2-yl)propoxy)phenyl)propanoic acid |
| 37a | | (2S)-2-(2,6-dichlorobenzamido)-3-(3-(3-(5,6,7,8-tetrahydro-1,8-naphthyridin-2-yl)propoxy)phenyl)propanoic acid |
| 37b | | (2R)-2-(2,6-dichlorobenzamido)-3-(3-(3-(5,6,7,8-tetrahydro-1,8-naphthyridin-2-yl)propoxy)phenyl)propanoic acid |
| 38 | 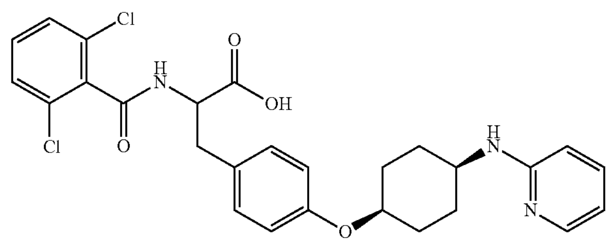 [SMILES: O=C(NC(Cc1ccc(O[C@H]2CC[C@@H](Nc3ccccn3)CC2)cc1)C(=O)O)c1c(Cl)cccc1Cl] | 2-[(2,6-dichlorobenzoyl)amino]-3-[4-[4-cis-(2-pyridylamino)cyclohexoxy]phenyl]propanoic acid |
| 38a | | (2S)-2-[(2,6-dichlorobenzoyl)amino]-3-[4-[4-cis-(2-pyridylamino)cyclohexoxy]phenyl]propanoic acid |
| 38b | | (2R)-2-[(2,6-dichlorobenzoyl)amino]-3-[4-[4-cis-(2-pyridylamino)cyclohexoxy]phenyl]propanoic acid |
| 39 | 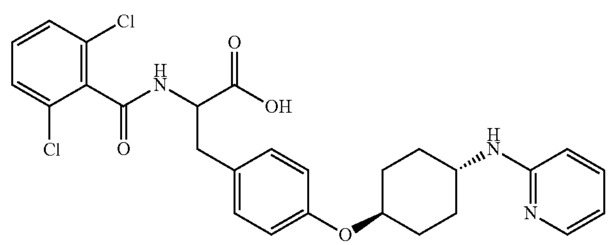 [SMILES: O=C(NC(Cc1ccc(O[C@H]2CC[C@H](Nc3ccccn3)CC2)cc1)C(=O)O)c1c(Cl)cccc1Cl] | 2-[(2,6-dichlorobenzoyl)amino]-3-[4-[4-trans-(2-pyridylamino)cyclohexoxy]phenyl]propanoic acid |
| 39a | | (2S)-2-[(2,6-dichlorobenzoyl)amino]-3-[4-[4-trans-(2-pyridylamino)cyclohexoxy]phenyl]propanoic acid |
| 39b | | (2R)-2-[(2,6-dichlorobenzoyl)amino]-3-[4-[4-trans-(2-pyridylamino)cyclohexoxy]phenyl]propanoic acid |

TABLE 1-continued

| Compound No. | Structure | Chemical Name [1] |
|---|---|---|
| 40 | 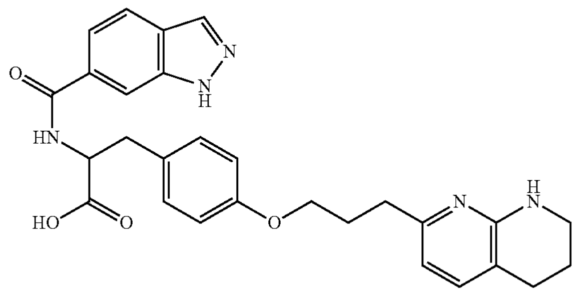 [SMILES: O=C(NC(Cc1ccc(OCCCc2ccc3c(n2)NCCC3)cc1)C(=O)O)c1ccc2cn[nH]c2c1] | 2-(1H-indazole-6-carboxamido)-3-(4-(3-(5,6,7,8-tetrahydro-1,8-naphthyridin-2-yl)propoxy)phenyl)propanoic acid |
| 40a | | (2S)-2-(1H-indazole-6-carboxamido)-3-(4-(3-(5,6,7,8-tetrahydro-1,8-naphthyridin-2-yl)propoxy)phenyl)propanoic acid |
| 40b | | (2R)-2-(1H-indazole-6-carboxamido)-3-(4-(3-(5,6,7,8-tetrahydro-1,8-naphthyridin-2-yl)propoxy)phenyl)propanoic acid |
| 41 | 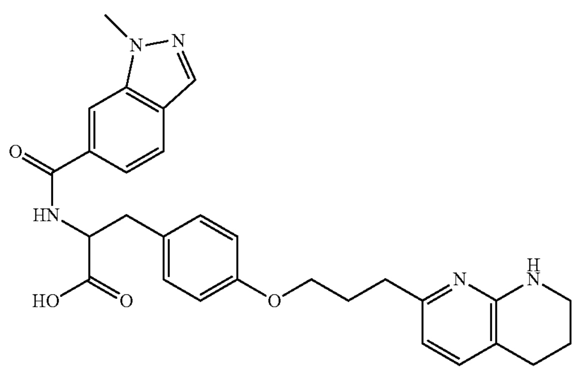 [SMILES: Cn1ncc2ccc(C(=O)NC(Cc3ccc(OCCCc4ccc5c(n4)NCCC5)cc3)C(=O)O)cc21] | 2-(1-methyl-1H-indazole-6-carboxamido)-3-(4-(3-(5,6,7,8-tetrahydro-1,8-naphthyridin-2-yl)propoxy)phenyl)propanoic acid |
| 41a | | (2S)-2-(1-methyl-1H-indazole-6-carboxamido)-3-(4-(3-(5,6,7,8-tetrahydro-1,8-naphthyridin-2-yl)propoxy)phenyl)propanoic acid |
| 41b | | (2R)-2-(1-methyl-1H-indazole-6-carboxamido)-3-(4-(3-(5,6,7,8-tetrahydro-1,8-naphthyridin-2-yl)propoxy)phenyl)propanoic acid |
| 42 | 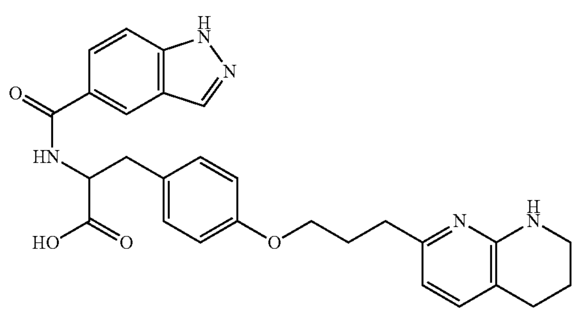 [SMILES: O=C(NC(Cc1ccc(OCCCc2ccc3c(n2)NCCC3)cc1)C(=O)O)c1ccc2[nH]ncc2c1] | 2-(1H-indazole-5-carboxamido)-3-(4-(3-(5,6,7,8-tetrahydro-1,8-naphthyridin-2-yl)propoxy)phenyl)propanoic acid |
| 42a | | (2S)-2-(1H-indazole-5-carboxamido)-3-(4-(3-(5,6,7,8-tetrahydro-1,8-naphthyridin-2-yl)propoxy)phenyl)propanoic acid |
| 42b | | (2R)-2-(1H-indazole-5-carboxamido)-3-(4-(3-(5,6,7,8-tetrahydro-1,8-naphthyridin-2-yl)propoxy)phenyl)propanoic acid |

TABLE 1-continued

| Compound No. | Structure | Chemical Name[1] |
|---|---|---|
| 43 | 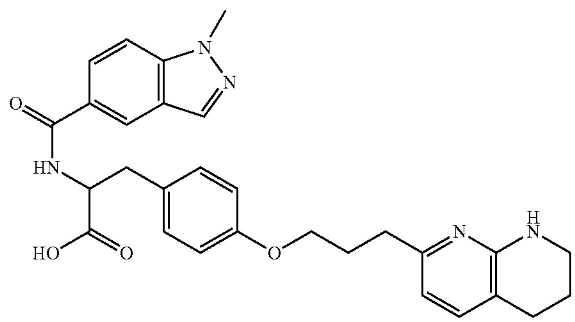 [SMILES: Cn1ncc2cc(C(=O)NC(Cc3ccc(OCCCc4ccc5c(n4)NCCC5)cc3)C(=O)O)ccc21] | 2-(1-methyl-1H-indazole-5-carboxamido)-3-(4-(3-(5,6,7,8-tetrahydro-1,8-naphthyridin-2-yl)propoxy)phenyl)propanoic acid |
| 43a | | (2S)-2-(1-methyl-1H-indazole-5-carboxamido)-3-(4-(3-(5,6,7,8-tetrahydro-1,8-naphthyridin-2-yl)propoxy)phenyl)propanoic acid |
| 43b | | (2R)-2-(1-methyl-1H-indazole-5-carboxamido)-3-(4-(3-(5,6,7,8-tetrahydro-1,8-naphthyridin-2-yl)propoxy)phenyl)propanoic acid |
| 44 | 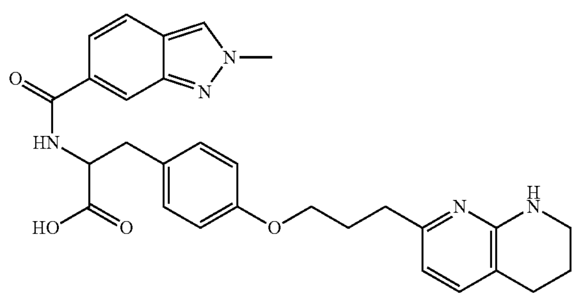 [SMILES: Cn1cc2ccc(C(=O)NC(Cc3ccc(OCCCc4ccc5c(n4)NCCC5)cc3)C(=O)O)cc2n1] | 2-(2-methyl-2H-indazole-6-carboxamido)-3-(4-(3-(5,6,7,8-tetrahydro-1,8-naphthyridin-2-yl)propoxy)phenyl)propanoic acid |
| 44a | | (2S)-2-(2-methyl-2H-indazole-6-carboxamido)-3-(4-(3-(5,6,7,8-tetrahydro-1,8-naphthyridin-2-yl)propoxy)phenyl)propanoic acid |
| 44b | | (2R)-2-(2-methyl-2H-indazole-6-carboxamido)-3-(4-(3-(5,6,7,8-tetrahydro-1,8-naphthyridin-2-yl)propoxy)phenyl)propanoic acid |
| 45 | 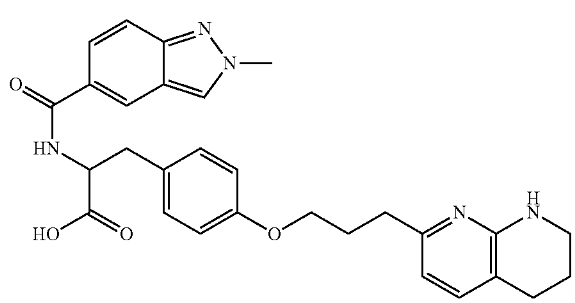 [SMILES: Cn1cc2cc(C(=O)NC(Cc3ccc(OCCCc4ccc5c(n4)NCCC5)cc3)C(=O)O)ccc2n1] | 2-(2-methyl-2H-indazole-5-carboxamido)-3-(4-(3-(5,6,7,8-tetrahydro-1,8-naphthyridin-2-yl)propoxy)phenyl)propanoic acid |
| 45a | | (2S)-2-(2-methyl-2H-indazole-5-carboxamido)-3-(4-(3-(5,6,7,8-tetrahydro-1,8-naphthyridin-2-yl)propoxy)phenyl)propanoic acid |
| 45b | | (2R)-2-(2-methyl-2H-indazole-5-carboxamido)-3-(4-(3-(5,6,7,8-tetrahydro-1,8-naphthyridin-2-yl)propoxy)phenyl)propanoic acid |

TABLE 1-continued

| Compound No. | Structure | Chemical Name [1] |
|---|---|---|
| 46 | 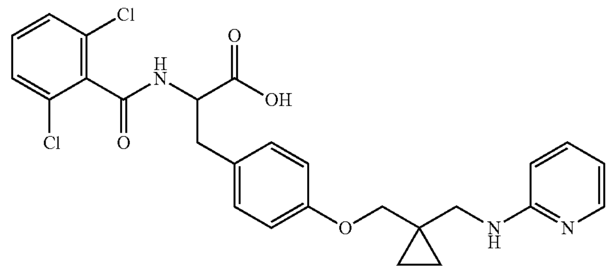 [SMILES: O=C(NC(Cc1ccc(OCC2(CNc3ccccn3)CC2)cc1)C(=O)O)c1c(Cl)cccc1Cl] | 2-(2,6-dichlorobenzamido)-3-(4-((1-((pyridin-2-ylamino)methyl)cyclopropyl)methoxy)phenyl)propanoic acid |
| 46a | | (2S)-2-(2,6-dichlorobenzamido)-3-(4-((1-((pyridin-2-ylamino)methyl)cyclopropyl)methoxy)phenyl)propanoic acid |
| 46b | | (2R)-2-(2,6-dichlorobenzamido)-3-(4-((1-((pyridin-2-ylamino)methyl)cyclopropyl)methoxy)phenyl)propanoic acid |
| 47 | 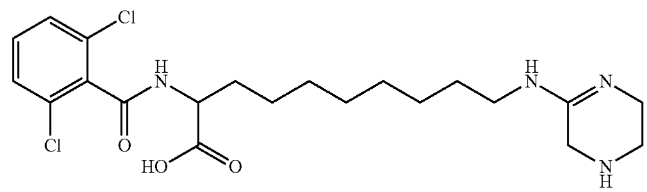 [SMILES: O=C(NC(CCCCCCCCNC1=NCCNC1)C(=O)O)c1c(Cl)cccc1Cl] | 2-(2,6-dichlorobenzamido)-10-((3,4,5,6-tetrahydropyrazin-2-yl)amino)decanoic acid |
| 47a | | (S)-2-(2,6-dichlorobenzamido)-10-((3,4,5,6-tetrahydropyrazin-2-yl)amino)decanoic acid |
| 47b | | (R)-2-(2,6-dichlorobenzamido)-10-((3,4,5,6-tetrahydropyrazin-2-yl)amino)decanoic acid |
| 48 | 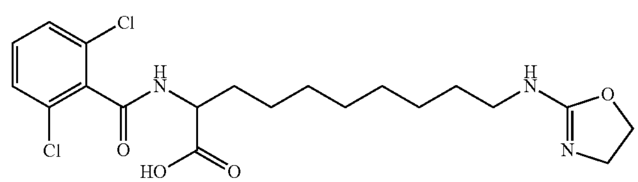 | 2-(2,6-dichlorobenzamido)-10-((4,5-dihydrooxazol-2-yl)amino)decanoic acid |
| 48a | | (S)-2-(2,6-dichlorobenzamido)-10-((4,5-dihydrooxazol-2-yl)amino)decanoic acid |
| 48b | | (R)-2-(2,6-dichlorobenzamido)-10-((4,5-dihydrooxazol-2-yl)amino)decanoic acid |
| 49 | 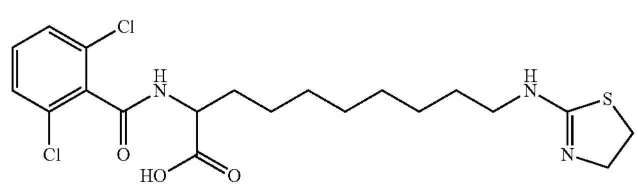 [SMILES: O=C(NC(CCCCCCCCNC1=NCCO1)C(=O)O)c1c(Cl)cccc1Cl] | 2-(2,6-dichlorobenzamido)-10-((4,5-dihydrothiazol-2-yl)amino)decanoic acid |
| 49a | | (S)-2-(2,6-dichlorobenzamido)-10-((4,5-dihydrothiazol-2-yl)amino)decanoic acid |
| 49b | | (R)-2-(2,6-dichlorobenzamido)-10-((4,5-dihydrothiazol-2-yl)amino)decanoic acid |

TABLE 1-continued

| Compound No. | Structure | Chemical Name [1] |
|---|---|---|
| 50 | 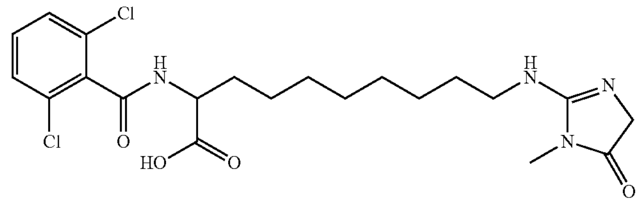 [SMILES: CN1C(=O)CN=C1NCCCCCCCCC(NC(=O)c1c(Cl)cccc1Cl)C(=O)O] | 2-(2,6-dichlorobenzamido)-10-((1-methyl-5-oxo-4,5-dihydro-1H-imidazol-2-yl)amino)decanoic acid |
| 50a | | (S)-2-(2,6-dichlorobenzamido)-10-((1-methyl-5-oxo-4,5-dihydro-1H-imidazol-2-yl)amino)decanoic acid |
| 50b | | (R)-2-(2,6-dichlorobenzamido)-10-((1-methyl-5-oxo-4,5-dihydro-1H-imidazol-2-yl)amino)decanoic acid |
| 51 | 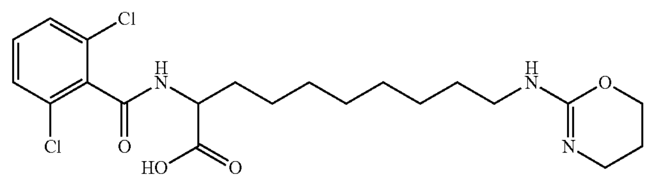 | 2-(2,6-dichlorobenzamido)-10-((5,6-dihydro-4H-1,3-oxazin-2-yl)amino)decanoic acid |
| 51a | | (S)-2-(2,6-dichlorobenzamido)-10-((5,6-dihydro-4H-1,3-oxazin-2-yl)amino)decanoic acid |
| 51b | | (R)-2-(2,6-dichlorobenzamido)-10-((5,6-dihydro-4H-1,3-oxazin-2-yl)amino)decanoic acid |
| 52 | 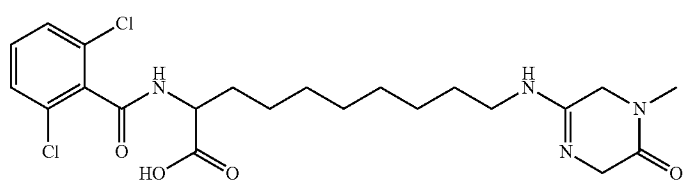 [SMILES: CN1CC(NCCCCCCCCC(NC(=O)c2c(Cl)cccc2Cl)C(=O)O)=NCC1=O] | 2-(2,6-dichlorobenzamido)-10-((4-methyl-5-oxo-3,4,5,6-tetrahydropyrazin-2-yl)amino)decanoic acid |
| 52a | | (S)-2-(2,6-dichlorobenzamido)-10-((4-methyl-5-oxo-3,4,5,6-tetrahydropyrazin-2-yl)amino)decanoic acid |
| 52b | | (R)-2-(2,6-dichlorobenzamido)-10-((4-methyl-5-oxo-3,4,5,6-tetrahydropyrazin-2-yl)amino)decanoic acid |
| 53 | 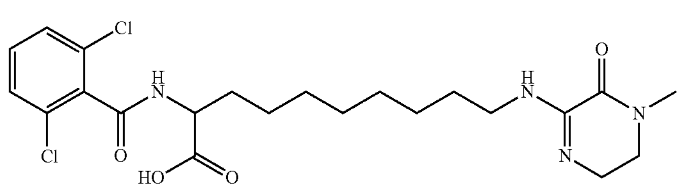 [SMILES: CN1CCN=C(NCCCCCCCCC(NC(=O)c2c(Cl)cccc2Cl)C(=O)O)C1=O] | 2-(2,6-dichlorobenzamido)-10-((4-methyl-3-oxo-3,4,5,6-tetrahydropyrazin-2-yl)amino)decanoic acid |
| 53a | | (S)-2-(2,6-dichlorobenzamido)-10-((4-methyl-3-oxo-3,4,5,6-tetrahydropyrazin-2-yl)amino)decanoic acid |
| 53b | | (R)-2-(2,6-dichlorobenzamido)-10-((4-methyl-3-oxo-3,4,5,6-tetrahydropyrazin-2-yl)amino)decanoic acid |

TABLE 1-continued

| Compound No. | Structure | Chemical Name [1] |
|---|---|---|
| 54 | 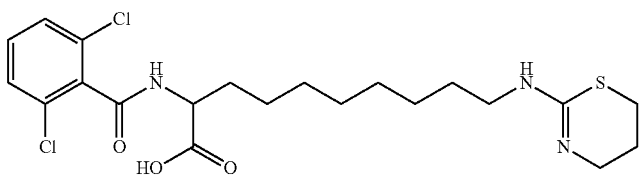 [SMILES: O=C(NC(CCCCCCCCNC1=NCCCS1)C(=O)O)c1c(Cl)cccc1Cl] | 2-(2,6-dichlorobenzamido)-10-((5,6-dihydro-4H-1,3-thiazin-2-yl)amino)decanoic acid |
| 54a | | (S)-2-(2,6-dichlorobenzamido)-10-((5,6-dihydro-4H-1,3-thiazin-2-yl)amino)decanoic acid |
| 54b | | (R)-2-(2,6-dichlorobenzamido)-10-((5,6-dihydro-4H-1,3-thiazin-2-yl)amino)decanoic acid |
| 55 | 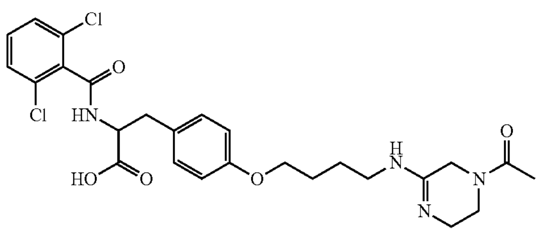 [SMILES: CC(=O)N1CCN=C(NCCCCOc2ccc(CC(NC(=O)c3c(Cl)cccc3Cl)C(=O)O)cc2)C1] | 3-(4-(4-((4-acetyl-3,4,5,6-tetrahydropyrazin-2-yl)amino)butoxy)phenyl)-2-(2,6-dichlorobenzamido)propanoic acid |
| 55a | | (S)-3-(4-(4-((4-acetyl-3,4,5,6-tetrahydropyrazin-2-yl)amino)butoxy)phenyl)-2-(2,6-dichlorobenzamido)propanoic acid |
| 55b | | (R)-3-(4-(4-((4-acetyl-3,4,5,6-tetrahydropyrazin-2-yl)amino)butoxy)phenyl)-2-(2,6-dichlorobenzamido)propanoic acid |
| 56 | 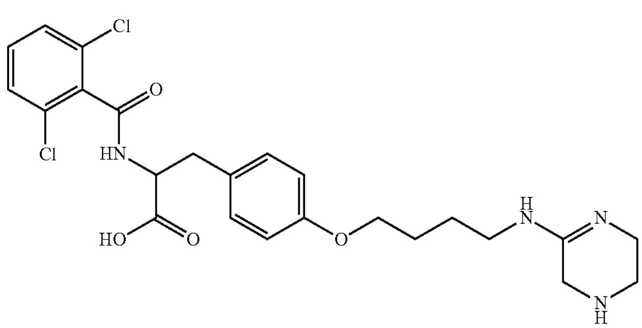 [SMILES: O=C(NC(Cc1ccc(OCCCCNC2=NCCNC2)cc1)C(=O)O)c1c(Cl)cccc1Cl] | 2-(2,6-dichlorobenzamido)-3-(4-(4-((3,4,5,6-tetrahydropyrazin-2-yl)amino)butoxy)phenyl)propanoic acid |
| 56a | | (S)-2-(2,6-dichlorobenzamido)-3-(4-(4-((3,4,5,6-tetrahydropyrazin-2-yl)amino)butoxy)phenyl)propanoic acid |
| 56b | | (R)-2-(2,6-dichlorobenzamido)-3-(4-(4-((3,4,5,6-tetrahydropyrazin-2-yl)amino)butoxy)phenyl)propanoic acid |

TABLE 1-continued

| Compound No. | Structure | Chemical Name [1] |
|---|---|---|
| 57 | 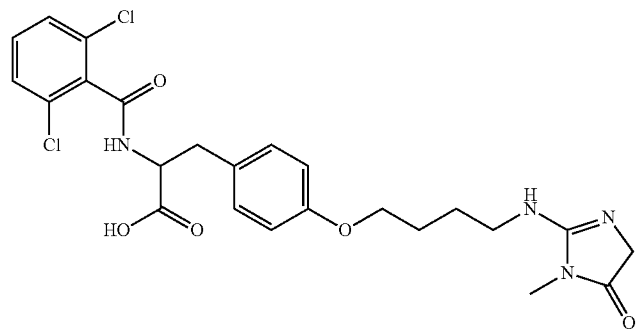 [SMILES: CN1C(=O)CN=C1NCCCCOc1ccc(CC(NC(=O)c2c(Cl)cccc2Cl)C(=O)O)cc1] | 2-(2,6-dichlorobenzamido)-3-(4-(4-((1-methyl-5-oxo-4,5-dihydro-1H-imidazol-2-yl)amino)butoxy)phenyl)propanoic acid |
| 57a | | (S)-2-(2,6-dichlorobenzamido)-3-(4-(4-((1-methyl-5-oxo-4,5-dihydro-1H-imidazol-2-yl)amino)butoxy)phenyl)propanoic acid |
| 57b | | (R)-2-(2,6-dichlorobenzamido)-3-(4-(4-((1-methyl-5-oxo-4,5-dihydro-1H-imidazol-2-yl)amino)butoxy)phenyl)propanoic acid |
| 58 | 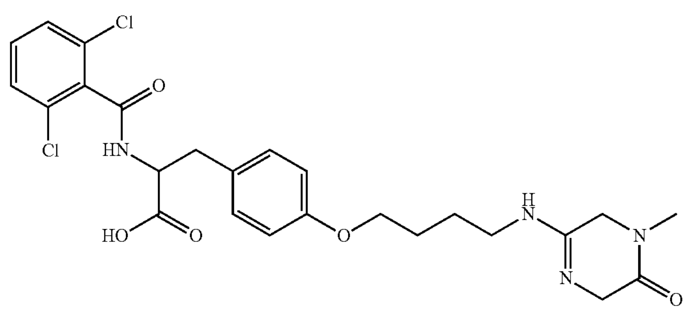 [SMILES: CN1CC(NCCCCOc2ccc(CC(NC(=O)c3c(Cl)cccc3Cl)C(=O)O)cc2)=NCC1=O] | 2-(2,6-dichlorobenzamido)-3-(4-(4-((4-methyl-5-oxo-3,4,5,6-tetrahydropyrazin-2-yl)amino)butoxy)phenyl)propanoic acid |
| 58a | | (S)-2-(2,6-dichlorobenzamido)-3-(4-(4-((4-methyl-5-oxo-3,4,5,6-tetrahydropyrazin-2-yl)amino)butoxy)phenyl)propanoic acid |
| 58b | | (R)-2-(2,6-dichlorobenzamido)-3-(4-(4-((4-methyl-5-oxo-3,4,5,6-tetrahydropyrazin-2-yl)amino)butoxy)phenyl)propanoic acid |
| 59 | 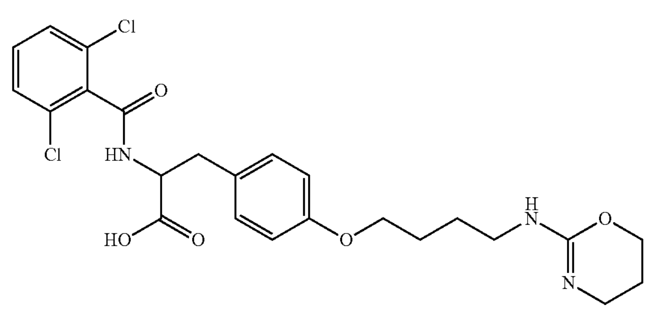 [SMILES: O=C(NC(Cc1ccc(OCCCCNC2=NCCCS2)cc1)C(=O)O)c1c(Cl)cccc1Cl] | 2-(2,6-dichlorobenzamido)-3-(4-(4-((5,6-dihydro-4H-1,3-oxazin-2-yl)amino)butoxy)phenyl)propanoic acid |
| 59a | | (S)-2-(2,6-dichlorobenzamido)-3-(4-(4-((5,6-dihydro-4H-1,3-oxazin-2-yl)amino)butoxy)phenyl)propanoic acid |
| 59b | | (R)-2-(2,6-dichlorobenzamido)-3-(4-(4-((5,6-dihydro-4H-1,3-oxazin-2-yl)amino)butoxy)phenyl)propanoic acid |

TABLE 1-continued

| Compound No. | Structure | Chemical Name [1] |
|---|---|---|
| 60 | 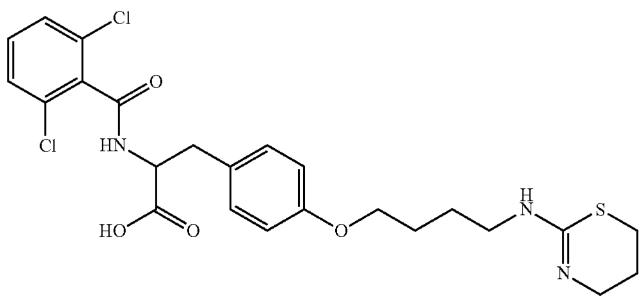 | 2-(2,6-dichlorobenzamido)-3-(4-(4-((5,6-dihydro-4H-1,3-thiazin-2-yl)amino)butoxy)phenyl)propanoic acid |
| 60a | | (S)-2-(2,6-dichlorobenzamido)-3-(4-(4-((5,6-dihydro-4H-1,3-thiazin-2-yl)amino)butoxy)phenyl)propanoic acid |
| 60b | | (R)-2-(2,6-dichlorobenzamido)-3-(4-(4-((5,6-dihydro-4H-1,3-thiazin-2-yl)amino)butoxy)phenyl)propanoic acid |
| 61 | 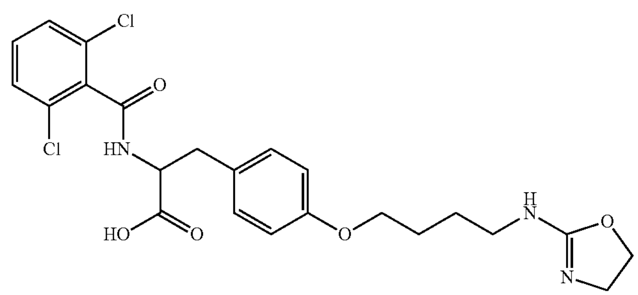 [SMILES: O=C(NC(Cc1ccc(OCCCCNC2=NCCS2)cc1)C(=O)O)c1c(Cl)cccc1Cl] | 2-(2,6-dichlorobenzamido)-3-(4-(4-((4,5-dihydrooxazol-2-yl)amino)butoxy)phenyl)propanoic acid |
| 61a | | (S)-2-(2,6-dichlorobenzamido)-3-(4-(4-((4,5-dihydrooxazol-2-yl)amino)butoxy)phenyl)propanoic acid |
| 61b | | (R)-2-(2,6-dichlorobenzamido)-3-(4-(4-((4,5-dihydrooxazol-2-yl)amino)butoxy)phenyl)propanoic acid |
| 62 | 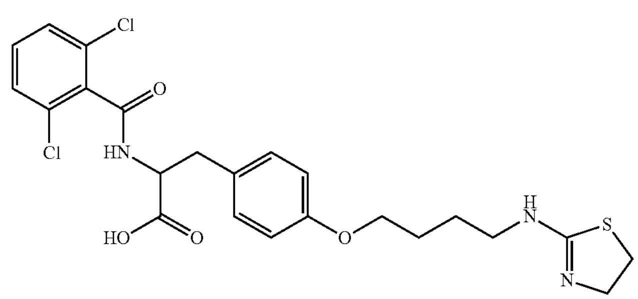 | 2-(2,6-dichlorobenzamido)-3-(4-(4-((4,5-dihydrothiazol-2-yl)amino)butoxy)phenyl)propanoic acid |
| 62a | | (S)-2-(2,6-dichlorobenzamido)-3-(4-(4-((4,5-dihydrothiazol-2-yl)amino)butoxy)phenyl)propanoic acid |
| 62b | | (R)-2-(2,6-dichlorobenzamido)-3-(4-(4-((4,5-dihydrothiazol-2-yl)amino)butoxy)phenyl)propanoic acid |

TABLE 1-continued

| Compound No. | Structure | Chemical Name [1] |
|---|---|---|
| 63 | 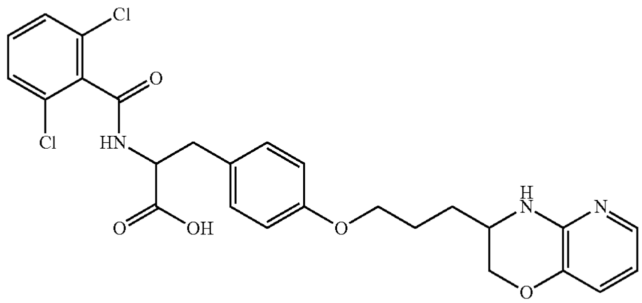 [SMILES: O=C(NC(Cc1ccc(OCCCC2COc3cccnc3N2)cc1)C(=O)O)c1c(Cl)cccc1Cl] | 2-(2,6-dichlorobenzamido)-3-(4-(3-(3,4-dihydro-2H-pyrido[3,2-b][1,4]oxazin-3-yl)propoxy)phenyl)propanoic acid |
| 63a | | (2S)-2-(2,6-dichlorobenzamido)-3-(4-(3-(3,4-dihydro-2H-pyrido[3,2-b][1,4]oxazin-3-yl)propoxy)phenyl)propanoic acid |
| 63b | | (2R)-2-(2,6-dichlorobenzamido)-3-(4-(3-(3,4-dihydro-2H-pyrido[3,2-b][1,4]oxazin-3-yl)propoxy)phenyl)propanoic acid |
| 64 | 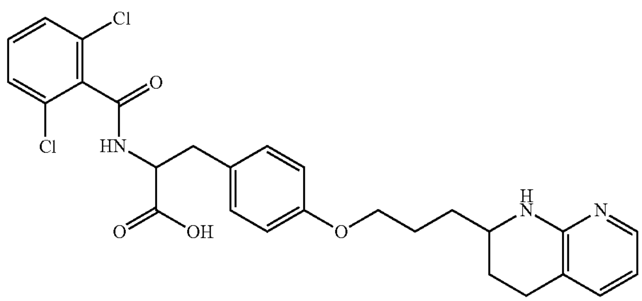 [SMILES: O=C(NC(Cc1ccc(OCCCC2CCc3cccnc3N2)cc1)C(=O)O)c1c(Cl)cccc1Cl] | 2-(2,6-dichlorobenzamido)-3-(4-(3-(1,2,3,4-tetrahydro-1,8-naphthyridin-2-yl)propoxy)phenyl)propanoic acid |
| 64a | | (2S)-2-(2,6-dichlorobenzamido)-3-(4-(3-(1,2,3,4-tetrahydro-1,8-naphthyridin-2-yl)propoxy)phenyl)propanoic acid |
| 64b | | (2R)-2-(2,6-dichlorobenzamido)-3-(4-(3-(1,2,3,4-tetrahydro-1,8-naphthyridin-2-yl)propoxy)phenyl)propanoic acid |
| 65 | 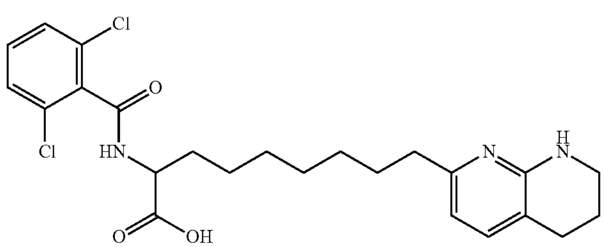 [SMILES: O=C(NC(CCCCCCCc1ccc2c(n1)NCCC2)C(=O)O)c1c(Cl)cccc1Cl] | 2-(2,6-dichlorobenzamido)-9-(5,6,7,8-tetrahydro-1,8-naphthyridin-2-yl)nonanoic acid |
| 65a | | (S)-2-(2,6-dichlorobenzamido)-9-(5,6,7,8-tetrahydro-1,8-naphthyridin-2-yl)nonanoic acid |
| 65b | | (R)-2-(2,6-dichlorobenzamido)-9-(5,6,7,8-tetrahydro-1,8-naphthyridin-2-yl)nonanoic acid |

TABLE 1-continued

| Compound No. | Structure | Chemical Name |
|---|---|---|
| 66 | 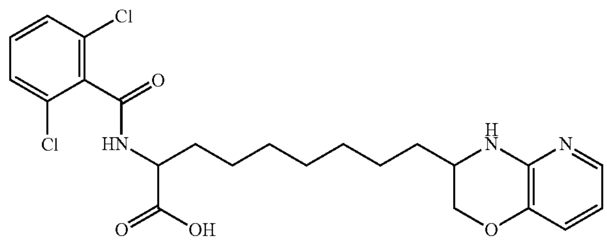 [SMILES: O=C(NC(CCCCCCCC1COc2cccnc2N1)C(=O)O)c1c(Cl)cccc1Cl] | 2-(2,6-dichlorobenzamido)-9-(3,4-dihydro-2H-pyrido[3,2-b][1,4]oxazin-3-yl)nonanoic acid |
| 66a | | (2S)-2-(2,6-dichlorobenzamido)-9-(3,4-dihydro-2H-pyrido[3,2-b][1,4]oxazin-3-yl)nonanoic acid |
| 66b | | (2R)-2-(2,6-dichlorobenzamido)-9-(3,4-dihydro-2H-pyrido[3,2-b][1,4]oxazin-3-yl)nonanoic acid |
| 67 | 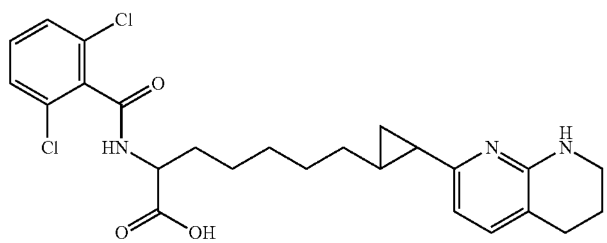 [SMILES: O=C(NC(CCCCCC1CC1c1ccc2c(n1)NCCC2)C(=O)O)c1c(Cl)cccc1Cl] | 2-(2,6-dichlorobenzamido)-7-(2-(5,6,7,8-tetrahydro-1,8-naphthyridin-2-yl)cyclopropyl)heptanoic acid |
| 67a | | (2S)-2-(2,6-dichlorobenzamido)-7-(2-(5,6,7,8-tetrahydro-1,8-naphthyridin-2-yl)cyclopropyl)heptanoic acid |
| 67b | | (2R)-2-(2,6-dichlorobenzamido)-7-(2-(5,6,7,8-tetrahydro-1,8-naphthyridin-2-yl)cyclopropyl)heptanoic acid |
| 68 | 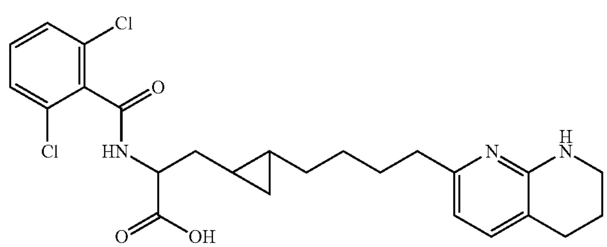 [SMILES: O=C(NC(CC1CC1CCCCc1ccc2c(n1)NCCC2)C(=O)O)c1c(Cl)cccc1Cl] | 2-(2,6-dichlorobenzamido)-3-(2-(4-(5,6,7,8-tetrahydro-1,8-naphthyridin-2-yl)butyl)cyclopropyl)propanoic acid |
| 68a | | (2S)-2-(2,6-dichlorobenzamido)-3-(2-(4-(5,6,7,8-tetrahydro-1,8-naphthyridin-2-yl)butyl)cyclopropyl)propanoic acid |
| 68b | | (2R)-2-(2,6-dichlorobenzamido)-3-(2-(4-(5,6,7,8-tetrahydro-1,8-naphthyridin-2-yl)butyl)cyclopropyl)propanoic acid |
| 69 | 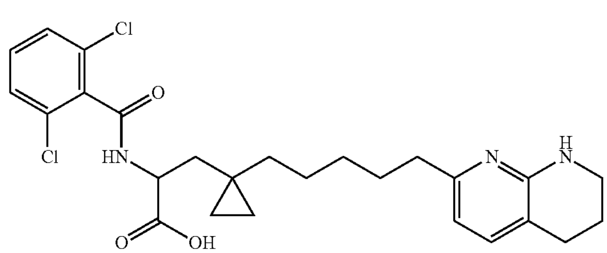 [SMILES: O=C(NC(CC1(CCCCCc2ccc3c(n2)NCCC3)CC1)C(=O)O)c1c(Cl)cccc1Cl] | 2-(2,6-dichlorobenzamido)-3-(1-(5-(5,6,7,8-tetrahydro-1,8-naphthyridin-2-yl)pentyl)cyclopropyl)propanoic acid |

TABLE 1-continued

| Compound No. | Structure | Chemical Name [1] |
|---|---|---|
| 69a | | (S)-2-(2,6-dichlorobenzamido)-3-(1-(5-(5,6,7,8-tetrahydro-1,8-naphthyridin-2-yl)pentyl)cyclopropyl)propanoic acid |
| 69b | | (R)-2-(2,6-dichlorobenzamido)-3-(1-(5-(5,6,7,8-tetrahydro-1,8-naphthyridin-2-yl)pentyl)cyclopropyl)propanoic acid |
| 70 | 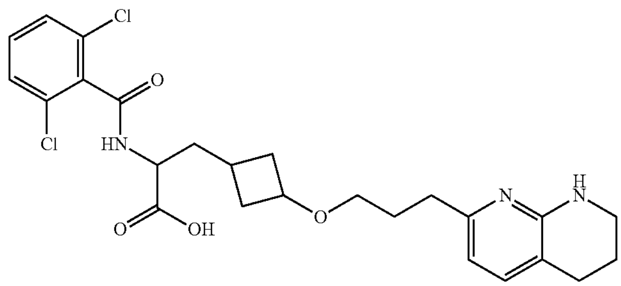 [SMILES: O=C(NC(CC1CC(OCCCc2ccc3c(n2)NCCC3)C1)C(=O)O)c1c(Cl)cccc1Cl] | 2-(2,6-dichlorobenzamido)-3-(3-(3-(5,6,7,8-tetrahydro-1,8-naphthyridin-2-yl)propoxy)cyclobutyl)propanoic acid |
| 70a | | (S)-2-(2,6-dichlorobenzamido)-3-(3-(3-(5,6,7,8-tetrahydro-1,8-naphthyridin-2-yl)propoxy)cyclobutyl)propanoic acid |
| 70b | | (R)-2-(2,6-dichlorobenzamido)-3-(3-(3-(5,6,7,8-tetrahydro-1,8-naphthyridin-2-yl)propoxy)cyclobutyl)propanoic acid |
| 71 | 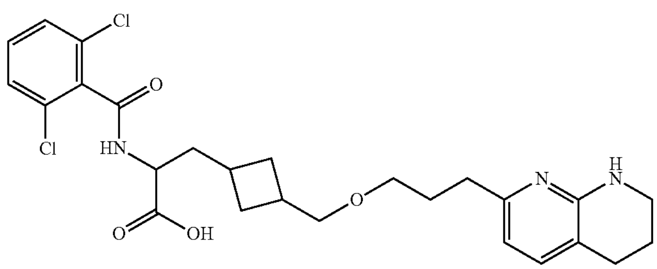 | 2-(2,6-dichlorobenzamido)-3-(3-((3-(5,6,7,8-tetrahydro-1,8-naphthyridin-2-yl)propoxy)methyl)cyclobutyl)propanoic acid |
| 71a | | (S)-2-(2,6-dichlorobenzamido)-3-(3-((3-(5,6,7,8-tetrahydro-1,8-naphthyridin-2-yl)propoxy)methyl)cyclobutyl)propanoic acid |
| 71b | | (R)-2-(2,6-dichlorobenzamido)-3-(3-((3-(5,6,7,8-tetrahydro-1,8-naphthyridin-2-yl)propoxy)methyl)cyclobutyl)propanoic acid |
| 72 | 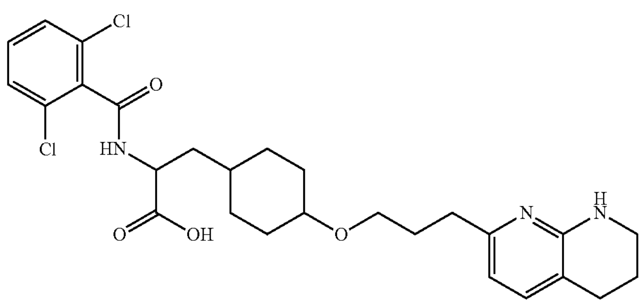 [SMILES: O=C(NC(CC1CCC(OCCCc2ccc3c(n2)NCCC3)CC1)C(=O)O)c1c(Cl)cccc1Cl] | 2-(2,6-dichlorobenzamido)-3-(4-(3-(5,6,7,8-tetrahydro-1,8-naphthyridin-2-yl)propoxy)cyclohexyl)propanoic acid |
| 72a | | (S)-2-(2,6-dichlorobenzamido)-3-(4-(3-(5,6,7,8-tetrahydro-1,8-naphthyridin-2-yl)propoxy)cyclohexyl)propanoic acid |

TABLE 1-continued

| Compound No. | Structure | Chemical Name [1] |
|---|---|---|
| 72b | | (R)-2-(2,6-dichlorobenzamido)-3-(4-(3-(5,6,7,8-tetrahydro-1,8-naphthyridin-2-yl)propoxy)cyclohexyl)propanoic acid |
| 73 | 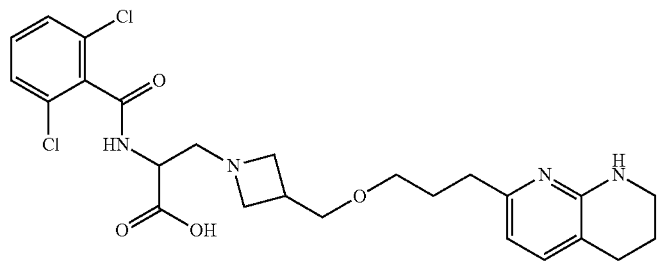 [SMILES: O=C(NC(CN1CC(COCCCc2ccc3c(n2)NCCC3)C1)C(=O)O)c1c(Cl)cccc1Cl] | 2-(2,6-dichlorobenzamido)-3-(3-((3-(5,6,7,8-tetrahydro-1,8-naphthyridin-2-yl)propoxy)methyl)azetidin-1-yl)propanoic acid |
| 73a | | (S)-2-(2,6-dichlorobenzamido)-3-(3-((3-(5,6,7,8-tetrahydro-1,8-naphthyridin-2-yl)propoxy)methyl)azetidin-1-yl)propanoic acid |
| 73b | | (R)-2-(2,6-dichlorobenzamido)-3-(3-((3-(5,6,7,8-tetrahydro-1,8-naphthyridin-2-yl)propoxy)methyl)azetidin-1-yl)propanoic acid |
| 74 | 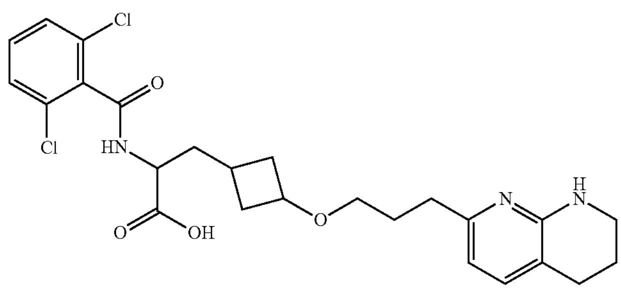 [SMILES: O=C(NC(CC1CC(OCCCc2ccc3c(n2)NCCC3)C1)C(=O)O)c1c(Cl)cccc1Cl] | 2-(2,6-dichlorobenzamido)-3-(3-(3-(5,6,7,8-tetrahydro-1,8-naphthyridin-2-yl)propoxy)azetidin-1-yl)propanoic acid |
| 74a | | (S)-2-(2,6-dichlorobenzamido)-3-(3-(3-(5,6,7,8-tetrahydro-1,8-naphthyridin-2-yl)propoxy)azetidin-1-yl)propanoic acid |
| 74b | | (R)-2-(2,6-dichlorobenzamido)-3-(3-(3-(5,6,7,8-tetrahydro-1,8-naphthyridin-2-yl)propoxy)azetidin-1-yl)propanoic acid |
| 75 | 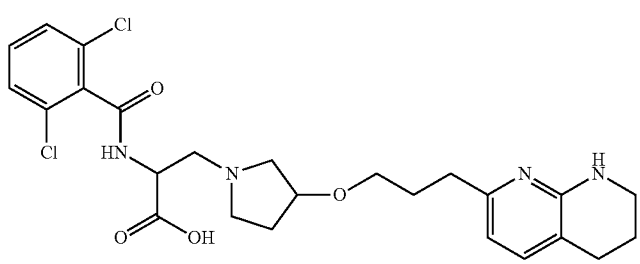 [SMILES: O=C(NC(CN1CCC(OCCCc2ccc3c(n2)NCCC3)C1)C(=O)O)c1c(Cl)cccc1Cl] | 2-(2,6-dichlorobenzamido)-3-(3-(3-(5,6,7,8-tetrahydro-1,8-naphthyridin-2-yl)propoxy)pyrrolidin-1-yl)propanoic acid |
| 75a | | (2S)-2-(2,6-dichlorobenzamido)-3-(3-(3-(5,6,7,8-tetrahydro-1,8-naphthyridin-2-yl)propoxy)pyrrolidin-1-yl)propanoic acid |
| 75b | | (2R)-2-(2,6-dichlorobenzamido)-3-(3-(3-(5,6,7,8-tetrahydro-1,8-naphthyridin-2-yl)propoxy)pyrrolidin-1-yl)propanoic acid |

TABLE 1-continued

| Compound No. | Structure | Chemical Name |
|---|---|---|
| 76 | 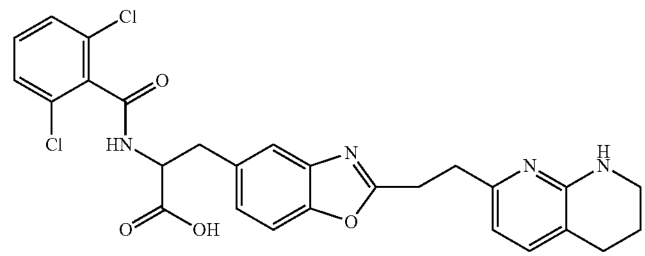 [SMILES: O=C(NC(Cc1ccc2oc(CCc3ccc4c(n3)NCCC4)nc2c1)C(=O)O)c1c(Cl)cccc1Cl] | 2-(2,6-dichlorobenzamido)-3-(2-(2-(5,6,7,8-tetrahydro-1,8-naphthyridin-2-yl)ethyl)benzo[d]oxazol-5-yl)propanoic acid |
| 76a | | (S)-2-(2,6-dichlorobenzamido)-3-(2-(2-(5,6,7,8-tetrahydro-1,8-naphthyridin-2-yl)ethyl)benzo[d]oxazol-5-yl)propanoic acid |
| 76b | | (R)-2-(2,6-dichlorobenzamido)-3-(2-(2-(5,6,7,8-tetrahydro-1,8-naphthyridin-2-yl)ethyl)benzo[d]oxazol-5-yl)propanoic acid |
| 77 | 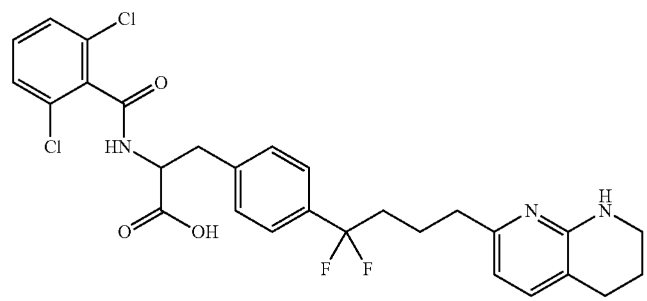 [SMILES: O=C(NC(Cc1ccc(C(F)(F)CCCc2ccc3c(n2)NCCC3)cc1)C(=O)O)c1c(Cl)cccc1Cl] | 2-(2,6-dichlorobenzamido)-3-(4-(1,1-difluoro-4-(5,6,7,8-tetrahydro-1,8-naphthyridin-2-yl)butyl)phenyl)propanoic acid |
| 77a | | (S)-2-(2,6-dichlorobenzamido)-3-(4-(1,1-difluoro-4-(5,6,7,8-tetrahydro-1,8-naphthyridin-2-yl)butyl)phenyl)propanoic acid |
| 77b | | (R)-2-(2,6-dichlorobenzamido)-3-(4-(1,1-difluoro-4-(5,6,7,8-tetrahydro-1,8-naphthyridin-2-yl)butyl)phenyl)propanoic acid |
| 78 | 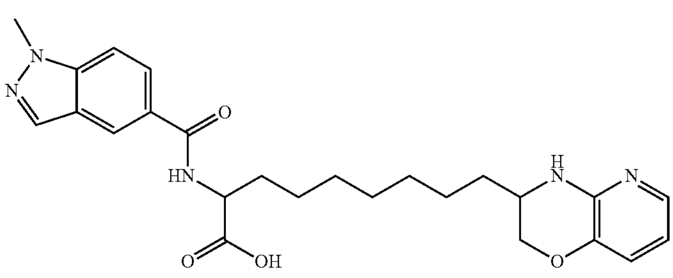 [SMILES: Cn1ncc2cc(C(=O)NC(CCCCCCCC3COc4cccnc4N3)C(=O)O)ccc21] | 9-(3,4-dihydro-2H-pyrido[3,2-b][1,4]oxazin-3-yl)-2-(1-methyl-1H-indazole-5-carboxamido)nonanoic acid |
| 78a | | (2S)-9-(3,4-dihydro-2H-pyrido[3,2-b][1,4]oxazin-3-yl)-2-(1-methyl-1H-indazole-5-carboxamido)nonanoic acid |
| 78b | | (2R)-9-(3,4-dihydro-2H-pyrido[3,2-b][1,4]oxazin-3-yl)-2-(1-methyl-1H-indazole-5-carboxamido)nonanoic acid |

TABLE 1-continued

| Compound No. | Structure | Chemical Name |
|---|---|---|
| 79 | 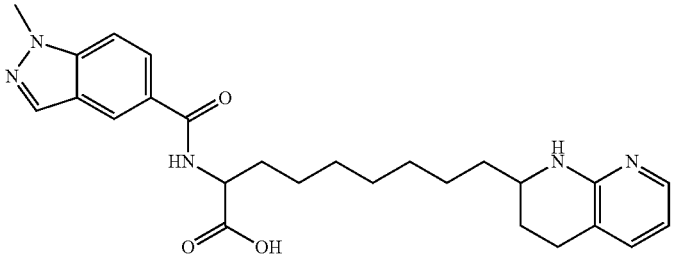 [SMILES: Cn1ncc2cc(C(=O)NC(CCCCCCCC3CCc4cccnc4N3)C(=O)O)ccc21] | 2-(1-methyl-1H-indazole-5-carboxamido)-9-(1,2,3,4-tetrahydro-1,8-naphthyridin-2-yl)nonanoic acid |
| 79a | | (2S)-2-(1-methyl-1H-indazole-5-carboxamido)-9-(1,2,3,4-tetrahydro-1,8-naphthyridin-2-yl)nonanoic acid |
| 79b | | (2R)-2-(1-methyl-1H-indazole-5-carboxamido)-9-(1,2,3,4-tetrahydro-1,8-naphthyridin-2-yl)nonanoic acid |
| 80 | 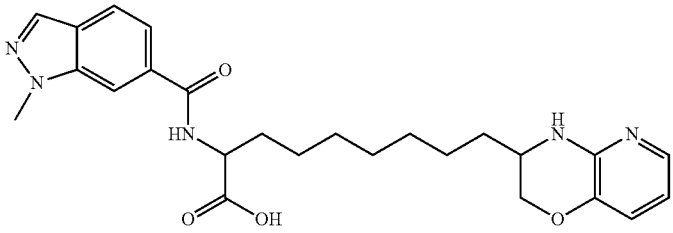 [SMILES: Cn1ncc2ccc(C(=O)NC(CCCCCCCC3COc4cccnc4N3)C(=O)O)cc21] | 9-(3,4-dihydro-2H-pyrido[3,2-b][1,4]oxazin-3-yl)-2-(1-methyl-1H-indazole-6-carboxamido)nonanoic acid |
| 80a | | (2S)-9-(3,4-dihydro-2H-pyrido[3,2-b][1,4]oxazin-3-yl)-2-(1-methyl-1H-indazole-6-carboxamido)nonanoic acid |
| 80b | | (2R)-9-(3,4-dihydro-2H-pyrido[3,2-b][1,4]oxazin-3-yl)-2-(1-methyl-1H-indazole-6-carboxamido)nonanoic acid |
| 81 | 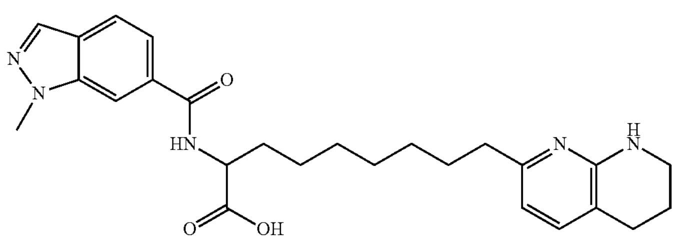 [SMILES: Cn1ncc2ccc(C(=O)NC(CCCCCCCc3ccc4c(n3)NCCC4)C(=O)O)cc21] | 2-(1-methyl-1H-indazole-6-carboxamido)-9-(5,6,7,8-tetrahydro-1,8-naphthyridin-2-yl)nonanoic acid |
| 81a | | (S)-2-(1-methyl-1H-indazole-6-carboxamido)-9-(5,6,7,8-tetrahydro-1,8-naphthyridin-2-yl)nonanoic acid |
| 81b | | (R)-2-(1-methyl-1H-indazole-6-carboxamido)-9-(5,6,7,8-tetrahydro-1,8-naphthyridin-2-yl)nonanoic acid |
| 82 | 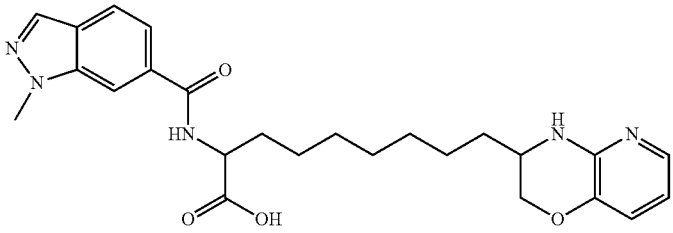 [SMILES: Cn1ncc2ccc(C(=O)NC(CCCCCCCC3COc4cccnc4N3)C(=O)O)cc21] | 2-(1-methyl-1H-indazole-5-carboxamido)-9-(5,6,7,8-tetrahydro-1,8-naphthyridin-2-yl)nonanoic acid |

TABLE 1-continued

| Compound No. | Structure | Chemical Name [1] |
|---|---|---|
| 82a | | (S)-2-(1-methyl-1H-indazole-5-carboxamido)-9-(5,6,7,8-tetrahydro-1,8-naphthyridin-2-yl)nonanoic acid |
| 82b | | (R)-2-(1-methyl-1H-indazole-5-carboxamido)-9-(5,6,7,8-tetrahydro-1,8-naphthyridin-2-yl)nonanoic acid |
| 83 | 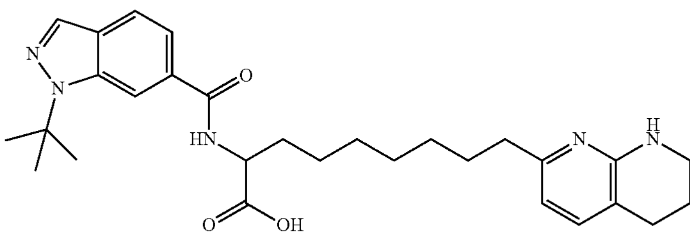 [SMILES: CC(C)(C)n1ncc2ccc(C(=O)NC(CCCCCCCc3ccc4c(n3)NCCC4)C(=O)O)cc21] | 2-(1-(tert-butyl)-1H-indazole-6-carboxamido)-9-(5,6,7,8-tetrahydro-1,8-naphthyridin-2-yl)nonanoic acid |
| 83a | | (S)-2-(1-(tert-butyl)-1H-indazole-6-carboxamido)-9-(5,6,7,8-tetrahydro-1,8-naphthyridin-2-yl)nonanoic acid |
| 83b | | (R)-2-(1-(tert-butyl)-1H-indazole-6-carboxamido)-9-(5,6,7,8-tetrahydro-1,8-naphthyridin-2-yl)nonanoic acid |
| 84 | 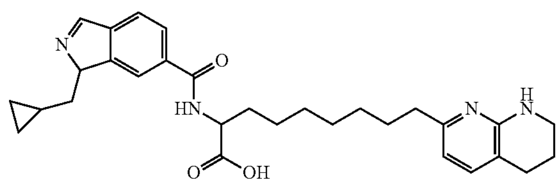 [SMILES: O=C(NC(CCCCCCCc1ccc2c(n1)NCCC2)C(=O)O)c1ccc2c(c1)C(CC1CC1)N=C2] | 2-(1-(cyclopropylmethyl)-1H-indazole-6-carboxamido)-9-(5,6,7,8-tetrahydro-1,8-naphthyridin-2-yl)nonanoic acid |
| 84a | | (S)-2-(1-(cyclopropylmethyl)-1H-indazole-6-carboxamido)-9-(5,6,7,8-tetrahydro-1,8-naphthyridin-2-yl)nonanoic acid |
| 84b | | (R)-2-(1-(cyclopropylmethyl)-1H-indazole-6-carboxamido)-9-(5,6,7,8-tetrahydro-1,8-naphthyridin-2-yl)nonanoic acid |
| 85 | 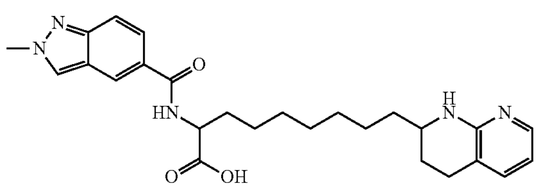 [SMILES: Cn1cc2cc(C(=O)NC(CCCCCCCC3CCc4cccnc4N3)C(=O)O)ccc2n1] | 2-(2-methyl-2H-indazole-5-carboxamido)-9-(1,2,3,4-tetrahydro-1,8-naphthyridin-2-yl)nonanoic acid |
| 85a | | (2S)-2-(2-methyl-2H-indazole-5-carboxamido)-9-(1,2,3,4-tetrahydro-1,8-naphthyridin-2-yl)nonanoic acid |
| 85b | | (2R)-2-(2-methyl-2H-indazole-5-carboxamido)-9-(1,2,3,4-tetrahydro-1,8-naphthyridin-2-yl)nonanoic acid |
| 86 | 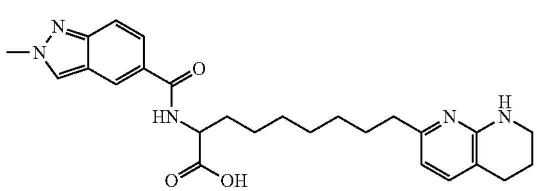 [SMILES: Cn1cc2cc(C(=O)NC(CCCCCCCc3ccc4c(n3)NCCC4)C(=O)O)ccc2n1] | 2-(2-methyl-2H-indazole-5-carboxamido)-9-(5,6,7,8-tetrahydro-1,8-naphthyridin-2-yl)nonanoic acid |

TABLE 1-continued

| Compound No. | Structure | Chemical Name [1] |
|---|---|---|
| 86a | | (S)-2-(2-methyl-2H-indazole-5-carboxamido)-9-(5,6,7,8-tetrahydro-1,8-naphthyridin-2-yl)nonanoic acid |
| 86b | | (R)-2-(2-methyl-2H-indazole-5-carboxamido)-9-(5,6,7,8-tetrahydro-1,8-naphthyridin-2-yl)nonanoic acid |

[1] Chemical names are generated using the ChemBioDraw ® Ultra version 14.0.0.117 software.

TABLE 2

| Compound No. | Structure |
|---|---|
| 87 | *[structure: 4-chlorobenzamide linked via amide to α-carbon of nonanoic acid bearing 5,6,7,8-tetrahydro-1,8-naphthyridin-2-yl group]* |
| 88 | *[structure: 4-fluorobenzamide linked via amide to α-carbon of nonanoic acid bearing 5,6,7,8-tetrahydro-1,8-naphthyridin-2-yl group]* |
| 89 | *[structure: 4-methoxybenzamide linked via amide to α-carbon of nonanoic acid bearing 5,6,7,8-tetrahydro-1,8-naphthyridin-2-yl group]* |
| 90 | *[structure: 4-cyanobenzamide linked via amide to α-carbon of nonanoic acid bearing 5,6,7,8-tetrahydro-1,8-naphthyridin-2-yl group]* |

TABLE 2-continued

| Compound No. | Structure |
|---|---|
| 91 | 3-chlorobenzoyl-NH-CH(COOH)-(CH2)6-[5,6,7,8-tetrahydro-1,8-naphthyridin-2-yl] |
| 92 | 3-fluorobenzoyl-NH-CH(COOH)-(CH2)6-[5,6,7,8-tetrahydro-1,8-naphthyridin-2-yl] |
| 93 | 3-methoxybenzoyl-NH-CH(COOH)-(CH2)6-[5,6,7,8-tetrahydro-1,8-naphthyridin-2-yl] |
| 94 | 3-cyanobenzoyl-NH-CH(COOH)-(CH2)6-[5,6,7,8-tetrahydro-1,8-naphthyridin-2-yl] |
| 95 | 2-fluorobenzoyl-NH-CH(COOH)-(CH2)6-[5,6,7,8-tetrahydro-1,8-naphthyridin-2-yl] |

TABLE 2-continued

| Compound No. | Structure |
|---|---|
| 96 | 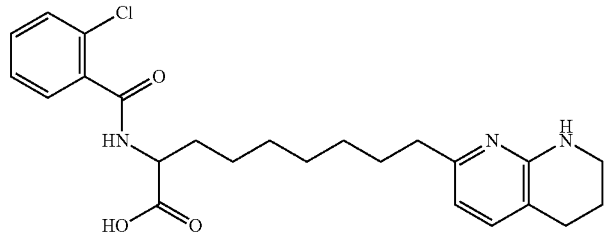 [SMILES: O=C(NC(CCCCCCCc1ccc2c(n1)NCCC2)C(=O)O)c1ccccc1F] |
| 97 | 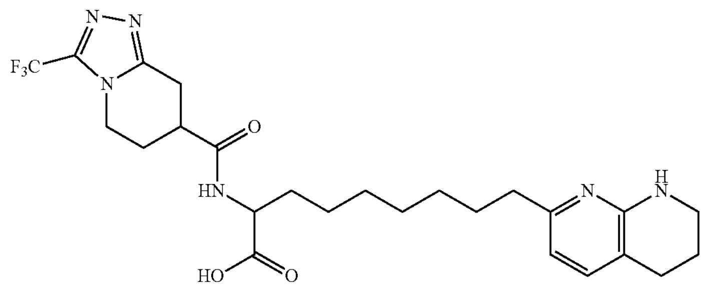 [SMILES: O=C(NC(CCCCCCCc1ccc2c(n1)NCCC2)C(=O)O)C1CCn2c(nnc2C(F)(F)F)C1] |
| 98 | 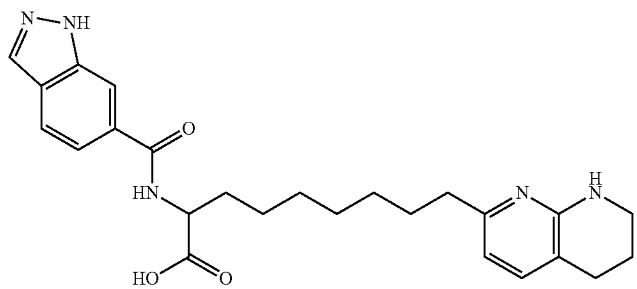 [SMILES: O=C(NC(CCCCCCCc1ccc2c(n1)NCCC2)C(=O)O)c1ccc2cn[nH]c2c1] |
| 99 | 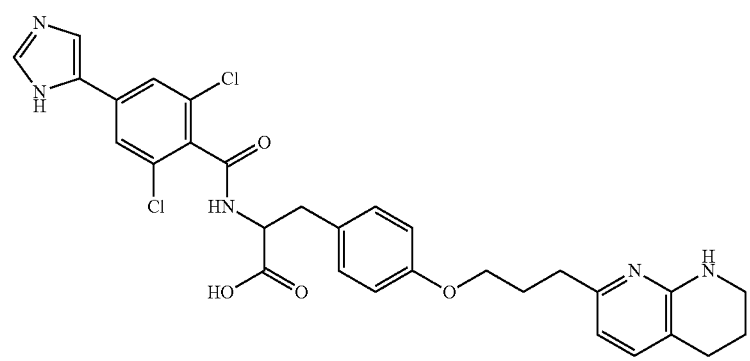 [SMILES: O=C(NC(Cc1ccc(OCCCc2ccc3c(n2)NCCC3)cc1)C(=O)O)c1c(Cl)cc(-c2cnc[nH]2)cc1Cl] |
| 100 | 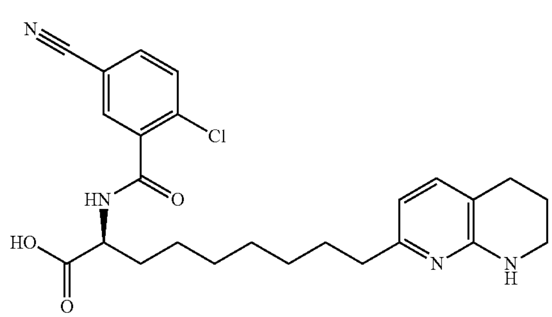 [SMILES: N#Cc1ccc(Cl)c(C(=O)N[C@@H](CCCCCCCc2ccc3c(n2)NCCC3)C(=O)O)c1] |

TABLE 2-continued
| Compound No. | Structure |
|---|---|
| 101 | 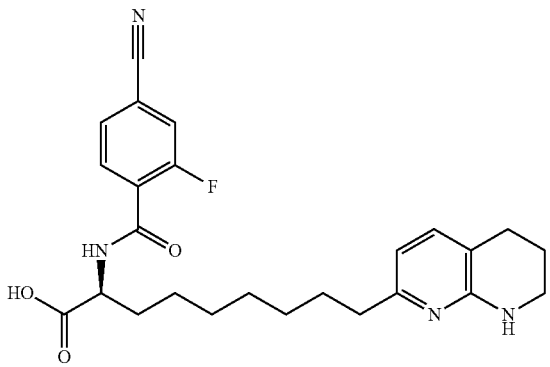 [SMILES: N#Cc1ccc(C(=O)N[C@@H](CCCCCCCc2ccc3c(n2)NCCC3)C(=O)O)c(F)c1] |
| 102 | 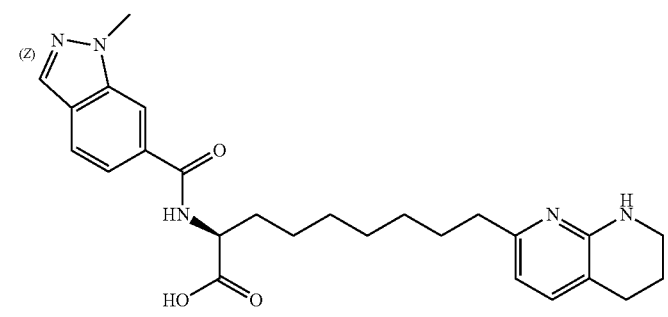 [SMILES: Cn1ncc2ccc(C(=O)N[C@@H](CCCCCCCc3ccc4c(n3)NCCC4)C(=O)O)cc21] |
| 103 | 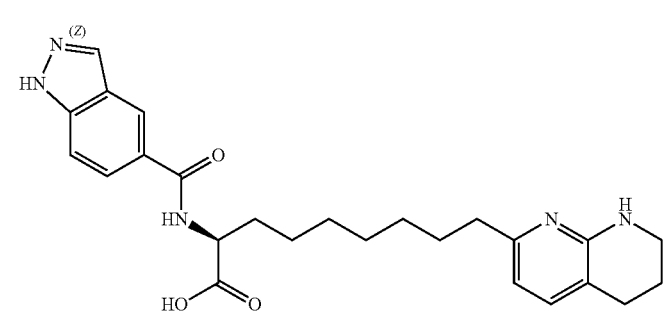 [SMILES: O=C(N[C@@H](CCCCCCCc1ccc2c(n1)NCCC2)C(=O)O)c1ccc2[nH]ncc2c1] |
| 104 | 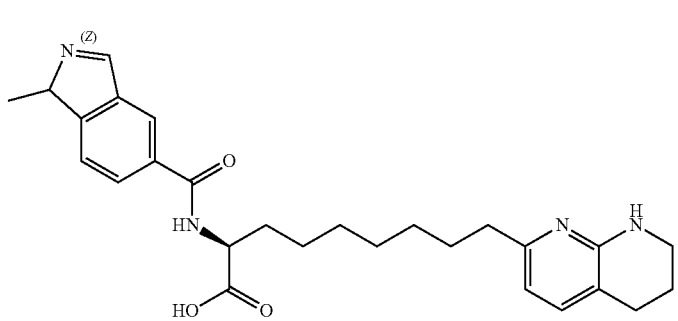 [SMILES: CC1N=Cc2cc(C(=O)N[C@@H](CCCCCCCc3ccc4c(n3)NCCC4)C(=O)O)ccc21] |

TABLE 2-continued

| Compound No. | Structure |
|---|---|
| 105 | 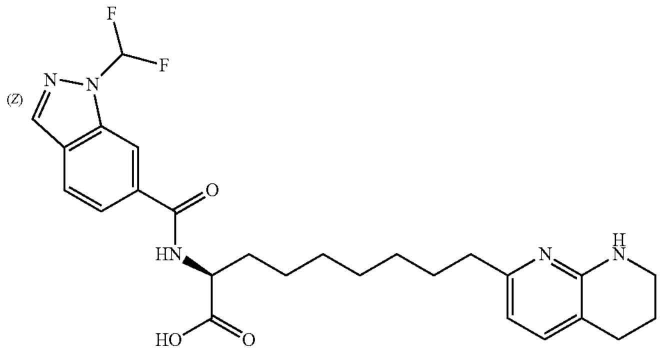 [SMILES: O=C(N[C@@H](CCCCCCCc1ccc2c(n1)NCCC2)C(=O)O)c1ccc2cnn(C(F)F)c2c1] |
| 106 | 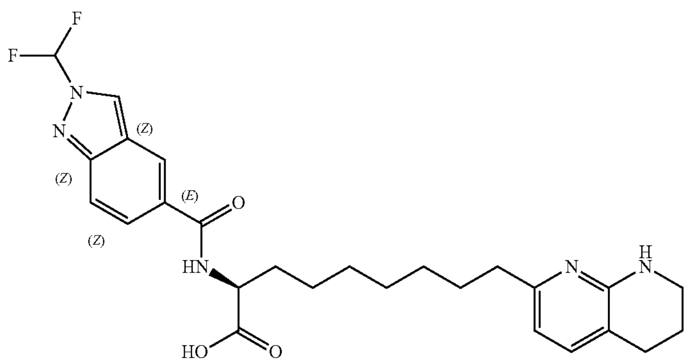 [SMILES: O=C(N[C@@H](CCCCCCCc1ccc2c(n1)NCCC2)C(=O)O)c1ccc2nn(C(F)F)cc2c1] |
| 107 | 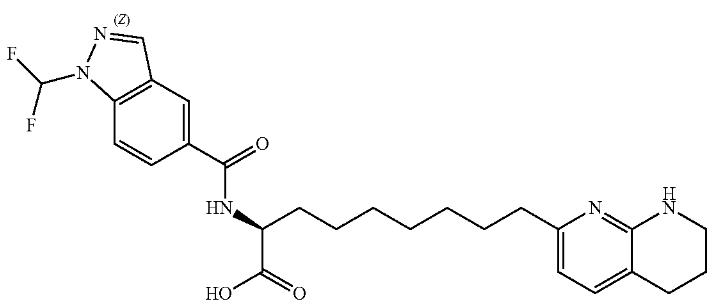 [SMILES: O=C(N[C@@H](CCCCCCCc1ccc2c(n1)NCCC2)C(=O)O)c1ccc2c(cnn2C(F)F)c1] |
| 108 | 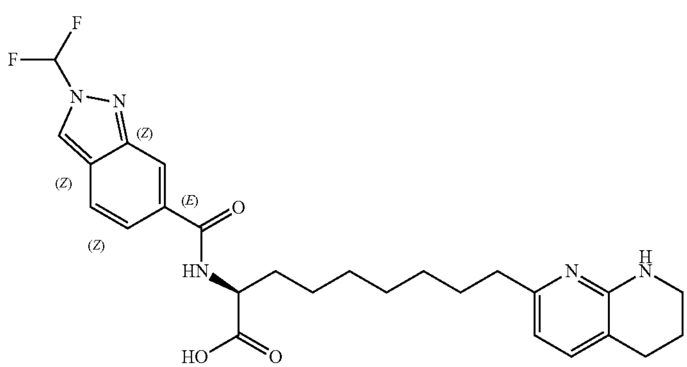 [SMILES: O=C(N[C@@H](CCCCCCCc1ccc2c(n1)NCCC2)C(=O)O)c1ccc2cn(C(F)F)nc2c1] |

TABLE 2-continued

| Compound No. | Structure |
| --- | --- |
| 109 | 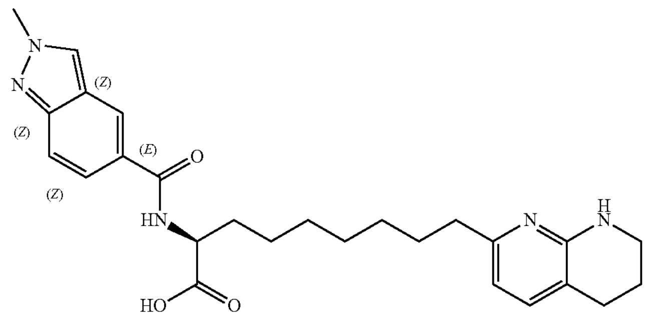 [SMILES: Cn1cc2cc(C(=O)N[C@@H](CCCCCCCc3ccc4c(n3)NCCC4)C(=O)O)ccc2n1] |
| 110 | 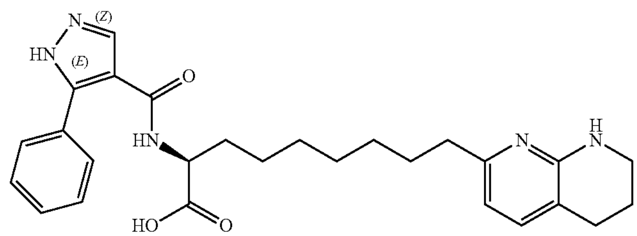 [SMILES: O=C(N[C@@H](CCCCCCCc1ccc2c(n1)NCCC2)C(=O)O)c1cn[nH]c1-c1ccccc1] |
| 111 | 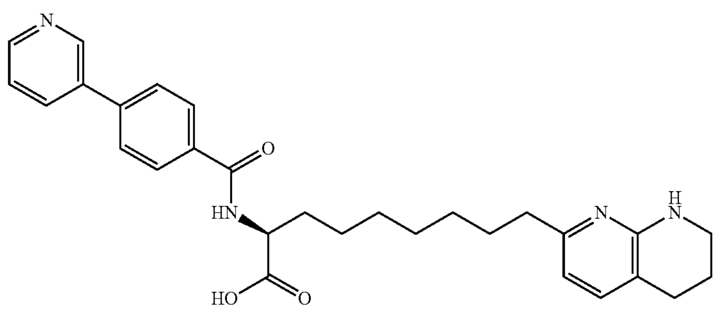 [SMILES: O=C(N[C@@H](CCCCCCCc1ccc2c(n1)NCCC2)C(=O)O)c1ccc(-c2cccnc2)cc1] |
| 112 | 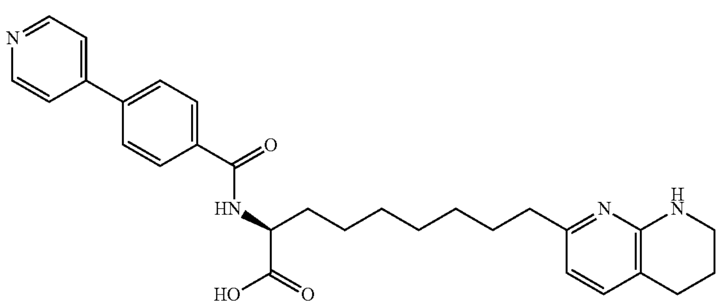 [SMILES: O=C(N[C@@H](CCCCCCCc1ccc2c(n1)NCCC2)C(=O)O)c1ccc(-c2ccncc2)cc1] |
| 113 | 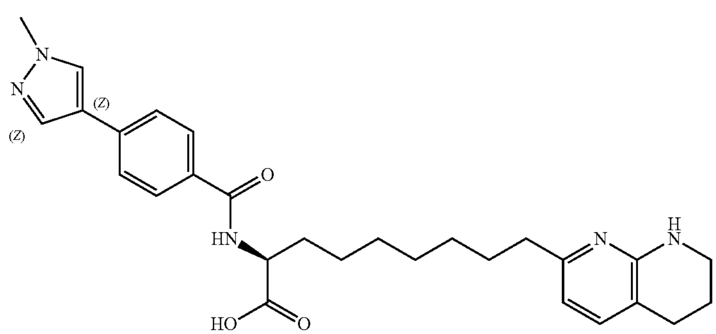 [SMILES: Cn1cc(-c2ccc(C(=O)N[C@@H](CCCCCCCc3ccc4c(n3)NCCC4)C(=O)O)cc2)cn1] |

TABLE 2-continued
| Compound No. | Structure |
| --- | --- |
| 114 | 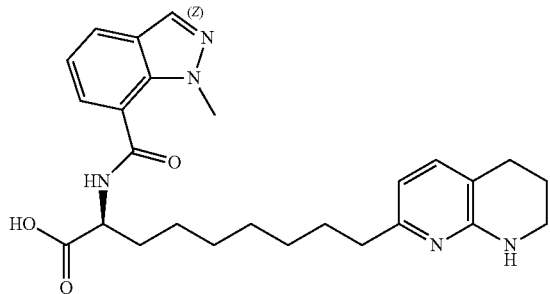 [SMILES: Cn1ncc2cccc(C(=O)N[C@@H](CCCCCCCc3ccc4c(n3)NCCC4)C(=O)O)c21] |
| 115 | 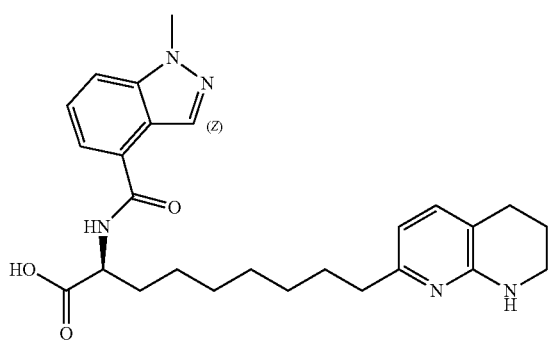 [SMILES: Cn1ncc2c(C(=O)N[C@@H](CCCCCCCc3ccc4c(n3)NCCC4)C(=O)O)cccc21] |
| 116 | 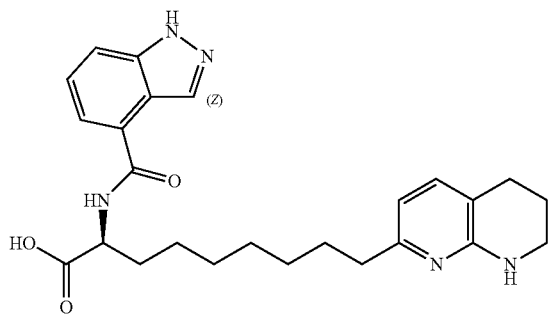 [SMILES: O=C(N[C@@H](CCCCCCCc1ccc2c(n1)NCCC2)C(=O)O)c1cccc2[nH]ncc12] |
| 117 | 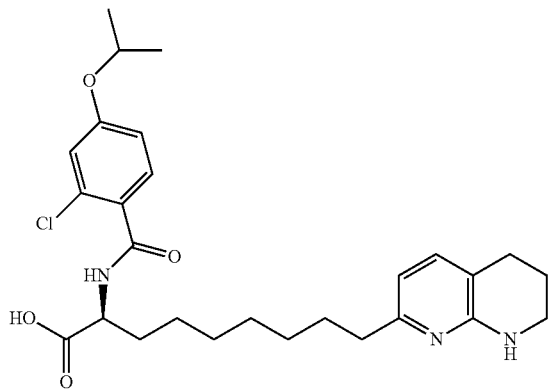 [SMILES: CC(C)Oc1ccc(C(=O)N[C@@H](CCCCCCCc2ccc3c(n2)NCCC3)C(=O)O)c(Cl)c1] |

TABLE 2-continued

| Compound No. | Structure |
|---|---|
| 118 | 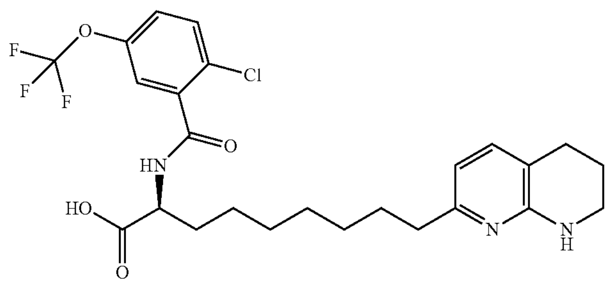 [SMILES: O=C(N[C@@H](CCCCCCCc1ccc2c(n1)NCCC2)C(=O)O)c1cc(OC(F)(F)F)ccc1Cl] |
| 119 | 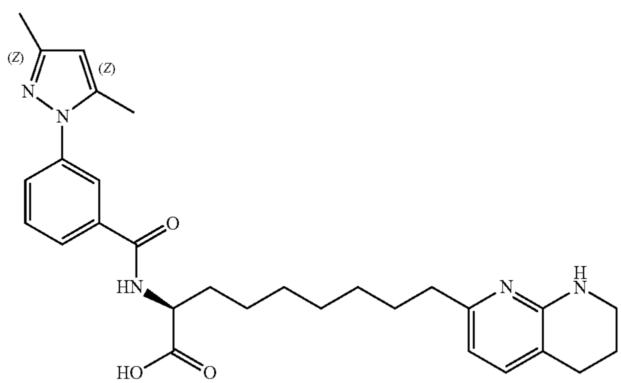 [SMILES: Cc1cc(C)n(-c2cccc(C(=O)N[C@@H](CCCCCCCc3ccc4c(n3)NCCC4)C(=O)O)c2)n1] |
| 121 | 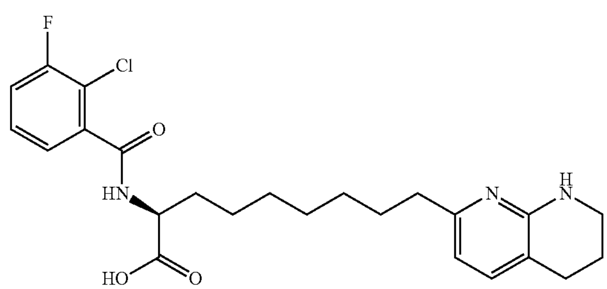 [SMILES: O=C(N[C@@H](CCCCCCCc1ccc2c(n1)NCCC2)C(=O)O)c1cccc(F)c1Cl] |
| 122 | 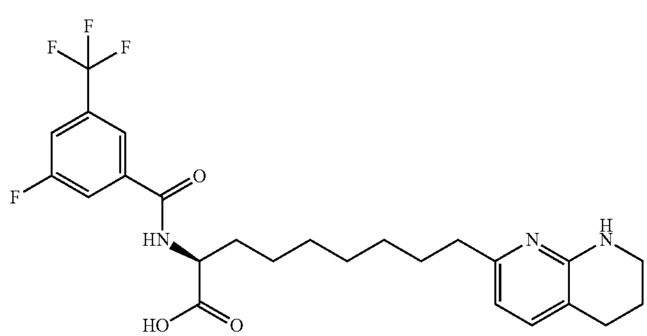 [SMILES: O=C(N[C@@H](CCCCCCCc1ccc2c(n1)NCCC2)C(=O)O)c1cc(F)cc(C(F)(F)F)c1] |

TABLE 2-continued
| Compound No. | Structure |
|---|---|
| 123 | 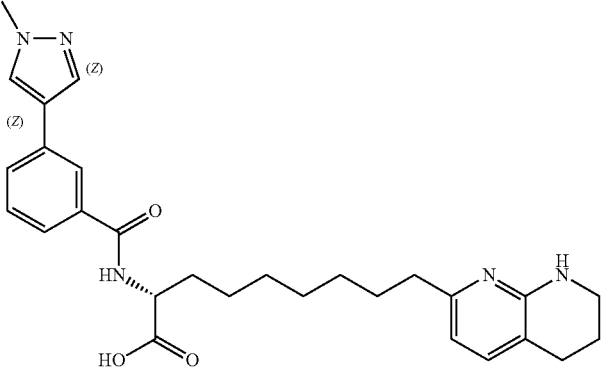 [SMILES: Cn1cc(-c2cccc(C(=O)N[C@H](CCCCCCCc3ccc4c(n3)NCCC4)C(=O)O)c2)cn1] |
| 124 | 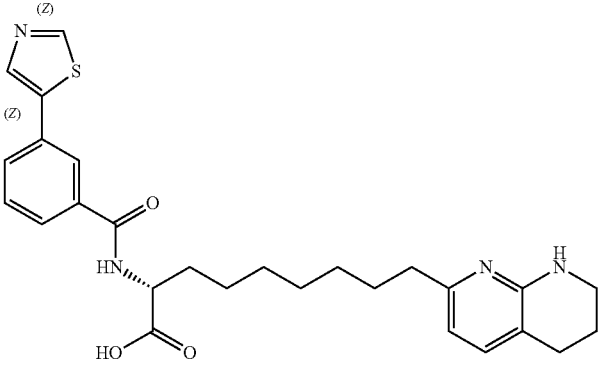 [SMILES: O=C(N[C@H](CCCCCCCc1ccc2c(n1)NCCC2)C(=O)O)c1cccc(-c2cncs2)c1] |
| 125 | 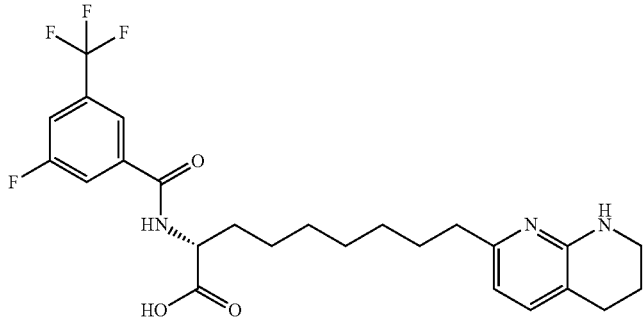 [SMILES: O=C(N[C@H](CCCCCCCc1ccc2c(n1)NCCC2)C(=O)O)c1cc(F)cc(C(F)(F)F)c1] |
| 126 | 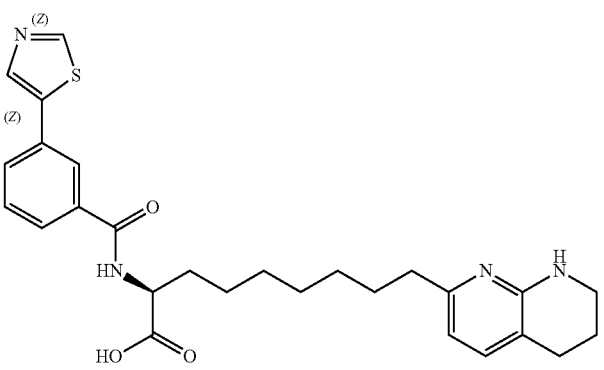 [SMILES: O=C(N[C@@H](CCCCCCCc1ccc2c(n1)NCCC2)C(=O)O)c1cccc(-c2cncs2)c1] |

In some embodiments, provided is a compound selected from Compound Nos. 1-62 in Table 1, or a salt thereof. In some embodiments, provided is a compound selected from Compound Nos. 1-86 in Table 1, or a salt thereof. In some embodiments, provided is a compound selected from Compound Nos. 87-126 in Table 2, or a salt thereof. In some embodiments, provided is a compound selected from Compound Nos. 1-62 in Table 1 or Compound Nos. 87-126 in Table 2, or a salt thereof. In some embodiments, the compound is selected from the group consisting of one or more of Compound Nos. 1-62 in Table 1, or a salt thereof. In some embodiments, the compound is selected from the group consisting of one or more of Compound Nos. 1-86 in Table 1, or a salt thereof. In some embodiments, the compound is selected from the group consisting of one or more of Compound Nos. 87-126 in Table 2, or a salt thereof. In some embodiments, the compound is selected from the group consisting of one or more of Compound Nos. 1-86 in Table 1 or Compound Nos. 87-126 in Table 2, or a salt thereof.

The invention also includes all salts of compounds referred to herein, such as pharmaceutically acceptable salts. The invention also includes any or all of the stereochemical forms, including any enantiomeric or diastereomeric forms, and any tautomers or other forms of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. It is also understood that prodrugs, solvates and metabolites of the compounds are embraced by this disclosure. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

Compounds described herein are αvβ1 integrin inhibitors. In some instances, it is desirable for the compound to inhibit other integrins in addition to αvβ1 integrin. In some embodiments, the compound inhibits αvβ1 integrin and one or more of αvβ6, αvβ3, αvβ5, α2β1, α3β1 and α6β1 integrin. In some embodiments, the compound inhibits αvβ1 integrin and αvβ6 integrin. In some embodiments, the compound inhibits αvβ1 integrin, αvβ3 integrin and αvβ5 integrin. In some embodiments, the compound inhibits αvβ1 integrin and α2β1 integrin. In some embodiments, the compound inhibits αvβ1 integrin, α2β1 integrin and α3β1 integrin. In some embodiments, the compound inhibits αvβ1 integrin and α6β1 integrin.

In some instances, it is desirable to avoid inhibition of other integrins. In some embodiments, the compound is a selective αvβ1 integrin inhibitor. In some embodiments, the compound does not inhibit substantially α4β1, αvβ8 and/or α2β3 integrin. In some embodiments, the compound inhibits αvβ1 integrin but does not inhibit substantially α4β1 integrin. In some embodiments, the compound inhibits αvβ1 integrin but does not inhibit substantially αvβ8 integrin. In some embodiments, the compound inhibits αvβ1 integrin but does not inhibit substantially α2β3 integrin.

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization, and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

Compounds of the formula (III) can be prepared according to Scheme 1, wherein $R^1$ and $R^2$ are as defined for formula (III), or any variation thereof detailed herein; $P^1$ is an amine protecting group (e.g., Cbz); $P^0$ is a carboxylic acid protecting group (e.g., methyl); and $R^{2p}$ is a protected $R^2$ group where applicable.

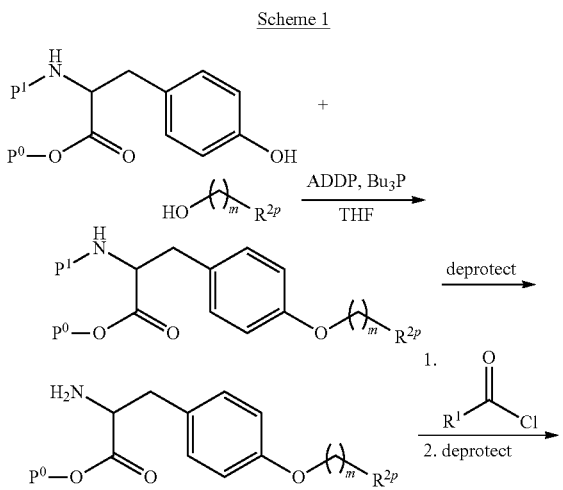

Scheme 1

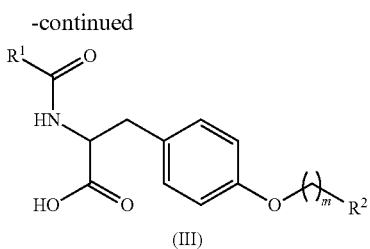

(III)

An exemplary embodiment of the preparative method in Scheme 1 is shown in Scheme 1a, where Ar is an optionally substituted aryl group.

Scheme 1a

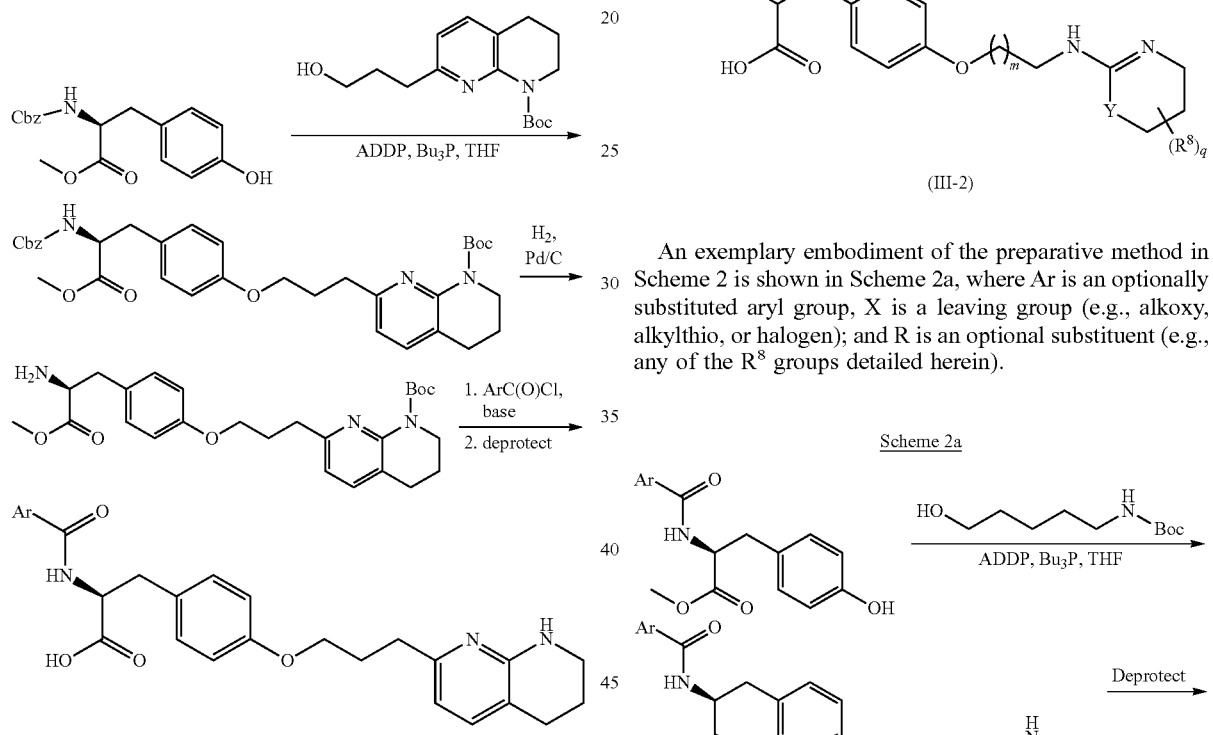

Compounds of the formula (III-2) can be prepared according to Scheme 2, wherein $R^1$, $R^8$ and Y are as defined for formula (III-2), or any variation thereof detailed herein; $P^2$ is an amine protecting group (e.g., Boc); $P^0$ is a carboxylic acid protecting group (e.g., methyl); X is a leaving group (e.g., alkoxy, alkylthio, or halogen); m is 1, 2, 3, 4 or 5; and q is 0, 1, 2 or 3.

Scheme 2

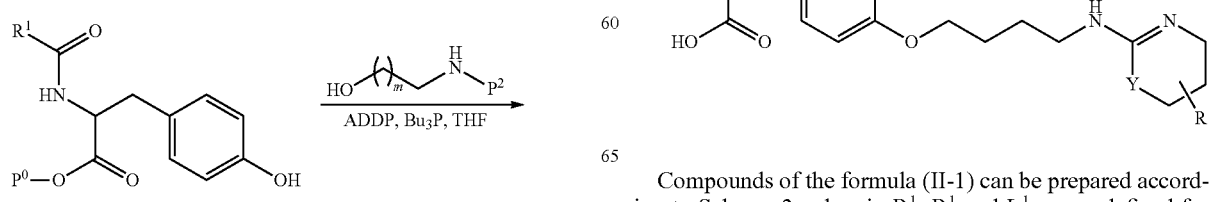

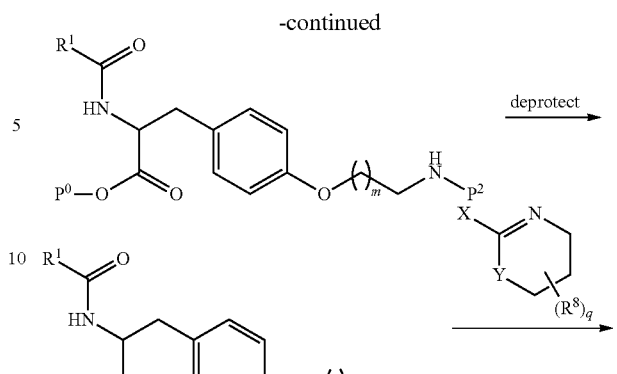

(III-2)

An exemplary embodiment of the preparative method in Scheme 2 is shown in Scheme 2a, where Ar is an optionally substituted aryl group, X is a leaving group (e.g., alkoxy, alkylthio, or halogen); and R is an optional substituent (e.g., any of the $R^8$ groups detailed herein).

Scheme 2a

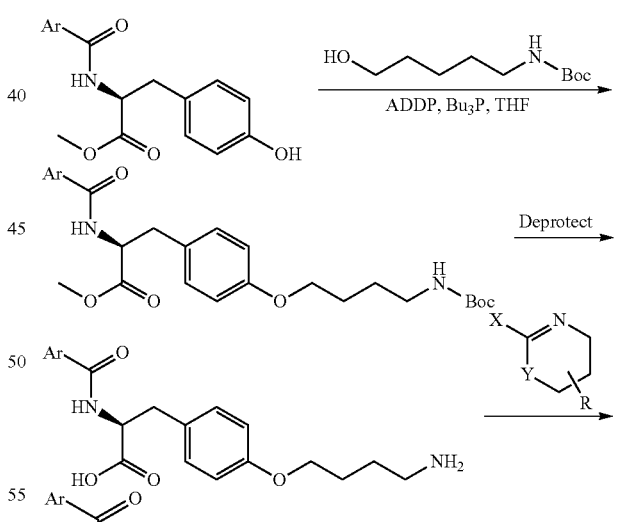

Compounds of the formula (II-1) can be prepared according to Scheme 3, wherein $R^1$, $R^1$ and $L^1$ are as defined for formula (II-1), or any variation thereof detailed herein; $P^3$ is an amine protecting group (e.g., Boc); and $P^0$ is a carboxylic acid protecting group (e.g., tert-butyl).

Scheme 3

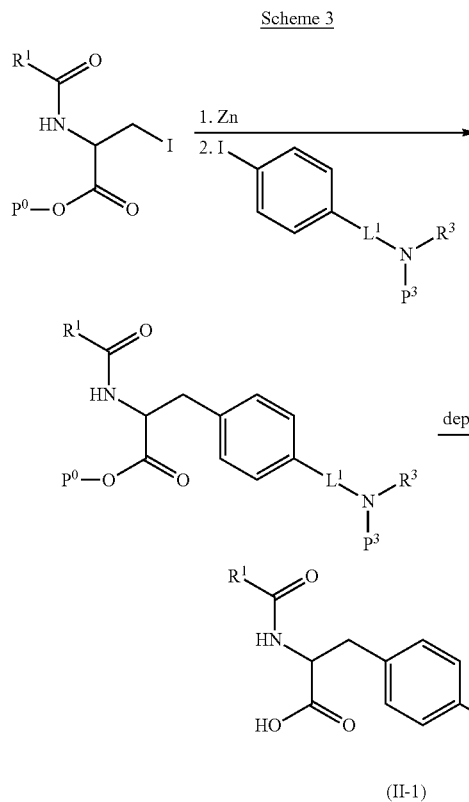

An exemplary embodiment of the preparative method in Scheme 3 is shown in Scheme 3a, where Ar is an optionally substituted aryl group, and L is a linker moiety (e.g., any of the $L^1$ groups detailed herein).

Scheme 3a

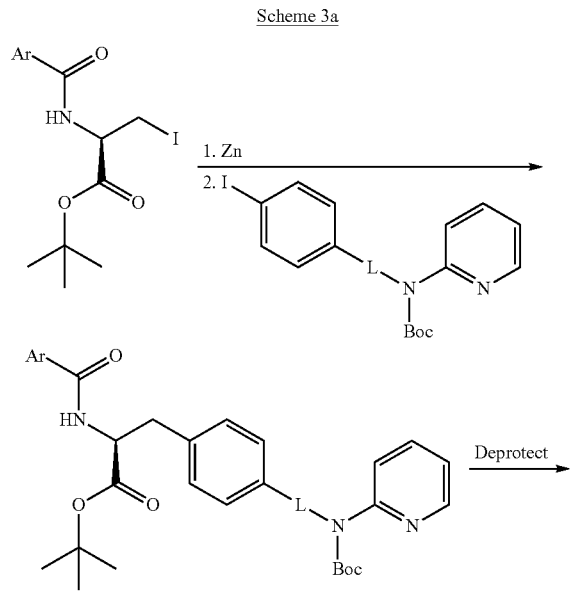

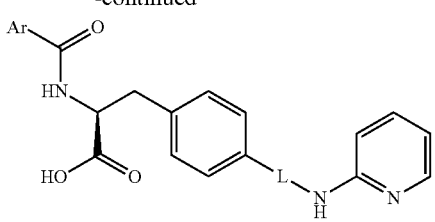

Compounds of the formula (IV) can be prepared according to Scheme 4, wherein $R^1$ and R are as defined for formula (IV), or any variation thereof detailed herein; $P^0$ is a carboxylic acid protecting group (e.g., methyl); p is 2, 3, 4, 5, 6 or 7; and $R^{2p}$ is a protected $R^2$ group where applicable.

Scheme 4

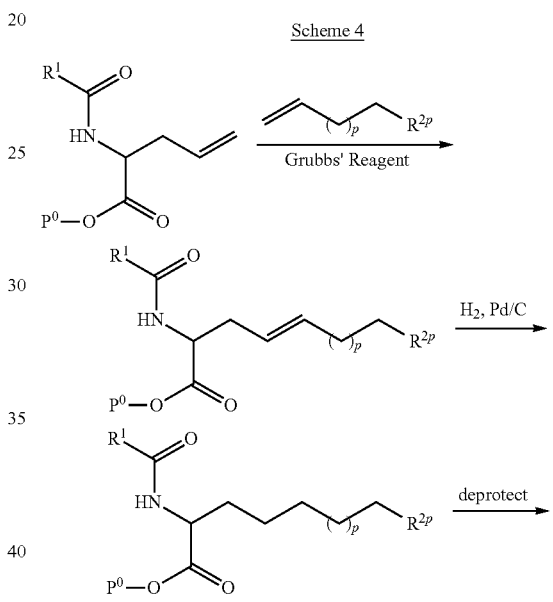

An exemplary embodiment of the preparative method in Scheme 4 is shown in Scheme 4a, where Ar is an optionally substituted aryl group.

Scheme 4a

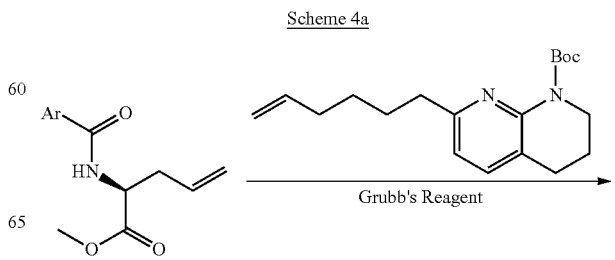

139

-continued

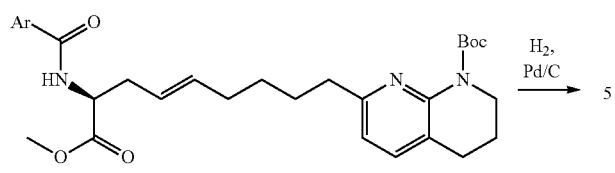

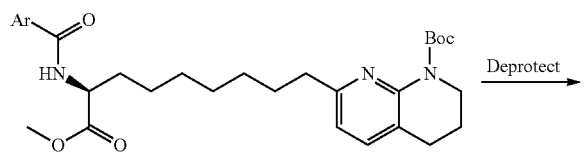

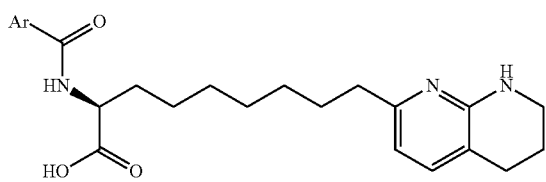

Compounds of the formula (IV-2) can be prepared according to Scheme 5, wherein $R^1$, $R^8$ and Y are as defined for formula (IV-2), or any variation thereof detailed herein; X is a leaving group (e.g., alkoxy, alkylthio, or halogen); $P^0$ is a carboxylic acid protecting group (e.g., methyl); p is 1, 2, 3, 4 or 5; and q is 0, 1, 2 or 3.

Scheme 5

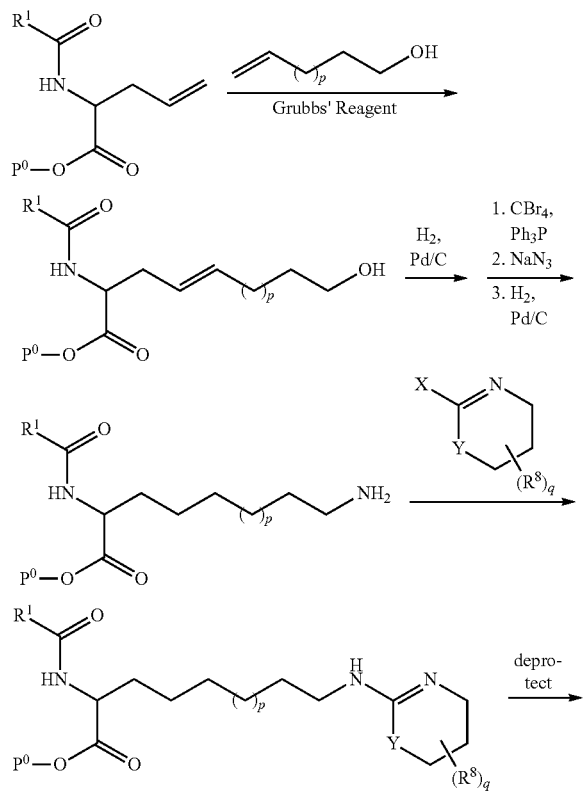

140

-continued

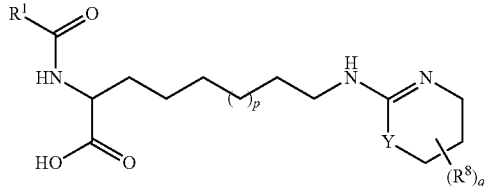

(IV-2)

An exemplary embodiment of the preparative method in Scheme 5 is shown in Scheme 5a, where Ar is an optionally substituted aryl group, X is a leaving group (e.g., alkoxy, alkylthio, or halogen); and R is an optional substituent (e.g., any of the $R^8$ groups detailed herein).

Scheme 5a

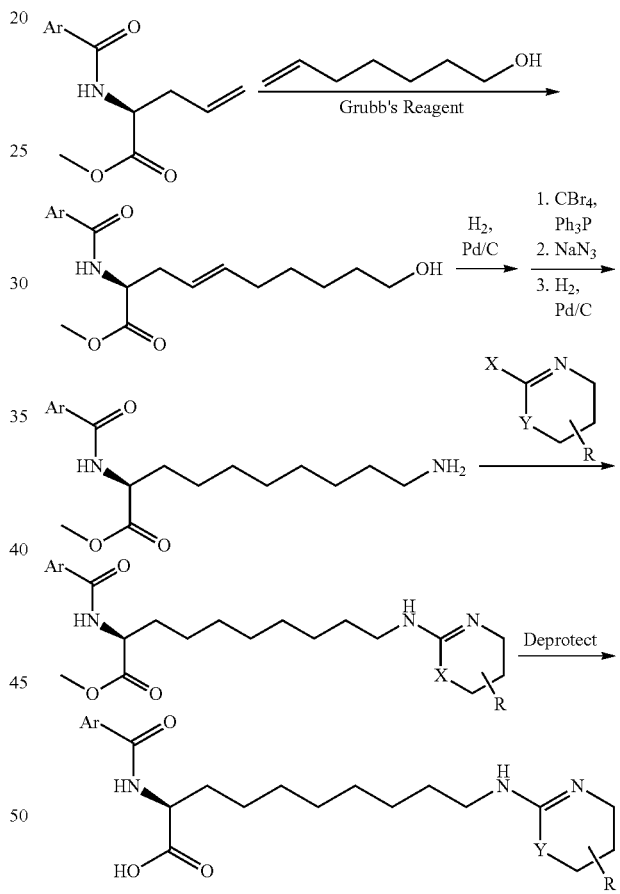

It is understood that the schemes above may be modified to arrive at various compounds of the invention by selection of appropriate reagents and starting materials. For a general description of protecting groups and their use, see P. G. M. Wuts and T. W. Greene, Greene's Protective Groups in Organic Synthesis 4th edition, Wiley-Interscience, New York, 2006.

Pharmaceutical Compositions and Formulations

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In one variation, "substantially pure" intends a composition that contains no more than 35% impurity, wherein the impurity denotes a compound other than the compound comprising the majority of the composition or a salt thereof. For example, a composition of a substantially pure compound selected from a compound of Table 1 or Table 2 intends a composition that contains no more than 35% impurity, wherein the impurity denotes a compound other than the compound or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure (S) compound means that the composition contains no more than 15% or no more than 10% or no more than 5% or no more than 3% or no more than 1% of the (R) form of the compound.

In one variation, the compounds herein are synthetic compounds prepared for administration to an individual such as a human. In another variation, compositions are provided containing a compound in substantially pure form. In another variation, the invention embraces pharmaceutical compositions comprising a compound detailed herein and a pharmaceutically acceptable carrier or excipient. In another variation, methods of administering a compound are provided. The purified forms, pharmaceutical compositions and methods of administering the compounds are suitable for any compound or form thereof detailed herein.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington: The Science and Practice of Pharmacy*, Lippincott Williams & Wilkins, $21^{st}$ ed. (2005), which is incorporated herein by reference.

Compounds as described herein may be administered to individuals (e.g., a human) in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

Compositions comprising a compound provided herein are also described. In one variation, the composition comprises a compound and a pharmaceutically acceptable carrier or excipient. In another variation, a composition of substantially pure compound is provided.

Methods of Use

Compounds and compositions of the invention, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

In one aspect, provided is a method of treating a fibrotic disease in an individual in need thereof comprising administering to the individual a therapeutically effective amount of a compound of formula (I), or any variation thereof, e.g., a compound of formula (I-A), (I-B), (II), (II-1), (III), (III-1), (III-2), (IV), (IV-1) or (IV-2), a compound selected from Compound Nos. 1-86 in Table 1, a compound selected from Compound Nos. 87-126 in Table 2, or a pharmaceutically acceptable salt thereof. In one aspect, the individual is a human. The individual, such as human, may be in need of treatment, such as a human who has or is suspected of having a fibrotic disease. In one aspect of the methods detailed herein, the methods described exclude use of a compound of Table 1x. In another aspect, the methods described herein include the use of a compound of Table 1X.

In another aspect, provided is a method of delaying the onset and/or development of a fibrotic disease in an individual (such as a human) who is at risk for developing a fibrotic disease. It is appreciated that delayed development may encompass prevention in the event the individual does not develop the fibrotic disease. An individual at risk of developing a fibrotic disease in one aspect has or is suspected of having one or more risk factors for developing a fibrotic disease. Risk factors for fibrotic disease may include an individual's age (e.g., middle-age or older adults), the presence of inflammation, having one or more genetic component associated with development of a fibrotic disease, medical history such as treatment with a drug or procedure believed to be associated with an enhanced susceptibility to fibrosis (e.g., radiology) or a medical condition believed to be associated with fibrosis, a history of smoking, the presence of occupational and/or environmental factors such as exposure to pollutants associated with development of a fibrotic disease.

In some embodiments, the fibrotic disease is fibrosis of a tissue such as the lung (pulmonary fibrosis), the liver, the skin, the heart (cardiac fibrosis), the kidney (renal fibrosis), or the gastrointestinal tract (gastrointestinal fibrosis).

In some embodiments, the fibrotic disease is a pulmonary fibrosis, e.g., idiopathic pulmonary fibrosis (IPF).

In some embodiments, the fibrotic disease is a liver fibrosis, e.g., infectious liver fibrosis (from pathogens such as HCV, HBV or parasites such as schistosomiasis), NASH, alcoholic steatosis induced liver fibrosis, and cirrhosis.

In another aspect, provided is a method of treating liver fibrosis in an individual, comprising administering to the individual a therapeutically effective amount of a compound of formula (I), or any variation thereof, e.g., a compound of formula (I-A), (I-B), (II), (II-1), (III), (III-1), (III-2), (IV), (IV-1) or (IV-2), a compound selected from Compound Nos. 1-86 in Table 1, a compound selected from Compound Nos. 87-126 in Table 2, or a pharmaceutically acceptable salt thereof. In one aspect, the individual is a human. The individual, such as the human, may be in need of treatment, such as a human who has or is suspected of having liver fibrosis. In some embodiments, the liver fibrosis is a result of or associated with nonalcoholic fatty liver disease (NAFLD), nonalcoholic steatohepatitis (NASH), alcoholic steatosis, or infection (such as viral hepatitis, which may be caused by HCV or HBV, or parasitic hepatitis, which may be caused by schistosomiasis). In one aspect of the methods detailed herein, the methods described exclude use of a compound of Table 1x. In another aspect, the methods described herein include the use of a compound of Table 1X.

In another aspect, provided is a compound of formula (I), or any variation thereof, e.g., a compound of formula (I-A), (I-B), (II), (II-1), (III), (III-1), (III-2), (IV), (IV-1) or (IV-2), a compound selected from Compound Nos. 1-86 in Table 1, a compound selected from Compound Nos. 87-126 in Table 2, or a pharmaceutically acceptable salt thereof, for use in the treatment of liver fibrosis.

Also provided is use of a compound of formula (I), or any variation thereof, e.g., a compound of formula (I-A), (I-B), (II), (II-1), (III), (III-1), (III-2), (IV), (IV-1) or (IV-2), a compound selected from Compound Nos. 1-86 in Table 1, a compound selected from Compound Nos. 87-126 in Table 2, or a pharmaceutically acceptable salt thereof, in the manufacture of a medicament for the treatment of liver fibrosis.

In another aspect, provided is a method of delaying the onset and/or development of liver fibrosis in an individual (such as a human) who is at risk for developing liver fibrosis. It is appreciated that delayed development may encompass prevention in the event the individual does not develop liver fibrosis. An individual at risk of developing a fibrotic disease in one aspect has or is suspected of having one or more risk factors for developing liver fibrosis. Risk factors for liver fibrosis may include an individual's age (e.g., middle-age or older adults), the presence of inflammation in the liver, having one or more genetic component associated with development of liver fibrosis, medical history such as treatment with a drug or procedure believed to be associated with an enhanced susceptibility to liver fibrosis or a medical condition believed to be associated with liver fibrosis (such as nonalcoholic fatty liver disease (NAFLD), nonalcoholic steatohepatitis (NASH), alcoholism, alcoholic steatosis, or liver infection (such as viral hepatitis, which may be caused by HCV or HBV, or parasitic hepatitis, which may be caused by schistosomiasis)), a history of smoking, the presence of occupational and/or environmental factors such as exposure to pollutants associated with development of liver fibrosis.

In some embodiments, the fibrotic disease is biliary tract fibrosis.

In some embodiments, the fibrotic disease is kidney fibrosis, e.g., diabetic nephrosclerosis, hypertensive nephrosclerosis, focal segmental glomerulosclerosis ("FSGS"), and acute kidney injury from contrast induced nephropathy.

In some embodiments, the fibrotic disease is systemic and local sclerosis or scleroderma, keloids and hypertrophic scars, or post surgical adhesions.

In some embodiments, the fibrotic disease is atherosclerosis or restenosis.

In some embodiments, the fibrotic disease is a gastrointestinal fibrosis, e.g., Crohn's disease.

In some embodiments, the fibrotic disease is cardiac fibrosis, e.g., post myocardial infarction induced fibrosis and inherited cardiomyopathy.

In one aspect, provided is a compound of formula (I), or any variation thereof, e.g., a compound of formula (I-A), (I-B), (II), (II-1), (III), (III-1), (III-2), (IV), (IV-1) or (IV-2), a compound selected from Compound Nos. 1-86 in Table 1, a compound selected from Compound Nos. 87-126 in Table 2, or a pharmaceutically acceptable salt thereof, for use in the treatment of a fibrotic disease.

Also provided is use of a compound of formula (I), or any variation thereof, e.g., a compound of formula (I-A), (I-B), (II), (II-1), (III), (III-1), (III-2), (IV), (IV-1) or (IV-2), a compound selected from Compound Nos. 1-86 in Table 1, a compound selected from Compound Nos. 87-126 in Table 2, or a pharmaceutically acceptable salt thereof, in the manufacture of a medicament for the treatment of a fibrotic disease.

In another aspect, provided is a method of inhibiting $\alpha v \beta 1$ integrin in an individual comprising administering a compound of formula (I), or any variation thereof, e.g., a compound of formula (I-A), (I-B), (II), (II-1), (III), (III-1), (III-2), (IV), (IV-1) or (IV-2), a compound selected from Compound Nos. 1-86 in Table 1, a compound selected from Compound Nos. 87-126 in Table 2, or a pharmaceutically acceptable salt thereof.

Also provided is a method of inhibiting TGFβ activation in a cell comprising administering to the cell a compound of formula (I), or any variation thereof, e.g., a compound of formula (I-A), (I-B), (II), (II-1), (III), (III-1), (III-2), (IV), (IV-1) or (IV-2), a compound selected from Compound Nos. 1-86 in Table 1, a compound selected from Compound Nos. 87-126 in Table 2, or a pharmaceutically acceptable salt thereof.

In any of the described methods, in one aspect the individual is a human, such as a human in need of the method. The individual may be a human who has been diagnosed with or is suspected of having a fibrotic disease. The individual may be a human who does not have detectable disease but who has one or more risk factors for developing a fibrotic disease.

Kits

The invention further provides kits for carrying out the methods of the invention, which comprises one or more compounds described herein or a pharmacological composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for use in the treatment of a fibrotic disease. In some embodiments, the kit contains instructions for use in the treatment of liver fibrosis.

Kits generally comprise suitable packaging. The kits may comprise one or more containers comprising any compound described herein. Each component (if there is more than one component) can be packaged in separate containers or some components can be combined in one container where cross-reactivity and shelf life permit. One or more components of a kit may be sterile and/or may be contained within sterile packaging.

The kits may be in unit dosage forms, bulk packages (e.g., multi-dose packages) or sub-unit doses. For example, kits may be provided that contain sufficient dosages of a compound as disclosed herein (e.g., a therapeutically effective amount) and/or a second pharmaceutically active compound useful for a disease detailed herein (e.g., fibrosis) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

EXEMPLARY EMBODIMENTS

The invention is further described by the following embodiments. The features of each of the embodiments are combinable with any of the other embodiments where appropriate and practical.

Embodiment 1

A compound of formula (I):

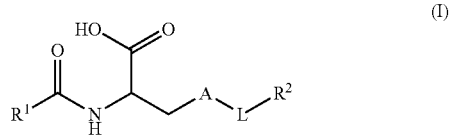

or a salt thereof, wherein:
$R^1$ is $C_6$-$C_{14}$ aryl or 5- to 10-membered heteroaryl, wherein the $C_6$-$C_{14}$ aryl and 5- to 10-membered heteroaryl of $R^1$ are independently optionally substituted by $R^{10}$;
$R^2$ is 5- to 10-membered heteroaryl containing at least 2 ring nitrogen atoms, 3- to 12-membered heterocyclyl containing at least 2 ring nitrogen atoms, or —NH—$R^3$, wherein the 5- to 10-membered heteroaryl and 3- to 12-membered heterocyclyl of $R^2$ are independently optionally substituted by $R^{10}$;
$R^3$ is 5- to 10-membered heteroaryl containing at least 1 ring nitrogen atom, or 3- to 12-membered heterocyclyl containing at least 1 ring nitrogen atom, wherein the 5- to 10-membered heteroaryl and 3- to 12-membered heterocyclyl of $R^3$ are independently optionally substituted by $R^{10}$;
-A-L- is -$A^1$-$L^1$-, -$A^2$-$L^2$-, or $A^3$;
$A^1$ is $C_3$-$C_8$ cycloalkylene, $C_3$-$C_8$ cycloalkenylene, $C_6$-$C_{14}$ arylene, 5- to 10-membered heteroarylene or 3- to 12-membered heterocyclylene, wherein the $C_3$-$C_8$ cycloalkylene, $C_3$-$C_8$ cycloalkenylene, $C_6$-$C_{14}$ arylene, 5- to 10-membered heteroarylene and 3- to 12-membered heterocyclylene of $A^1$ are independently optionally substituted by $R^{10}$;
$A^2$ is $C_3$-$C_8$ alkylene or $C_3$-$C_8$ alkenylene, wherein the $C_3$-$C_8$ alkylene and $C_3$-$C_8$ alkenylene of $A^2$ are independently optionally substituted by $R^9$;
$A^3$ is $C_5$-$C_{10}$ alkylene or $C_5$-$C_{10}$ alkenylene, wherein the $C_5$-$C_{10}$ alkylene and $C_5$-$C_{10}$ alkenylene of $A^3$ are independently optionally substituted by $R^9$;
$L^1$ is —O—Z—, —O—Z—$X^1$—, —O—$Y^1$—, —O—$Y^1$—$X^1$—, —O—Z—$Y^1$—, —O—Z—$Y^1$—$X^1$—, —O—Z—$X^1$—$Y^1$—, —O—Z—$X^1$—$Y^1$—$X^1$—, —Z—O—Z—, —$X^1$—Z—O—Z—, —Z—O—Z—$X^1$—, —$X^1$—Z—O—Z—$X^1$—, —Z—O—$Y^1$—, —Z—O—$Y^1$—$X^1$—, —$X^1$—Z—O—$Y^1$—, —$X^1$—Z—O—$Y^1$—$X^1$—, —N($R^4$)—Z—, —N($R^4$)—Z—$X^1$—, $X^2$, —$X^2$—$Y^1$—, $Y^2$, or —$Y^2$—$X^2$—;
$L^2$ is $C_3$-$C_6$ cycloalkylene optionally substituted by $R^{10}$;
each $X^1$ is independently $C_1$-$C_6$ alkylene or $C_2$-$C_6$ alkenylene, wherein the $C_1$-$C_6$ alkylene and $C_2$-$C_6$ alkenylene of $X^1$ are independently optionally substituted by $R^{10}$;
each $X^2$ is independently $C_1$-$C_6$ alkylene or $C_2$-$C_6$ alkenylene, wherein the $C_1$-$C_6$ alkylene and $C_2$-$C_6$ alkenylene of $X^2$ are independently optionally substituted by $R^9$;
each $Y^1$ is independently $C_3$-$C_6$ cycloalkylene optionally substituted by $R^{10}$;
each $Y^2$ is independently saturated 3- to 4-membered heterocyclylene optionally substituted by $R^{10}$;
each Z is independently —$CR^{5a}R^{5b}$—;
each $R^4$, $R^{5a}$ and $R^{5b}$ is independently H or $C_1$-$C_6$ alkyl;
each $R^9$ is independently $C_1$-$C_6$ alkyl, $C_2$-$C_6$ alkenyl, $C_2$-$C_6$ alkynyl,
halogen, —CN, —$OR^{11}$, —$SR^{11}$, —$NR^{12}R^{13}$, —$NO_2$, —C=NH($OR^{11}$), —C(O)$R^{11}$, —OC(O)$R^{11}$, —C(O)$OR^{11}$, —C(O)$NR^{12}R^{13}$, —$NR^{11}$C(O)$R^{12}$, —$NR^{11}$C(O)$OR^{12}$, —NR$^{11}$C(O)NR$^{12}$R$^{13}$, —S(O)R$^{11}$, —S(O)$_2$R$^{11}$, —NR$^{11}$S(O)R$^{12}$, —NR$^{11}$S(O)$_2$R$^{12}$, —S(O)NR$^{12}$R$^{13}$, —S(O)$_2$NR$^{12}$R$^{13}$, —P(O)(OR$^{12}$)(OR$^{13}$), C$_3$-C$_8$ cycloalkyl, 3- to 12-membered heterocyclyl, 5- to 10-membered heteroaryl or C$_6$-C$_{14}$ aryl, wherein each R$^9$ is independently optionally substituted by halogen, oxo, —OR$^{14}$, —NR$^{14}$R$^{15}$, —C(O)R$^{14}$, —CN, —S(O)R$^{14}$, —S(O)$_2$R$^{14}$, —P(O)(OR$^{14}$)(OR$^{15}$), C$_3$-C$_8$ cycloalkyl, 3- to 12-membered heterocyclyl, 5- to 10-membered heteroaryl, C$_6$-C$_{14}$ aryl, or C$_1$-C$_6$ alkyl optionally substituted by oxo, —OH or halogen;

each R$^{10}$ is independently oxo or R$^9$;

R$^{11}$ is independently hydrogen, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 6-membered heteroaryl or 3- to 6-membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 6-membered heteroaryl and 3- to 6-membered heterocyclyl are independently optionally substituted by halogen, oxo, —CN, —OR$^{16}$, —NR$^{16}$R$^{17}$, —P(O)(OR$^{16}$)(OR$^{17}$), or C$_1$-C$_6$ alkyl optionally substituted by halogen, —OH or oxo;

R$^{12}$ and R$^{11}$ are each independently hydrogen, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 6-membered heteroaryl or 3- to 6-membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 6-membered heteroaryl and 3- to 6-membered heterocyclyl are independently optionally substituted by halogen, oxo, —CN, —OR$^{16}$, —NR$^{16}$R$^{17}$ or C$_1$-C$_6$ alkyl optionally substituted by halogen, —OH or oxo;

or R$^{12}$ and R$^{11}$ are taken together with the atom to which they attached to form a 3- to 6-membered heterocyclyl optionally substituted by halogen, oxo, —OR$^{16}$, —NR$^{16}$R$^{17}$ or C$_1$-C$_6$ alkyl optionally substituted by halogen, oxo or —OH;

R$^{14}$ and R$^{15}$ are each independently hydrogen, C$_1$-C$_6$ alkyl optionally substituted by halogen or oxo, C$_2$-C$_6$ alkenyl optionally substituted by halogen or oxo, or C$_2$-C$_6$ alkynyl optionally substituted by halogen or oxo;

or R$^{14}$ and R$^{15}$ are taken together with the atom to which they attached to form a 3- to 6-membered heterocyclyl optionally substituted by halogen, oxo or C$_1$-C$_6$ alkyl optionally substituted by halogen or oxo; and R$^{16}$ and R$^{17}$ are each independently hydrogen, C$_1$-C$_6$ alkyl optionally substituted by halogen or oxo, C$_2$-C$_6$ alkenyl optionally substituted by halogen or oxo, or C$_2$-C$_6$ alkynyl optionally substituted by halogen or oxo;

or R$^{16}$ and R$^{17}$ are taken together with the atom to which they attached to form a 3-6 membered heterocyclyl optionally substituted by halogen, oxo or C$_1$-C$_6$ alkyl optionally substituted by oxo or halogen;

provided that the compound is other than a compound in Table 1X and salts thereof.

Embodiment 2

The compound of embodiment 1, or a salt thereof, wherein R$^1$ is a fused bicyclic C$_9$-C$_{14}$ aryl optionally substituted by R$^{10}$ or a fused bicyclic 7- to 10-membered heteroaryl optionally substituted by R$^{10}$.

Embodiment 3

The compound of embodiment 1 or 2, or a salt thereof, wherein R$^1$ is a fused bicyclic 7- to 10-membered heteroaryl optionally substituted by R$^{10}$.

Embodiment 4

The compound of embodiment 3, or a salt thereof, wherein R$^1$ is indazolyl optionally substituted by R$^{10}$, benzimidazolyl optionally substituted by R$^{10}$, or benzoxazolyl optionally substituted by R$^{10}$.

Embodiment 5

The compound of embodiment 1, or a salt thereof, wherein R$^1$ is phenyl optionally substituted by R$^{10}$.

Embodiment 6

The compound of embodiment 1, or a salt thereof, wherein R$^1$ is a monocyclic 5- or 6-membered heteroaryl optionally substituted by R$^{10}$.

Embodiment 7

The compound of any one of embodiments 1 to 6, or a salt thereof, wherein the -A-L-moiety is -A$^1$-L$^1$-.

Embodiment 8

The compound of embodiment 7, or a salt thereof, wherein A$^1$ is C$_6$-C$_{14}$ arylene optionally substituted by R$^{10}$.

Embodiment 9

The compound of embodiment 7, or a salt thereof, wherein A$^1$ is C$_3$-C$_8$ cycloalkylene optionally substituted by R$^{10}$.

Embodiment 10

The compound of embodiment 7, or a salt thereof, wherein A$^1$ is 5- to 10-membered heteroarylene optionally substituted by R$^{10}$.

Embodiment 11

The compound of embodiment 7, or a salt thereof, wherein A$^1$ is 3- to 12-membered heterocyclylene optionally substituted by R$^{10}$.

Embodiment 12

The compound of embodiment 7, or a salt thereof, wherein A$^1$ is selected from the group consisting of 1,4-phenylene, 1,3-phenylene, 1,1-cyclopropylene, 1,2-cyclopropylene, 1,3-cyclobutylene, 1,4-cyclohexylene, 1,3-azetidinylene, 1,3-pyrrolidinylene, and 2,5-benzo[d]oxazolylene.

Embodiment 13

The compound of any one of embodiments 7 to 12, or a salt thereof, wherein L$^1$ is —O—Z—, —O—Z—X$^1$—, —O—Y$^1$—, —O—Z—Y$^1$—, —O—Z—X$^1$—Y$^1$—, —Z—O—Z—, —X$^1$—Z—O—Z—, —Z—O—Z—X$^1$—, —X$^1$—Z—O—Z—X$^1$—, —Z—O—Y$^1$—, or —X$^1$—Z—O—Y$^1$—.

Embodiment 14

The compound of embodiment 13, or a salt thereof, wherein Z is —CR$^{5a}$R$^{5b}$— where each of R$^{5a}$ and R$^{5b}$ is H.

Embodiment 15

The compound of embodiment 13, or a salt thereof, wherein $L^1$ is selected from the group consisting of —O—(CH$_2$)$_3$—, —O—(CH$_2$)$_4$—, —CH$_2$—O—(CH$_2$)$_3$—, —CH$_2$—O—(CH$_2$)$_2$—, —CH(CH$_3$)—O—(CH$_2$)$_2$—, —CH$_2$—O—(CH$_2$)$_3$—,

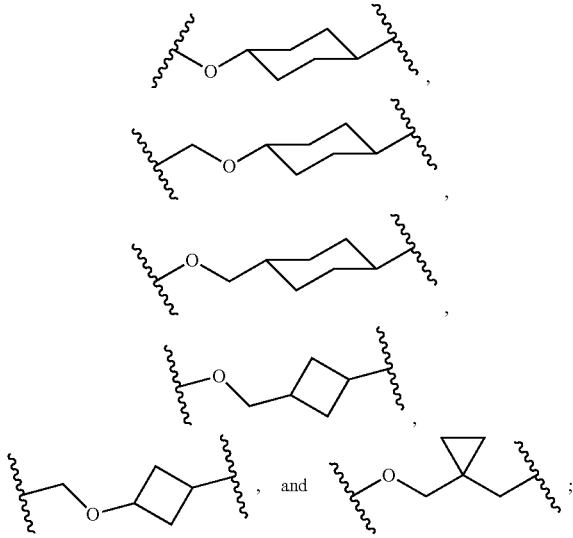

wherein the wavy lines denote attachment points to the parent molecule.

Embodiment 16

The compound of any one of embodiments 7 to 12, or a salt thereof, wherein $L^1$ is —N(R$^4$)—Z— or —N(R$^4$)—Z—X$^1$—.

Embodiment 17

The compound of embodiment 16, or a salt thereof, wherein R$^4$ is H and Z is —CR$^{5a}$R$^{5b}$— where each of R$^{5a}$ and R$^{5b}$ is H.

Embodiment 18

The compound of embodiment 17, or a salt thereof, wherein $L^1$ is —NH—C(CH$_3$)$_2$—(CH$_2$)$_2$—.

Embodiment 19

The compound of any one of embodiments 7 to 12, or a salt thereof, wherein $L^1$ is X$^2$ or —X$^2$—Y$^1$—.

Embodiment 20

The compound of embodiment 19, or a salt thereof, wherein $L^1$ is selected from the group consisting of —(CH$_2$)$_2$—, —(CH$_2$)$_4$—, —(CH$_2$)$_5$—, —CF$_2$—(CH$_2$)$_3$— and

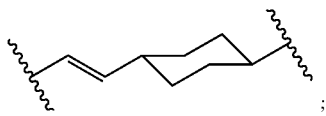 [SMILES: */C=C/C1CCC(*)CC1]

wherein the wavy lines denote attachment points to the parent molecule.

Embodiment 21

The compound of any one of embodiments 7 to 12, or a salt thereof, wherein $L^1$ is Y$^2$, or —Y$^2$—X$^2$—.

Embodiment 22

The compound of embodiment 21, or a salt thereof, wherein Y$^2$ is saturated 4-membered heterocyclylene optionally substituted by R$^{10}$.

Embodiment 23

The compound of embodiment 21, or a salt thereof, wherein Y$^2$ is 1,3-azetidinylene.

Embodiment 24

The compound of embodiment 21, or a salt thereof, wherein $L^1$ is selected from the group consisting of

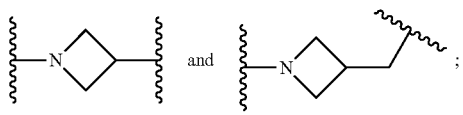 [SMILES: *C1CN(*)C1 ; *CC1CN(*)C1]

wherein the wavy lines denote attachment points to the parent molecule.

Embodiment 25

The compound of any one of embodiments 1 to 6, or a salt thereof, wherein the -A-L- moiety is -A$^2$-L$^2$- or A$^3$.

Embodiment 26

The compound of embodiment 25, or a salt thereof, wherein A$^2$ is C$_3$-C$_8$ alkylene optionally substituted by R$^9$.

Embodiment 27

The compound of embodiment 25, or a salt thereof, wherein A$^3$ is C$_5$-C$_{10}$ alkenylene optionally substituted by R$^9$.

Embodiment 28

The compound of embodiment 25, or a salt thereof, wherein the -A-L-moiety is selected from the group consisting of —CH$_2$(CH$_2$)$_5$CH$_2$—, —CH$_2$(CH$_2$)$_4$CH$_2$—, —CH=CH—(CH$_2$)$_3$CH$_2$—, and

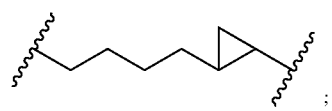 [SMILES: *CCCCC1CC1*]

wherein the wavy lines denote attachment points to the parent molecule.

Embodiment 29

The compound of any one of embodiments 1 to 28, or a salt thereof, wherein $R^2$ is 5- to 10-membered heteroaryl containing at least 2 ring nitrogen atoms optionally substituted by $R^{10}$, or 3- to 12-membered heterocyclyl containing at least 2 ring nitrogen atoms optionally substituted by $R^{10}$.

Embodiment 30

The compound of embodiment 29, or a salt thereof, wherein $R^2$ is selected from the group consisting of 5,6,7,8-tetrahydro-naphthyridinyl, 1,2,3,4-tetrahydro-1,8-naphthyridinyl, 3,4-dihydro-2H-pyrido[3,2-b][1,4]oxazinyl, and 2,3-dihydro-1H-pyrrolo[2,3-b]pyridinyl.

Embodiment 31

The compound of any one of embodiments 1 to 28, or a salt thereof, wherein $R^2$ is —NH—$R^3$.

Embodiment 32

The compound of embodiment 31, or a salt thereof, wherein $R^3$ is 5- to 10-membered heteroaryl containing at least 1 ring nitrogen atom optionally substituted by $R^{10}$.

Embodiment 33

The compound of embodiment 32, or a salt thereof, wherein $R^3$ is selected from the group consisting of 4,5-dihydro-1H-imidazolyl, 5,6-dihydro-4H-1,3-oxazinyl, 4,5-dihydrothiazolyl, 3,4,5,6-tetrahydropyrazinyl, 5,6-dihydro-4H-1,3-thiazinyl.

Embodiment 34

The compound of embodiment 31, or a salt thereof, wherein $R^3$ is pyridinyl optionally substituted by $R^{10}$.

Embodiment 35

The compound of embodiment 34, or a salt thereof, wherein $R^3$ is selected from the group consisting of 4,5-dihydro-1H-imidazolyl, 5,6-dihydro-4H-1,3-oxazinyl, 4,5-dihydrothiazolyl, 3,4,5,6-tetrahydropyrazinyl, 5,6-dihydro-4H-1,3-thiazinyl.

Embodiment 36

The compound of embodiment 1, wherein the compound is selected from Compound Nos. 1-86 in Table 1, or a salt thereof.

Embodiment 37

A pharmaceutical composition comprising a compound of any one of embodiments 1 to 36, or a salt thereof, and a pharmaceutically acceptable carrier or excipient.

Embodiment 38

A method of treating a fibrotic disease in an individual in need thereof comprising administering to the individual a therapeutically effective amount of a compound of any one of embodiments 1 to 36 or a pharmaceutically acceptable salt thereof.

Embodiment 39

The method of embodiment 38, wherein the fibrotic disease is pulmonary fibrosis, liver fibrosis, skin fibrosis, cardiac fibrosis, kidney fibrosis, or gastrointestinal fibrosis.

Embodiment 40

A kit comprising a compound of any one of embodiments 1 to 36, or a pharmaceutically acceptable salt thereof.

Embodiment 41

The kit of embodiment 40, further comprising instructions for the treatment of a fibrotic disease.

Embodiment 42

A method of inhibiting αvβ1 integrin in an individual comprising administering a compound of any one of embodiments 1 to 36 or a pharmaceutically acceptable salt thereof.

Embodiment 43

A method of inhibiting TGFβ activation in a cell comprising administering to the cell a compound of any one of embodiments 1 to 36 or a pharmaceutically acceptable salt thereof.

Embodiment 44

Use of a compound of any one of embodiments 1 to 36 or a pharmaceutically acceptable salt thereof in the manufacture of a medicament for the treatment of a fibrotic disease.

SYNTHETIC EXAMPLES

The chemical reactions in the Synthetic Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

Example 1
Synthesis of (S)-2-benzamido-3-(4-(3-(5,6,7,8-tetrahydro-1,8-naphthyridin-2-yl)propoxy)phenyl)propanoic acid
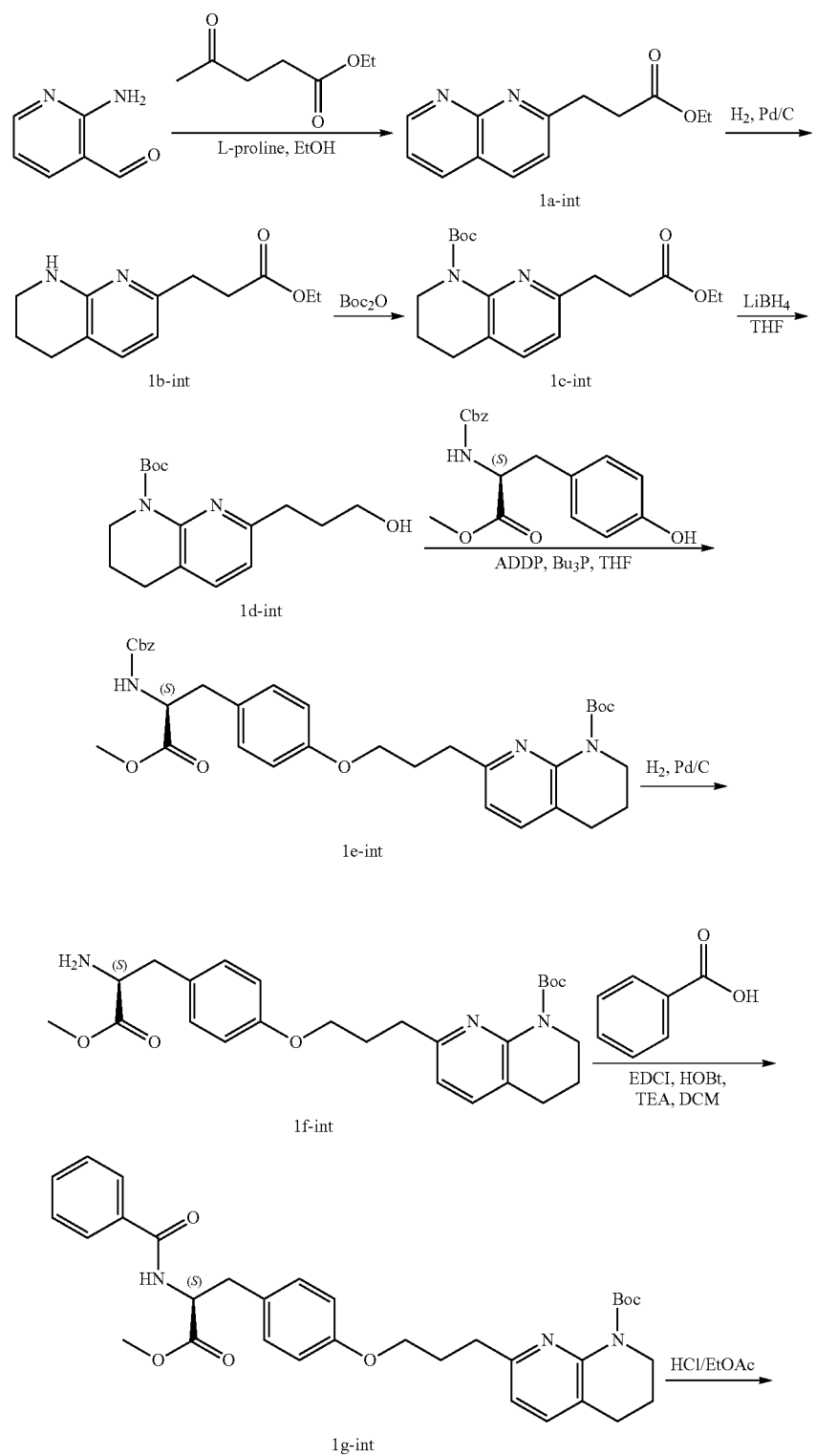

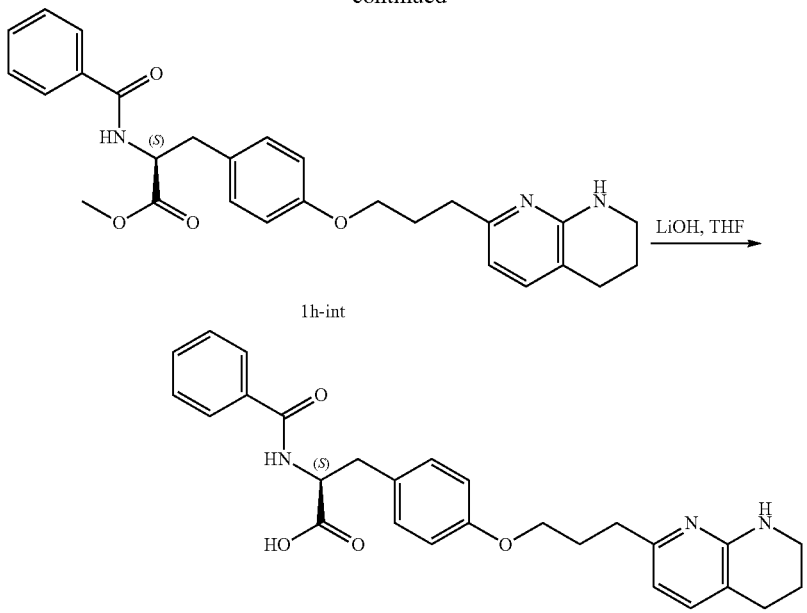

Example 1

Compound 1a-int: To a mixture of 2-aminonicotinaldehyde (50 g, 409.4 mmol) in EtOH (600 mL) was added ethyl 4-oxopentanoate (59.02 g, 409.4 mmol, 58.44 mL) and L-proline (23.57 g, 204.7 mmol). The reaction was refluxed at 80° C. for 12 hrs. TLC (PE:EtOAc=1:1, $R_f$=0.5) showed the reaction was complete. The reaction mixture was concentrated to give a residue. The residue was purified by column chromatography (SiO$_2$, PE:EtOAc=3:1 to 1:1) to obtain a pure product compound 1a-int. LCMS (ESI+): m/z=231.0 (M+H)$^+$, RT=0.72 min.

Compound 1b-int: To a solution of compound 1a-int (39 g, 169.37 mmol) in MeOH (500 mL) was added Pd/C (12 g) under N$_2$. The suspension was degassed under vacuum and purged with H$_2$ several times. The mixture was stirred under H$_2$ (50 psi) at 50° C. for 6 hrs. TLC (PE:EtOAc=10:1, $R_f$=0.6) indicated the compound 1a-int was consumed completely. The catalyst was removed by filtration and washed with MeOH (500 mL) 2 times. The mixture concentrated under reduced pressure to give compound 1b-int, which was used directly in the next step without any further purification.

Compound 1c-int: Compound 1b-int (36.00 g, 153.66 mmol) was added to the Boc$_2$O (300 mL) at 25° C. The reaction mixture was allowed to stir at 50° C. for 12 hrs. LCMS indicated the desired product and the reaction was complete. The crude product was purified by column chromatography (SiO$_2$, PE:EtOAc=10:1 to 1:1) to give a pure compound 1c-int. LCMS (ESI+): m/z=335.2 (M+H)$^+$, RT=0.64 min.

Compound 1d-int: To a solution of compound 1c-int (20 g, 59.81 mmol) in THF (200 mL) was added LiBH$_4$ (2.61 g, 119.62 mmol) at 0° C. The reaction was stirred at 30° C. for 30 min and at 40° C. for 5 hrs. TLC (PE:EtOAc=10:1, $R_f$=0.5) indicated the compound 1c-int was consumed completely. The desired product was detected by LCMS. The mixture was poured into saturated NH$_4$Cl (500 mL). The product was extracted with EtOAc (500 mL). The organic layer was washed with brine (200 mL), dried by NaSO$_4$ and concentrated in vacuo. The residue was purified by column chromatography (SiO$_2$, PE:EtOAc=10:1 to 1:1) to give compound 1d-int. LCMS (ESI+): m/z=335.2 (M+H)$^+$, RT=0.695 min; $^1$H NMR (400 MHz, CHLOROFORM-d): δ ppm 1.29 (t, J=7.02 Hz, 1H) 1.56 (s, 8H) 1.54-1.57 (m, 1H) 1.92-1.99 (m, 4H) 2.75 (t, J=6.58 Hz, 2H) 2.92 (t, J=6.58 Hz, 2H) 3.66-3.74 (m, 2H) 3.75-3.82 (m, 2H) 4.19-4.33 (m, 1H) 4.25 (br s, 1H) 6.86 (d, J=7.45 Hz, 1H) 7.34 (d, J=7.45 Hz, 1H).

Compound 1e-int: To a solution of 1d-int (3 g, 10.26 mmol) and methyl (2S)-2-(benzyloxycarbonyl amino)-3-(4-hydroxyphenyl)propanoate (4.06 g, 12.31 mmol) in dry THF (10 mL) was added ADDP (6.47 g, 25.65 mmol) at 0° C. under N$_2$. Bu$_3$P (5.19 g, 25.65 mmol, 6.33 mL) was added drop-wisedly to the reaction mixture at 0° C. After the addition was complete, the reaction mixture was allowed to warm to 20° C. with stirring over 2 hr then maintained at 40° C. over 12 hr. TLC (PE:EtOAc=2:1, $R_f$=0.2) indicated 1d-int (3 g, 10.26 mmol) remained, but some new spots were detected. LCMS indicated that 1e-int was present. The mixture was concentrated to give the crude product. The crude product was purified by column chromatography (SiO$_2$, PE:EtOAc=10:1 to 1:1) to obtain compound 1e-int. LCMS (ESI+): m/z=604.3 (M+H)$^+$; RT: 2.355 min.

Compound 1f-int: To a solution of compound 1e-int (3.00 g, 4.97 mmol) in MeOH (30 mL) was added Pd/C (0.5 g). The suspension was degassed under vacuum and purged with H$_2$ several times. The mixture was stirred under H$_2$ (15 psi) at 30° C. for 3 hrs. TLC (PE:EtOAc=1:1, $R_f$=0.3) indicated compound 1e-int was consumed completely. LCMS indicated the desired product was present. The product was filtered and concentrated under reduced pressure. The crude product was purified by column chromatography (SiO$_2$, PE:EtOAc=1:1 to 10:1) to give compound 1f-int. LCMS (ESI+): m/z=470.2 (M+H)$^+$; RT=0.63 min.

Compound 1g-int: A solution of compound 1f-int (200 mg, 425.92 umol), benzoic acid (52.01 mg, 425.92 umol), EDCI (106.14 mg, 553.7 umol), HOBt (74.82 mg, 553.7 umol) and DIEA (82.57 mg, 638.88 umol) in DMF (2 mL) was stirred at 25° C. for 10 hrs. LCMS showed that 1g-int was present. The reaction was poured into water (10 mL) and extracted with ethyl acetate (15 mL×3). The organic layers were combined, washed with brine (20 mL), dried over sodium sulfate and evaporated under reduced pressure. The crude product was purified by prep-TLC (PE:EtOAc=5: 1, $R_f$=0.5) to give compound 1g-int. LCMS (ESI+): m/z 574.3 (M+H)+, RT: 0.95 min.

Compound 1h-int: A solution of compound 1g-int (90 mg, 156.88 umol) in HCl/EtOAc (10 mL) was stirred at 25° C. for 12 hrs. LCMS showed that the desired product was present. The solvent was removed in vacuo to give compound 1h-int. The crude product was used directly in the next step. LCMS (ESI+): m/z 474.2 (M+H)$^+$, RT: 0.84 min.

Example 1

To a solution of compound 1h-int (100 mg, 196.07 umol) in THF (3 mL) and H$_2$O (3 mL) was added LiOH. H$_2$O (41.14 mg, 980.35 umol) at 25° C. The mixture was stirred at 25° C. for 12 hrs. LCMS showed that the desired product was present. The reaction mixture was adjusted to pH 6 with 10% citric acid and the solvent was removed. The crude product was purified by prep-HPLC to give Example 1.

HPLC purification conditions: Gilson 281 semi-preparative HPLC system; Mobile phase A: TFA/H$_2$O=0.075% v/v; B: ACN (gradient of B 15% at T=0 to 45% at T=10 min); Column: Luna C18 100×30 5 u; Flow rate: 25 mL/min; Monitor wavelength: 220 & 254 nm.

$^1$H NMR (400 MHz, METHANOL-d$_4$) δ=7.71-7.75 (m, 2H) 7.49-7.55 (m, 2H) 7.40-7.46 (m, 2H) 7.19 (d, J=8.60 Hz, 2H) 6.78 (d, J=8.60 Hz, 2H) 6.60 (d, J=7.28 Hz, 1H) 4.80 (dd, J=9.48, 4.85 Hz, 1H) 4.00 (t, J=5.73 Hz, 2H) 3.45-3.51 (m, 2H) 3.24-3.30 (m, 2H) 3.03 (dd, J=13.89, 9.70 Hz, 1H) 2.87 (t, J=7.50 Hz, 2H) 2.79 (t, J=6.28 Hz, 2H) 2.09-2.17 (m, 2H) 1.94 (quin, J=5.95 Hz, 2H); LCMS (ESI+): m/z 460. (M+H)$^+$, RT: 2.2 min; HPLC purity: 99.6%, RT: 5 min; Chiral SFC purity: 97.5%, e.e. value: 95.0%, RT: 3.0 min.

Example 2

Synthesis of (S)-2-(1-methyl-1H-benzo[d]imidazole-6-carboxamido)-3-(4-(3-(5,6,7,8-tetrahydro-1,8-naphthyridin-2-yl)propoxy)phenyl)propanoic acid Example 2

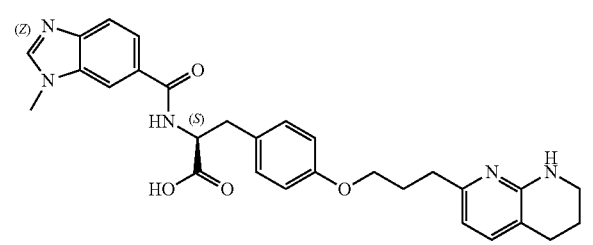

Example 2 was prepared by the same procedure used to prepare Example 1 with the exception that benzoic acid was replaced by 1-methyl-1H-benzo[d]imidazole-6-carboxylic acid in the reaction with intermediate 1f-int.

HPLC purification conditions: Gilson 281 semi-preparative HPLC system; Mobile phase A: TFA/H$_2$O=0.075% v/v; B: ACN (gradient: % B at T=0: 20; at T=12 min: 50%); Column: YMC-Actus Triart C18 150×30 5 u; Flow rate: 25 mL/min; Monitor wavelength: 220 & 254 nm.

$^1$H NMR (400 MHz, METHANOL-d$_4$): δ ppm 8.95 (s, 1H) 8.20 (s, 1H) 7.88-7.90 (d, J=8.80 Hz, 1H) 7.79-7.81 (d, J=8.80 Hz, 1H) 7.51-7.53 (d, J=7.20 Hz, 2H) 7.20-7.22 (d, J=8.40 Hz, 2H) 6.78-6.80 (d, J=8.40 Hz, 2H) 6.58-6.60 7.20-7.22 (d, J=8.40 Hz, 1H) 4.80 (m, 1H) 4.07 (s, 3H) 3.98-4.01 (t, J=5.73 Hz, 2H) 3.46-3.49 (t, J=5.51 Hz, 2H) 3.31 (m, 1H) 3.04-3.10 (m, 1H) 2.77-2.88 (m, 4H) 2.10-2.14 (m, 2H) 1.91-1.94 (m, 2H); LCMS (ESI+): m/z 513.6 (M+H)$^+$, RT: 1.83 min; HPLC purity: 99.1%, RT: 2.95 min; Chiral SFC purity: 95.3%, e.e. value: 90.58%, RT: 2.5 min.

Example 3

Synthesis of (S)-2-(5-(difluoromethyl)pyrazine-2-carboxamido)-3-(4-(3-(5,6,7,8-tetrahydro-1,8-naphthyridin-2-yl)propoxy)phenyl)propanoic acid Example 3

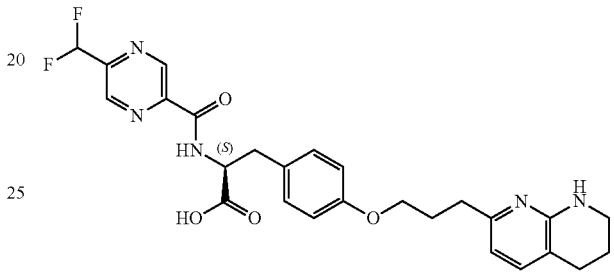

Example 3 was prepared by the same procedure used to prepare Example 1 with the exception that benzoic acid was replaced by 5-(difluoromethyl)pyrazine-2-carboxylic acid in the reaction with intermediate 1f-int.

HPLC purification conditions: Gilson 281 semi-preparative HPLC system; Mobile phase A: TFA/H$_2$O=0.075% v/v; B: ACN (gradient: % B at T=0: 23; at T=10 min: 53); Column: Luna C18 100*30 5 u; Flow rate: 25 mL/min; Monitor wavelength: 220 & 254 nm.

$^1$H NMR (400 MHz, METHANOL-d$_4$): δ ppm 1.95 (br s, 2H) 2.08-2.17 (m, 2H) 2.81 (br s, 2H) 2.87 (br t, J=7.89 Hz, 2H) 3.14 (dd, J=14.03, 7.89 Hz, 1H) 3.26-3.30 (m, 1H) 3.28 (br s, 1H) 3.49 (br s, 2H) 3.98 (br d, J=5.26 Hz, 2H) 6.56-6.64 (m, 1H) 6.73-6.78 (m, 2H) 6.89-6.95 (m, 1H) 6.92 (d, J=2.19 Hz, 1H) 7.06 (s, 1H) 7.04-7.07 (m, 1H) 7.10-7.17 (m, 2H) 7.54 (br s, 1H) 8.88-9.01 (m, 1H) 8.95 (br s, 1H) 9.21-9.29 (m, 1H) 9.25 (s, 1H); LCMS (ESI+): m/z=512.1 (M+H)$^+$, RT: 2.6 min.

Example 4

Synthesis of (S)-2-(6-phenylpyrazine-2-carboxamido)-3-(4-(3-(5,6,7,8-tetrahydro-1,8-naphthyridin-2-yl)propoxy)phenyl)propanoic acid Example 4

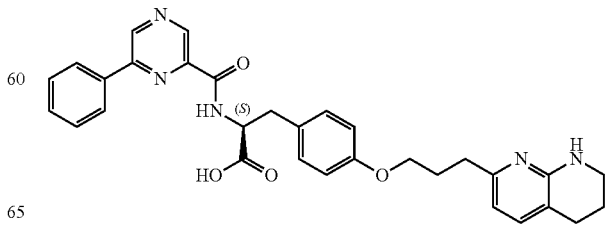

Example 4 was prepared by the same procedure used to prepare Example 1 with the exception that benzoic acid was replaced by 6-phenylpyrazine-2-carboxylic acid in the reaction with intermediate 1f-int.

HPLC purification conditions: Gilson 281 semi-preparative HPLC system; Mobile phase A: 10 mM $NH_4HCO_3$ in $H_2O$; B: AcN (gradient: % B at T=0: 30; at T=12 min: 60); Column: YMC-Actus Triart C18 150×30 5 u; Flow rate: 25 mL/min; Monitor wavelength: 220 & 254 nm.

$^1$H NMR (400 MHz, DMSO-$d_6$): δ ppm 9.41 (s, 1H), 9.05 (s, 1H), 8.19 (br d, J=7.50 Hz, 2H), 7.54 (br d, J=6.39 Hz, 3H), 7.13 (br d, J=8.16 Hz, 1H), 7.10-7.16 (m, 1H), 7.06 (br d, J=7.28 Hz, 1H), 6.72 (br d, J=8.38 Hz, 2H), 6.26 (d, J=7.06 Hz, 1H), 4.61 (br t, J=5.95 Hz, 1H), 3.80 (br t, J=6.06 Hz, 2H), 3.22 (br t, J=5.18 Hz, 2H), 3.16 (br d, J=5.95 Hz, 2H), 2.56 (br d, J=5.95 Hz, 4H), 1.86-1.95 (m, 2H), 1.72 (br d, J=4.85 Hz, 2H); LCMS (ESI+): m/z 538.1. (M+H)$^+$, RT: 2.4 min; HPLC purity: 97.8%, RT=5.1 min; Chiral SFC purity: 100%, ee value: 100%, RT=2.8 min.

Example 5

Synthesis of (S)-2-(2,6-dichloro-4-cyanobenzamido)-3-(4-(3-(5,6,7,8-tetrahydro-1,8-naphthyridin-2-yl)propoxy)phenyl)propanoic acid

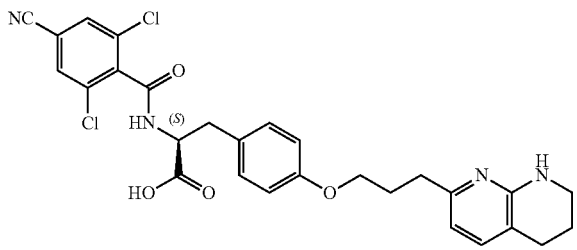

Example 5

Example 5 was prepared by the same procedure used to prepare Example 1 with the exception that benzoic acid was replaced by 2,6-dichloro-4-cyanobenzoic acid in the reaction with intermediate 1f-int.

HPLC purification conditions: Gilson 281 semi-preparative HPLC system; Mobile phase A: TFA/$H_2O$=0.075% v/v; B: AcN (gradient % B at T=0: 20%; at T=11.5 min: 50%); Column: Boston Green ODS 150×30 5 u; Flow rate: 25 mL/min; Monitor wavelength: 220 & 254 nm.

$^1$H NMR (400 MHz, METHANOL-$d_4$): δ ppm 7.83 (s, 2H), 7.56 (d, J=7.50 Hz, 1H), 7.19 (d, J=8.60 Hz, 2H), 6.73-6.84 (m, 2H), 6.62 (d, J=7.50 Hz, 1H), 4.88-4.93 (m, 1H), 4.00 (t, J=5.84 Hz, 2H), 3.42-3.53 (m, 2H), 3.22 (dd, J=14.22, 5.18 Hz, 1H), 2.83-2.96 (m, 3H), 2.80 (t, J=6.28 Hz, 2H), 2.07-2.22 (m, 2H), 1.93 (dt, J=12.02, 5.90 Hz, 2H); LCMS (ESI+): m/z=553.0 (M+H)$^+$; RT: 2.3 min; HPLC purity: 100%, RT: 4.9 min; Chiral SFC purity: 100%, e.e. value: 100%, RT: 3.0 min.

Example 6

Synthesis of (S)-2-(2-fluoro-6-(trifluoromethyl)benzamido)-3-(4-(3-(5,6,7,8-tetrahydro-1,8-naphthyridin-2-yl)propoxy)phenyl)propanoic acid

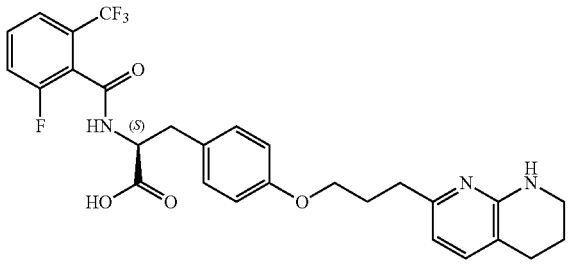

Example 6

Example 6 was prepared by the same procedure used to prepare Example 1 with the exception that benzoic acid was replaced by 2-fluoro-6-(trifluoromethyl)benzoic acid in the reaction with intermediate 1f-int.

HPLC purification conditions: Gilson 281 semi-preparative HPLC system; Mobile phase A: TFA/$H_2O$=0.075% v/v; B: AcN (gradient % B at T=0: 21%; at T=10 min: 51%); Column: Luna C18 100×30 5 u; Flow rate: 25 mL/min; Monitor wavelength: 220 & 254 nm.

$^1$H NMR (400 MHz, METHANOL-$d_4$): δ ppm 7.62-7.63 (m, 1H), 7.54-7.56 (d, J=7.2 Hz, 2H), 7.42-7.46 (m, 2H), 7.17-7.19 (d, J=8.4 Hz, 2H), 6.78-6.80 (d, J=8.4 Hz, 2H), 6.61-6.63 (d, J=7.6 Hz, 1H), 4.82 (m, 1H), 4.01-4.03 (t, 2H), 3.47-3.50 (t, 2H), 3.15 (dd, 1H), 2.87-2.98 (m, 3H), 2.79-2.82 (t, 2H), 2.15 (m, 2H), 1.93-1.96 (m, 2H); LCMS (ESI+): m/z=546.1 (M+H)$^+$, RT: 2.3 min; HPLC purity=99.6% RT: 4.9 min; Chiral SFC purity: 94.5%, ee value: 89.0%, RT: 6.3 min.

Example 7

Synthesis of (S)-2-(2,6-difluorobenzamido)-3-(4-(3-(5,6,7,8-tetrahydro-1,8-naphthyridin-2-yl)propoxy) phenyl)propanoic acid

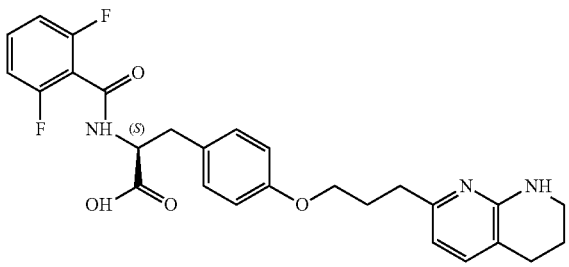

Example 7

Example 7 was prepared by the same procedure used to prepare Example 1 with the exception that benzoic acid was replaced by 2,6-difluorobenzoic acid in the reaction with intermediate 1 f-int.

HPLC purification conditions: Gilson 281 semi-preparative HPLC system; Mobile phase A: TFA/$H_2O$=0.075% v/v;

B: AcN (gradient % B at T=0: 20%; at T=11.5 min: 45%); Column: Boston Green ODS 150×30 5 u; Flow rate: 25 mL/min; Monitor wavelength: 220 & 254 nm.

$^1$H NMR (400 MHz, METHANOL-$d_4$): δ ppm 7.60 (d, J=7.50 Hz, 1H), 7.46-7.55 (m, 1H), 2.85 (t, J=6.17 Hz, 2H), 7.23 (d, J=8.60 Hz, 2H), 7.05 (t, J=8.05 Hz, 2H), 6.84 (d, J=8.60 Hz, 2H), 6.67 (d, J=7.28 Hz, 1H), 4.78-4.83 (m, 1H), 4.08 (t, J=5.84 Hz, 2H), 3.51-3.56 (m, 2H), 3.26 (dd, J=14.00, 5.18 Hz, 1H), 3.00 (dd, J=14.00, 8.93 Hz, 1H), 2.94 (t, J=7.50 Hz, 2H), 2.15-2.24 (m, 2H), 1.99 (quin, J=5.95 Hz, 2H); LCMS (ESI+): m/z=496.1 (M+H)$^+$, RT=2.2 min; HPLC purity: 99.1%, RT: 4.5 min; Chiral SFC purity: 100%, e.e. value: 100%, RT: 3.0 min.

Example 8

Synthesis of (S)-2-(2-methylpyrimidine-4-carboxamido)-3-(4-(3-(5,6,7,8-tetrahydro-1,8-naphthyridin-2-yl)propoxy)phenyl)propanoic acid Example 8

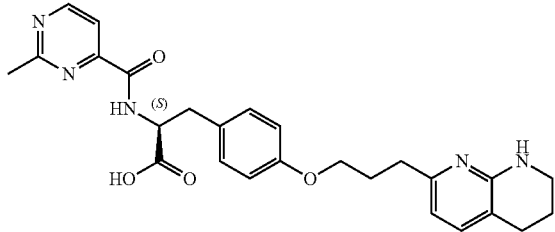

Example 8 was prepared by the same procedure used to prepare Example 1 with the exception that benzoic acid was replaced by 2-methylpyrimidine-4-carboxylic acid in the reaction with intermediate 1f-int.

HPLC purification conditions: Gilson 281 semi-preparative HPLC system; Mobile phase A: TFA/H$_2$O=0.075% v/v; B: AcN (gradient % B at T=0: 17%; at T=11.5 min: 47%); Column: Boston Green ODS 150×30 5 u; Flow rate: 25 mL/min; Monitor wavelength: 220 & 254 nm.

$^1$H NMR (400 MHz, METHANOL-$d_4$): δ 8.86 (d, J=5.0 Hz, 1H) 7.81 (d, J=5.0 Hz, 1H) 7.53 (d, J=7.2 Hz, 1H) 7.06-7.15 (m, 2H) 6.71-6.79 (m, 2H) 6.59 (d, J=7.2 Hz, 1H) 4.77-4.81 (m, 1H) 3.97 (t, J=5.8 Hz, 2H) 3.42-3.50 (m, 2H) 3.22-3.27 (m, 1H) 3.08-3.16 (m, 1H) 2.82-2.89 (m, 2H) 2.78 (t, J=6.1 Hz, 2H) 2.72 (s, 3H) 2.05-2.16 (m, 2H) 1.86-1.96 ppm (m, 2H); LCMS (ESI+): m/z=575.5 (M+H)$^+$, RT=2.1 min; HPLC purity=100%, RT: 4.3 min; Chiral SFC purity: 95.7%, ee value: 91.2%, RT: 3.8 min.

Example 9

Synthesis of (S)-2-(1-methyl-1H-benzo[d]imidazole-5-carboxamido)-3-(4-(3-(5,6,7,8-tetrahydro-1,8-naphthyridin-2-yl)propoxy)phenyl)propanoic acid Example 9

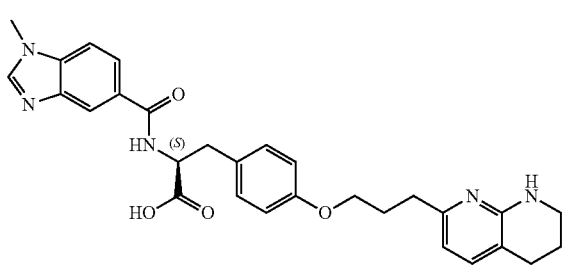

Example 9 was prepared by the same procedure used to prepare Example 1 with the exception that benzoic acid was replaced by 1-methyl-1H-benzo[d]imidazole-5-carboxylic acid in the reaction with intermediate 1f-int.

HPLC purification conditions: Gilson 281 semi-preparative HPLC system; Mobile phase A: TFA/H$_2$O=0.075% v/v; B: AcN (gradient % B at T=0: 15%; at T=12 min: 45%); Column: YMC-Actus Triart C18 150×30 5 u; Flow rate: 25 mL/min; Monitor wavelength: 220 & 254 nm.

$^1$H NMR (400 MHz, METHANOL-$d_4$): δ 9.09 (s, 1H), 8.19 (d, J=0.88 Hz, 1H), 7.94-7.98 (m, 1H), 7.84-7.89 (m, 1H), 7.52 (d, J=7.28 Hz, 1H), 7.21 (d, J=8.60 Hz, 2H), 6.79 (d, J=8.60 Hz, 2H), 6.59 (d, J=7.28 Hz, 1H), 4.82-4.85 (m, 1H), 4.09 (s, 3H), 3.99 (t, J=5.84 Hz, 2H), 3.44-3.50 (m, 2H), 3.27-3.30 (m, 1H), 3.08 (br d, J=9.70 Hz, 1H), 2.86 (d, J=7.72 Hz, 2H), 2.76-2.82 (m, 2H), 2.08-2.17 (m, 2H), 1.87-1.97 ppm (m, 2H); LCMS (ESI+): m/z=514.2 (M+H)$^+$, RT=1.8 min; HPLC: RT=3.1 min, purity: 100%; Chiral SFC purity: 100%, ee value: 100%, RT=3.3 min.

Examples 10-12

Synthesis of (S)-2-(benzo[d]oxazole-5-carboxamido)-3-(4-(3-(5,6,7,8-tetrahydro-1,8-naphthyridin-2-yl)propoxy)phenyl)propanoic acid (Example 10)

Example 10

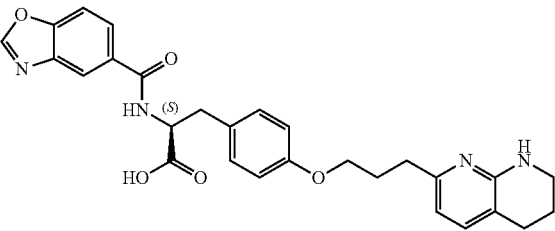

(S)-2-(3-amino-4-hydroxybenzamido)-3-(4-(3-(5,6,7,8-tetrahydro-1,8-naphthyridin-2-yl)propoxy)phenyl)propanoic acid (Example 11)

Example 11

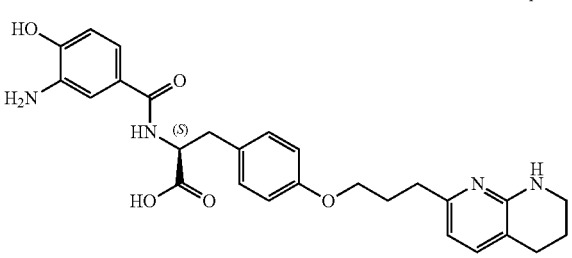

(S)-2-(3-formamido-4-hydroxybenzamido)-3-(4-(3-(5,6,7,8-tetrahydro-1,8-naphthyridin-2-yl)propoxy)phenyl)propanoic acid (Example 12)

Example 12

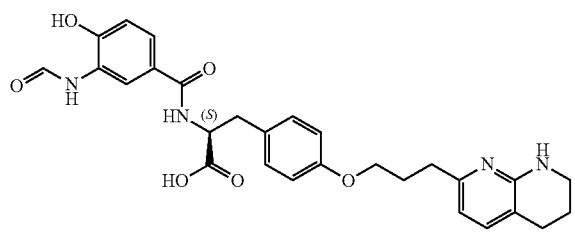

Examples 10, 11 and 12 were prepared by the same procedure used to prepare Example 1 with the exception that benzoic acid was replaced by benzo[d]oxazole-5-carboxylic acid in the reaction with intermediate 1f-int. Subsequent treatment with LiOH as in Example 1 resulted in the formation of Examples 10, 11 and 12 as a separable mixture.

HPLC purification condition: Gilson 281 semi-preparative HPLC system; Mobile phase A: TFA/H$_2$O=0.075% v/v; B: AcN (gradient % B at T=0: 10%; at T=12 min: 40%); Column: YMC-Actus Triart C18 150×30 5 u; Flow rate: 25 mL/min; Monitor wavelength: 220 & 254 nm.

Example 10

$^1$H NMR (400 MHz, DMSO-d$_6$): δ ppm 8.81 (s, 1H), 8.75 (br d, J=8.16 Hz, 1H), 8.24 (s, 1H), 7.86-7.92 (m, 1H), 7.79-7.84 (m, 1H), 7.20 (d, J=8.60 Hz, 2H), 6.98 (d, J=7.06 Hz, 1H), 6.78 (d, J=8.60 Hz, 2H), 6.32 (br s, 1H), 6.22 (d, J=7.28 Hz, 1H), 4.50-4.60 (m, 1H), 3.86 (br t, J=6.39 Hz, 2H), 3.19 (br s, 2H), 3.09 (br d, J=4.19 Hz, 1H), 3.00 (br d, J=10.80 Hz, 1H), 2.51-2.60 (m, 4H), 1.89-1.99 (m, 2H), 1.70 (quin, J=5.73 Hz, 2H); LCMS (ESI+): m/z=501.1 (M+H)$^+$, RT: 2.1 min; HPLC purity: 99.5%, RT: 2.3 min; Chiral SFC purity: 100%, ee value: 100%, RT=2.6 min.

Example 11

$^1$H NMR (400 MHz, METHANOL-d$_4$): δ ppm 7.59 (d, J=1.98 Hz, 1H), 7.48-7.57 (m, 2H), 7.15 (d, J=8.60 Hz, 2H), 6.93 (d, J=8.60 Hz, 1H), 6.76 (d, J=8.60 Hz, 2H), 6.58 (d, J=7.28 Hz, 1H), 4.74 (dd, J=9.26, 5.07 Hz, 1H), 3.98 (t, J=5.84 Hz, 2H), 3.42-3.49 (m, 2H), 3.23 (dd, J=14.11, 5.07 Hz, 1H), 3.01 (dd, J=14.00, 9.37 Hz, 1H), 2.85 (t, J=7.50 Hz, 2H), 2.77 (t, J=6.28 Hz, 2H), 2.07-2.16 (m, 2H), 1.92 (quin, J=5.95 Hz, 1H), 1.87-1.96 (m, 1H); LCMS (ESI+): m/z=491.1 (M+H)$^+$, RT: 2.1 min; HPLC purity: 100%, RT: 3.0 min; Chiral SFC purity: 100%, e.e. value: 100%, RT=2.5 min.

Example 12

$^1$H NMR (400 MHz, DMSO-d$_6$): δ ppm 9.59 (s, 1H), 8.44 (d, J=2.20 Hz, 1H), 8.24-8.29 (m, 2H), 7.39 (dd, J=8.38, 2.21 Hz, 1H), 7.15 (d, J=8.60 Hz, 2H), 6.98 (d, J=7.28 Hz, 1H), 6.84 (d, J=8.38 Hz, 1H), 6.76 (d, J=8.82 Hz, 2H), 6.34 (br s, 1H), 6.22 (d, J=7.28 Hz, 1H), 4.41-4.50 (m, 1H), 3.86 (t, J=6.28 Hz, 2H), 3.19 (br s, 2H), 3.04 (br dd, J=13.78, 4.52 Hz, 1H), 2.95 (br dd, J=13.78, 9.81 Hz, 1H), 2.49-2.57 (m, 4H), 1.89-1.97 (m, 2H), 1.66-1.74 (m, 2H); LCMS (ESI+): m/z=519.1 (M+H)$^+$, RT: 1.9 min; HPLC purity: 92.7%, RT: 3.8 min; Chiral SFC purity: 100%, e.e. value: 100%, RT=3.5 min.

Example 13

Synthesis of (S)-2-(isonicotinamido)-3-(4-(3-(5,6,7,8-tetrahydro-1,8-naphthyridin-2-yl)propoxy)phenyl)propanoic acid Example 13

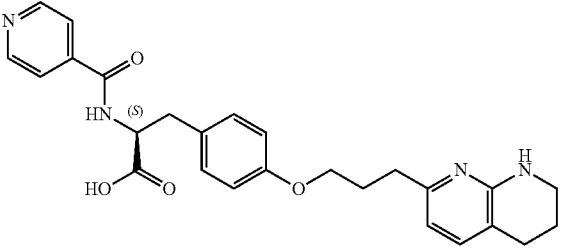

Example 13 was prepared by the same procedure used to prepare Example 1 with the exception that benzoic acid was replaced by isonicotinic acid in the reaction with intermediate 1f-int.

HPLC purification conditions: Gilson 281 semi-preparative HPLC system; Mobile phase A: TFA/H$_2$O=0.075% v/v; B: AcN (gradient % B at T=0: 10%; at T=12 min: 40%); Column: YMC-Actus Triart C18 150×30 5 u; Flow rate: 25 mL/min; Monitor wavelength: 220 & 254 nm.

$^1$H NMR (400 MHz, METHANOL-d$_4$): δ ppm 8.76 (br d, J=3.97 Hz, 2H), 7.85 (d, J=6.17 Hz, 2H), 7.54 (d, J=7.50 Hz, 1H), 7.19 (d, J=8.60 Hz, 2H), 6.80 (d, J=8.60 Hz, 2H), 6.60 (d, J=7.28 Hz, 1H), 4.81-4.84 (m, 1H), 4.00 (t, J=5.84 Hz, 1H), 3.94-4.07 (m, 1H), 3.43-3.55 (m, 2H), 3.33-3.37 (m, 1H), 3.27-3.30 (m, 1H), 3.32-3.37 (m, 1H), 3.02 (dd, J=14.11, 9.92 Hz, 1H), 2.87 (t, J=7.61 Hz, 2H), 2.80 (t, J=6.17 Hz, 1H), 2.76-2.83 (m, 1H), 2.06-2.21 (m, 2H), 1.94 (quin, J=5.95 Hz, 2H); HPLC purity: 98.2%, RT: 3.3 min; LCMS (ESI+): m/z=460.1 (M+H)$^+$, RT=1.8 min; Chiral SFC purity: 99.7%, ee value: 99.3%, RT=3.4 min.

Example 14

Synthesis of (S)-2-(nicotinamido)-3-(4-(3-(5,6,7,8-tetrahydro-1,8-naphthyridin-2-yl)propoxy)phenyl)propanoic acid Example 14

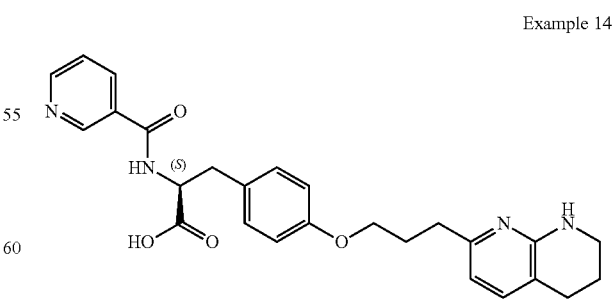

Example 14 was prepared by the same procedure used to prepare Example 1 with the exception that benzoic acid was replaced by nicotinic acid in the reaction with intermediate 1f-int.

HPLC purification conditions: Gilson 281 semi-preparative HPLC system; Mobile phase A: TFA/H$_2$O=0.075% v/v; B: AcN (gradient % B at T=0: 10%; at T=12 min: 40%); Column: YMC-Actus Triart C18 150×30 5 u; Flow rate: 25 mL/min; Monitor wavelength: 220 & 254 nm.

$^1$H NMR (400 MHz, DMSO-d$_6$): δ ppm 8.93 (s, 1H), 8.88-8.90 (d, J=8.00 Hz, 1H), 8.69-8.70 (d, J=4.00 Hz, 1H), 7.47-7.50 (m, 1H), 7.19-7.21 (d, J=8.40 Hz, 2H), 7.00-7.02 (d, J=7.60 Hz, 1H), 6.80-6.82 (d, J=8.40 Hz, 2H), 6.39 (s, 1H), 6.24-6.26 (d, J=7.20 Hz, 1H), 4.53-4.59 (m, 1H), 3.87-3.90 (m, 2H), 3.22 (m, 1H), 3.10-3.13 (m, 1H), 2.93-2.99 (m, 1H), 2.55-2.60 (m, 4H), 1.95-1.99 (m, 2H), 1.72-1.74 (m, 2H); HPLC purity: 99.7%, RT: 3.3 min; LCMS (ESI+): m/z=461.1 (M+H)$^+$, RT=1.9 min; Chiral SFC purity: 98.0%, ee value: 96.0%, RT=3.0 min.

Example 15

Synthesis of (S)-2-(3,5-dichloroisonicotinamido)-3-(4-(3-(5,6,7,8-tetrahydro-1,8-naphthyridin-2-yl)propoxy)phenyl)propanoic acid

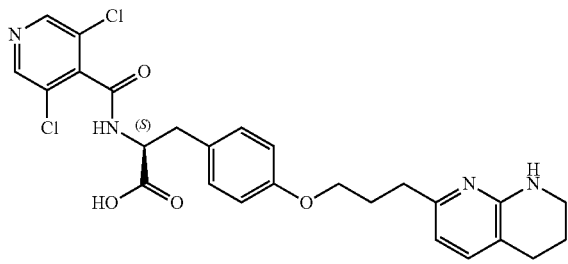

Example 15

Example 15 was prepared by the same procedure used to prepare Example 1 with the exception that benzoic acid was replaced by 3,5-dichloroisonicotinic acid in the reaction with intermediate 1f-int.

HPLC purification conditions: Gilson 281 semi-preparative HPLC system; Mobile phase A: TFA/H$_2$O=0.075% v/v; B: AcN (gradient % B at T=0: 10%; at T=12 min: 40%); Column: YMC-Actus Triart C18 150×30 5 u; Flow rate: 25 mL/min; Monitor wavelength: 220 & 254 nm.

$^1$H NMR (400 MHz, DMSO-d$_6$): δ ppm 9.19 (d, J=8.38 Hz, 1H), 8.60 (s, 2H), 7.14 (d, J=8.60 Hz, 2H), 7.00 (d, J=7.28 Hz, 1H), 6.79 (d, J=8.60 Hz, 2H), 6.33 (br s, 1H), 6.24 (d, J=7.28 Hz, 1H), 4.61 (td, J=8.88, 4.96 Hz, 1H), 3.89 (t, J=6.39 Hz, 2H), 3.20 (br s, 2H), 3.04 (dd, J=14.00, 4.96 Hz, 1H), 2.82 (dd, J=14.00, 9.37 Hz, 1H), 2.51-2.60 (m, 4H), 1.91-2.01 (m, 2H), 1.67-1.76 (m, 2H); LCMS (ESI+): m/z=529.2 (M+H)$^+$, RT: 2.4 min; HPLC purity: 97.8%, RT: 4.4 min; Chiral SFC purity: 100%, ee value: 100%, RT=2.5. min.

Example 16

Synthesis of (S)-2-(2,6-dichlorobenzamido)-3-(4-(3-(5,6,7,8-tetrahydro-1,8-naphthyridin-2-yl)propoxy)phenyl)propanoic acid

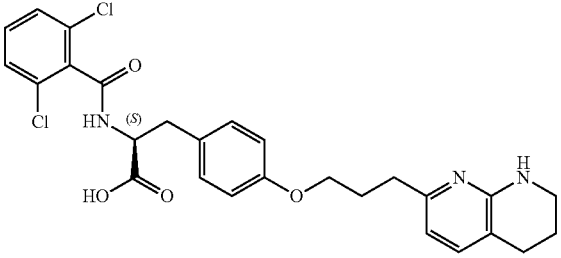

Example 16

Example 16 was prepared by the same procedure used to prepare Example 1 with the exception that benzoic acid was replaced by 2,6-dichlorobenzoic acid in the reaction with intermediate 1f-int.

HPLC purification conditions: Gilson 281 semi-preparative HPLC system; Mobile phase A: 10 mM NH$_4$HCO$_3$ in H$_2$O; B: AcN (gradient % B at T=0:25%; at T=12 min: 45%); Column: YMC-Actus Triart C18 150×30 5 u; Flow rate: 25 mL/min; Monitor wavelength: 220 & 254 nm.

$^1$H NMR (400 MHz, METHANOL-d$_4$): δ ppm 1.93-1.89 (m, 2H) 2.12-2.09 (m, 2H) 2.86-2.76 (m, 4H) 2.96-2.87 (m, 1H) 3.21-3.16 (m, 1H) 3.46 (t, J=6.0 Hz, 2H) 3.97 (d, J=5.6 Hz, 2H) 4.86-4.85 (m, 1H) 6.60 (d, J=8.0 Hz, 1H) 6.74 (d, J=8.4 Hz, 2H) 7.20 (d, J=8.4 Hz, 2H) 7.35-7.30 (m, 3H) 7.52 (d, J=6.4 Hz, 1H); LCMS (ESI+): m/z=528.1 (M+H)$^+$, RT: 2.25 min; HPLC purity: 100%, RT: 4.7 min; Chiral SFC purity: 100%, ee value: 100%, RT: 2.7 min.

Example 17

Synthesis of (S)-2-(2,6-dichlorobenzamido)-3-(4-((4-methyl-3-oxo-3,4,5,6-tetrahydropyrazin-2-yl)amino)butoxy)phenyl)propanoic acid

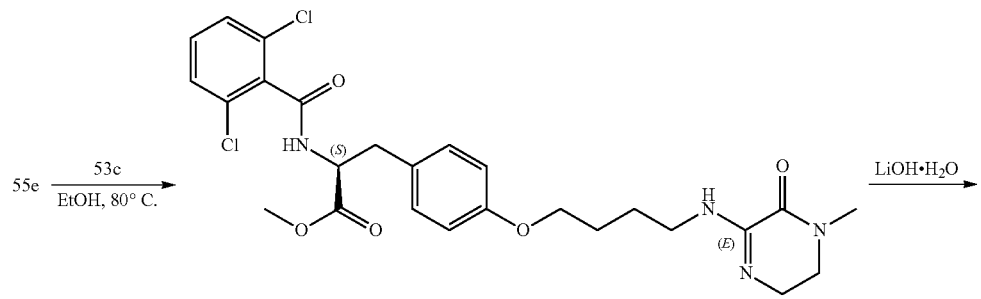

17a

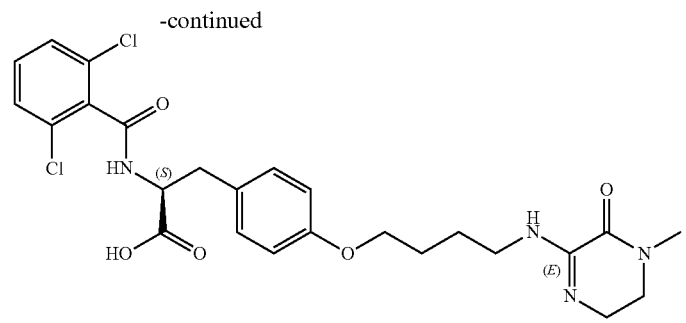

Example 17

Compound 17a: 51e (150 mg, 0.34 mmol) and 53c (54 mg, 0.34 mmol) in EtOH (5 mL) were heated at reflux for 3 hrs. LCMS showed desired product was formed, TLC (Ethyl acetate:Methanol=10:1, $R_f$=0.22) showed new a product spot. The mixture was concentrated and the residue was purified by prep-TLC (EtOAc:MeOH=10:1) to give 17a.

Example 17

17a (95 mg, 0.17 mmol) and LiOH.H$_2$O (14.5 mg, 0.35 mmol) in THF (5 mL)/H$_2$O (1 mL) were stirred at 20° C. for 2 hrs. LCMS showed Example 17 was present. The mixture was concentrated and the residue was purified by prep-HPLC to give Example 17.

HPLC purification conditions: Gilson 281 semi-preparative HPLC system; Mobile phase A: TFA/H$_2$O=0.075% v/v; B: AcN (gradient % B at T=0: 10%; at T=12 min: 45%); Column: Luna C18 100×30 5 u; Flow rate: 20 mL/min; Monitor wavelength: 220 & 254 nm.

$^1$H NMR (400 MHz, METHANOL-d$_4$): δ ppm 7.49-7.61 (m, 3H), 7.42 (d, J=8.6 Hz, 2H), 6.99-7.08 (m, 2H), 5.09 (br s, 1H), 4.16-4.24 (m, 2H), 3.88 (s, 3H), 3.56-3.67 (m, 2H), 3.50 (dt, J=3.31, 1.65 Hz, 4H), 3.41 (dd, J=14.11, 5.29 Hz, 1H), 3.15 (dd, J=14.11, 9.26 Hz, 1H), 1.99-2.09 (m, 4H); LCMS (ESI+): m/z=535.0 (M+H)$^+$, RT: 2.3 min; HPLC purity: 97.3%, RT: 7.6 min; Chiral SFC purity: 100%, ee value: 100%, RT: 3.0 min.

Example 18

Synthesis of 2-(2,6-dichlorobenzamido)-3-(4-(3-(2,3-dihydro-1H-pyrrolo[2,3-b]pyridin-2-yl)propoxy)phenyl)propanoic acid

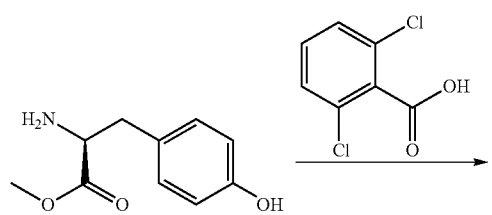

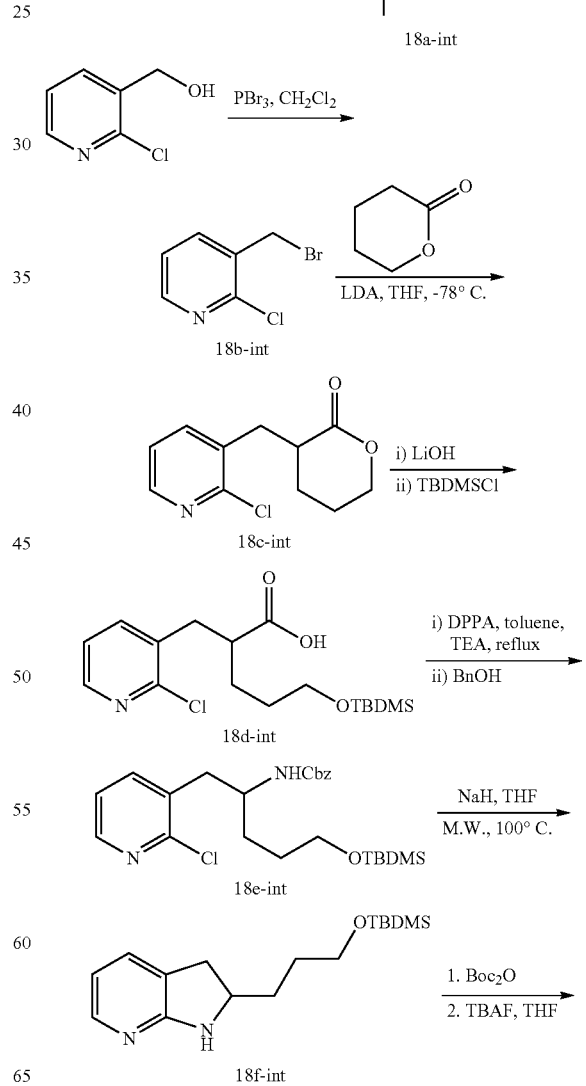

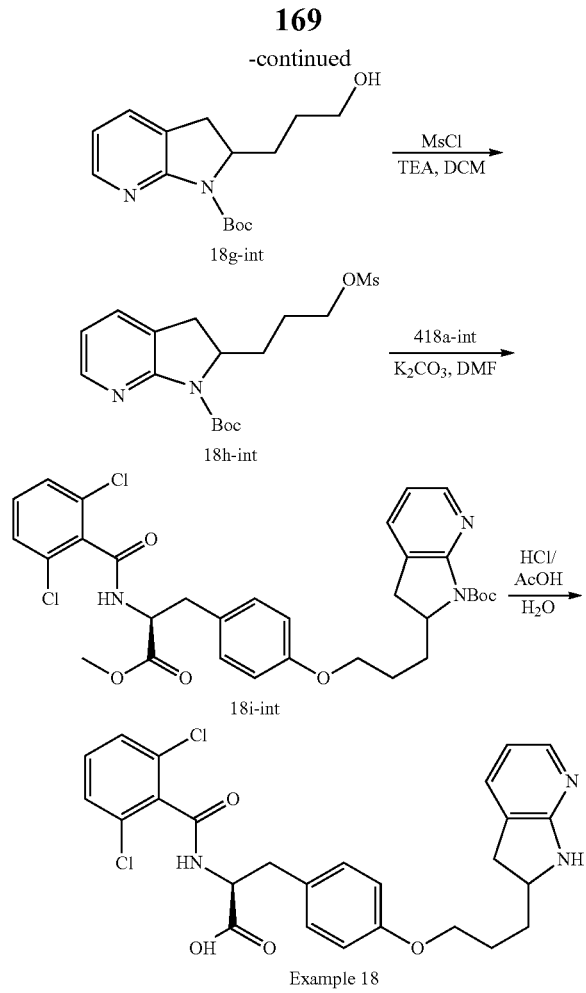

Example 18

Compound 18a-int: To a solution of 2,6-dichlorobenzoic acid (2.29 g, 12 mmol) in DMF (60 mL) was added EDCI (2.3 g, 12 mmol), HOBt (1.62 g, 12 mmol) and TEA (2.02 g, 20 mmol, 2.77 mL) at 5-10° C. The mixture was stirred at 5-10° C. for 1 hr, then methyl (2S)-2-amino-3-(4-nitrophenyl)propanoate (3.6 g, 16.06 mmol) in DMF (20 mL) was added and stirred at 10-20° C. for 2 hrs. TLC (PE:EtOAc=1:1, $R_f$=0.5) indicated the reaction was completed. The mixture was poured into water (100 mL), extracted with EtOAc (200 mL×2). The combined organic layers were washed with 1N HCl (100 mL), $H_2O$ (100 mL), sat. $NaHCO_3$ (100 mL), brine (50 mL), dried over $Na_2SO_4$ then concentrated to give a crude product, which was crystallized from PE:DCM=10:1 to afford 18a-int; $^1H$ NMR (400 MHz, CHLOROFORM-d): δ ppm 7.28-7.34 (m, 3H), 7.08 (d, J=8.53 Hz, 2H), 6.72-6.77 (m, 2H), 6.28 (d, J=7.78 Hz, 1H), 5.15 (dt, J=8.00, 5.60 Hz, 1H), 4.82 (s, 1H), 3.75-3.78 (m, 3H), 3.21 (d, J=5.65 Hz, 2H).

Compound 18b-int: To a solution of (2-chloropyridin-3-yl)methanol (50 g, 348 mmol) in dry DCM (500 mL) was added $PBr_3$ (94.3 g, 348 mmol) at 20° C. The reaction mixture was stirred at 20° C. for 2 hr. LCMS indicated 18b-int was detected. Water (50 mL) was added slowly at 0° C. Then saturated aqueous $K_2CO_3$ was added to pH 7. The organic layer was separated and water phase was extracted with DCM (200 mL). The organic layer was concentrated to give crude product which was purified by silica gel column chromatography (PE:EtOAc=20:1~5:1) to give 18b-int; $^1H$ NMR (400 MHz, METHANOL-$d_4$): δ ppm 7.81 (s, 2H), 7.56 (d, J=7.50 Hz, 1H), 7.19 (d, J=8.60 Hz, 2H), 6.73-6.84 (m, 2H), 6.62 (d, J=7.50 Hz, 1H), 4.88-4.93 (m, 1H), 4.00 (t, J=5.84 Hz, 2H), 3.42-3.53 (m, 2H), 3.22 (dd, J=14.22, 5.18 Hz, 1H), 2.83-2.96 (m, 3H), 2.80 (t, J=6.28 Hz, 2H), 2.07-2.22 (m, 2H), 1.93 (dt, J=12.02, 5.90 Hz, 2H).

Compound 18c-int: To a solution of tetrahydropyran-2-one (26.67 g, 266.38 mmol, 24.03 mL) in THF (50 mL) was added LDA (2 M, 146.51 mL, 1.10 eq) at −75° C. drop-wise. After the addition was complete, the reaction mixture was stirred at −75° C. for 0.5 hr. Compound 18b-int (55.00 g, 266.38 mmol) was added to the reaction mixture. The reaction mixture was warmed to −30° C. over 3 hr. The reaction mixture was poured into saturated $NH_4Cl$ (50 mL) then the organic layer was separated and concentrated. The crude product was purified by silica gel column (PE:EA=10:1 to 3:1) to give 18c-int.

Compound 18d-int: To 18c-int (22 g, 97.49 mmol) in THF (100 mL) and water (100 mL) was added LiOH. $H_2O$ (12.27 g, 292.47 mmol). The reaction mixture was stirred at 20° C. for 2 hrs. LCMS showed a peak with desired MS was detected. THF was evaporated and to the mixture was added citric acid until the pH 5 was attained. The product was extracted with EtOAc (300 mL×3). The combined organic layer was dried over $Na_2SO_4$ and concentrated to give 2-[(2-chloro-3-pyridyl)methyl]-5-hydroxy-pentanoic acid (23.00 g, crude) as an oil. The product was used in the next step without purification. A solution of 2-[(2-chloro-3-pyridyl)methyl]-5-hydroxy-pentanoic acid (23.00 g, 94.38 mmol) in DMF (150 mL) was added imidazole (12.85 g, 188.76 mmol) and TBDMSCl (21.34 g, 141.57 mmol, 17.35 mL). The reaction mixture was stirred at 40° C. for 16 hrs. LCMS indicated that the reaction was complete. Water (500 mL) was added and the product was extracted with EtOAc (500 mL×2). The combined organic layer was concentrated and the crude product was purified by silica gel column (PE:EtOAc=10:1 to 1:2) to give compound 18d-int; LCMS (ESI+): m/z=357.9 (M+H)$^+$, RT=1.5 min.

Compound 18e-int: To a solution of compound 18d-int (15 g, 41.91 mmol) in toluene (100 mL) was added DPPA (13.84 g, 50.29 mmol, 10.90 mL), TEA (12.72 g, 125.73 mmol, 17.42 mL) and BnOH (13.6 g 125.73 mmol 13.08 mL) at 20° C. Then the reaction mixture was stirred at 80° C. for 2 hr. LCMS indicated the starting material was consumed completely. The reaction mixture was concentrated and the crude product was purified by silica gel column (PE:EtOAc=20:1 to 4:1) to give compound 18e-int; LCMS (ESI+): m/z=463.0 (M+H)$^+$, RT=1.7 min.

Compound 18f-int: To compound 18e-int (1 g, 2.16 mmol) in THF (20 mL) was added NaH (259.13 mg, 6.48 mmol, 60% purity). The reaction mixture was stirred at 100° C. under microwave conditions for 1 hr. LCMS showed the desired product was present and the reactant was consumed. The solvent was evaporated under reduced pressure and the product was purified by silica gel column (PE:EtOAc=10:1 to 1:1) to give 18f-int; LCMS (ESI+): m/z=293.1 (M+H)$^+$, RT=1.1 min.

Compound 18g-int: Compound 18f-int (1.2 g, 4.1 mmol) in THF (10 mL) was added to TBAF (1M, 8.2 mL) and the reaction mixture was stirred at 20° C. for 16 hrs. LCMS and TLC (DCM:MeOH=10:1, $R_f$=0.3) indicated the reaction was complete. The solvent was evaporated and the product was purified by silica gel column (DCM:MeOH=1:0 to 10:1) to give 3-(2,3-dihydro-1H-pyrrolo[2,3-b]pyridin-2-yl)propan-1-ol (530 mg, 2.97 mmol, 72.53% yield) as a yellow oil. 500 mg (2.81 mmol) of this material was dissolved in THF and $Boc_2O$ (4.91 g, 22.48 mmol, 5.16 mL), then the reaction mixture was stirred at 50° C. for 5 hrs. LCMS and TLC (PE:EtOAc=1:1) showed the reaction was complete. The crude product was purified by silica gel column (PE:EtOAc=1:0 to 1:1) to give 18g-int; LCMS (ESI+): m/z=279.0 (M+H)$^+$, RT=0.9 min.

Compound 18h-int: To Compound 18g-int (110 mg, 395.19 umol) in DCM (2 mL) was added MsCl (54.32 mg, 474.23 umol, 36.70 uL) and TEA (79.98 mg, 790.38 umol, 109.56 uL). The reaction mixture was stirred at 20° C. for 1 hr. TLC (PE:EtOAc=1:1, R$_f$=0.6) indicated the reaction was complete. Water (1 mL) was added and the organic layer was separated. The solvent was evaporated under reduced pressure to give compound 18h, which was used in the next step without further purification.

Compound 18i-int: To a mixture of 18h-int (120 mg, 336.66 umol) and methyl (2S)-2-[(2,6-dichlorobenzoyl) amino]-3-(4-hydroxyphenyl)propanoate (123.96 mg, 336.66 umol) in DMF (2 mL) was added K$_2$CO$_3$ (139.59 mg, 1.01 mmol). The reaction mixture was stirred at 110° C. for 16 hrs. LCMS showed the reaction mixture was complete. The solvent was evaporated and the crude product was purified by prep-TLC (PE:EA=1:1, R$_f$=0.7) to give compound 18i-int; LCMS (ESI+): m/z=628.1 (M+H)$^+$, RT=1.4 min.

Example 18

A solution of 18i-int (50.00 mg, 79.55 umol) in MeCN (1 mL) and H$_2$O (1 mL) was added to AcOH (9.55 mg, 159.10 umol, 9.1 uL) and HCl (10N, 159.1 uL). The reaction mixture was stirred at 70° C. for 16 hrs. LCMS showed the reaction was completed, then the solvent was removed by evaporation under reduced pressure. The crude product was purified by prep-HPLC to give Example 18.

HPLC purification conditions: Gilson 281 semi-preparative HPLC system; Mobile phase A: TFA/H$_2$O=0.075% v/v; B: AcN (gradient % B at T=0: 20%; at T=12 min: 50%); Column: YMC-Actus Triart C18 150×30 5 u; Flow rate: 25 mL/min; Monitor wavelength: 220 & 254 nm.

$^1$H NMR (400 MHz, CHLOROFORM-d): δ ppm 7.58-7.59 (m, 1H), 7.34-7.35 (m, 1H), 7.33-7.34 (m, 3H), 7.23 (d, J=8.40 Hz, 2H), 6.84 (d, J=8.80 Hz, 2H), 6.70 (t, J=6.80 Hz, 1H), 4.30-4.35 (m, 1H), 4.02 (t, J=5.60 Hz, 2H), 3.29-3.39 (m, 1H), 3.19-3.20 (m, 1H), 2.94-2.97 (m, 2H), 1.83-1.91 (M, 4H); LCMS (ESI+): m/z=514.0 (M+H)$^+$, RT=2.2 min; HPLC purity: 99.0%, RT: 2.3 min. Chiral SFC showed an equal mixture of all four diastereomers.

Example 19

Synthesis of (S)-2-(2,6-dichlorobenzamido)-9-(5,6,7,8-tetrahydro-1,8-naphthyridin-2-yl)nonanoic acid

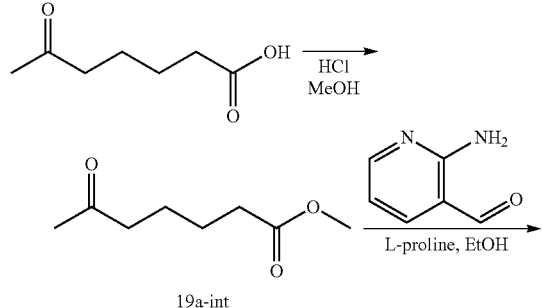

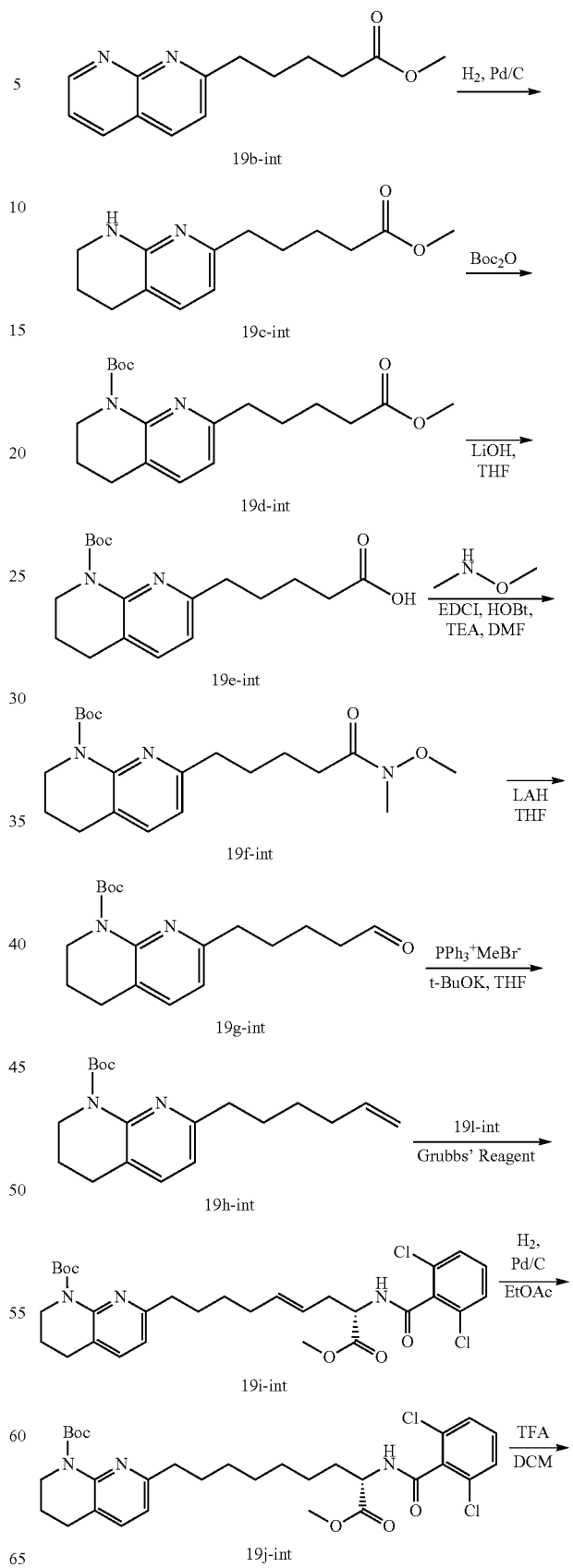

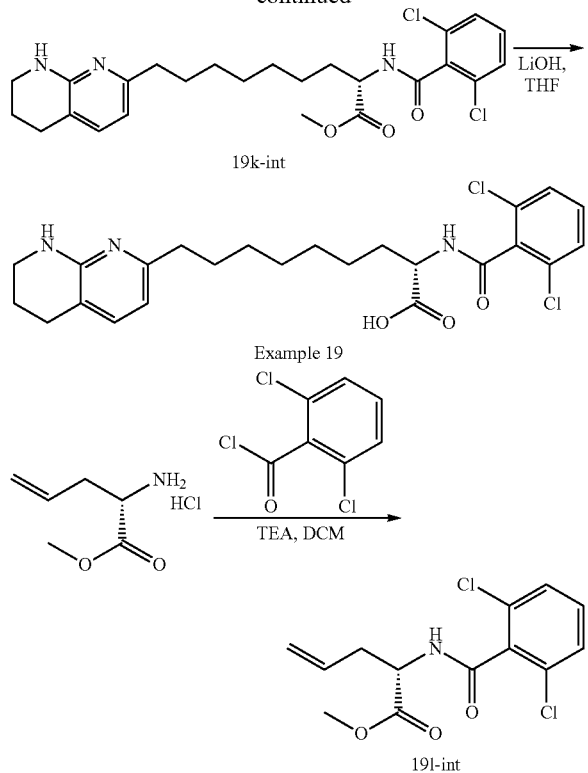

Compound 19a-int: A solution of 6-oxoheptanoic acid (25 g, 173.41 mmol) in HCl/MeOH (250 mL) was stirred at 80° C. for 10 hr. LCMS showed that the product was present. The solvent was removed and the residue was dissolved in ethyl acetate (200 mL). Then the organic layer was washed with saturated NaHCO$_3$ (150 mL), brine (150 mL) then concentrated to give 19a-int; LCMS (ESI+): m/z=159.1 (M+H)$^+$, RT=0.51 min.

Compound 19b-int: 19a-int (21 g, 132.75 mmol), 2-aminopyridine-3-carbaldehyde (17.83 g, 146.03 mmol) and L-proline (7.64 g, 66.38 mmol) in EtOH (200 mL) were stirred at 80° C. for 10 hrs. LCMS showed that the 19b-int was formed. The solvent was removed and the crude product was purified by chromatography on silica gel (PE: EtOAc=10:1 to 1:1, R$_f$=0.3) to give 19b-int; LCMS (ESI+): m/z=245.0 (M+H)$^+$, RT=0.75 min.

Compound 19c-int: To 19b-int (8.6 g, 35.20 mmol) in MeOH (100 mL) was added Pd/C (1 g) at 0° C. The mixture was degassed with N$_2$ then saturated with H$_2$; the reaction was stirred at 0-20° C. under H$_2$ (50 psi) for 12 hrs. TLC (PE:EtOAc=2:1, R$_f$=0.25) showed the reaction was complete. The catalyst was removed by filtration and the filtrate was concentrated to give 19c-int.

Compound 19d-int: A solution of compound 19c-int (8 g, 32.22 mmol) in Boc$_2$O (56.26 g, 257.76 mmol, 59.22 mL) was stirred at 40-60° C. for 12 hrs. TLC (PE:EtOAc=2:1, R$_f$=0.5) indicated the reaction was complete. The reaction mixture was applied to silica gel and purified by silica gel chromatography (PE:EtOAc=10:1 to 1:1, R$_f$=0.3) to give 19d-int.

Compound 19e-int: To 19d-int in dioxane (100 mL)/H$_2$O (5 mL) was added LiOH.H$_2$O (2.53 g, 60.27 mmol). The mixture was stirred at 20° C. for 12 hrs. TLC (PE:EtOAc=1:1, R$_f$=0.15) indicated the reaction was complete. The mixture was concentrated and the residue was poured into H$_2$O (100 mL) and DCM (200 mL), then adjusted to pH 6 with 1N HCl; the organic layer was separated and the aqueous layer was extracted with DCM (200 mL). The combined organics were dried over Na$_2$SO$_4$, then concentrated to give 19e-int.

Compound 19f-int: To a solution of 19e-int (10 g, 29.9 mmol) in DCM (100 mL) was added EDCI (6.88 g, 35.88 mmol), HOBt (4.85 g, 35.88 mmol) and TEA (6.05 g, 59.81 mmol, 8.29 mL) at 20° C. The mixture was stirred at 10-20° C. for 0.5 hrs; N-methoxymethanamine hydrochloride (3.5 g, 35.88 mmol) was added and the mixture stirred at 10-20° C. for 2.5 hrs. TLC (PE:EtOAc=1:1, R$_f$=0.5) indicated the reaction was complete by the end of this period. The mixture was poured into H$_2$O (100 mL), extracted with DCM (100 mL×2) and the combined organics were dried over Na$_2$SO$_4$, concentrated in vacuo. The residue was purified by silica gel chromatography (PE:EtOAc=5:1 to 2:1) to give 19f-int; LCMS (ESI+): m/z=378.1 (M+H)+, RT=0.33 min.

Compound 19g-int: To 19f-int (7.5 g) in THF (120 mL) was added dropwise DIBALH (1M THF solution, 29.8 mL) at −78° C. The mixture was stirred at −78° C. for 3 hrs. TLC (PE:EtOAc=2:1, R$_f$=0.5) indicated the reaction was complete. The mixture was poured into ice water (100 mL) and extracted with EtOAc (100 mL×2). The combined organics were dried over Na$_2$SO$_4$ then the solvent removed to give 19g-int.

Compound 19h-int: To a mixture of methyl(triphenyl)phosphonium bromide (13.46 g, 37.68 mmol) in THF (100 mL) was added t-BuOK (1 M solution in THF, 37.68 mL, 37.68 mmol) at 0° C. The mixture was stirred at 20° C. for 1 hr then 19g-int (6 g, 18.84 mmol, 1.00 eq) was added. This mixture was stirred at 20° C. for 2 hrs, after this time TLC (PE:EtOAc=2:1, R$_f$=0.43) indicated that reaction was complete. The mixture was quenched with aq. NH$_4$Cl (1M, 40 mL), extracted with EtOAc (100 mL×2), dried over Na$_2$SO$_4$ then concentrated. The residue was purified by silica gel chromatography (PE:EtOAc=10:1) to give 19h-int; LCMS (ESI+): m/z=317.3 (M+H)+, RT=0.79 min.

Compound 19i-int: To a mixture of compound 19l-int (2 g, 6.62 mmol) and compound 19h-int (2.09 g, 6.62 mmol) in DCM (200 mL) was added Grubbs II catalyst (561.95 mg, 662 umol). The mixture was purged with N$_2$ (3×) then stirred at 40° C. for 24 hrs, after this time TLC (PE:EtOAc=2:1, R$_f$=0.50) indicated the reaction was complete. The mixture was concentrated and the residue was purified by silica gel chromatography (PE:EtOAc=5:1) to give 19i-int; LCMS (ESI+): m/z=590.4 (M+H)$^+$, RT=0.81 min.

Compound 19j-int: To 19i-int (390 mg, 660.41 umol) in EtOAc (50 mL) was added Pd/C (50 mg, 660.41 umol). The mixture was purged with N$_2$ (3×) then stirred at 20-30° C. for 4 hrs under an atmosphere of H$_2$ gas. After this time LCMS indicated the most of 19i-int was consumed so mixture was filtered to remove the catalyst. The filtrate was concentrated in vacuum to give 19j-int; LCMS (ESI+): m/z=592.4 (M+H)+, RT=0.78 min.

Compound 19k-int: Compound 19j-int (370 mg, 624.42 umol) in TFA/DCM (5 mL) was stirred at 25° C. for 10 hrs; after this time LCMS showed that the reaction was complete. The solvent was removed to give 19k-int; LCMS (ESI+): m/z=492.2 (M+H)$^+$, RT=0.92 min.

Compound 19l-int: Methyl (2S)-2-aminopent-4-enoate (45 g, 348.41 mmol) in DCM (500 mL) was added dropwise to TEA (88.14 g, 871.03 mmol, 120.74 mL) and 2,6-dichlorobenzoyl chloride (21 g, 100.26 mmol, 14.38 mL) in DCM at 20° C. The mixture was stirred at 20-40° C. for 12 hrs and was poured into H$_2$O (500 mL). The organic layer was separated and washed with 1N HCl (200 mL), sat.

NaHCO$_3$ (200 mL), brine (200 mL) and dried over Na$_2$SO$_4$. The solvent was removed by evaporation under reduced pressure and dried in vacuo to give 19l-int.

Example 19

A solution of 19k-int (300 mg, 0.61 mmol) and LiOH.H$_2$O (51.13 mg, 1.22 mmol) in THF (5 mL)/H$_2$O (5 mL) was stirred at 25° C. for 10 hrs. LCMS showed that Example 19 was present and the reaction complete. The solvent was removed and the crude product was purified by prep-HPLC to give Example 19.

HPLC purification conditions: Gilson 281 semi-preparative HPLC system; Mobile phase A: TFA/H$_2$O=0.075% v/v; B: AcN (gradient % B at T=0: 15%; at T=10 min: 45%); Column: Luna C18 100×30 5 u; Flow rate: 25 mL/min; Monitor wavelength: 220 & 254 nm.

$^1$H NMR (400 MHz, METHANOL-d$_4$): δ ppm 7.59 (d, J=7.28 Hz, 1H), 7.36-7.45 (m, 3H), 6.63 (d, J=7.28 Hz, 1H), 4.63 (dd, J=9.48, 4.63 Hz, 1H), 3.47-3.52 (m, 2H), 2.81 (t, J=6.17 Hz, 2H), 2.70 (t, J=7.83 Hz, 2H), 1.90-2.00 (m, 3H), 1.66-1.84 (m, 3H), 1.52 (br d, J=4.85 Hz, 2H), 1.40 (br s, 6H); LCMS (ESI+): m/z=478.0 (M+H)$^+$, RT=2.3 min; HPLC: RT=5.0 min, purity: 92.9%; Chiral SFC purity: 100%, e. e. value: 100%, RT=3.3 min.

Example 20

Synthesis of (S,E)-2-(2,6-dichlorobenzamido)-9-(5,6,7,8-tetrahydro-1,8-naphthyridin-2-yl)non-4-enoic acid

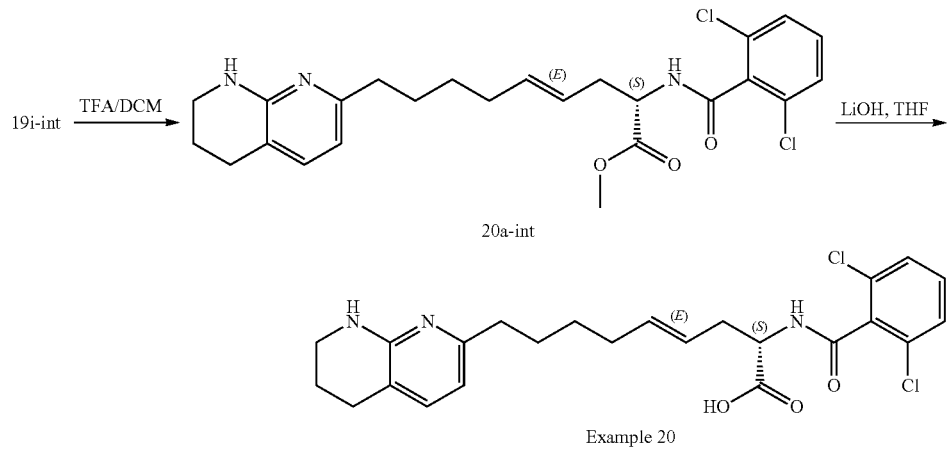

20a-int

Example 20

Compound 20a-int: To compound 19i-int (200 mg, 338.67 umol) in DCM (40 mL) was added TFA (5 mL); the mixture was stirred at 20° C. for 4 hrs. After this time LCMS indicated the reaction was complete. The mixture was concentrated and the residue was poured into H$_2$O (10 mL) and sat. NaHCO$_3$ (20 mL) then extracted with DCM (50 mL×2). The combined organics were dried over Na$_2$SO$_4$ and concentrated to give compound 20a. This material was used in next step without further purification; LCMS (ESI+): m/z=490.3 (M+H)$^+$, RT=0.77 min.

Example 20

To a solution of 20a-int (150 mg, 305.86 umol) in THF (2 mL)/H$_2$O (2 mL) was added LiOH.H$_2$O (12.83 mg, 305.86 umol). This was stirred for 12 hrs at 20° C. after which LCMS showed the desired product was present and the reaction complete. The solvent was removed and the crude material was purified by prep-HPLC to give Example 20.

HPLC purification conditions: Gilson 281 semi-preparative HPLC system; Mobile phase A: TFA/H$_2$O=0.075% v/v; B: AcN (gradient % B at T=0: 20%; at 11.5 min: 40%); Column: Boston Green ODS 150×30 5 u; Flow rate: 25 mL/min; Monitor wavelength: 220 & 254 nm.

$^1$H NMR (400 MHz, METHANOL-d$_4$): 7.56 (d, J=7.2 Hz, 1H), 7.35-7.41 (m, 3H), 6.60 (d, J=7.2 Hz, 1H), 5.52-5.63 (m, 1H), 4.60-4.64 (m, 1H), 3.44-3.46 (m, 2H), 2.78-2.79 (m, 2H), 2.68-2.76 (m, 2H), 2.64-2.66 (m, 1H), 2.05-2.08 (m, 2H), 1.89-1.92 (m, 2H), 1.65-1.67 (m, 2H), 1.43-1.46 ppm (m, 2H); LCMS (ESI+): m/z=476.0 (M+H)+, RT=2.3 min; HPLC: RT=4.9 min, purity: 90.9%; Chiral SFC purity: 100%, e.e. value: 100%, RT=3.3 min.

Example 21

Synthesis of (S)-2-(2,6-dichlorobenzamido)-3-(4-(3-((5,6,7,8-tetrahydro-1,8-naphthyridin-2-yl)methyl)azetidin-1-yl)phenyl)propanoic acid

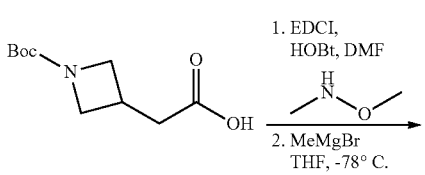

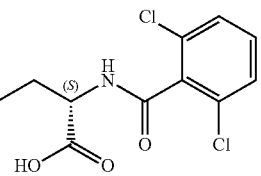

21a-int

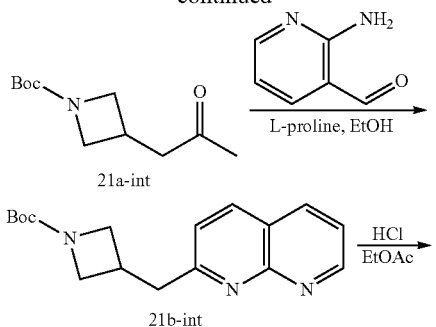

21b-int

-continued

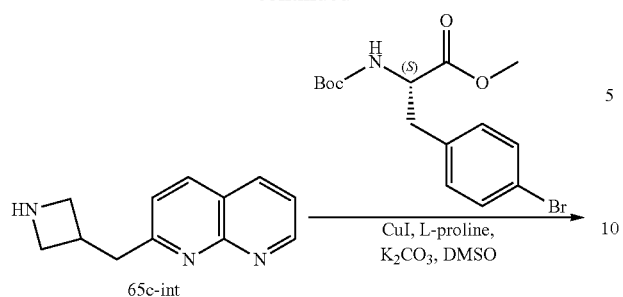

65c-int

CuI, L-proline, K₂CO₃, DMSO

-continued

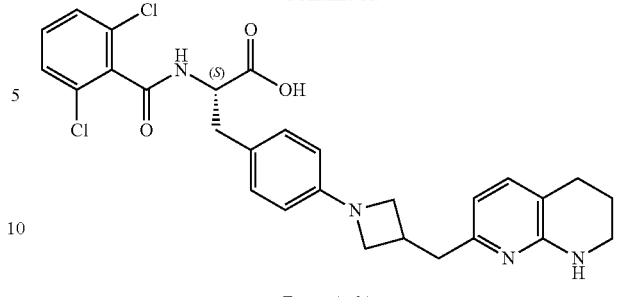

Example 21

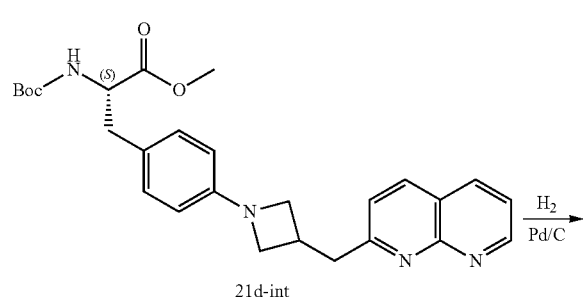

21d-int

H₂
Pd/C

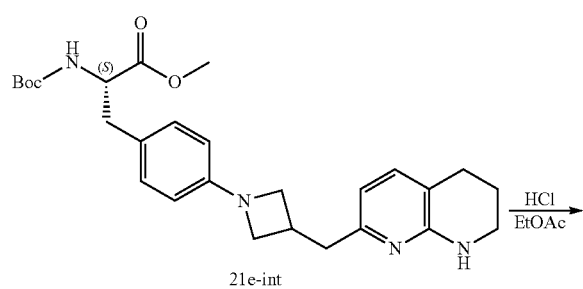

21e-int

HCl
EtOAc

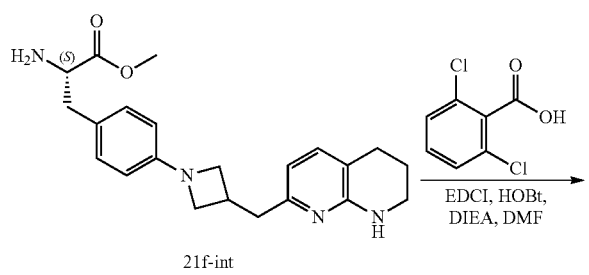

21f-int

EDCI, HOBt,
DIEA, DMF

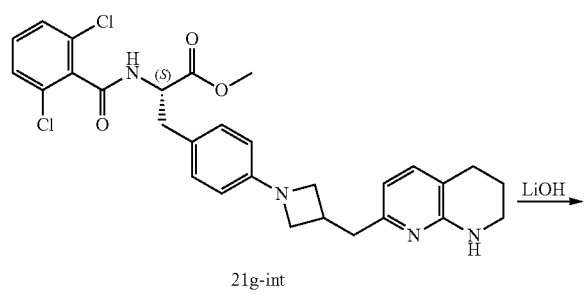

21g-int

LiOH

Compound 21a-int: To 2-(1-tert-butoxycarbonylazetidin-3-yl)acetic acid (4.8 g, 22.3 mmol), HOBt (3.62 g, 26.76 mmol) and TEA (5.64 g, 55.75 mmol, 7.73 mL) in DCM (100 mL) was added EDCI (5.13 g, 26.76 mmol) at 0° C. The mixture was stirred at 20° C. for 1 hr then N-methoxymethanamine hydrogen chloride salt (2.39 g, 24.53 mmol) was added. The mixture was stirred at 20° C. for 2 hrs then poured into H₂O (50 mL). The organic layer was separated, was washed with H₂O (50 mL), brine (50 mL) and dried over Na₂SO₄. The solvent was removed to give tert-butyl 3-[2-[methoxy(methyl)amino]-2-oxo-ethyl]azetidine-1-carboxylate (5.5 g, 19.36 mmol, 86.8% yield). To this material (5.5 g) in THF (100 mL) was added dropwise a THF solution of bromo(methyl)magnesium (3.55 g, 29.81 mmol) at −78° C.; the reaction was stirred at −78° C. for 3 hrs. TLC (PE:EtOAc=3:1, R_f=0.5) indicated the reaction was complete. The mixture was quenched with sat. NH4Cl (50 mL), extracted with EtOAc (100 mL×2), then the combined organic layers were dried over Na₂SO₄ and concentrated to give 21a-int.

Compound 21b-int: A mixture of 21a-int (5 g, 23.44 mmol), 2-aminopyridine-3-carbaldehyde (2.86 g, 23.44 mmol) and L-proline (1.35 g, 11.72 mmol) in EtOH (80 mL) was stirred at 80-90° C. for 12 hrs. TLC (PE:EtOAc=1:1, R_f=0.15) indicated the reaction was completed. The mixture was concentrated and the residue was poured into H₂O (50 mL) then extracted with EtOAc (100 mL×3). The combined organics layers were dried over Na₂SO₄, filtered and concentrated. The residue was purified by silica gel chromatography (PE:EtOAc=1:1) to give 21b-int.

Compound 21c-int: 21b-int (3.50 g, 11.69 mmol) in HCl/MeOH (4N, 40 mL) was stirred at 20° C. for 12 hrs. TLC (PE:EtOAc=10:1, R_f=0.15) indicated the reaction was complete. The mixture was concentrated to give compound 21c-int.

Compound 21d-int: To 21c-int (200 mg, 1 mmol) in DMSO (3 mL) was added (S)-methyl 3-(4-bromophenyl)-2-((tert-butoxycarbonyl)amino)propanoate (610.13 mg, 1.51 mmol), CuI (38.23 mg, 200.75 umol), Cs₂CO₃ (654.09 mg, 2.01 mmol) and L-proline (46.23 mg, 401.51 umol). The mixture was stirred at 90° C. for 12 hrs under N₂. LCMS indicated the reaction was complete. The reaction mixture was diluted with H₂O (20 mL) and extracted with ethyl acetate (20 mL×3). The combined organic phases were washed with brine (30 mL), dried with anhydrous Na₂SO₄, filtered and concentrated. The residue was purified by silica gel chromatography (PE:EA=10:1, 0:1) to give 21d-int.

Compound 21e-int: To 21d-int (170 mg, 356.72 umol) in MeOH (10 mL) was added Pd/C (50 mg), then the mixture was stirred at 40° C. for 12 hrs under H₂; TLC showed the starting material was consumed completely. The mixture was filtered and concentrated in vacuum to give 21e-int.

$^1$H NMR (400 MHz, CHLOROFORM-d): δ ppm 7.19-7.37 (m, 1H), 7.15 (s, 1H), 6.98 (br d, J=8.16 Hz, 2H), 6.42-6.48 (m, 2H), 4.01 (dt, J=14.44, 7.33 Hz, 1H), 3.66-3.81 (m, 5H), 3.27-3.36 (m, 2H), 3.12 (d, J=1.10 Hz, 2H), 2.96-3.05 (m, 2H), 2.71 (br t, J=6.28 Hz, 2H), 2.29-2.38 (m, 3H), 1.94 (dt, J=11.42, 5.65 Hz, 2H), 1.43 (s, 9H).

Compound 21f-int: To 21e-int (160 mg, 332.92 umol) in DCM (5.00 mL) was added TFA (1.54 g, 13.51 mmol, 1.00 mL), then the mixture was stirred at 25° C. for 12 hrs. LCMS showed the reaction was complete. The mixture was concentrated to give 21f-int; LCMS (ESI+): m/z=381.3 (M+H)$^+$, RT: 0.59 min.

Compound 21g-int: To 2,6-dichlorobenzoic acid (60.24 mg, 315.40 umol) in DCM was added HOBt (35.51 mg, 262.83 umol) and EDCI (65.50 mg, 341.68 umol), then the mixture was stirred 0.5 hrs. Compound 21f-int (100 mg, 262.83 umol) and Et$_3$N (66.49 mg, 657.08 umol, 91.08 uL) was added to the mixture and stirred at 25° C. for 12h. LCMS showed the reaction was complete. The mixture was added to H$_2$O (10 mL) and extracted with ethyl acetate (20 mL×2). The combined organic phases were washed with brine (20 mL×5), dried with anhydrous Na$_2$SO$_4$, filtered and concentrated. After purification by prep-TLC (PE:EtOAc=0:1) there was obtained 21g-int; LCMS (ESI+): m/z=553.2 (M+H)$^+$, RT: 0.72 min.

Example 21

To 21g-int (70 mg, 126.47 umol) in THF (5 mL)/H$_2$O (2 mL) was added LiOH.H$_2$O (15.92 mg, 379.42 umol). This mixture was stirred at 40° C. for 12 hrs whereupon LCMS showed the reaction was complete. The mixture was concentrated and purified by prep-HPLC to give Example 21.

HPLC purification conditions: Gilson 281 semi-preparative HPLC system; Mobile phase A: TFA/H$_2$O=0.075% v/v; B: AcN (gradient % B at T=0: 20%; at T=10 min: 40%); Column: Boston Green ODS 150×30 5 u; Flow rate: 25 mL/min; Monitor wavelength: 220 & 254 nm.

$^1$H NMR (400 MHz, METHANOL-d$_4$): δ ppm 7.88 (s, 1H), 7.31-7.36 (m, 3H), 7.16 (d, J=8.60 Hz, 2H), 6.49 (d, J=8.38 Hz, 2H), 4.82-4.83 (m, 1H), 4.22 (t, J=7.61 Hz, 2H), 3.99 (s, 1H), 3.73-3.79 (m, 2H), 3.45-3.49 (m, 2H), 3.15 (d, J=5.73 Hz, 2H), 2.91 (dd, J=14.00, 9.15 Hz, 1H), 2.83 (t, J=6.17 Hz, 2H), 1.90-1.98 (m, 2H); LCMS (ESI+): m/z=539.0 (M+H)$^+$, RT: 2.2 min; HPLC purity: 96.3%, RT: 6.3 min; Chiral SFC: racemate.

Example 22

Synthesis of (S)-2-(2,6-dichlorobenzamido)-3-(4-(3-(5,6,7,8-tetrahydro-1,8-naphthyridin-2-yl)azetidin-1-yl)phenyl)propanoic acid

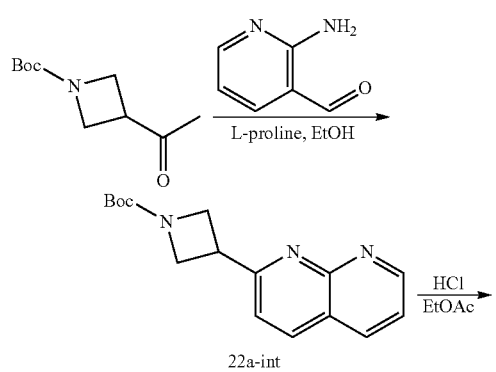

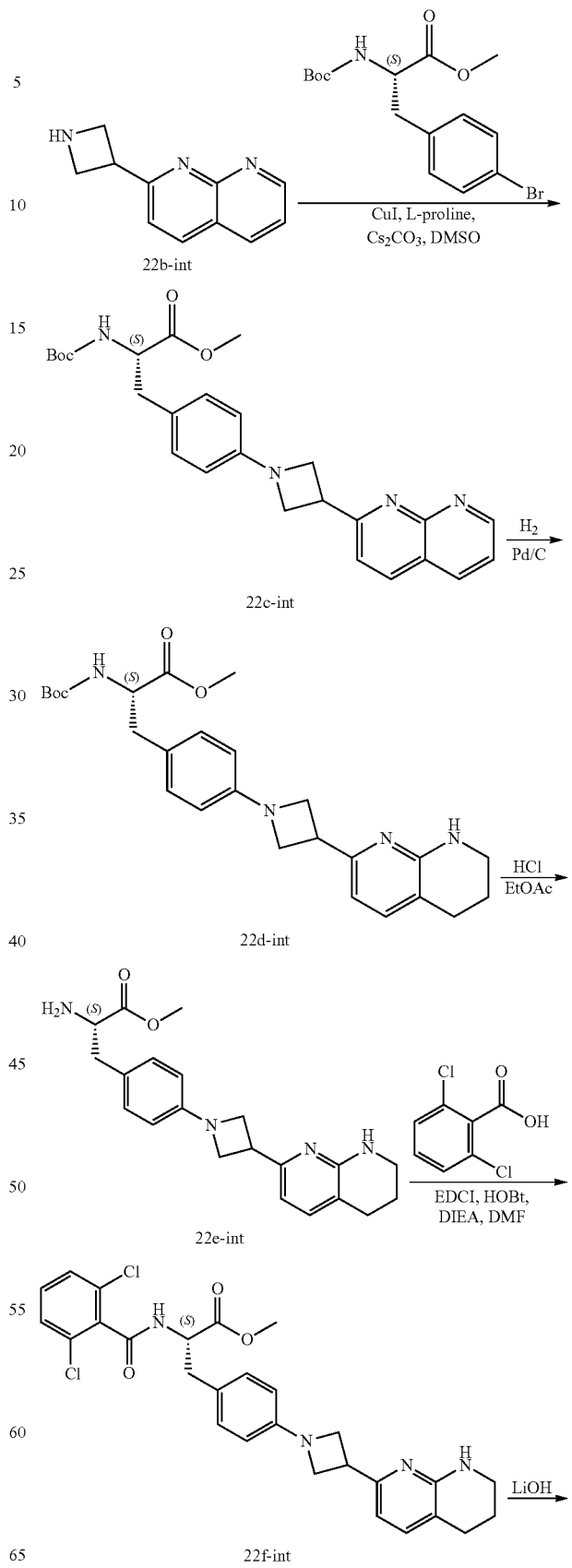

181

-continued

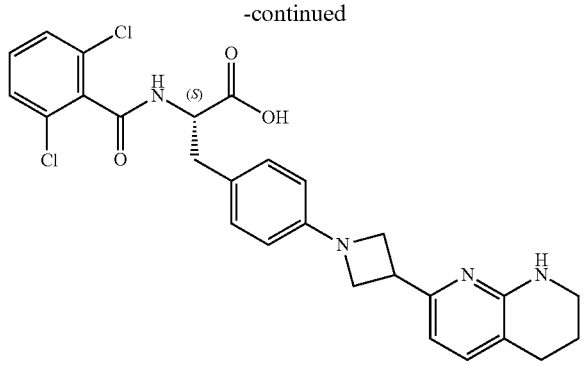

Example 22

Compound 22a-int: To the solution of tert-butyl 3-acetylazetidine-1-carboxylate (4.8 g, 24.09 mmol) in EtOH (70 mL) was added L-proline (1.39 g, 12.05 mmol) and 2-aminonicotinaldehyde (2.94 g, 24.09 mmol). The mixture was stirred at 70° C. for 12 hrs after which LCMS showed the reaction was completed. The mixture was concentrated in vacuum and purified by silica gel chromatography (PE:EtOAc=5:1 to 0:1) to give 22a-int; $^1$H NMR (400 MHz, CHLOROFORM-d): δ ppm 9.10-9.22 (m, 1H), 8.17-8.30 (m, 2H), 7.46-7.60 (m, 2H), 4.39 (br s, 4H), 4.03-4.29 (m, 1H), 1.42-1.53 (m, 9H).

Compound 22b-int: 22a-int (1.50 g, 5.26 mmol, 1.00 eq) in HCl/EtOAc (50 mL) was stirred at 25° C. for 12 hrs. LCMS and TLC showed the reaction was completed. The mixture was concentrated to give 22b-int; $^1$H NMR (400 MHz, METHANOL-d$_4$): δ ppm 9.11-9.27 (m, 1H), 8.52-8.77 (m, 2H), 7.67-7.89 (m, 2H), 4.51-4.64 (m, 3H), 4.10-4.33 (m, 1H), 3.73-4.00 (m, 1H).

Compound 22c-int: To 22b-int (500 mg, 2.70 mmol) in DMSO (10 mL) was added (S)-methyl 3-(4-bromophenyl)-2-((tert-butoxycarbonyl)amino) propanoate (1.64 g, 4.05 mmol) and Cs$_2$CO$_3$ (1.76 g, 5.40 mmol), CuI (102.82 mg, 540.00 umol) and L-proline (124.32 mg, 1.08 mmol). The mixture was stirred at 90° C. for 18 hrs under N$_2$; after this time LCMS showed that the reaction was complete. The mixture was diluted with H$_2$O (20 mL) and extracted with ethyl acetate (20 mL×3). The combined organic phases were washed with brine (30 mL), dried with anhydrous Na$_2$SO$_4$, filtered and concentrated, then purified by silica gel chromatography (PE:EtOAc=1:1) to give 22c-int; $^1$H NMR (400 MHz, CHLOROFORM-d): δ ppm 9.10 (dd, J=4.41, 1.98 Hz, 1H), 8.15-8.24 (m, 2H), 7.62 (d, J=8.38 Hz, 1H), 7.48 (dd, J=8.05, 4.30 Hz, 1H), 6.97 (d, J=8.38 Hz, 2H), 6.49 (d, J=8.16 Hz, 2H), 4.96 (br d, J=7.72 Hz, 1H), 4.36-4.38 (m, 2H), 4.26 (br d, J=2.87 Hz, 2H), 3.71 (s, 3H), 1.42 (s, 9H).

Compound 22d-int: To 22c-int (300 mg, 648.59 umol) in MeOH (7 mL) was added Pd/C (100 mg); the mixture was degassed with N$_2$ then saturated with H$_2$. The reaction was stirred under H$_2$ (50 psi) at 40° C. for 12 hrs. TLC showed the starting material was consumed completely; the mixture was filtered and concentrated to give 22d-int; LCMS (ESI+): m/z=467.3 (M+H)$^+$, RT: 0.75 min.

Compound 22e-int: 22d-int was added to HCl/MeOH (10 mL) and stirred at 25° C. for 12 hrs. After this time LCMS showed the reaction was complete. The mixture was concentrated to give 22e-int.

Compound 22f-int: To 2,6-dichlorobenzoic acid (175.13 mg, 916.88 umol) in DMF (5 mL) was added EDCI (190.41 mg, 993.29 umol) and HOBt (103.24 mg, 764.07 umol); this mixture was stirred 0.5h. Compound 22e-int (280 mg, 764.07 umol) and Et$_3$N (193.29 mg, 1.91 mmol, 264.78 uL) were added to the mixture and stirred at 25° C. for 2 hrs. LCMS showed the reaction was complete. The mixture was diluted with H$_2$O (10 mL) and extracted with ethyl acetate (20 mL×2). The combined organic phases were washed with brine (20 mL×5), dried over anhydrous Na$_2$SO$_4$, filtered and concentrated. The residue was purified by prep-TLC (PE:EtOAc=1:1) to give 22f-int; LCMS (ESI+): m/z=539.2 (M+H)$^+$, RT: 0.75 min.

Example 22

To 22f-int (100 mg, 185.37 umol) in THF (5 mL) was added LiOH (13.32 mg, 556.12 umol) and H$_2$O (2 mL), then the mixture was stirred at 40° C. for 12 hrs. After this time LCMS showed the reaction was complete. The mixture was concentrated then purified by prep-HPLC to give Example 22.

HPLC purification conditions: Gilson 281 semi-preparative HPLC system; Mobile phase A: TFA/H$_2$O=0.075% v/v; B: AcN (gradient % B at T=0: 12%; at 10.5 min: 34%); Column: Boston Green ODS 150×30 5 u; Flow rate: 25 mL/min; Monitor wavelength: 220 & 254 nm.

$^1$H NMR (400 MHz, METHANOL-d$_4$): δ ppm 7.63 (d, J=7.2 Hz, 1H), 7.32-7.36 (m, 3H), 7.17 (d, J=8.4 Hz, 2H), 6.83 (d, J=7.5 Hz, 1H), 6.50 (d, J=8.4 Hz, 2H), 4.81 (br s, 1H), 4.16-4.23 (m, 2H), 3.90 (br d, J=2.8 Hz, 2H), 3.47-3.53 (m, 2H), 3.27-3.28 (m, 1H), 3.17 (dd, J=14.0, 5.52 Hz, 1H), 2.92 (dd, J=14.2, 9.2 Hz, 1H), 2.83 (t, J=6.4 Hz, 2H), 1.92-2.00 (m, 2H); LCMS (ESI+): m/z=525.0 (M+H)$^+$, RT: 2.5 min; HPLC purity: 90.5%, RT: 6.2 min; Chiral SFC purity: 87.3%, ee value: 74.5%, RT: 1.3 min.

Example 23

Synthesis of (S)-2-(2,6-dichlorobenzamido)-3-(4-(((1s,3R)-3-(pyridin-2-ylamino)cyclobutyl)methoxy)phenyl)propanoic acid

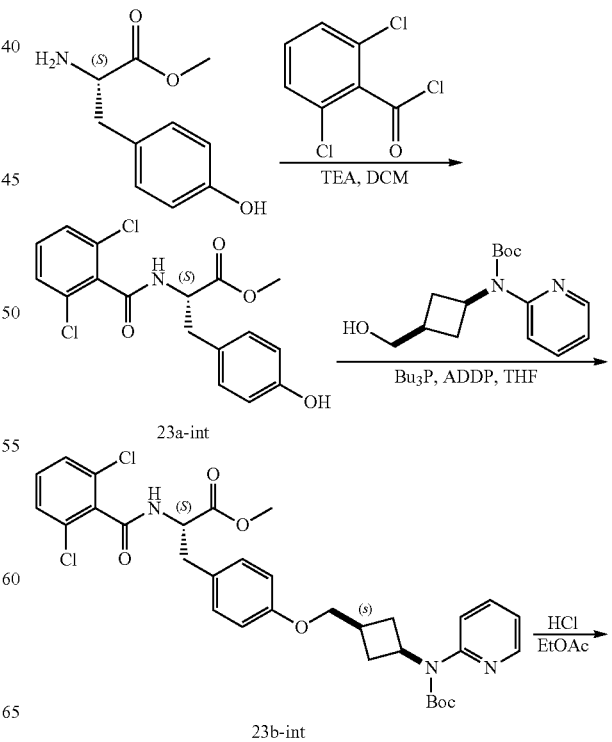

183
-continued

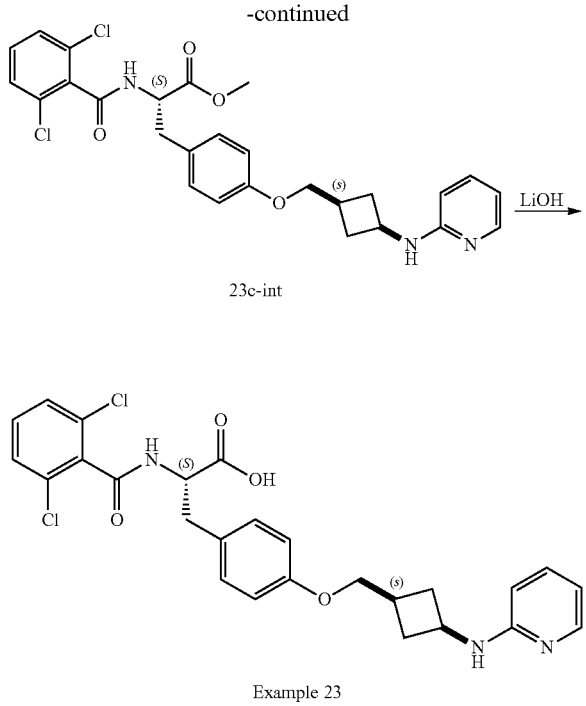

Example 23

Compound 23a-int: See the procedure for compound 18a-int.

Compound 23b-int: To 23a-int (0.4 g, 1.09 mmol) in THF (20 mL) was added tert-butyl ((1s,3s)-3-(hydroxymethyl)cyclobutyl)(pyridin-2-yl)carbamate (0.3 g, 1.09 mmol) and PPh₃ (0.63 mg, 2.4 mmol) at 0° C., then portions of ADDP (0.6 g, 2.40 mmol) were added at 0° C. The mixture was stirred for 12 hrs at 30° C. then concentrated. The crude product was purified by column chromatography (PE:EtOAc=5:1 to 1:1) to give 23b-int; LCMS (ESI+): m/z=628.2 (M+H)⁺, RT: 0.91 min.

Compound 23c-int: 23b-int (0.9 g) in HCl/MeOH (50 mL, 4M) was stirred for 2 h at 15° C. The mixture was concentrated to give 23c-int; LCMS (ESI+): m/z=528.2 (M+H)⁺, RT: 0.75 min.

Example 23

To 23c-int (0.4 g) in THF (10 mL)/H₂O (10 mL) was added LiOH. H₂O (0.16 g, 3.78 mmol). The mixture was stirred for 2 h at 30° C. then was concentrated and purified by prep-HPLC to give Example 23.

HPLC purification conditions: Gilson 281 semi-preparative HPLC system; Mobile phase A: TFA/H₂O=0.075% v/v; B: AcN (gradient % B at T=0: 10%; at T=12 min: 30%); Column: Luna C18 100×30 5 u; Flow rate: 20 mL/min; Monitor wavelength: 220 & 254 nm.

¹H NMR (400 MHz, CHLOROFORM-d): δ ppm 2.03-1.97 (m, 2H) 2.59-2.49 (m, 3H) 3.21 (t, J=10.4 Hz, 2H) 3.89 (d, J=5.2 Hz, 3H) 5.12-5.07 (m, 1H) 5.42 (s, 1H) 6.38 (d, J=7.6 Hz, 1H) 6.69-6.63 (m, 2H) 6.77 (d, J=8.8 Hz, 2H) 7.15 (d, J=8.8 Hz, 2H) 7.28-7.22 (m, 3H) 7.79-7.74 (m, 2H) 9.67 (s, 1H); LCMS (ESI+): m/z=514.0 (M+H)⁺, RT: 2.2 min; HPLC purity: 95.3%, RT: 6.2 min; Chiral SFC purity: 100%, ee value: 100%, RT: 3.4 min.

184

Example 24

Synthesis of (S)-2-(2,6-dichlorobenzamido)-3-(4-((E)-2-((1s,4R)-4-(pyridin-2-ylamino)cyclohexyl)vinyl)phenyl)propanoic acid

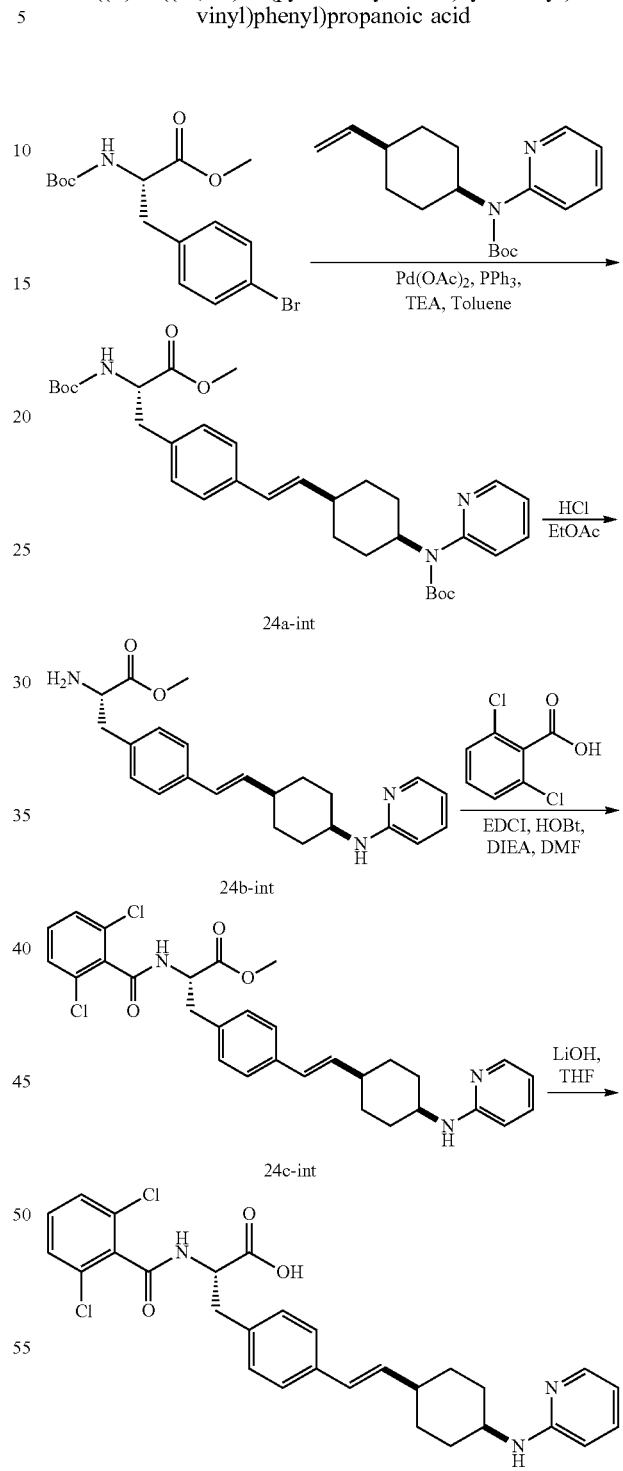

Compound 24a-int: To a solution of tert-butyl pyridin-2-yl((1s,4s)-4-vinylcyclohexyl)carbamate (1 g, 3.31 mmol) in toluene (15 mL) was added Pd(OAc)₂ (37.12 mg, 165.5 umol) and PPh₃ (86.82 mg, 331.00 umol) under N₂, then (S)-methyl 3-(4-bromophenyl)-2-((tert-butoxycarbonyl)

amino)propanoate (2.37 g, 6.62 mmol) and TEA (669.22 mg, 6.62 mmol, 916.74 uL) was added to the mixture; the mixture was stirred at 70° C. under N₂ for 14 hrs. LCMS showed the reaction was complete after this time. The mixture was filtered and concentrated, then partitioned between water (50 mL) and EtOAc (50 mL) then the organic layer was washed with saturated NH₄Cl aqueous solution (100 mL), brine (100 mL), dried over Na₂SO₄ (10 g) and concentrated. The residue was purified by column chromatography (SiO₂, PE:EtOAc=5:1 to 1:1) to give 24a-int; ¹H NMR (400 MHz, CHLOROFORM-d): δ ppm 8.48 (dd, J=10.58, 4.41 Hz, 1H), 7.66-7.71 (m, 1H), 7.23 (d, J=7.94 Hz, 2H), 7.12-7.18 (m, 2H), 7.00-7.06 (m, 3H), 6.25-6.35 (m, 1H), 4.00-4.11 (m, 1H), 3.71-3.73 (m, 3H), 3.27 (d, J=7.06 Hz, 1H), 3.06 (br. s., 1H), 1.94-2.04 (m, 1H), 1.57-1.92 (m, 8H), 1.38-1.42 (m, 18H).

Compound 24b-int: To 24a-int (150 mg, 258.74 umol) in EtOAc (5 mL) was added HCl/EtOAc (4 M, 50 mL); the mixture was stirred at 20° C. for 2 h after which LCMS showed the reaction was complete. The mixture was concentrated under reduced pressure and the crude compound 24b-int was used into the next step without further purification; LCMS (ESI+): m/z=380.3, (M+H)⁺, RT: 0.63 min Compound 24c-int: To a solution of 2,6-dichlorobenzoic acid (83.05 mg, 434.80 umol) in DMF (8 mL) was added HOBt (58.75 mg, 434.80 umol) and EDCI (83.35 mg, 434.8 umol); the mixture was stirred at 20° C. for 0.5 hr. Compound 24b-int (150 mg, 395.27 umol) in DMF (2 mL) and TEA (120 mg, 1.19 mmol, 164.37 uL) was added; the mixture was stirred at 20° C. for 5.5 hr. LCMS showed the reaction was completed. H₂O (50 mL) and EtOAc (15 mL) were added into the mixture, separated, the organic layer was dried over Na₂SO₄ and concentrated. The residue was purified by prep-TLC (SiO₂, PE:EtOAc=1:2) to give 24c-int; LCMS (ESI+): m/z=552.3, (M+H)⁺, RT: 0.78 min.

Example 24

To a solution of 24c-int in THF (10 mL) was added LiOH.H₂O (151.9 mg, 3.62 mmol). The mixture was stirred at 60° C. for 2 hours. The reaction mixture was concentrated under reduced pressure to remove solvent. The residue was purified by prep-HPLC to give Example 24.

HPLC purification method: Gilson 281 semi-preparative HPLC system; Mobile phase A: TFA/H₂O=0.075% v/v; B: AcN (gradient % B at T=0: 12%; at T=12 min: 45%); Column: Luna C18 100×30 5 u; Flow rate: 20 mL/min; Monitor wavelength: 220 & 254 nm.

¹H NMR (400 MHz, METHANOL-d₄): δ ppm 7.87-7.90 (m, 1H), 7.80-7.82 (m, 1H), 7.25-7.39 (m, 6H), 7.10-7.13 (m, 1H), 7.05 (m, 1H), 6.85-6.87 (m, 1H), 6.43 (s, 1H), 6.26-6.28 (m, 1H), 4.92 (m, 1H), 3.83 (m, 1H), 3.35 (m, 1H), 3.25 (m, 1H), 2.97-3.03 (m, 2H), 2.44 (m, 1H), 1.73-1.87 (m, 6H); LCMS (ESI+): m/z=538.1 (M+H)⁺, RT: 2.0 min; HPLC purity: 98.7%, RT: 7.0; Chiral SFC purity: 79.3%, e.e. value: 58.6%, RT: 4.53.

Example 25

Synthesis of (S)-2-(2,6-dichlorobenzamido)-3-(4-(((1s,4R)-4-(pyridin-2-ylamino)cyclohexyl)methoxy)phenyl)propanoic acid

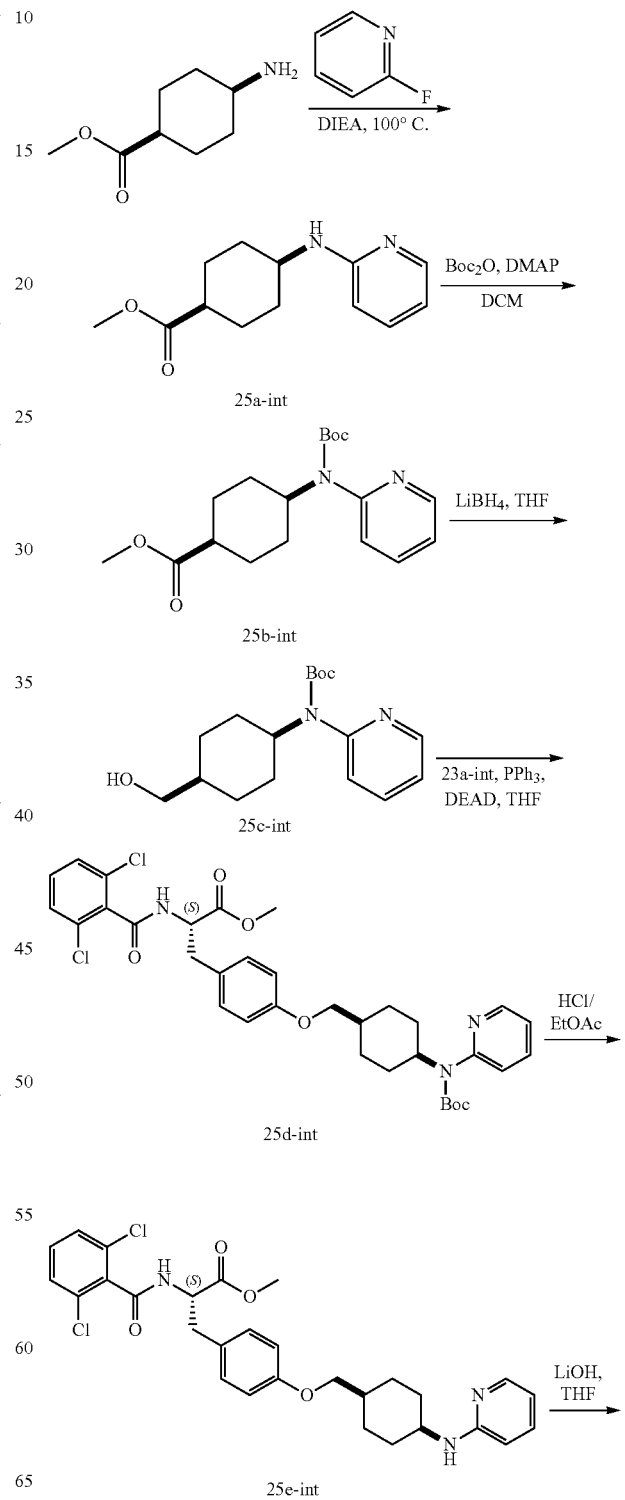

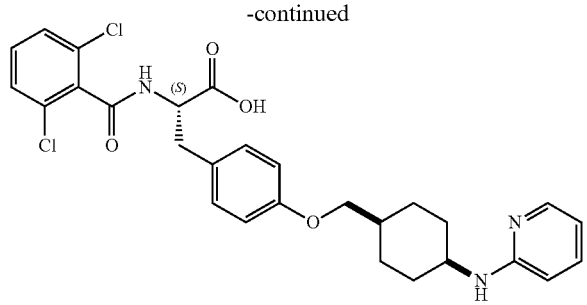

Example 25

Compound 25a-int: To a mixture of methyl 4-aminocyclohexanecarboxylate (14 g, 68.67 mmol, HCl salt) in 2-fluoropyridine (99.75 g, 1.03 mol, 88.27 mL) was added DIEA (8.88 g, 68.67 mmol, 11.99 mL). The mixture was stirred at 120° C. for 16 hr; LCMS showed the reaction was complete. The mixture was concentrated and taken up in EtOAc (200 mL) dried and concentrated. The residue was purified by silica gel chromatography (PE:EtOAc=1:1) to give 25a-int; LCMS (ESI+): m/z=235.1 (M+H)+, RT: 0.63 min.

Compound 25b-int: To 25a-int (2 g, 8.11 mmol), TEA (2.46 g, 24.33 mmol, 3.37 mL), DMAP (99.08 mg, 811.00 umol) in DCM (20 mL) was added Boc₂O (1.95 g, 8.92 mmol, 2.05 mL). The mixture was stirred at 15° C. for 19 hrs; LCMS showed the reaction was complete. The mixture was washed with H₂O, dried over Na₂SO₄ and concentrated. This material was purified by silica gel chromatography (PE:EtOAc=1:1) to give 25b-int; ¹H NMR (400 MHz, METHANOL-d₄): δ 1.37 (d, J=0.88 Hz, 9H), 1.46-1.64 (m, 4H), 1.80 (br d, J=13.01 Hz, 2H), 2.17 (br d, J=13.01 Hz, 2H), 2.60 (br s, 1H), 3.58 (d, J=0.88 Hz, 3H), 4.03 (td, J=11.52, 2.98 Hz, 1H), 7.14-7.39 (m, 2H), 7.85 (br t, J=7.72 Hz, 1H), 8.32-8.49 (m, 1H).

Compound 25c-int: To 25b-int (1.35 g, 3.84 mmol) in THF (8 mL) was added LiBH4 (250.91 mg, 11.52 mmol). The mixture was stirred at 50° C. for 16 hr; LCMS showed the reaction was complete. The mixture was quenched by H₂O (10 mL) and EtOAc (15 mL) was poured into the mixture. The organic layer was separated, dried over Na₂SO₄ and concentrated. The crude material was purified by silica gel chromatography (PE:EtOAc=1:1) to give 25c-int; LCMS (ESI+): m/z=307.1 (M+H)+, RT: 0.93.

Compound 25d-int: To 25c-int (350 mg, 950.54 umol), 23a-int (270 mg, 837.14 umol), PPh₃ (373.98 mg, 1.43 mmol) in THF (3 mL) was added DEAD (248.32 mg, 1.43 mmol, 258.67 uL) at 0° C. The mixture was stirred at 45° C. for 76 hr; LCMS showed the reaction was complete. The mixture was concentrated to residue and purified by silica gel chromatography (PE:EtOAc=2:1), then by HPLC to give compound 25d-int; LCMS (ESI+): m/z=656.3 (M+H)+, RT: 0.98 min.

Compound 25e-int: To 25d-int (130.00 mg, 142.55 umol) in DCM (5 mL) was added HCl/EtOAc (4 M, 1.07 mL). The mixture was stirred at 30° C. for 1 hr; LCMS showed the reaction was complete. The mixture was concentrated to give 25e-int; LCMS (ESI+): m/z=556.3 (M+H)+, RT: 0.80 min.

Example 25

To 25e-int (80 mg, 97.14 umol) in THF (3 mL) was added LiOH.H₂O (4.08 mg, 97.14 umol). The mixture was stirred at 50° C. for 14 hrs; LCMS showed the reaction was complete. The mixture was purified by prep-HPLC to give Example 25.

HPLC purification method: Gilson 281 semi-preparative HPLC system; Mobile phase A: TFA/H₂O=0.075% v/v; B: AcN (gradient % B at T=0: 10%; at T=12 min: 45%); Column: Luna C18 100×30 5 u; Flow rate: 20 mL/min; Monitor wavelength: 220 & 254 nm.

¹H NMR (400 MHz, METHANOL-d₄): δ ppm 7.72-7.99 (m, 2H), 7.27-7.41 (m, 3H), 7.22 (d, J=8.60 Hz, 2H), 7.13 (d, J=9.26 Hz, 1H), 6.81-6.90 (m, 3H), 4.87-4.93 (m, 1H), 3.81-3.93 (m, 3H), 3.22 (dd, J=14.22, 5.18 Hz, 1H), 2.95 (dd, J=14.11, 9.48 Hz, 1H), 2.01 (br s, 1H), 1.74-1.89 (m, 6H), 1.54-1.73 (m, 2H); LCMS (ESI+): m/z=542.1 (M+H)+, RT: 2.6 min; HPLC purity: 97.9%, RT: 6.8 min; Chiral SFC purity: 79.2%, e.e. value: 68.3%, RT: 3.2 min.

Example 26

Synthesis of (S)-2-(2,6-dichlorobenzamido)-3-(4-((2-methyl-4-(pyridin-2-ylamino)butan-2-yl)amino)phenyl)propanoic acid

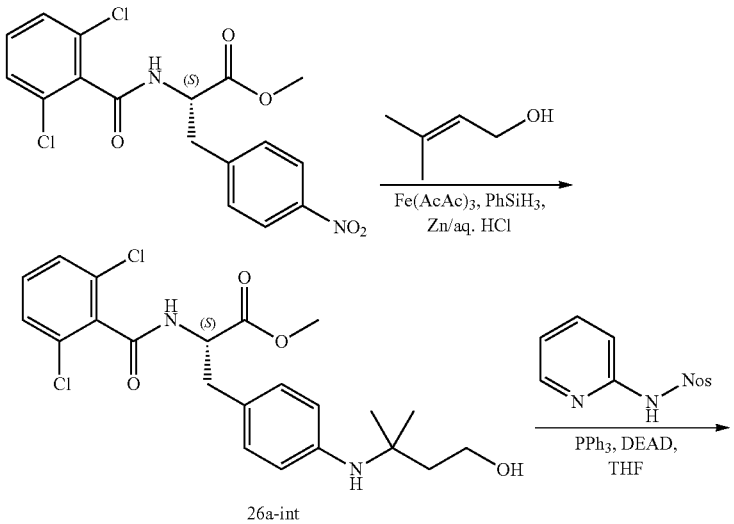

26a-int

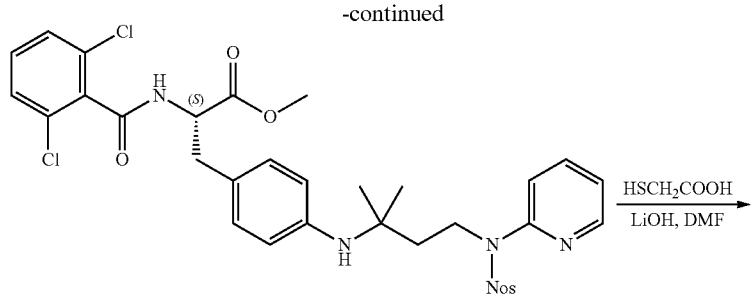

26b-int

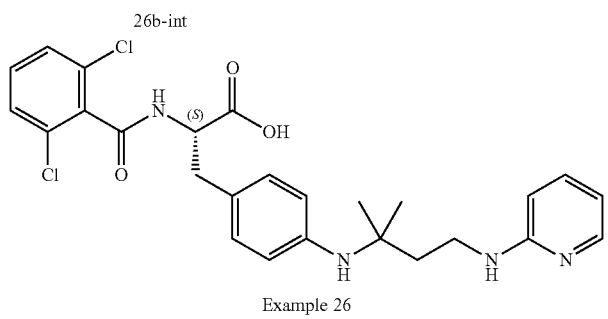

Example 26

Compound 26a-int: To a solution of (S)-methyl 2-(2,6-dichlorobenzamido)-3-(4-nitrophenyl)propanoate (5 g, 12.59 mmol) and 3-methylbut-2-en-1-ol (3.25 g, 37.76 mmol, 3.78 mL) in EtOH (50 mL) was added Fe(AcAc)$_3$ (1.33 g, 3.78 mmol) and PhSiH$_3$ (2.72 g, 25.18 mmol); this mixture was stirred at 60° C. for 1 hr. Zn metal (16.46 g, 251.76 mmol) was added, followed by HCl (10 mL); the reaction was heated at 60° C. for 1 hr. When LCMS indicated the reaction was complete, the solvent was removed by evaporation under reduced pressure. The residue was poured into sat. NaHCO$_3$ (50 mL) and DCM (100 mL) and was filtered then washed with DCM (100 mL). The organic layer was separated and dried over Na$_2$SO$_4$ then concentrated. The crude product was purified by column chromatography on silica gel (PE:EtOAc=2:1) to give compound 26a-int; $^1$H NMR (400 MHz, CHLOROFORM-d): δ ppm 1.25-1.32 (m, 8H) 1.76 (br t, J=5.62 Hz, 1H) 1.87 (br s, 2H) 3.19 (br d, J=5.51 Hz, 2H) 3.76 (s, 2H) 3.86-3.98 (m, 3H) 5.08-5.20 (m, 1H) 6.28 (br d, J=7.94 Hz, 1H) 6.80 (br d, J=7.94 Hz, 2H) 7.00-7.08 (m, 2H) 7.30-7.37 (m, 3H).

Compound 26b-int: 26a-int (1 g, 2.21 mmol), 4-nitro-N-(pyridin-2-yl)benzenesulfonamide (1 g, 2.21 mmol), PPh$_3$ (1.39 g, 5.29 mmol) and DEAD (1.38 g, 7.94 mmol, 1.44 mL) in THF (100 mL) was stirred at 0-20° C. for 12 hrs; LCMS indicated the reaction was complete. The mixture was evaporated and purified by prep-HPLC to give 26b-int; LCMS (ESI+): m/z=714.1 (M+H)$^+$, RT=0.82 min.

Example 26

26b-int (300 mg, 419.81 umol) and mercaptoacetic acid (193.36 mg, 2.10 mmol, 143.23 uL) and LiOH (50.27 mg, 2.10 mmol) in DMF (10 mL) was stirred at 50° C. for 3 hrs; LCMS indicated the reaction was complete. The mixture was poured into H$_2$O (50 mL), washed with TBME (50 mL×2) and the aqueous layer was concentrated. The crude product was purified by prep-HPLC to give Example 26.

HPLC purification method: Gilson 281 semi-preparative HPLC system; Mobile phase A: TFA/H$_2$O=0.075% v/v; B: AcN (gradient % B at T=0: 10%; at 12 min: 45%); Column: Luna C18 100×30 5 u; Flow rate: 20 mL/min; Monitor wavelength: 220 & 254 nm.

$^1$H NMR (400 MHz, METHANOL-d): δ ppm 7.92 (t, J=7.91 Hz, 1H), 7.86 (d, J=6.65 Hz, 1H), 7.58 (d, J=8.41 Hz, 2H), 7.34-7.39 (m, 5H), 7.04 (d, J=9.03 Hz, 1H), 6.91 (t, J=6.78 Hz, 1H), 5.01 (dd, J=10.23, 4.58 Hz, 1H), 3.47-3.52 (m, 2H), 3.40 (d, J=5.02 Hz, 1H), 3.07 (dd, J=14.18, 10.16 Hz, 1H), 2.06-2.13 (m, 2H), 1.49 (d, J=5.40 Hz, 6H); LCMS (ESI+): m/z=515.1 (M+H)$^+$, RT: 1.7 min; HPLC purity: 100%, RT: 4.1 min; Chiral SFC purity: 100%, e.e. value: 100%, RT: 2.2 min.

Example 27

Synthesis of (2S)-2-(2,6-dichlorobenzamido)-3-(4-(3-(1,2,3,4-tetrahydro-1,8-naphthyridin-2-yl)propoxy)phenyl)propanoic acid

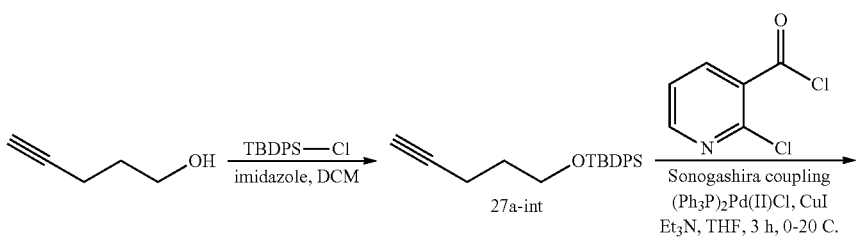

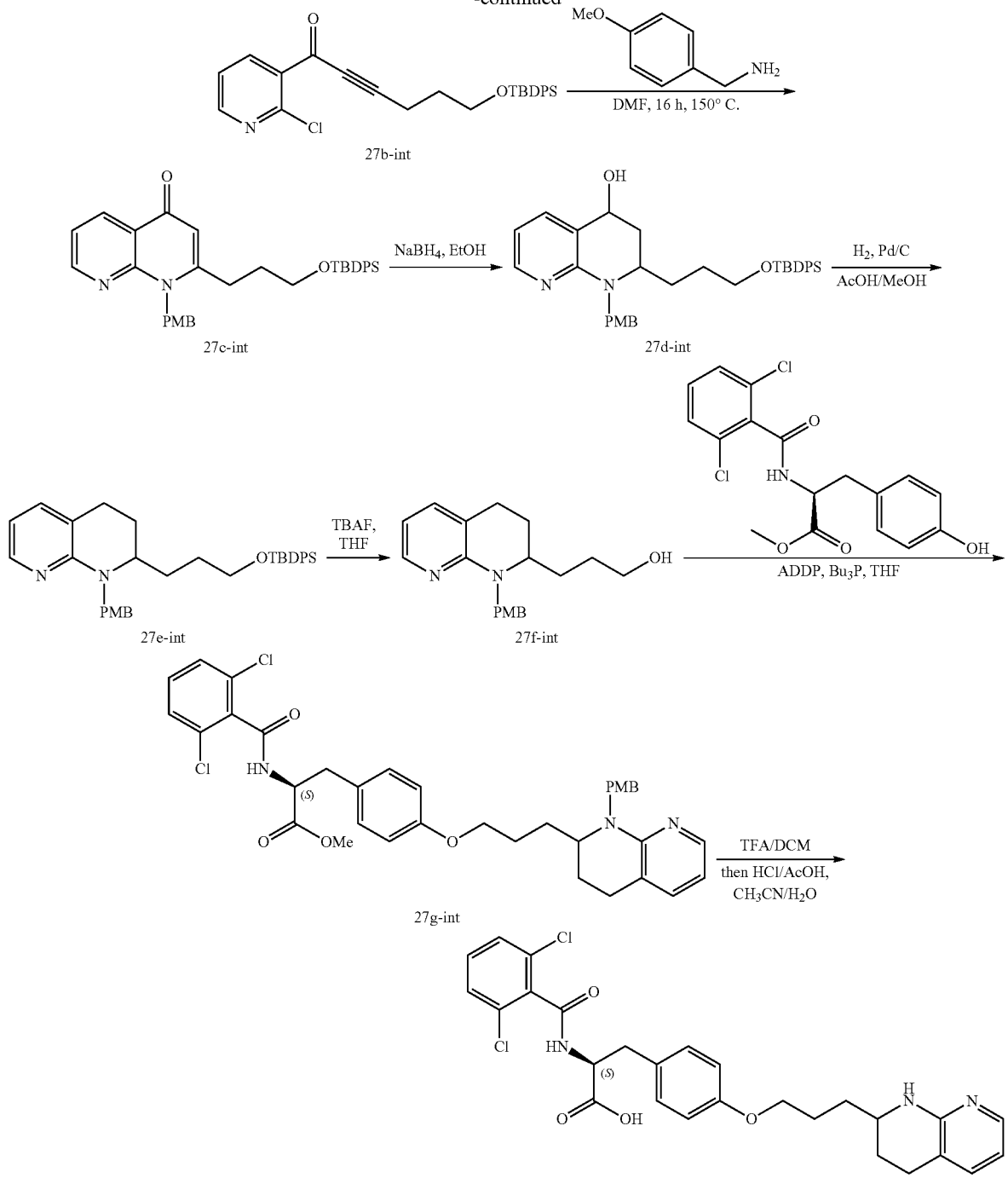

Example 27

Compound 27a-int: To the solution of pent-4-yn-1-ol (4.67 g, 55.52 mmol) in DCM (50 mL) was added imidazole (4.91 g, 72.17 mmol), then there was added a solution of tert-butyl-chlorodiphenylsilane (15.56 g, 56.63 mmol, 14.55 mL) in DCM (30 mL) drop-wise at 0° C. The mixture was stirred at 25° C. for 12 hrs when TLC (Petroleum ether: Ethyl acetate=10:1, Rf=0.5) indicated the reaction was complete. The mixture was poured into HCl solution (0.5N, 50 mL) diluted with $H_2O$ (50 mL), then extracted with DCM (100 mL×2). The combined organics layers were dried over $Na_2SO_4$, filtered and concentrated to give compound 27a-int; $^1H$ NMR (400 MHz, CHLOROFORM-d) δ ppm 7.70 (dd, J=7.89, 1.75 Hz, 4H) 7.38-7.46 (m, 6H) 3.78 (t, J=6.14 Hz, 2H) 2.37 (td, J=7.02, 2.63 Hz, 2H) 1.93 (t, J=2.63 Hz, 1H) 1.76-1.84 (m, 2H) 1.09 (s, 9H).

Compound 27b-int: To a solution of compound 27a-int (17.5 g, 54.26 mmol) in THF (150 mL) was added 2-chloropyridine-3-carbonyl chloride (9.55 g, 54.26 mmol) and CuI (516.69 mg, 2.71 mmol), followed by $Pd(PPh_3)_2Cl_2$ (1.90 g, 2.71 mmol) under $N_2$. The mixture was cooled to 0° C., then TEA was added (5.49 g, 54.26 mmol, 7.52 mL) under $N_2$. The reaction mixture was allowed to warm to 25°

C. with stirring for 12 hrs. after which TLC (Petroleum ether: Ethyl acetate=5:1, Rf=0.25) indicated the reaction was complete. The mixture was eluted with EtOAc (100 mL), filtered. The filtrate was washed with $H_2O$ (100 mL), brine (100 mL) and dried over $Na_2SO_4$. The mixture was filtered and concentrated in vacuo. The residue was purified by column chromatography on silica gel (Petroleum ether: Ethyl acetate=10:1) to give compound 27b-int (16.50 g, 35.71 mmol, 65.81% yield) as a yellow oil; $^1$H NMR (400 MHz, CHLOROFORM-d) δ ppm 8.52 (dd, J=4.60, 1.97 Hz, 1H), 8.22 (dd, J=7.67, 1.97 Hz, 1H), 7.65 (dd, J=7.67, 1.53 Hz, 4H), 7.32-7.41 (m, 6H) 3.78 (t, J=5.92 Hz, 2H) 2.70-2.71 (m, 1H) 2.67 (t, J=7.02 Hz, 1H) 1.89 (quin, J=6.47 Hz, 2H) 1.06 (s, 9H).

Compound 27c-int: A mixture of compound 27b-int (17.5 g, 37.87 mmol) and (4-methoxyphenyl)methanamine (5.20 g, 37.87 mmol, 4.91 mL) in DMF (200 mL) was added $K_2CO_3$ (10.47 g, 75.74 mmol) at 20° C. Then the reaction mixture was stirred at 100° C. TLC (Petroleum ether: Ethyl acetate=3:1, Rf=0.2) indicated the reaction was complete after 16 hrs. The mixture was poured into $H_2O$ (200 mL), then extracted with EtOAc (100 mL×3). The combined organics were dried over $Na_2SO_4$, filtered and concentrated. The residue was purified by column chromatography on silica gel (Petroleum ether: Ethyl acetate=5:1 to 1:1) to give compound 27c-int; $^1$H NMR (400 MHz, CHLOROFORM-d) δ ppm 8.74 (dd, J=7.83, 1.87 Hz, 1 H) 8.69 (dd, J=4.41, 1.76 Hz, 1H) 7.59-7.65 (m, 4H) 7.32-7.45 (m, 7H) 6.91 (d, J=8.60 Hz, 2H) 6.78 (d, J=8.82 Hz, 2H) 3.71-3.77 (m, 5H) 2.79-2.87 (m, 2H) 1.84-1.94 (m, 2H) 1.03 (s, 9H).

Compound 27d-int: To a solution of compound 27c-int (16.50 g, 29.32 mmol) in EtOH (250 mL) was added $NaBH_4$ (13.31 g, 351.83 mmol) in portions. The mixture was stirred at 25° C. for 12 hrs. TLC (Petroleum ether: Ethyl acetate=3:1, Rf=0.25) indicated the reaction was complete. The mixture was poured into $H_2O$ (100 mL) and concentrated in vacuum. The mixture was extracted with EtOAc (200 mL×3), then the combined organics were washed with brine (100 mL), dried over $Na_2SO_4$, filtered and concentrated in vacuo. The residue was purified by column chromatography on silica gel (Petroleum ether: Ethyl acetate=5:1) to give compound 27d-int; LCMS (ESI+): m/z=567.5 (M+H)$^+$, RT: 0.899 min.

Compound 27e-int: A mixture of compound 27d-int (12.00 g, 21.17 mmol) and Pd/C (500 mg) in MeOH (60 mL) and AcOH (20.00 mL) was degassed with $N_2$ three times and then with $H_2$ three times. The mixture was hydrogenated under a $H_2$ (50 psi) atmosphere at 40° C. for 12 hrs. TLC (Petroleum ether: Ethyl acetate=5:1, $R_f$=0.35) indicated that the reaction was complete. The mixture was filtered to remove the catalyst, then the filtrate was concentrated by distillation under vacuum. The residue was purified by column chromatography on silica gel (Petroleum ether: Ethyl acetate=5:1) to give compound 27e-int; LCMS (ESI+): m/z=551.5 (M+H)$^+$, RT=0.943 min.

Compound 27f-int: To a mixture of compound 27e-int (2 g, 3.63 mmol) in THF (30 mL) was added TBAF (1 M, 20 mL). The mixture was stirred at 20° C. for 16 hrs, then EtOAc (50 mL) was poured into the mixture. The mixture was washed with $H_2O$ (3×20 mL), dried over $Na_2SO_4$ and concentrated to a residue. The residue was purified by prep-HPLC to give compound 27f-int; LCMS (ESI+): m/z=313.2 (M+H)$^+$, RT=0.62 min; Chiral SFC: racemate. HPLC purification method: Shimadzu LC-8A preparative HPLC system; Mobile phase A: $TFA/H_2O$=0.09% v/v; B: AcN (gradient % B at T=0: 5%; at 20 min: 35%); Column: Luna C18 250×50 10 u; Flow rate: 80 mL/min; Monitor wavelength: 220 & 254 nm.

Compound 27g-int: To a mixture of compound 27f-int (150 mg, 480.14 umol), (S)-methyl 2-(2,6-dichlorobenzamido)-3-(4-hydroxyphenyl)propanoate (176.79 mg, 480.14 umol) and tributylphosphine (145.71 mg, 720.21 umol, 177.70 uL) was added ADDP (181.72 mg, 720.21 umol) at 0° C. This mixture was stirred at 45° C. for 16 hrs whereupon the reaction was complete by LCMS. EtOAc (50 mL) was poured into the mixture and the mixture was washed with $H_2O$ (3×20 mL), dried over $Na_2SO_4$, concentrated to give a residue. This crude product was purified by TLC (Petroleum ether: Ethyl acetate=1:1) to give 27g-int; LCMS (ESI+): m/z=662.2 (M+H)$^+$, RT=2.26 min.

Example 27

To a mixture of 27g-int (140 mg, 211.29 umol) in DCM (3 mL) was added TFA (24.1 mg, 211.29 umol, 15.64 uL). The mixture was stirred at 30° C. for 16 hrs then the solvent was removed. The residue was dissolved in MeCN (1.5 mL) then $H_2O$ (1.5 mL) and HCl (1N, 633.87 umol, 22.66 uL) and AcOH (neat, 422.58 umol, 24.17 uL) were added. This mixture was stirred at 70° C. for 16 hrs, the solvent was removed and the residue was purified by prep-HPLC to give Example 27.

HPLC purification method: Gilson 281 semi-preparative HPLC system; Mobile phase: A: $TFA/H_2O$=0.075% v/v; B: ACN (gradient % B at T=0: 20%; at 3.1 min: 50%); Column: Luna C18 100×30 5 u; Flow rate: 25 mL/min; Monitor wavelength: 220 & 254 nm.

$^1$H NMR (400 MHz, METHANOL-d$^4$) δ ppm 7.63-7.74 (m, 2H), 7.35 (s, 3H), 7.22 (d, J=8.60 Hz, 2H) 6.71-6.92 (m, 3H), 4.90-4.92 (m, 1H), 3.96-4.11 (m, 2H), 3.70 (br s, 1H), 3.13-3.25 (m, 1H), 2.78-3.00 (m, 3H), 2.03-2.15 (m, 1H), 1.66-1.98 (m, 5H). LCMS (ESI+): m/z=527.7 (M+H)$^+$, RT=2.273 min; HPLC purity: 98.7%, RT: 4.9 min; Chiral SFC: two diastereomers indicated.

Example 28

Synthesis of (+/−)-2-(2,6-dichlorobenzamido)-3-(3-(3-(5,6,7,8-tetrahydro-1,8-naphthyridin-2-yl)propoxy)azetidin-1-yl)propanoic acid

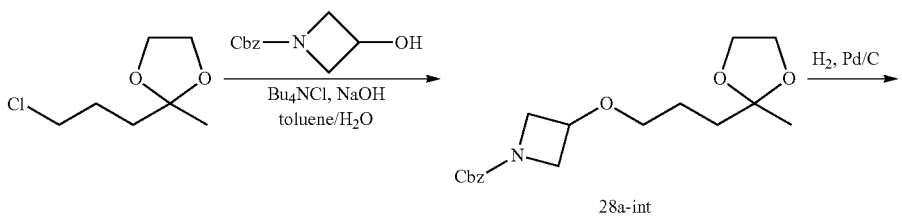

28a-int

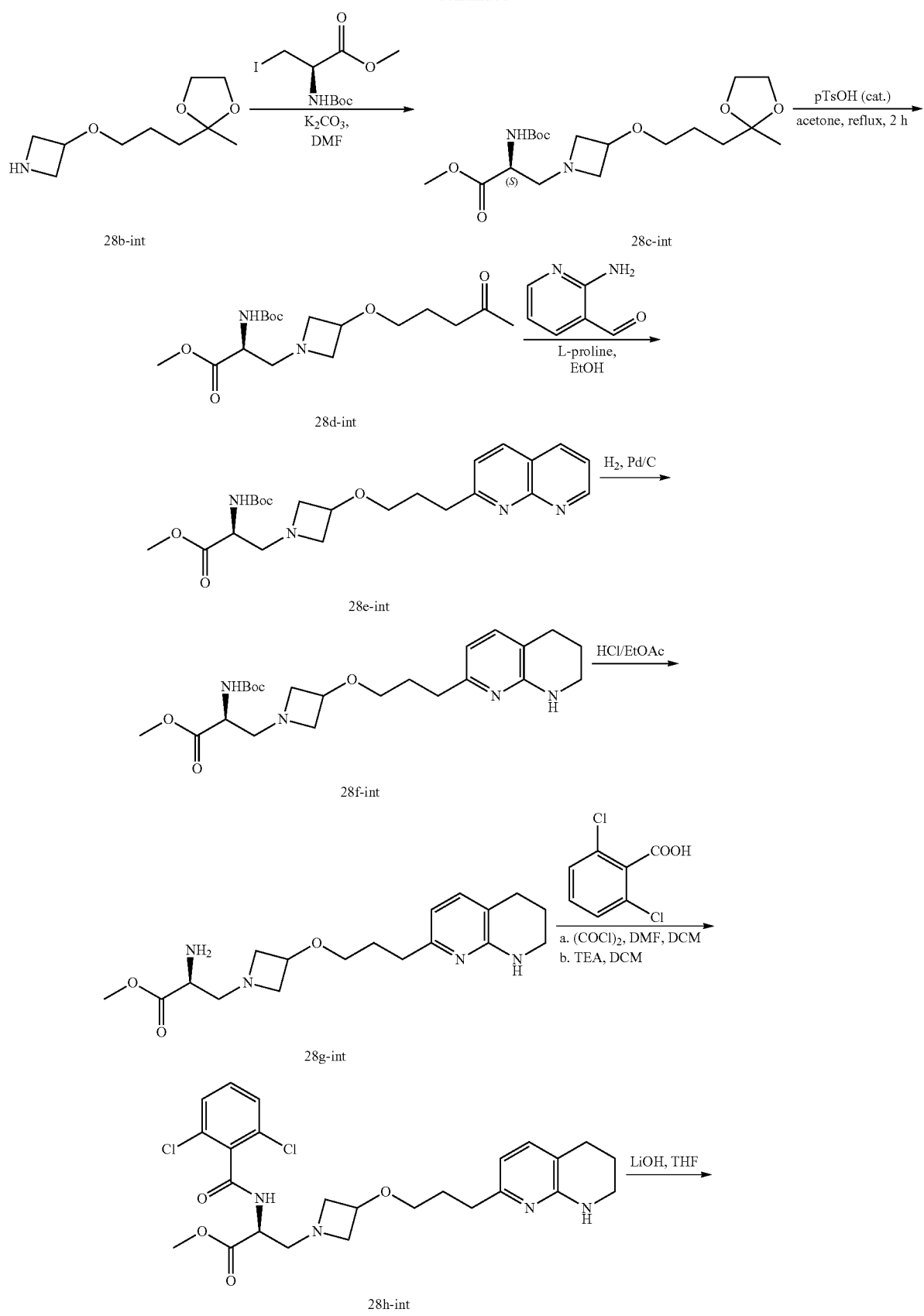

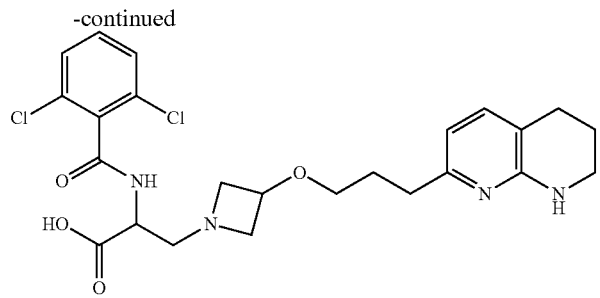

Example 28

Compound 28a-int: To a mixture of benzyl 3-hydroxyazetidine-1-carboxylate (0.17 g, 0.82 mmol) in toluene (5 mL) was added NaOH/H$_2$O (0.79 g, 9.84 mmol, 50% purity) and TBAB (0.07 g, 0.21 mmol) at 10° C. under N$_2$. The mixture was stirred at 10° C. for 30 min, then 2-(3-chloropropyl)-2-methyl-1,3-dioxolane (0.2 g, 1.22 mmol) was added and stirred at 60° C. for 16 hrs. The desired product was detected by LCMS. Nine batches run in parallel at this scale were combined together and the solvent removed. The residue was diluted with H$_2$O (20 mL), then extracted with EtOAc (15 mL×3). The combined organic phase was washed with brine (20 mL), dried over anhydrous Na$_2$SO$_4$ and concentrated in vacuum. This material was purified by column chromatography (SiO$_2$, Petroleum ether: Ethyl acetate=6:1~1:1) to afford compound 28a-int; LCMS (ESI+): m/z=336.1 (M+H)$^+$, RT=0.81 min. $^1$H NMR (400 MHz, CHLOROFORM-d) δ ppm 7.28-7.39 (m, 5H), 5.10 (s, 2H), 4.20-4.28 (m, 1H), 4.11-4.18 (m, 2H), 3.86-3.99 (m, 6H), 3.37 (t, J=5.51 Hz, 2H), 1.70 (br s, 4H), 1.32 (s, 3H).

Compound 28b-int: To a mixture of 28a-int (1.00 g, 2.98 mmol) in MeOH (20 mL) was added Pd/C (30.00 mg, 0.3 mmol, 10%) at 20° C. The mixture was stirred at 20° C. under H$_2$ (15 psi) for 16 hours. TLC (Petroleum Ether: Ethyl Acetate=1:1, R$_f$=0.27) showed compound 28a-int was consumed completely. The reaction was purged with N$_2$, filtered through a pad of Celite® then concentrated to give compound 28b-int; $^1$H NMR (400 MHz, CHLOROFORM-d) δ ppm 4.23-4.39 (m, 1H), 3.88-4.00 (m, 5H), 3.55-3.76 (m, 4H), 3.36 (br t, J=5.95 Hz, 2H), 1.72 (br d, J=5.73 Hz, 4H), 1.33 (s, 3H).

Compound 28c-int: To a mixture of (R)-methyl 2-((tert-butoxycarbonyl)amino)-3-iodopropanoate (1.01 g, 3.06 mmol) in CH$_3$CN (5 mL) was added 28b-int (0.56 g, 2.78 mmol) and DIEA (0.9 g, 6.96 mmol). This mixture was stirred at 70° C. for 16 hours, then LCMS indicated the desired product was present and the reaction complete. The solvent was removed and the residue was poured into water (20 mL) and extracted with EtOAc (15 mL×3). The combined organic phases were washed with brine (20 mL), dried over anhydrous Na$_2$SO$_4$, filtered and concentrated in vacuo. The residue was purified by column chromatography (SiO$_2$, Petroleum ether: Ethyl acetate=6:1~1:1) to afford compound 28c-int; LCMS (ESI+): m/z=403.2 (M+H)$^+$, RT=1.5 min; $^1$H NMR (400 MHz, CHLOROFORM-d) δ ppm 5.38-5.47 (m, 1H), 4.17-4.24 (m, 1H), 4.00-4.08 (m, 1H), 3.87-4.00 (m, 4H), 3.74 (s, 2H), 3.52-3.66 (m, 2H), 3.28-3.37 (m, 2H), 2.75-3.02 (m, 4H), 1.72-1.87 (m, 4H), 1.57-1.71 (m, 4H), 1.44 (s, 9H), 1.31 (s, 3H).

Compound 28d-int: To a mixture of 28c-int (0.78 g, 1.94 mmol) in acetone (20 mL) and H$_2$O (1 mL) was added TsOH.H$_2$O (73.81 mg, 0.39 mmol) at 20° C. The mixture was stirred at 20° C. for 16 hrs after which TLC (Petroleum ether: Ethyl acetate=1:2, R$_f$=0.37) indicated that 28c-int was consumed. NaHCO$_3$ solution was added to adjust to pH 8; the solvent was removed. This residue was poured into water (30 mL) and extracted with DCM (20 mL×3). The combined organic phases were washed with brine (30 mL), dried over anhydrous Na$_2$SO$_4$, filtered, concentrated and purified by prep-TLC (Petroleum ether: Ethyl acetate=1:2, R$_f$=0.37) to give 28d-int.

HPLC purification conditions: Gilson 281 semi-preparative HPLC system; Mobile phase A: TFA/H$_2$O=0.075% v/v; B: ACN (gradient of B: 2% at T=0 to 32% at T=10 min); Column: Luna C18 100×30 5 u; Flow rate: 25 mL/min; Monitor wavelength: 220 & 254 nm.

$^1$H NMR (400 MHz, CHLOROFORM-d) δ ppm 5.40 (br s, 1H), 4.21 (br s, 1H), 4.03 (t, J=5.92 Hz, 1H), 3.74 (s, 3H), 3.51-3.65 (m, 2H), 3.31 (t, J=6.14 Hz, 2H), 2.75-3.01 (m, 4H), 2.51 (t, J=7.02 Hz, 2H), 2.15 (s, 3H), 1.81 (q, J=6.69 Hz, 2H), 1.45 (s, 9H).

Compound 28e-int: To 28d-int (0.35 g, 0.98 mmol) and 2-aminonicotinaldehyde (0.16 g, 1.27 mmol) in MeOH (3 mL) was added L-proline (56.21 mg, 0.49 mmol) under N$_2$. The mixture was stirred at 80° C. for 48 hrs, then TLC (Petroleum ether: Ethyl acetate=1:2, Rf=0.05) showed a new product and the 28d-int was consumed completely. The solvent was removed to give a residue and this material was poured into water (30 mL) then extracted with EtOAc (20 mL×3). The combined organic phases were washed with brine (15 mL), dried with anhydrous Na$_2$SO$_4$, filtered, concentrated and purified by column chromatography (Petroleum ether: Ethyl acetate=1:1~1:5). There was obtained 150 mg of 28e-int which was purified further by prep-HPLC to give pure 28e-int.

HPLC purification conditions: Gilson 281 semi-preparative HPLC system; Mobile phase A: TFA/H$_2$O=0.075% v/v; B: ACN (gradient of B: 2% at T=0 to 32% at T=10 min); Column: Luna C18 100×30 5 u; Flow rate: 25 mL/min; Monitor wavelength: 220 & 254 nm.

$^1$H NMR (400 MHz, CHLOROFORM-d) δ ppm 9.27 (br s, 1H), 8.43 (br d, J=8.38 Hz, 1H), 8.30 (br d, J=8.16 Hz, 1H), 7.69 (br s, 1H), 7.57 (br d, J=7.72 Hz, 1H), 6.14 (br s, 1H), 4.38-4.59 (m, 3H), 3.88 (br s, 1H), 3.78 (s, 3H), 3.69 (br d, J=8.38 Hz, 1H), 3.57-3.65 (m, 1H), 3.52 (br s, 2H), 3.24 (br t, J=6.06 Hz, 2H), 2.15-2.26 (m, 3H), 1.43 (s, 9H); LCMS (ESI+): m/z=445.2 (M+H)$^+$; RT: 1.05 min.

Compound 28f-int: To 28e-int (80.00 mg, 0.18 mmol) in MeOH (10 mL) was added Pd/C (10.00 mg, 10%) under N$_2$. The suspension was degassed under vacuum and purged with H$_2$ several times. The mixture was stirred under H$_2$ (50 psi) at 50° C. for 5 hours. LCMS showed the starting material was consumed completely and had desired MS. The reaction was purged with N$_2$, then filtrated through a pad of diatomaceous earth and concentrated to give 28f-int which was used directly for next step. LCMS (ESI+): m/z=449.3 (M+H)$^+$; RT: 1.1 min.

Compound 28g-int: 28f-int (74 mg, 0.16 mmol) in HCl/EtOAc (30 mL, 4N) was stirred at 20° C. for 16 hrs. LCMS showed that 28g-int was present and the reaction complete; the solvent was removed to give 28g-int, which was used for next step without further processing; LCMS (ESI+): m/z 349.2 (M+H)$^+$, RT: 0.56 min.

Compound 28h-int: To a solution of 2,6-dichlorobenzoic acid (0.1 g, 0.52 mmol) in DCM (5 mL) was added DMF (3.83 mg, 52.35 umol) at 0° C. under N$_2$, then oxalyl dichloride (0.20 g, 1.57 mmol) was added drop-wise at 0° C. and the reaction mixture was stirred at 0 to 20° C. for 2 hours. TLC (Petroleum ether: Ethyl acetate=5:1, R$_f$=0.77) showed the starting material was consumed completely. And the solvent was removed to give 2,6-dichlorobenzoyl chloride (0.11 g, 0.37 mmol, 70% yield) which was used for next step directly. To 28g-int (65 mg, 0.17 mmol, HCl salt) and DIEA (87.3 mg, 0.68 mmol) in DCM (10 mL), was added drop-wise a solution of 2,6-dichlorobenzoyl chloride (88.43 mg, 0.42 mmol) in DCM (5 mL) at 0° C. under N$_2$. The reaction mixture was stirred at 0-20° C. for 16 hrs after which LCMS indicated that 28h-int was present and 28g-int was consumed. The solvent was removed and the residue was purified by prep-HPLC to give pure 28h-int; LCMS (ESI+): m/z 521.3 (M+H)$^+$, RT: 1.1 min.

HPLC purification conditions: Gilson 281 semi-preparative HPLC system; Mobile phase: A: TFA/H$_2$O=0.075% v/v; B: ACN (gradient of B: 20% at T=0 to 40% at T=12 min); Column: YMC-Actus Triart C18 150×30 5 u; Flow rate: 20 mL/min; Monitor wavelength: 220 & 254 nm.

Example 28

To 28h-int (10 mg, 19.18 umol) in THF (3 mL) and H$_2$O (1 mL) was added LiOH.H$_2$O (2.41 mg, 57.54 umol) at 20° C. and this mixture was stirred at 20° C. for 2 hours. LCMS showed the reaction was complete, then 1N HCl was added to adjust the solution to pH 7 and the solvent was removed and the residue was purified by prep-HPLC to give Example 28.

HPLC purification conditions: Gilson 281 semi-preparative HPLC system; Mobile phase: A: TFA/H$_2$O=0.075% v/v; B: ACN (gradient of B: 15% at T=0 to 40% at T=12 min); Column: YMC-Actus Triart C18 150×30 5 u; Flow rate: 25 mL/min; Monitor wavelength: 220 & 254 nm.

$^1$H NMR (400 MHz, METHANOL-d4) δ ppm 7.58 (d, J=7.28 Hz, 1H), 7.39-7.49 (m, 3H), 6.64 (d, J=7.50 Hz, 1H), 4.72-4.77 (m, 1H), 4.57 (br dd, J=10.69, 5.40 Hz, 2H), 4.38-4.46 (m, 1H), 4.19 (br dd, J=10.03, 4.30 Hz, 2H), 3.79 (dd, J=13.01, 7.50 Hz, 1H), 3.63 (dd, J=12.79, 5.29 Hz, 1H), 3.54 (t, J=5.95 Hz, 2H), 3.45-3.51 (m, 2H), 2.78-2.87 (m, 4H), 1.91-2.04 (m, 4H); LCMS (ESI+): m/z 506.9 (M+H)$^+$, RT: 2.1 min; HPLC purity: 97.5%, RT: 4.8 min; Chiral SFC purity: 51.8%, e.e.: 3.7%, RT: 3.9 min.

Example 29

Synthesis of (S)-2-(2,6-dichlorobenzamido)-3-(4-((2-(5,6,7,8-tetrahydro-1,8-naphthyridin-2-yl)ethoxy)methyl)phenyl)propanoic acid trifluoroacetate

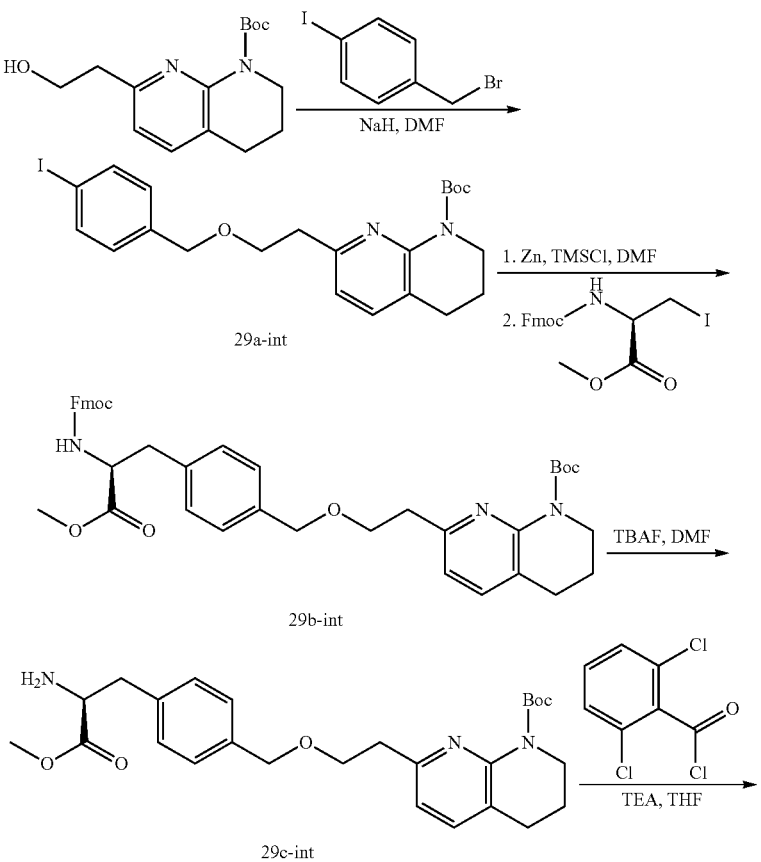

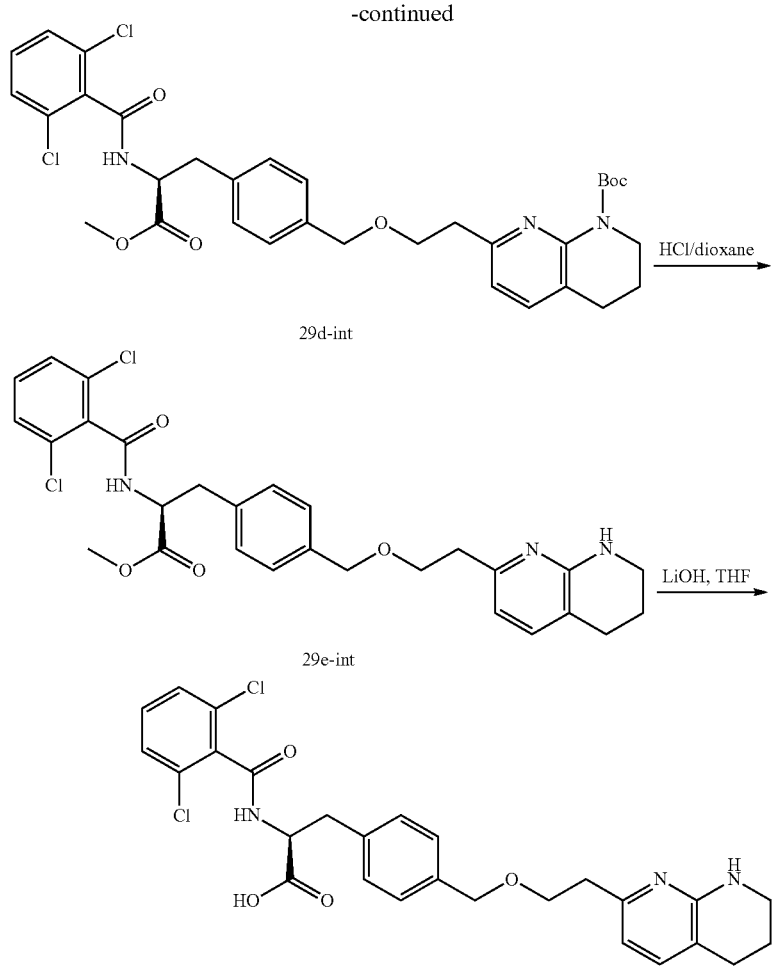

Example 29

Compound 29a-int. To a stirred solution 4-iodobenzyl bromide (800 mg, 2.69 mmol) in 8.0 mL dry DMF cooled to 0° C. in an ice bath was added tert-butyl 7-(2-hydroxyethyl)-3,4-dihydro-1,8-naphthyridine-1(12H)-carboxylate (825 mg, 2.96 mmol), followed by sodium hydride (60% in mineral oil, 162 mg, 4.04 mmol) and the reaction stirred at ambient temperature for 1 hour. The reaction mixture was diluted with water, extracted into diethyl ether, and the organics pooled and washed with brine, dried over sodium sulfate, filtered, concentrated and purified over silica eluted with 0-40% ethyl acetate in hexane to afford the compound 29a-int. $^1$H NMR (400 MHz, DMSO-d6) δ=7.68 (d, J=8.2 Hz, 2H), 7.41 (d, J=7.7 Hz, 1H), 7.09 (d, J=8.3 Hz, 2H), 6.93 (d, J=7.5 Hz, 1H), 4.44 (s, 2H), 3.74 (t, J=6.9 Hz, 2H), 3.64-3.58 (m, 2H), 2.89 (t, J=7.0 Hz, 2H), 2.68 (t, J=6.6 Hz, 2H), 1.80 (quin, J=6.3 Hz, 2H), 1.38 (s, 9H).

Compound 29b-int. To a sealed vial with a stir bar and zinc metal (140 mg, 2.15 mmol) in 1 mL dry DMF under argon was added TMS-Cl (0.045 mL, 0.354 mmol). The reaction was then heated to 50° C. for 15 min. The reaction was allowed to cool to ambient temperature, stirring stopped such that zinc dust settled, and the solvent was withdrawn by syringe. The zinc residue was washed 2×0.500 mL dry DMF using a syringe to introduce and withdraw the solvent from the vial. After two washes, the supernatant was clear. To the activated zinc, Fmoc-iodoalanine methyl ester (228 mg, 0.506 mmol) in 1.5 mL dry DMF was added at once, and the mixture stirred and heated at 55° C. for 15 minutes. A separate solution 29a-int (250 mg, 0.506 mmol) and palladium dichloride bistriphenylphosphine (10.7 mg, 0.015 mmol) in 1 mL dry DMF was prepared, sealed and sparged with argon for 5 minutes. The organozinc was transferred under argon to the mixture of aryl iodide and catalyst, and heated to 55° C. overnight. The reaction was then allowed to cool to ambient temperature, diluted 5 ml water, extracted into 1×5 mL EtOAc, washed 3×5 ml brine, organics pooled and dried over sodium sulfate, filtered, concentrated and purified over silica 0-30% ethyl acetate in hexane to yield the compound 29b-int. $^1$H NMR (400 MHz, DMSO-d$_6$) δ=7.87 (d, J=7.8 Hz, 3H), 7.63 (t, J=6.5 Hz, 2H), 7.43-7.35 (m, 3H), 7.34-7.26 (m, 2H), 7.23-7.16 (m, 4H), 7.13-7.08 (m, 1H), 6.90 (d, J=7.5 Hz, 1H), 4.42 (s, 2H), 4.27-4.18 (m, 3H), 4.18-4.12 (m, 1H), 3.72 (t, J=6.9 Hz, 2H), 3.62 (s, 2H), 3.61-3.56 (m, 2H), 3.03 (dd, J=4.9, 13.6 Hz, 1H), 2.92-2.84 (m, 3H), 2.66 (t, J=6.6 Hz, 2H), 1.79 (quin, J=6.3 Hz, 2H), 1.39 (s, 9H).

Compound 29c-int. To a stirred solution 29b-int (90 mg, 0.130 mmol) in DMF (3.38 mL) and isopropanol (0.1 mL) was added a solution of 1 M TBAF in THF (0.267 mL, 0.267 mmol) in DMF (2.77 mL). The reaction stirred at ambient temperature overnight, and was then diluted with EtOAc (10 mL), washed brine (2×10 mL), dried over magnesium sulfate, filtered and concentrated. The residue was partitioned between acetonitrile and hexanes, and the acetonitrile layer concentrated to afford the 29c-int.

Compound 29d-int. To a stirred solution 29c-int (57 mg, 121 mmol) and TEA (24.6 mg, 0.243 mmol) in 1.7 mL dry THF at 0° C. 2,6-dichlorobenzoyl chloride (25.4 mg, 12.6 mmol) in 1.7 mL dry THF. The reaction was allowed to warm to ambient temperature over 1 hr. The reaction was diluted with water, extracted into ethyl acetate, separated and the organics washed with 0.1N HCl, washed with brine, dried over sodium sulfate, filtered, concentrated and purified over silica gel eluted with 0-100% ethyl acetate in hexane to afford the 29d-int.

Compound 29e-int. 29d-int (44 mg, 0.685 mmol) was stirred at ambient temperature in 4 ml HCl solution in dioxane (3.0 mL) overnight, and then concentrated. The sample was thrice redissolved in methanol and concentrated to afford 29d-int. LCMS (+ESI, calc. M+H+=542.2, obs. 542.2).

Example 29

A solution of 29e-int (36 mg, 0.064 mmol) in 0.5 mL THF and 0.25 mL water with lithium hydroxide monohydrate (5.85 mg, 139 mmol) was stirred at ambient temperature for one hour. The pH of the reaction was adjusted to pH 5-6. A white solid precipitate was formed, washed with water, and the material purified using preparative HPLC (Mobile Phase A: 0.1% TFA in $H_2O$, B: ACN; Flow rate: 20 ml/min; Gradient: 0 min 10% B; 5 min 10% B; 20 min 95% B; 32 min 95% B; 35 min 10% B Column: Phenomenex Gemini 5 micron C18 110 A, 150×21.20 mm 5 micron size), followed by lyophilization to afford the Example 29 as a white solid. $^1$H NMR (400 MHz, METHANOL-d4) δ=7.80 (s, 1H), 7.68 (br s, 1H), 7.59 (d, J=7.4 Hz, 1H), 7.36-7.34 (m, 3H), 7.28 (d, J=7.9 Hz, 2H), 7.18 (d, J=8.0 Hz, 2H), 6.64 (d, J=7.4 Hz, 1H), 4.95-4.91 (m, 2H), 4.54-4.45 (m, 2H), 3.77-3.69 (m, 2H), 3.66-3.63 (m, 1H), 3.51-3.46 (m, 2H), 3.27 (br d, J=5.1 Hz, 1H), 3.00 (dd, J=9.5, 14.1 Hz, 1H), 2.93 (t, J=5.9 Hz, 2H), 2.82 (t, J=6.2 Hz, 2H), 1.99-1.91 (m, 2H). LCMS (+ESI, calc. M+H+=528.1, obs. 527.9).

Example 30

Synthesis of (S)-2-(2,6-dichlorobenzamido)-3-(4-((3-(pyridin-2-ylamino)propoxy) methyl) phenyl) propanoic acid trifluoroacetate

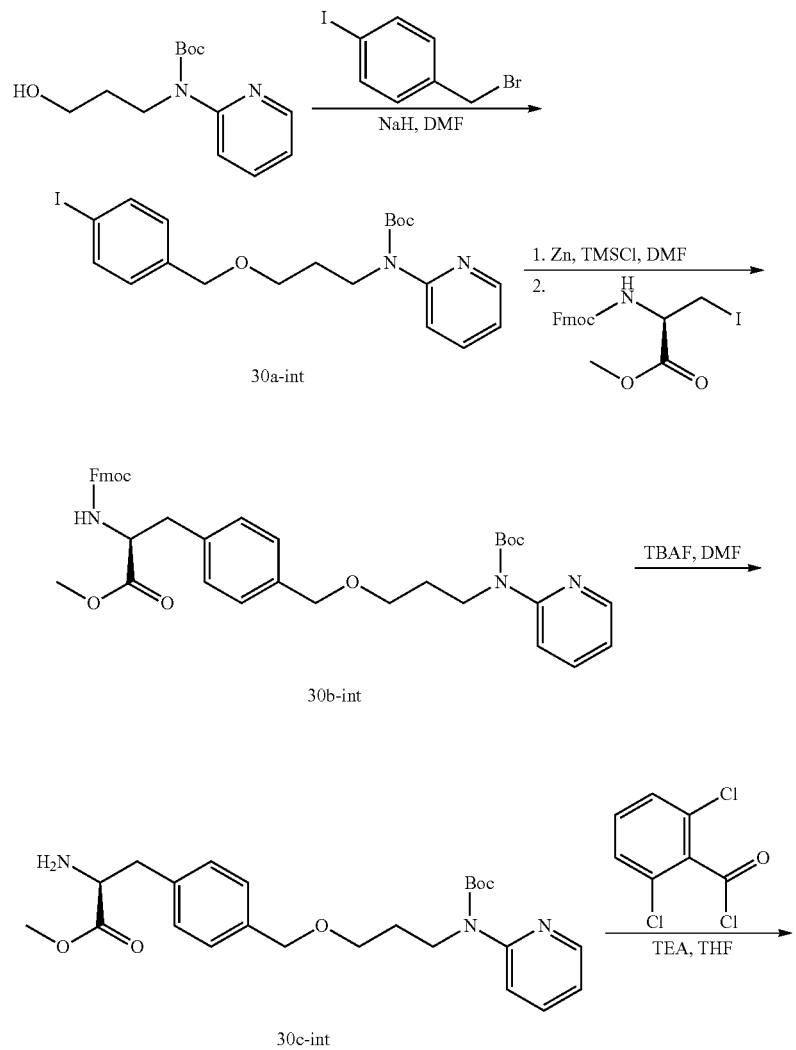

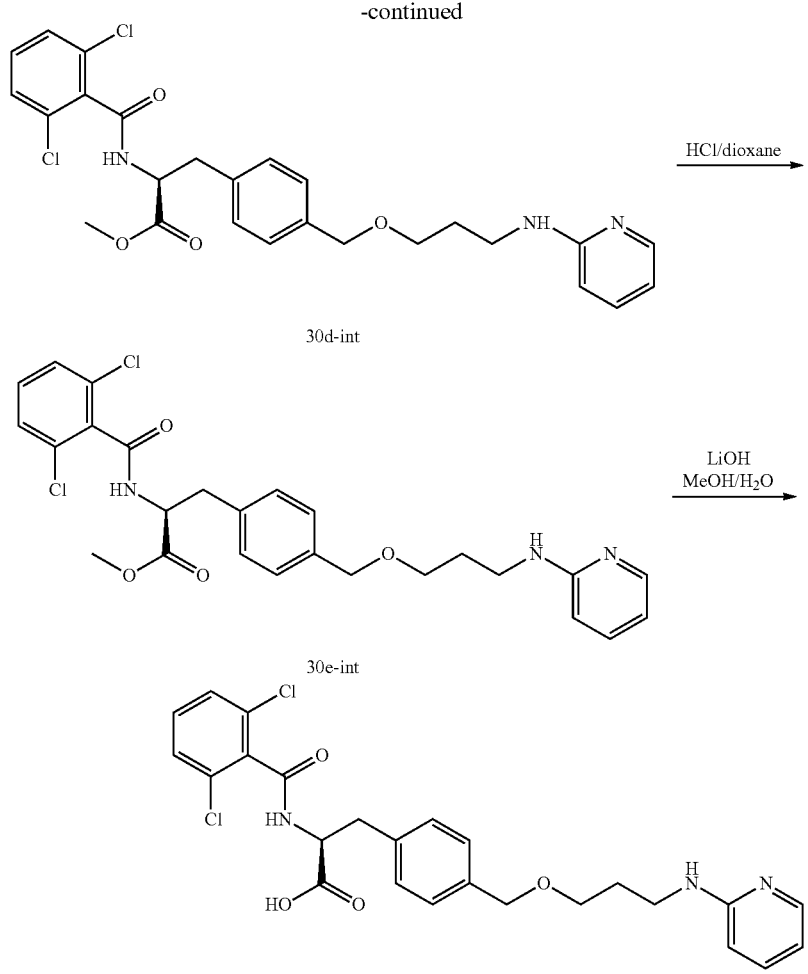

Example 30

Compound 30a-int. To a stirred solution 4-iodobenzyl-bromide (4.0 g, 13.5 mmol) in 40 mL dry DMF was added tert-butyl ((3-hydroxypropyl)pyridine-2-yl)carbamate (3.74 g, 14.8 mmol) and sodium hydride (60% in mineral oil) (808 mg, 20.2 mmol) and the reaction stirred at ambient temperature for one hour. The reaction mixture was diluted with water, extracted into diethyl ether, and the organics pooled, washed with brine, dried over sodium sulfate, filtered, concentrated and purified over silica gel eluted with 0-40% ethyl acetate in hexanes to provide 30a-int; $^1$H NMR (400 MHz, DMSO-d6) δ=8.42-8.33 (m, 1H), 7.74 (ddd, J=2.0, 7.3, 8.3 Hz, 1H), 7.71-7.67 (m, 2H), 7.52 (d, J=8.4 Hz, 1H), 7.13 (ddd, J=0.9, 4.9, 7.3 Hz, 1H), 7.08 (d, J=8.4 Hz, 2H), 4.34 (s, 2H), 3.97-3.88 (m, 2H), 3.43 (t, J=6.2 Hz, 2H), 1.90-1.77 (m, 2H), 1.43 (s, 9H).

Compound 30b-int. To a sealed vial with a stir bar and zinc metal (123 mg, 1.89 mmol) in 0.2 mL dry DMF under argon was added TMS-Cl (0.039 mL, 0.310 mmol) and the reaction was then heated to 50° C. for 15 min. The reaction was allowed to cool to ambient temperature, stirring stopped such that zinc dust settled, and the solvent was withdrawn by syringe. The zinc residue was washed 2×0.75 mL dry DMF using a syringe to introduce and withdraw the solvent from the vial. After two washes, the supernatant was clear. To the activated zinc, Fmoc-iodoalanine methyl ester (200 mg, 0.443 mmol) in 0.2 mL dry DMF was added at once, and the mixture stirred and heated at 55° C. for 15 minutes. A separate solution aryl iodide 1298.5 (208 mg, 0.443 mmol) and palladium dichloride bistriphenylphosphine (9.3 mg, 0.013 mmol) in 0.2 mL dry DMF was prepared, sealed and sparged with argon for 5 minutes. The organozinc was transferred under argon to the mixture of aryl iodide and catalyst, and heated to 55° C. for 1 hr. The reaction was then allowed to cool to ambient temperature, diluted 3 ml water, extracted into 1×2 mL EtOAc, washed 3×3 ml brine, organics pooled and dried over sodium sulfate, filtered, concentrated and purified over silica 0-30% ethyl acetate in hexane to afford 30b-int as a white solid. $^1$H NMR (400 MHz, DMSO-d6) δ=8.39-8.33 (m, 1H), 7.92-7.83 (m, 3H), 7.77-7.70 (m, 1H), 7.63 (br t, J=6.5 Hz, 2H), 7.51 (br d, J=8.2 Hz, 1H), 7.40 (dt, J=4.4, 7.2 Hz, 2H), 7.36-7.24 (m, 3H), 7.23-7.14 (m, 3H), 7.14-7.08 (m, 1H), 4.32 (s, 2H), 4.28-4.19 (m, 3H), 4.20-4.11 (m, 1H), 3.95-3.85 (m, 2H), 3.62 (s, 3H), 3.39 (br t, J=6.1 Hz, 2H), 3.08-3.00 (m, 1H), 2.92-2.84 (m, 1H), 1.85-1.73 (m, 2H), 1.42 (s, 9H).

Compound 30c-int. To a stirred solution of 30b-int (80 mg, 0.120 mmol) in DMF (3.38 mL) and isopropanol (0.092 mL) was added a solution of 1 M TBAF in THF (0.246 mL, 0.246 mmol) in DMF (6.0 mL). The reaction was stirred at ambient temperature overnight, and was then diluted with EtOAc. The organic layer was washed with water, dried over sodium sulfate, filtered and concentrated. The residue was partitioned between acetonitrile and hexanes. The acetonitrile layer was washed 6× with hexanes and concentrated to afford 30c-int.

Compound 30d-int. To a stirred solution of 30c-int (53 mg, 120 mmol) and TEA (24.6 mg, 0.243 mmol) in 1.6 mL dry THF was added 2,6-dichlorobenzoyl chloride (16.9 mg, 0.120 mmol) in 1.6 mL dry THF. The reaction was allowed to warm to ambient temperature over 1 hr. The reaction was partitioned with aq. sodium bicarbonate and ethyl acetate. The organic layer was dried over sodium sulfate, filtered, and concentrated. The crude residue was purified over 4g silica eluted with a gradient of ethyl acetate in hexane to afford 30d-int.

Compound 30e-int. 30d-int (49 mg, 0.795 mmol) was stirred at ambient temperature in 4 M HCl in dioxane at 40° C. for 1.5 hr. The mixture was concentrated, dissolved in MeOH and reconcentrated five times to afford the crude hydrochloride salt of 30e-int.

Example 30

A solution of 30e-int (45 mg, 0.087 mmol) in 0.5 mL THF, 0.25 mL methanol and 0.25 mL of water with lithium hydroxide monohydrate (11 mg, 261 mmol) was stirred at 50° C. for one hour. The pH of the reaction was adjusted to pH 5-6 and the product was extracted into DCM. The organic layer was dried over sodium sulfate, filtered, and concentrated. The residue was purified using preparative HPLC (Mobile Phase A: 0.1% TFA in $H_2O$, B: ACN; Flow rate: 20 ml/min; Gradient: 0 min 10% B; 5 min 10% B; 20 min 95% B; 32 min 95% B; 35 min 10% B Column: Phenomenex Gemini 5 micron C18 110 A, 150×21.20 mm 5 micron size), followed by lyophilization to afford Example 30. $^1$H NMR (400 MHz, DMSO-d6) δ=13.25-13.01 (br s, 1H), 12.86-12.70 (br s, 1H), 9.08 (d, J=8.3 Hz, 1H), 8.66-8.49 (m, 1H), 7.92-7.87 (m, 1H), 7.84 (br t, J=7.9 Hz, 1H), 7.47-7.37 (m, 3H), 7.28-7.20 (m, 3H), 6.98 (br d, J=8.9 Hz, 1H), 6.82 (br t, J=6.6 Hz, 1H), 6.61-6.44 (br s, 1H), 4.71-4.62 (m, 1H), 4.44 (s, 2H), 3.51 (br t, J=6.0 Hz, 2H), 3.41-3.35 (m, 2H), 3.16-3.08 (m, 1H), 2.90 (br dd, J=9.7, 14.0 Hz, 1H), 1.92-1.82 (m, 2H). LCMS (+ESI, calc. M+H+=502.1, obs. 501.8).

Example 31

Synthesis of (S)-2-(2,6-dichlorobenzamido)-3-(4-((((1s,4R)-4-(pyridin-2-ylamino)cyclohexyl) oxy) methyl)phenyl)propanoic acid trifluoroacetate

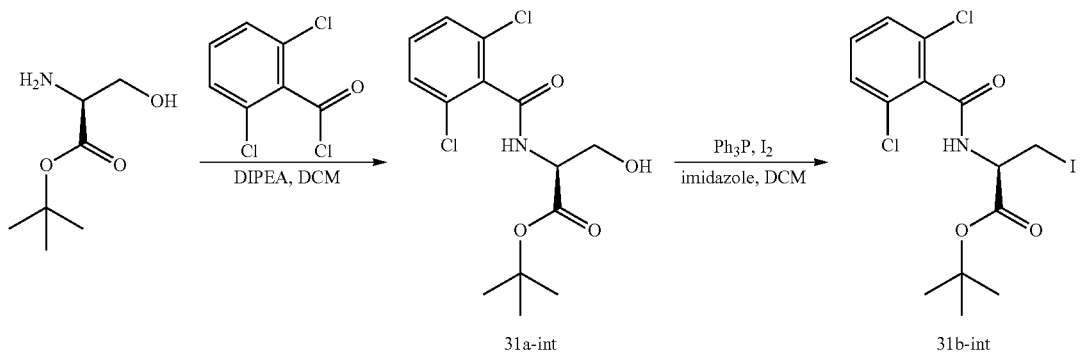

31a-int 31b-int

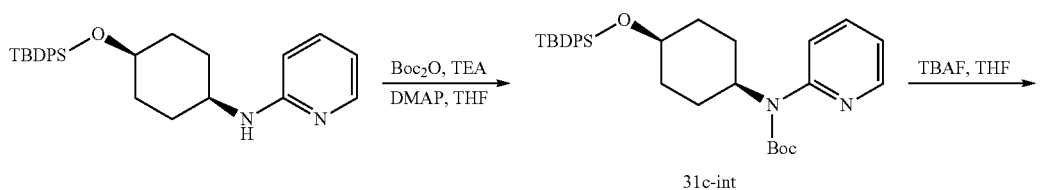

31c-int

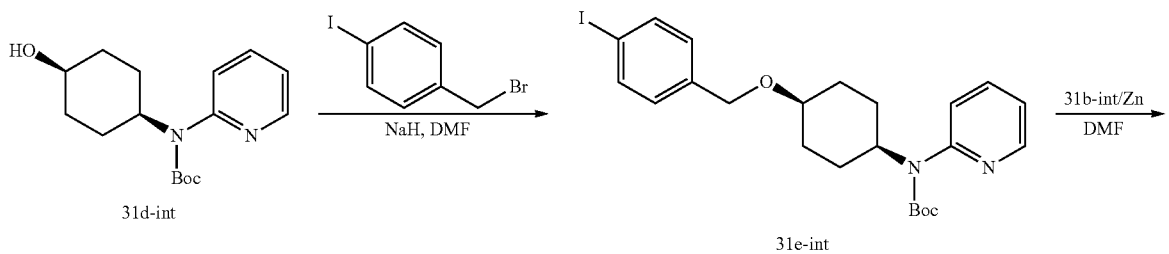

31d-int 31e-int

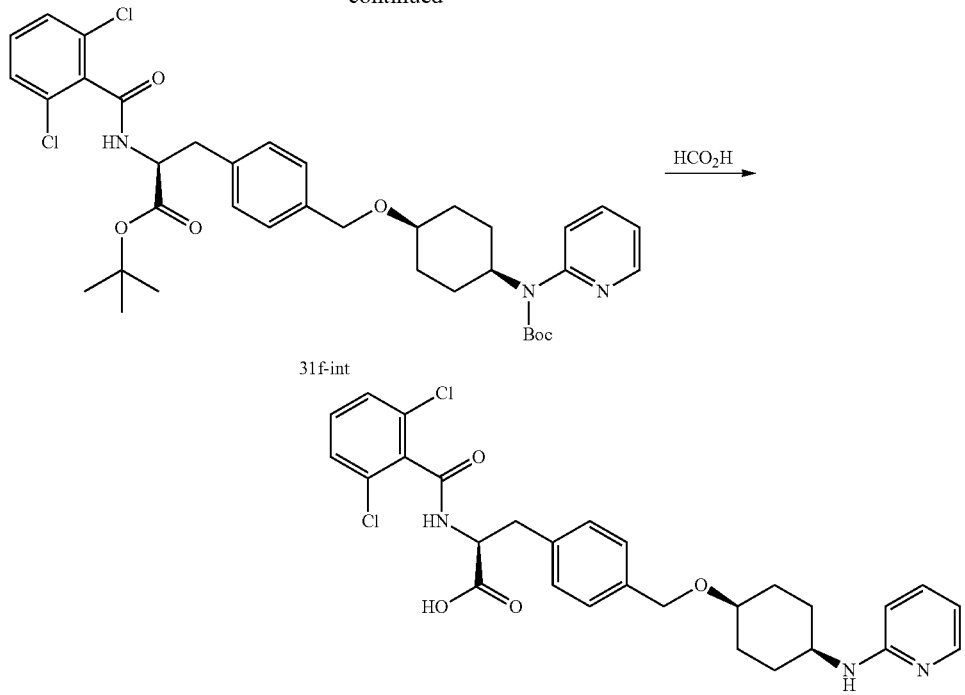

Example 31

Compound 31a-int. To a stirred solution tert-butyl-L-serinate (2.5 g, 12.6 mmol) and DIPEA (6.99 mL, 37.9 mmol) in 100 mL DCM at 0° C. in an ice bath was added 2,6-dichlorobenzoyl chloride (1.81 mL, 12.6 mmol). The reaction was allowed to warm to ambient temperature over 1 hr. The reaction was diluted with 100 mL 10% aqueous citric acid, separated and the organics washed brine (1×100 mL), dried over sodium sulfate, filtered and concentrated to afford 31a-int. $^1$H NMR (400 MHz, DMSO-$d_6$) δ=8.95 (d, J=7.9 Hz, 1H), 7.51-7.47 (m, 2H), 7.45-7.39 (m, 1H), 4.65 (br. s, 1H) 4.42 (td, J=5.6, 7.9 Hz, 1H), 3.69 (d, J=5.6 Hz, 2H), 1.44 (s, 9H).

Compound 31b-int. To a stirred solution of 31a-int (4.05g, 12.1 mmol) in 50 mL DCM was added triphenylphosphine (3.81 g, 14.5 mmol) and imidazole (949 mg, 13.9 mmol), followed by iodine (3.54 g, 13.9 mmol). A brief exotherm brought the reaction to reflux, and the orange color quickly dissipated. After stirring 0.5 hours, the reaction was diluted 1×100 mL water, organics separated and washed 1×100 mL 10% aqueous citric acid, 1×100 mL brine, dried over sodium sulfate, filtered and concentrated to afford a red-orange oil which was purified over silica gel eluted with 0-50% ethyl acetate in hexane to afford 31b-int. LCMS (+ESI, calc. M-tert-butyl+2H$^+$=387.9, obs. 387.8; calc. M-tert-butyl+2H$^+$+CH3CN=428.9, obs. 428.8).

Compound 31c-int. To a stirred solution of N-((1 s,4s)-5-(tert-butyldiphenylsilyl)oxy)cyclohexyl)pyridine-2-amine (3.30 g, 8.20 mmol) in 33 mL of dry THF was added DMAP (100 mg, 0.820 mmol), Boc anhydride (2.15 g, 9.84 mmol) and triethylamine (1.66 g, 16.4 mmol) and the reaction stirred overnight at ambient temperature under argon. The reaction was concentrated and purified over silica gel eluted with 0-25% ethyl acetate in hexane to afford 31c-int. $^1$H NMR (400 MHz, DMSO-$d_6$) δ=8.48-8.40 (m, 1H), 7.82 (dt, J=1.9, 7.7 Hz, 1H), 7.61 (dd, J=1.9, 7.5 Hz, 1H), 7.57-7.51 (m, 4H), 7.46-7.38 (m, 6H), 7.29-7.26 (m, 1H), 3.99-3.89 (m, 2H), 2.46-2.35 (m, 2H), 1.96-1.87 (m, 2H), 1.45-1.38 (m, 1H), 1.35-1.34 (m, 9H), 1.34-1.31 (m, 1H), 1.00-0.98 (m, 1H), 0.98-0.95 (m, 1H), 0.93-0.90 (m, 9H).

Compound 31d-int. 31c-int (4.4g, 8.55 mmol) in 40 mL of THF under argon was added 1.0 M TBAF solution in THF (13.2 mL, 13.2 mmol). The reaction was heated in an oil bath at 50° C. for 24 hrs. The reaction was diluted 1×100 mL water and extracted into 1×100 mL ethyl acetate. The organic layer was washed 1×100 mL water, 1×100 mL brine, and then dried over sodium sulfate, filtered, concentrated and purified over silica gel eluted with 0-50% ethyl acetate in hexanes to afford 31d-int. $^1$H NMR (400 MHz, DMSO-$d_6$) δ=8.46 (dd, J=1.8, 4.9 Hz, 1H), 7.81 (dt, J=1.9, 7.7 Hz, 1H), 7.29 (dd, J=4.9, 7.3 Hz, 1H), 7.19 (d, J=7.9 Hz, 1H), 3.97 (tt, J=3.4, 12.1 Hz, 1H), 3.75 (br d, J=2.3 Hz, 1H), 1.84-1.69 (m, 2H), 1.65 (br d, J=14.0 Hz, 2H), 1.55-1.39 (m, 4H), 1.32 (s, 9H).

Compound 31e-int. To a stirred solution of 4-iodobenzyl bromide (400 mg, 1.35 mmol) and 31d-int (197 mg, 0.674 mmol) in 3.5 mL of dry DMF, under argon, and cooled to 0° C. in an ice bath, was added sodium hydride (60% in mineral oil) (24.2 mg, 1.01 mmol). The reaction was stirred in the bath which was allowed to warm to ambient temperature overnight. The reaction was quenched 1×5 mL water and extracted into 1×10 mL ethyl acetate. The organic layer was washed 3×20 mL brine, dried over sodium sulfate, filtered, and concentrated. The crude residue was purified over silica eluted with 0-50% ethyl acetate in hexane to afford 31e-int. LCMS (+ESI, calc. M-tert-butyl+2H$^+$=453.1, obs. 453.1; calc. M-Boc+2H$^+$=409.1, obs. 409.0, calc. M+Na$^+$=531.1, obs. 531.0).

Compound 31f-int. To a sealed vial with a stir bar and zinc metal (43.6 mg, 0.670 mmol) in 0.3 mL of dry DMF under argon was added TMS-Cl (0.014 mL, 0.110 mmol). The reaction was then heated to 50° C. for 15 min. The reaction was allowed to cool to ambient temperature, and the solvent was withdrawn by syringe. The zinc residue was washed 2×0.25 mL dry DMF using a syringe to introduce and withdraw the solvent from the vial. After two washes, the supernatant was clear. To the activated zinc, 31b (140 mg, 0.315 mmol) in 1 mL dry DMF was added at once, and the mixture stirred and heated at 55° C. for 15 minutes. A separate solution of 31e-int (80 mg, 0.157 mmol) and palladium dichloride bistriphenylphosphine (3.3 mg, 0.0047 mmol) in 1 mL dry DMF was prepared, sealed and sparged with argon for 5 minutes. The organozinc was transferred under argon to the mixture of aryl iodide and catalyst, and heated to 55° C. for 1 hr. The reaction was then allowed to cool to ambient temperature, diluted with 3 ml of water and extracted into 1×2 mL EtOAc. The organic layer was washed 3×3 ml brine, dried over sodium sulfate, filtered, concentrated and purified over silica 0-30% ethyl acetate in hexane to afford 31f-int. $^1$H NMR (400 MHz, DMSO-d$_6$) δ=9.14-9.10 (m, 1H), 8.49-8.44 (m, 1H), 7.85-7.76 (m, 1H), 7.48-7.40 (m, 3H), 7.31-7.26 (m, 1H), 7.24-7.23 (m, 1H), 7.22-7.19 (m, 2H), 7.17-7.12 (m, 2H), 4.66-4.56 (m, 1H), 4.33 (s, 2H), 4.09-3.98 (m, 1H), 3.08-3.02 (m, 1H), 2.96-2.90 (m, 1H), 2.97-2.89 (m, 1H), 1.97-1.86 (m, 2H), 1.79 (br d, J=12.8 Hz, 2H), 1.55 (br d, J=11.8 Hz, 2H), 1.45-1.39 (m, 2H), 1.39-1.37 (m, 9H), 1.33 (s, 9H).

Example 31

Compound 31 f-int (45 mg, 0.064 mmol) was stirred overnight in neat formic acid (1 mL). The solvent was removed under vacuum, and the residue twice concentrated from acetonitrile (2 mL). The residue was purified by prep. HPLC (Mobile Phase A: H$_2$O, B: 0.1% TFA in ACN; Flow rate: 20 ml/min; Gradient: 0 min 10% B; 5 min 10% B; 20 min 95% B; 32 min 95% B; 35 min 10% B Column: Phenomenex Gemini 5 micron C18 110 A, 150×21.20 mm 5 micron size) and lyophilized to afford the Example 31. $^1$H NMR (400 MHz, DMSO-d$_6$) δ=13.11 (br s, 1H), 12.77 (br s, 1H), 9.09 (d, J=8.3 Hz, 1H), 8.67 (br s, 1H), 7.95-7.75 (m, 1H), 7.51-7.33 (m, 2H), 7.32-7.16 (m, 3H), 7.02 (br d, J=8.9 Hz, 1H), 6.83 (t, J=6.6 Hz, 1H), 4.79-4.56 (m, 1H), 4.45 (s, 1H), 3.77 (br s, 4H), 3.68 (br s, 2H), 3.60 (br s, 2H), 3.35 (br s, 1H), 3.26-3.03 (m, 1H), 2.92 (br dd, J=9.7, 14.0 Hz, 1H), 2.77-2.52 (m, 1H), 2.47-2.21 (m, 1H), 2.07 (s, 1H), 1.92 (br d, J=11.1 Hz, 1H), 1.76-1.51 (m, 4H), 1.12 (br d, J=17.9 Hz, 1H), 0.85 (br s, 1H), 0.40 (br s, 1H), 0.07 (br s, 1H), −0.20 (br d, J=5.5 Hz, 1H). LCMS (+ESI, calc. M+H+=542.2, obs. 542.2).

Example 32

Synthesis of (S)-2-(2,6-dichlorobenzamido)-3-(4-(((1s,3R)-3-(pyridin-2-ylamino)cyclobutoxy)methyl)phenyl)propanoic acid trifluoroacetate

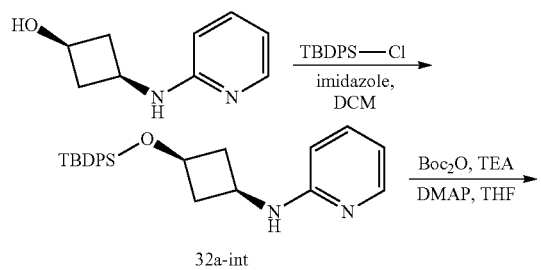

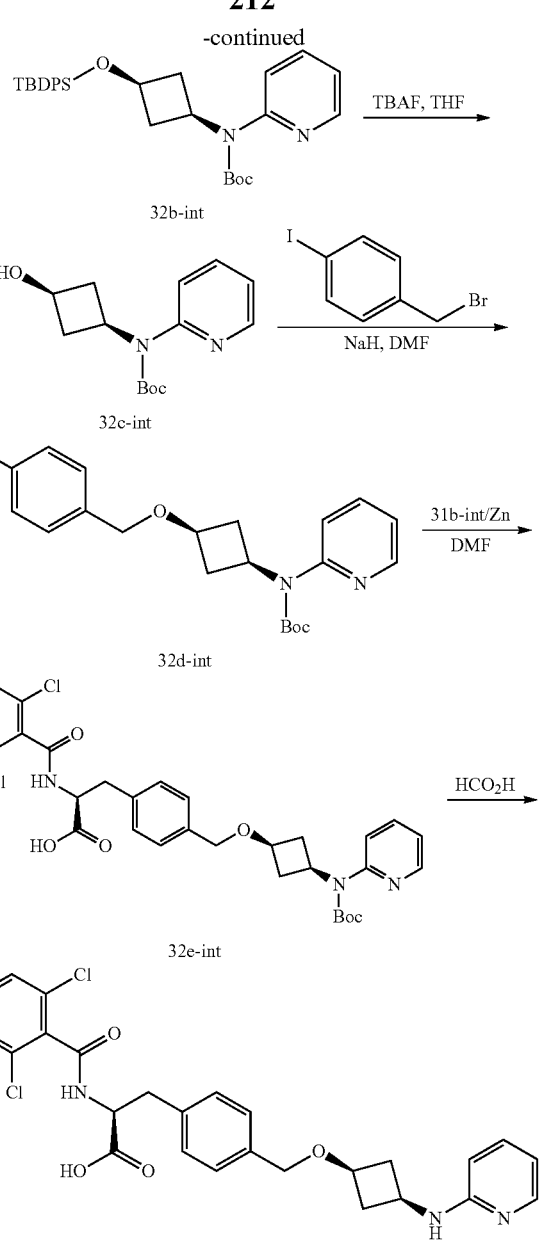

Compound 32a-int. To a solution of (1 s,3s)-3-(pyridin-2-ylamino)cyclobutan-1-ol (1.00 equiv; 1.37 g, 8.34 mmol) in DCM (41.1 mL) at 0° C., imidazole (2.00 equiv; 1.14 g, 16.7 mmol) and tert-butyldiphenylsilyl chloride (TBDPSCl) (1.30 equiv; 2.98 g, 10.8 mmol) were added and the mixture was stirred at 0° C. overnight. Then the reaction mixture was concentrated and purified by flash chromatography with 0-10% MeOH in DCM to give 32a-int. $^1$H NMR (400 MHz, DMSO-d6) δ=7.93 (s, 1H), 7.90 (dd, J=1.3, 4.8 Hz, 1H), 7.62 (dd, J=1.8, 7.5 Hz, 4H), 7.49-7.41 (m, 6H), 6.44 (dd, J=5.5, 6.6 Hz, 1H), 6.37 (d, J=8.4 Hz, 1H), 4.01 (quin, J=7.2 Hz, 1H), 3.75-3.61 (m, 1H), 2.64-2.54 (m, 2H), 1.98-1.82 (m, 2H), 1.03-0.94 (m, 9H). LCMS (+ESI, calc. M+H+=403.21, obs. 403.6).

Compound 32b-int. To a solution of starting material 32a-int (1.00 equiv; 3.30 g, 8.20 mmol), 4-(dimethylamino)pyridine (DMAP) (0.10 equiv; 100 mg, 0.82 mmol), triethylamine (2.00 equiv; 1.66g, 16.4 mmol) in THF (33 mL), Boc anhydride (1.20 equiv; 2.15 g, 9.84 mmol) was added and the mixture was stirred at room temperature overnight under argon. The reaction mixture was concentrated and purified by flash chromatography with 0-30% ethyl acetate in hexane to give 32b-int. LCMS (+ESI, calc. M+H+=503.27, obs. M-t-butyl+2H+=447.1, M-Boc+H+=403.1).

Compound 32c-int. To a solution of starting material 32b-int (1.00 equiv; 2.30g, 4.85 mmol) in THF (23 mL), tetrabutylammonium fluoride solution (TBAF) 1.0 M in THF (5.03 mL) was added and the mixture was stirred for 2 hours at room temperature. The reaction mixture was concentrated and purified by flash chromatography with 0-50% ethyl acetate in hexane to give 32c-int. LCMS (+ESI, calc. M+H+=265.15, obs. M-t-butyl+2H+=209.1, M-Boc+H+=165.1).

Compound 32d-int. To a solution of 1-(bromomethyl)-4-iodobenzene (1.00 equiv; 920 mg, 3.10 mmol) in DMF (9.2 mL), starting material 32c-int (1.10 equiv; 901 mg, 3.41 mmol) and sodium hydride (1.00 equiv; 74.4 mg, 3.10 mmol) were added and the mixture was stirred at room temperature overnight. Then the reaction mixture was diluted with water and extracted with ether. The organic layer was washed with brine, dried over sodium sulphate, filtered and concentrated to obtain 32d-int. $^1$H NMR (400 MHz, DMSO-d6) δ=8.52-8.40 (m, 1H), 7.82 (dt, J=2.1, 7.7 Hz, 1H), 7.67 (d, J=8.2 Hz, 2H), 7.34-7.21 (m, 2H), 7.06 (d, J=8.2 Hz, 2H), 4.25 (s, 2H), 4.16-4.06 (m, 1H), 3.77-3.64 (m, 1H), 2.57-2.51 (m, 2H), 1.85-1.69 (m, 2H), 1.41-1.21 (m, 9H). LCMS (+ESI, calc. M+H+=481.09, obs. M-t-butyl+2H+=425.7, M-Boc+H+=381.0).

Compound 32e-int. To a mixture of zinc dust (4.26 equiv; 116 mg, 1.77 mmol) and anhydrous DMF (0.2 mL) under argon, trimethyl silyl chloride (0.70 equiv; 37.0 µL, 0.291 mmol) was added. The mixture was heated to 55° C. and stirred for 20 min. Then allowed the reaction mixture to settle down, DMF was removed. The activated zinc powder was washed with anhydrous DMF under argon until it stopped giving brown color. To the activated zinc powder, 31b-int (2.00 equiv; 370 mg, 0.833 mmol) in 200 µL anhydrous DMF was added. After 5 min, the reaction mixture was heated up to 50° C. and then allowed to cool down to room temperature for 20 min. The supernatant of the above mixture was added to a solution of 32d-int (1.00 equiv; 200 mg, 0.416 mmol) and bis(triphenylphosphine) palladium(II) dichloride (0.030 equiv; 8.77 mg, 12.5 µmol) in anhydrous DMF (200 µL). The reaction mixture was stirred at 50° C. and monitored by TLC and LCMS. After the reaction was completed, the reaction mixture was partitioned with aqueous sodium bicarbonate and ethyl acetate. The organic layer was dried over sodium sulphate, then filtered and concentrated under vacuum. The product was purified by flash chromatography with 0-30% ethyl acetate in hexane to give 32e-int. LCMS (+ESI, calc. M+H+=670.24, obs. 670.2, M-Boc+H+=570.2).

Example 32

A reaction mixture of 32e-int (1.00 equiv; 200 mg, 0.298 mmol) and formic acid (2 mL) was stirred at 40° C. for 2 hours. Then the mixture was concentrated under vacuum. Example 32 was purified by Prep-HPLC (Mobile Phase A: 0.1% TFA in H$_2$O, B: ACN; Flow rate: 20 ml/min; Gradient: 0 min 1% B; 5 min 1% B; 18 min 65% B, 20 min 95% B, 32 min 95% B, Column: Phenomenex Gemini 5 micron C18 110 A, 150×21.20 mm 5 micron size). Example 32 was obtained by combining the pure fractions and lyophilizing. $^1$H NMR (400 MHz, DMSO-d6) δ=12.87 (br, 1H), 12.69 (br, 1H), 9.08 (br d, J=8.3 Hz, 1H), 7.91 (br d, J=5.4 Hz, 1H), 7.86-7.73 (m, 1H), 7.47-7.35 (m, 4H), 7.31-7.19 (m, 3H), 6.97-6.85 (m, 2H), 6.81 (br s, 1H), 4.66 (dt, J=4.9, 8.9 Hz, 1H), 4.37 (s, 2H), 3.87-3.69 (m, 2H), 3.12 (br dd, J=4.7, 14.1 Hz, 1H), 2.91 (br dd, J=9.8, 13.9 Hz, 1H), 2.83-2.73 (m, 2H), 1.98-1.84 (m, 2H). LCMS (+ESI, calc. M+H+=514.12, obs. 514.1).

Example 33

Synthesis of (2S)-2-(2,6-dichlorobenzamido)-3-(4-(1-(2-(5,6,7,8-tetrahydro-1,8-naphthyridin-2-yl)ethoxy)ethyl)phenyl)propanoic acid

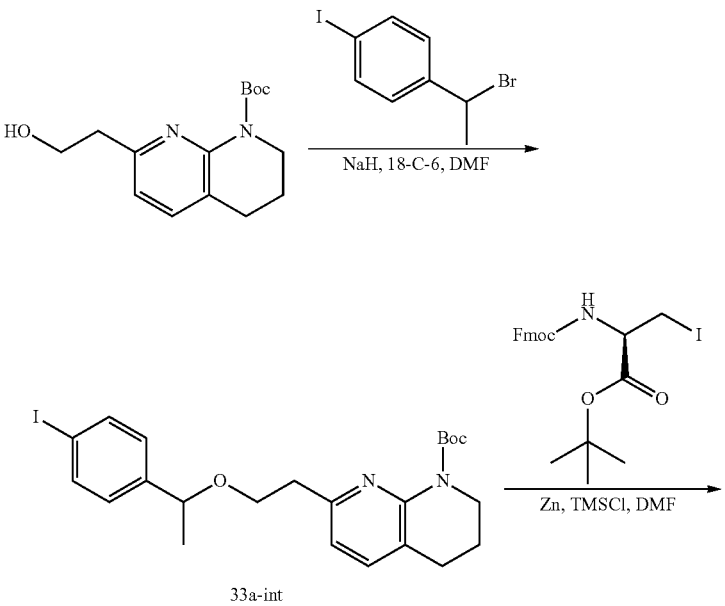

33a-int

-continued

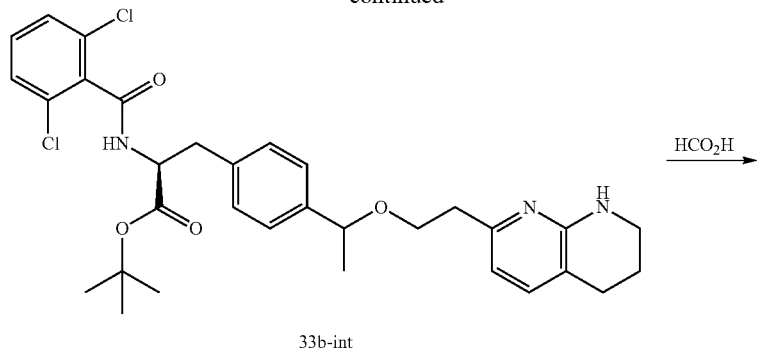

33b-int

HCO₂H →

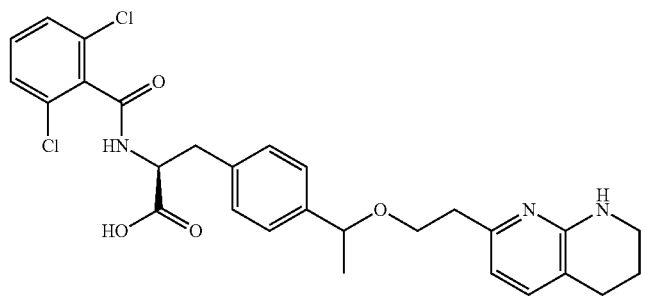

Example 33

Compound 33a-int. To a solution of 1-bromo-1-(4-iodophenyl)ethane (1.00 equiv; 500 mg, 1.61 mmol), tert-butyl 7-(2-hydroxyethyl)-3,4-dihydro-1,8-naphthyridine-1(2H)-carboxylate (1.00 equiv; 448 mg, 1.61 mmol), and 18-crown-6 (0.10 equiv; 42.5 mg, 0.161 mmol) in DMF (1 mL) at 0° C., sodium hydride (2.00 equiv; 129 mg, 3.22 mmol) was added. The reaction mixture was then heated at 55° C. After one hour, the reaction mixture was cooled to 0° C., diluted with ether, quenched by cautious addition of saturated ammonium chloride. Then the mixture was poured into water, washed with brine, dried over sodium sulphate and concentrated under vacuum to give 33a-int. ¹H NMR (400 MHz, DMSO-d6) δ=7.67 (d, J=8.3 Hz, 2H), 7.40 (d, J=7.7 Hz, 1H), 7.08 (d, J=8.3 Hz, 2H), 6.90 (d, J=7.7 Hz, 1H), 4.43 (q, J=6.4 Hz, 1H), 3.68-3.49 (m, 4H), 2.92-2.75 (m, 2H), 2.67 (t, J=6.6 Hz, 2H), 1.85-1.72 (m, 2H), 1.32 (s, 9H), 1.28 (d, J=6.5 Hz, 3H). LCMS (+ESI, calc. M+H+=509.12, obs. M-t-butyl+2H+=452.8, M-Boc+H+=409.0).

Compound 33b-int. To a mixture of zinc dust (4.5 equiv; 57.9 mg, 0.885 mmol) and anhydrous DMF (0.1 mL) under argon, trimethyl silyl chloride (0.75 equiv; 18.7 μL, 0.148 mmol) was added. The mixture was heated to 55° C. and stirred for 20 min. Then allowed the reaction mixture to settle down, DMF was removed. The activated zinc powder was washed with anhydrous DMF under argon until it stopped giving brown color. To the activated zinc powder, 31b-int (2.00 equiv; 175 mg, 0.393 mmol) in 100 μL anhydrous DMF was added. After 5 min, the reaction mixture was heated up to 50° C. and then allowed to cool down to room temperature for 20 min. The supernatant of the above mixture was added to a solution of 33a-int (1.00 equiv; 100 mg, 0.197 mmol) and bis(triphenylphosphine) palladium(II) dichloride (0.030 equiv; 4.14 mg, 5.90 μmol) in anhydrous DMF (100 μL). The reaction mixture was stirred at 50° C. and monitored by TLC and LCMS. After the reaction was completed, the reaction mixture was partitioned with aqueous sodium bicarbonate and ethyl acetate. The organic layer was dried over sodium sulphate, then filtered and concentrated under vacuum. The product 33b-int was purified by flash chromatography with 0-70% ethyl acetate in hexane. The compound was further purified by prep-HPLC (Mobile Phase A: 0.1% TFA in H₂O, B: ACN; Flow rate: 20 ml/min; Gradient: 0 min 10% B; 5 min 10% B; 35 min 60% B, 37 min 90% B, 47 min 90% B, 50 min 10% B. LCMS (+ESI, calc. M+H+=698.27, obs. M-t-butyl+2H+=642.2). The fractions from the prep run containing the desired product were combined, partially concentrated, and taken onto the next step as a solution.

Example 33

The reaction mixture of 33b-int (1.00 equiv; 53 mg, 0.076 mmol) and formic acid (2 mL) was stirred at 40° C. for 2 hours. Then the mixture was concentrated under vacuum and purified by flash chromatography with 0-30% water in acetonitrile. Example 33 was obtained by lyophilization. ¹H NMR (400 MHz, DMSO-d6) δ=8.97-8.58 (m, 1H), 8.35-8.03 (m, 1H), 7.45-7.34 (m, 3H), 7.23 (d, J=8.0 Hz, 2H), 7.19-7.09 (m, 2H), 7.01 (br d, J=7.3 Hz, 1H), 6.37-6.27 (m, 1H), 6.27-6.23 (m, 1H), 4.57 (br s, 1H), 4.38 (q, J=6.4 Hz, 1H), 3.20 (br s, 2H), 3.13 (br dd, J=4.8, 13.9 Hz, 2H), 2.92 (br dd, J=9.3, 13.7 Hz, 2H), 2.71-2.61 (m, 2H), 2.58 (br t, J=6.2 Hz, 2H), 1.77-1.67 (m, 2H), 1.27 (d, J=6.5 Hz, 3H). LCMS (+ESI, calc. M+H+=542.15, obs. 542.1).

Example 34

Synthesis of (2S)-2-[(4-cyclopropylbenzoyl)amino]-3-[4-[3-(5,6,7,8-tetrahydro-1,8-naphthyridin-2-yl)propoxy]phenyl]propanoic acid

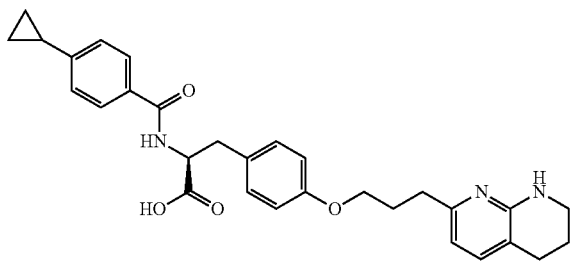

Example 34

Example 34 was prepared by the same procedure used to prepare Example 1 with the exception that benzoic acid was replaced by 4-cyclopropylbenzoyl chloride in the reaction with intermediate 1f-int.

m/z [M+H] for $C_{30}H_{34}N_3O_4$: theoretical: 500.25; found: 500.2.

$^1$H NMR (500 MHz, Methanol-d4) δ 7.70-7.59 (m, 2H), 7.53 (m, 1H), 7.22-7.16 (m, 2H), 7.16-7.09 (m, 2H), 6.83-6.75 (m, 2H), 6.61 (d, J=7.4 Hz, 1H), 4.85-4.76 (m, 1H), 4.02 (m, 2H), 3.49 (t, J=5.7 Hz, 2H), 3.28 (dd, J=13.9, 5.0 Hz, 1H), 3.04 (dd, J=14.0, 9.6 Hz, 1H), 2.88 (t, J=7.5 Hz, 2H), 2.81 (t, J=6.2 Hz, 2H), 2.22-2.07 (m, 2H), 2.04-1.89 (m, 3H), 1.05 (m, 2H), 0.79-0.71 (m, 2H).

Example 35

Synthesis of (2S)-2-[(3,5-dichlorobenzoyl)amino]-3-[4-[3-(5,6,7,8-tetrahydro-1,8-naphthyridin-2-yl)propoxy]phenyl]propanoic acid

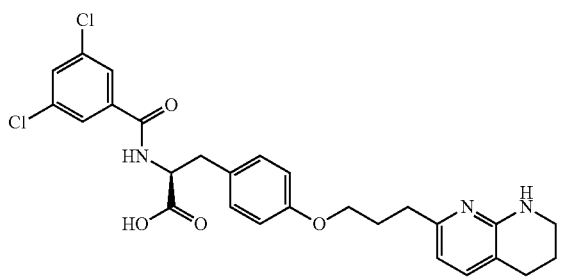

Example 35

Example 35 was prepared by the same procedure used to prepare Example 1 with the exception that benzoic acid was replaced by 3,5-dichlorobenzoyl chloride in the reaction with intermediate 1f-int.

m/z [M+H] for $C_{27}H_{28}Cl_2N_3O_4$: theoretical: 528.14; found: 528.1.

$^1$H NMR (500 MHz, Methanol-d4) δ 7.68 (d, J=1.9 Hz, 2H), 7.64 (t, J=1.9 Hz, 1H), 7.56 (dd, J=7.4, 1.2 Hz, 1H), 7.23-7.16 (m, 2H), 6.85-6.78 (m, 2H), 6.63 (d, J=7.4 Hz, 1H), 4.84-4.76 (m, 1H), 4.03 (t, J=5.8 Hz, 2H), 3.54-3.46 (m, 2H), 3.30-3.26 (m, 1H), 3.01 (dd, J=14.0, 10.2 Hz, 1H), 2.94-2.85 (m, 2H), 2.82 (t, J=6.2 Hz, 2H), 2.21-2.10 (m, 2H), 2.03-1.91 (m, 2H).

Example 36

Synthesis of (2S)-2-[(2-chloro-5-fluoro-benzoyl)amino]-3-[4-[3-(5,6,7,8-tetrahydro-1,8-naphthyridin-2-yl)propoxy]phenyl]propanoic acid

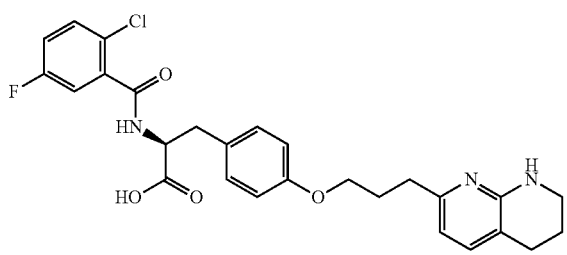

Example 36

Example 36 was prepared by the same procedure used to prepare Example 1 except that benzoic acid was replaced with 2-chloro-5-fluorobenzoylchloride in the reaction with 1f-int.

m/z [M+H] for $C_{27}H_{28}ClFN_3O_4$: theoretical: 512.17; found: 512.2.

$^1$H NMR (500 MHz, Methanol-d4) δ 7.58 (dd, J=7.3, 1.1 Hz, 1H), 7.45 (m, 1H), 7.25-7.16 (m, 3H), 7.03 (dd, J=8.3, 3.0 Hz, 1H), 6.88-6.80 (m, 2H), 6.65 (d, J=7.3 Hz, 1H), 4.83 (m, 1H), 4.05 (t, J=5.8 Hz, 2H), 3.51 (t, J=5.7 Hz, 2H), 3.32-3.23 (m, 1H), 3.00-2.91 (m, 3H), 2.83 (t, J=6.3 Hz, 2H), 2.18 (m, 2H), 1.98 (m, 2H).

Example 37

Synthesis of (2S)-2-((2,6-dichlorobenzoyl)amino)-3-(3-(3-(5,6,7,8-tetrahydro-1,8-naphthyridin-2-yl)propoxy)phenyl)propanoic acid

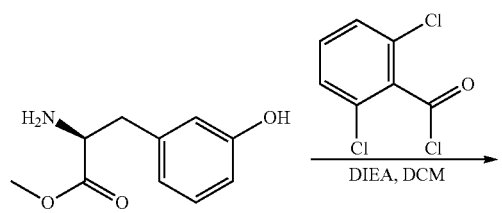

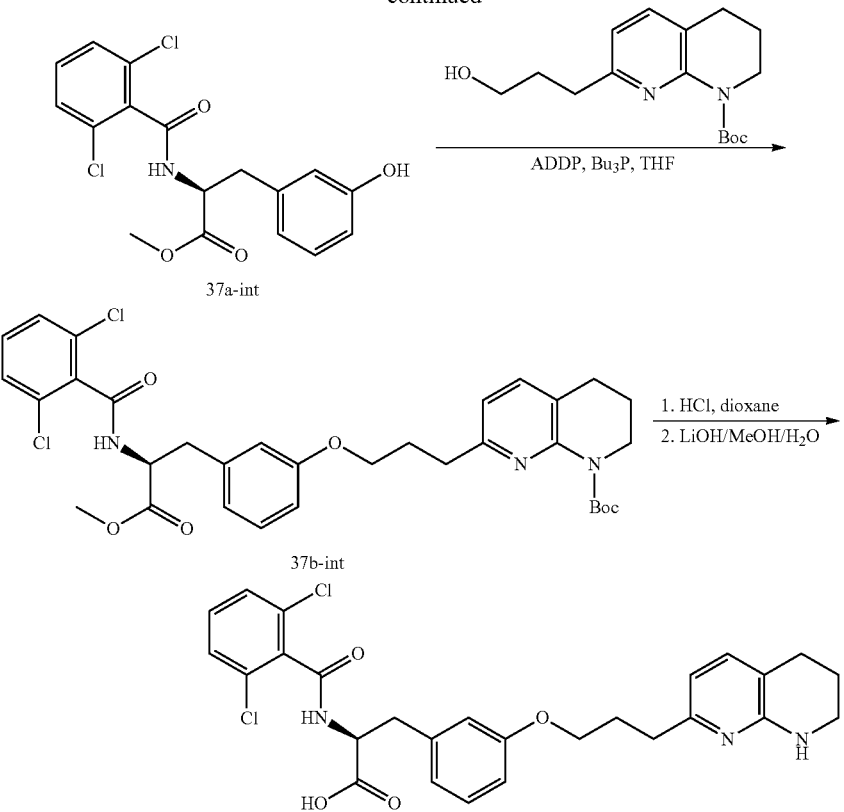

Example 37

Compound 37a-int. To a mixture of methyl (2S)-2-amino-3-(3-hydroxyphenyl)propanoate hydrochloride (100. mg, 0.4300 mmol) in DCM (2.1581 mL) at r. t. was added diisopropylethylamine (0.38 mL, 2.16 mmol) followed by 2,6-dichlorobenzoyl chloride (0.06 mL, 0.4300 mmol) dropwise. The resulting mixture was stirred at r. t. for 1 hr. The reaction was concentrated, the residue was then partitioned between EtOAc (5.0 mL) and 1N HCl (2.0 mL). the layers were separated and the organic layer was washed with saturated sodium bicarbonate (2.0 mL) followed by brine (2.0 mL), dried over sodium sulfate, filtered and concentrated to give 37a-int.

Compound 37b-int. To the mixture of methyl (2S)-2-[(2,6-dichlorobenzoyl)amino]-3-(3-hydroxyphenyl)propanoate (158. mg, 0.4300 mmol) and tert-butyl 7-(3-hydroxypropyl)-3,4-dihydro-2H-1,8-naphthyridine-1-carboxylate (100.37 mg, 0.3400 mmol) in THF (1.4303 mL) at r.t. was added ADDP (129.92 mg, 0.5100 mmol). The resulting mixture was sonicated to aid dissolving, tributylphosphine (0.13 mL, 0.5100 mmol) was added dropwise to the reaction mixture. The newly formed mixture was stirred at r.t. for 2 hrs. TLC showed starting material still present. Additional ADDP (129.92 mg, 0.5100 mmol) was added and the reaction was heated at 60° C., and tributylphosphine (0.13 mL, 0.5100 mmol) was added dropwise to the warm mixture. The reaction was stirred at 60° C. for another 2 hrs and then at ambient temperature for 2 days. The reaction was then diluted with EtOAc (10.0 mL) and washed with water (2.0 mL). The organic layer was concentrated to give a purplish solid, retreated with EtOAc (5.0 mL), mixed with silica gel, concentrated down with rotavapor, purified by combiflash (12g silica gel, 0-50% EtOAc/Hexanes, dry loading). Desired fractions were combined and concentrated to 37b-int. m/z [M+H] for $C_{33}H_{38}Cl_2N_3O_6$: theoretical: 642.21; found: 642.7.

Example 37 tert-Butyl 7-(3-(3-(((2S)-2-((2,6-dichlorobenzoyl)amino)-3-methoxy-3-oxo-propyl)phenoxy)propyl)-3,4-dihydro-2H-1,8-naphthyridine-1-carboxylate (85. mg, 0.1300 mmol) was treated with 4N HCl in 1,4-dioxane (1.0 mL) at r.t. for overnight. The reaction was concentrated, coevaporated with EtOAc (3×1.0 mL). The resulting residue was then dissolved in a mixture of MeOH (2.0 mL) and water (0.8 mL) and then was treated with lithium hydroxide (19.01 mg, 0.7900 mmol). The resulting mixture was stirred at r.t. for 1 hour before it was concentrated. The resulting residue was then redissolved in 1:1 AcOH:H2O (3.0 mL), filtered and purified by reverse phase prep HPLC (50g C18 Gold column, 10-60% ACN/H2O with 0.1% TFA). Desired fractions were combined and frozen dried to Example 37. m/z [M+H] for $C_{27}H_{28}Cl_2N_3O_4$: theoretical: 528.14; found: 528.1

$^1$H NMR (500 MHz, Methanol-d4) δ 7.59 (dt, J=7.4, 1.2 Hz, 1H), 7.41-7.33 (m, 3H), 7.19 (dd, J=8.7, 7.5 Hz, 1H), 6.92-6.84 (m, 2H), 6.76 (ddd, J=8.4, 2.6, 1.1 Hz, 1H), 6.67 (d, J=7.4 Hz, 1H), 5.00 (dd, J=9.8, 5.1 Hz, 1H), 4.09 (q, J=5.7 Hz, 2H), 3.50 (q, J=5.2 Hz, 2H), 3.31-3.25 (m, 1H), 3.00 (dd, J=14.2, 9.9 Hz, 1H), 2.92 (t, J=7.5 Hz, 2H), 2.83 (t, J=6.3 Hz, 2H), 2.26-2.17 (m, 2H), 1.99-1.94 (m, 2H).

Example 38

Synthesis of (2S)-2-[(2,6-dichlorobenzoyl)amino]-3-[4-[4-cis-(2-pyridylamino)cyclohexoxy]phenyl]propanoic acid

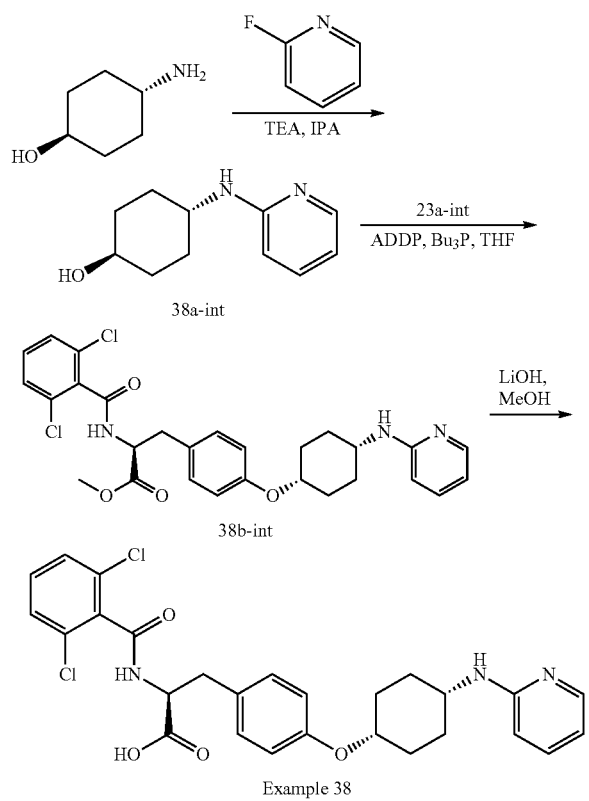

Compound 38a-int. 2-Fluoropyridine (1 g, 10 mmol), 4-trans-aminocyclohexanol (1.42 g, 12.36 mmol) and triethylamine (2.15 mL, 15.45 mmol) were stirred in isopropanol (5 mL) at 100° C. for seven days. The reaction mixture was evaporated and purified by combiflash chromatography (EtOAc in Hexanes=20-100%) to give 38a-int.

Compound 38b-int. To a reaction solution of 38a-int (300 mg, 1.56 mmol), 23a-int (689 mg, 1.87 mmol) and tributylphosphine (631 mg, 3.12 mmol) in THF (10 mL) at 60° C., was added 1,1-(azodicarbonyl)dipiperidine (787 mg, 3.12 mmol) portion-wise. The reaction mixture was stirred at 60° C. for two hours. It was then evaporated and purified by combiflash chromatography (EtOAc in Hexanes=20-100%) to give 38b-int. $^1$H NMR (500 MHz, Chloroform-d) δ 8.03 (dd, J=5.1, 1.9 Hz, 1H), 7.38 (td, J=8.7, 1.9 Hz, 1H), 7.32-7.19 (m, 3H), 7.12 (d, J=10 Hz, 2H), 6.83 (d, J=10 Hz, 2H), 6.61 (d, J=10 Hz, 1H), 6.52 (m, 1H), 6.37 (d, J=8.5 Hz, 1H), 5.15 (m, 1H), 4.64 (d, J=8.0 Hz, 1H), 4.45 (br, 1H), 3.75 (s, 3H), 3.71 (m, 1H), 3.19 (m, 2H), 2.00 (m, 2H), 1.87 (m, 2H), 1.73 (m, 4H). LCMS [M+H$^+$]: 543.

Example 38

Compound 38b-int (100 mg, 0.18 mmol) and lithium hydroxide (60 mg, 2.5 mmol) were stirred in methanol (2 mL) at room temperature for three hours. The reaction mixture was evaporated and purified by reverse-phase combiflash chromatography (CH3CN (0.1% TFA) in water (0.1% TFA)=10-100%) to Example 38. $^1$H NMR (500 MHz, Methanol-d$_4$) δ 7.90 (ddd, J=8.9, 6.9, 1.7 Hz, 1H), 7.82 (dd, J=6.5, 1.6 Hz, 1H), 7.41-7.31 (m, 3H), 7.26 (m, 2H), 7.07 (d, J=9.1 Hz, 1H), 6.95-6.85 (m, 3H), 4.96-4.89 (m, 1H), 4.62 (br, 1H), 3.70 (p, J=7.9 Hz, 1H), 3.25 (m, 1H), 2.97 (dd, J=14.1, 9.7 Hz, 1H), 2.13 (m, 2H), 1.93-1.74 (m, 6H). LCMS [M+H$^+$]: 529.

Example 39

Synthesis of (2S)-2-[(2,6-dichlorobenzoyl)amino]-3-[4-[4-trans-(2-pyridylamino)cyclohexoxy]phenyl]propanoic acid

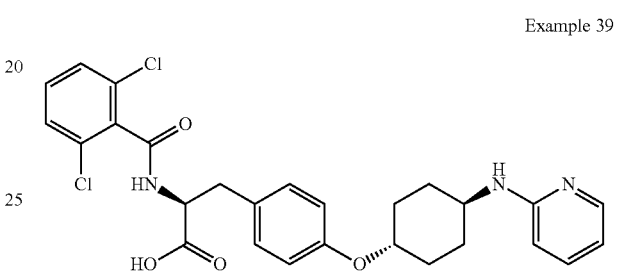

Example 39 was prepared by the same procedure used to prepare Example 38 with the exception that trans-4-aminocyclohexanol was replaced by cis-4-aminocyclohexanol in the reaction with 2-fluoropyridine. $^1$H NMR (500 MHz, Methanol-d$_4$) δ 7.90 (t, J=9 Hz, 1H), 7.83 (d, J=5 Hz, 1H), 7.40-7.35 (m, 3H), 7.25 (d, J=10 Hz, 1H), 7.14 (d, J=10 Hz, 1H), 7.06 (d, J=5 Hz, 1H), 6.91-6.88 (m, 2H), 6.72 (m, 1H), 4.93-4.88 (m, 1H), 4.35 (m, 1H), 3.67 (m, 1H), 3.33 (m, 1H), 2.97 (m, 1H), 2.20 (m, 2H), 1.63 (m, 6H). LCMS [M+H$^+$]: 529.

Example 40

Synthesis of (2S)-2-(1H-indazole-6-carbonylamino)-3-[4-[3-(5,6,7,8-tetrahydro-1,8-naphthyridin-2-yl)propoxy]phenyl]propanoic acid

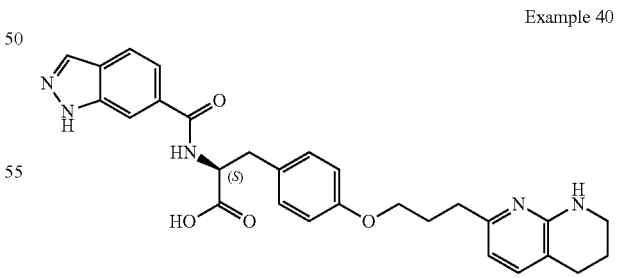

Example 40 was prepared by the same procedure used to prepare Example 1 with the exception that benzoic acid was replaced by 1H-indazole-6-carboxylic acid in the reaction with intermediate if-int. $^1$H NMR (500 MHz, Methanol-d$_4$) δ 8.19 (s, 1H), 8.05 (s, 1H), 7.83 (d, J=7.5 Hz, 1H), 7.50 (d, J=7.5 Hz, 2H), 7.24 (d, J=7.5 Hz, 2H), 6.81 (d, J=7.5 Hz, 2H), 6.59 (d, J=7.2 Hz, 1H), 4.10 (t, J=3.3 Hz, 2H), 3.49 (t, J=3.5 Hz, 2H), 3.16-2.99 (m, 1H), 2.89 (t, J=3.2 Hz, 2H), 2.77 (t, J=3.0 Hz, 2H), 2.22-2.08 (m, 2H), 1.98-1.85 (m, 2H); LCMS [M+H$^+$]: 500.

Example 41

Synthesis of (2S)-2-[(1-methylindazole-6-carbonyl)amino]-3-[4-[3-(5,6,7,8-tetrahydro-1,8-naphthyridin-2-yl)propoxy]phenyl]propanoic acid

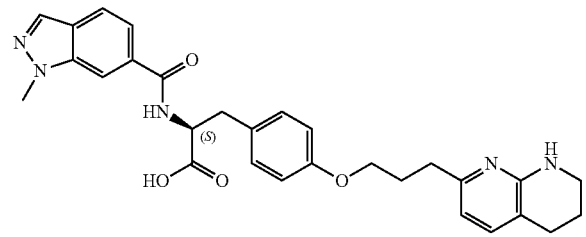

Example 41

Example 41 was prepared by the same procedure used to prepare Example 1 with the exception that benzoic acid was replaced by 1-methylindazole-6-carboxylic acid in the reaction with intermediate 1f-int. $^1$H NMR (500 MHz, Methanol-d$_4$) δ 8.14 (s, 1H), 8.03 (s, 1H), 7.81 (d, J=7.5 Hz, 1H), 7.52 (d, J=7.5 Hz, 2H), 7.24 (d, J=7.5 Hz, 2H), 6.82 (d, J=7.5 Hz, 2H), 6.61 (d, J=7.2 Hz, 1H), 4.14 (s, 3H), 4.10 (t, J=3.9 Hz, 2H), 3.49 (t, J=3.5 Hz, 2H), 3.17-3.00 (m, 1H), 2.90 (t, J=3.0 Hz, 2H), 2.78 (t, J=3.0 Hz, 2H), 2.22-2.06 (m, 2H), 2.02-1.86 (m, 2H); LCMS [M+H$^+$]: 514.

Example 42

Synthesis of (2S)-2-(1H-indazole-5-carbonylamino)-3-[4-[3-(5,6,7,8-tetrahydro-1,8-naphthyridin-2-yl)propoxy]phenyl]propanoic acid

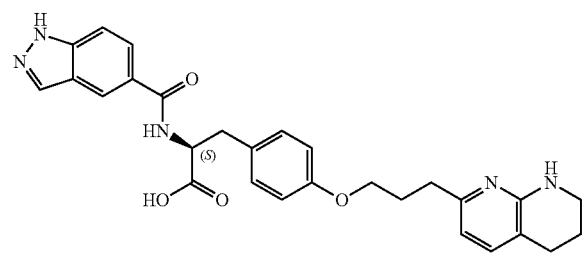

Example 42

Example 42 was prepared by the same procedure used to prepare Example 1 with the exception that benzoic acid was replaced by 1H-indazole-5-carboxylic acid in the reaction with intermediate 1f-int. $^1$H NMR (500 MHz, Methanol-d$_4$) δ 8.26 (s, 1H), 8.16 (s, 1H), 7.81 (d, J=7.3 Hz, 1H), 7.61 (d, J=5.5 Hz, 1H), 7.50 (d, J=5.4 Hz, 1H), 7.24 (d, J=7.4 Hz, 2H), 6.81 (d, J=7.4 Hz, 2H), 6.60 (d, J=7.1 Hz, 1H), 4.02 (t, J=3.8 Hz, 2H), 3.49 (t, J=3.5 Hz, 2H), 3.16-3.04 (m, 1H), 2.89 (t, J=3.0 Hz, 2H), 2.77 (t, J=3.0 Hz, 2H), 2.22-2.06 (m, 2H), 2.02-1.86 (m, 2H); LCMS [M+H$^+$]: 500.

Example 43

Synthesis of (2S)-2-[(1-methylindazole-5-carbonyl)amino]-3-[4-[3-(5,6,7,8-tetrahydro-1,8-naphthyridin-2-yl)propoxy]phenyl]propanoic acid

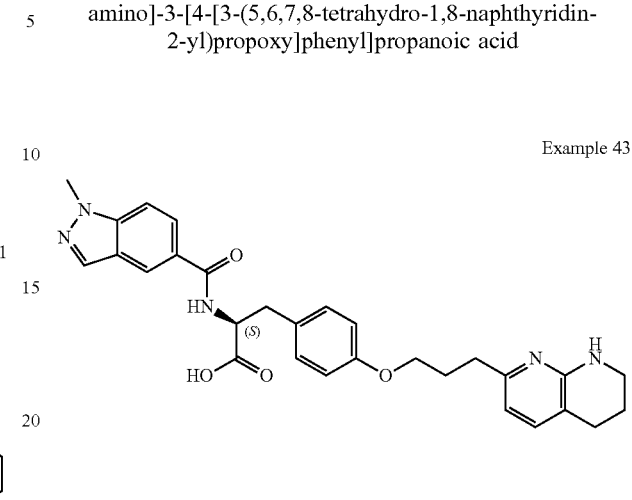

Example 43

Example 43 was prepared by the same procedure used to prepare Example 1 with the exception that benzoic acid was replaced by 1-methylindazole-5-carboxylic acid in the reaction with intermediate 1f-int. $^1$H NMR (500 MHz, Methanol-d$_4$) δ 8.24 (s, 1H), 8.12 (s, 1H), 7.84 (d, J=7.3 Hz, 1H), 7.63 (d, J=5.9 Hz, 1H), 7.51 (d, J=5.7 Hz, 1H), 7.23 (d, J=7.5 Hz, 2H), 6.81 (d, J=7.6 Hz, 2H), 6.61 (d, J=7.1 Hz, 1H), 4.12 (s, 3H), 4.01 (t, J=3.1 Hz, 2H), 3.49 (t, J=3.5 Hz, 2H), 3.16-2.99 (m, 1H), 2.89 (t, J=3.0 Hz, 2H), 2.77 (t, J=2.9 Hz, 2H), 2.22-2.06 (m, 2H), 1.99-1.87 (m, 2H); LCMS [M+H$^+$]: 514.

Example 44

Synthesis of (2S)-2-[(2-methylindazole-6-carbonyl)amino]-3-[4-[3-(5,6,7,8-tetrahydro-1,8-naphthyridin-2-yl)propoxy]phenyl]propanoic acid

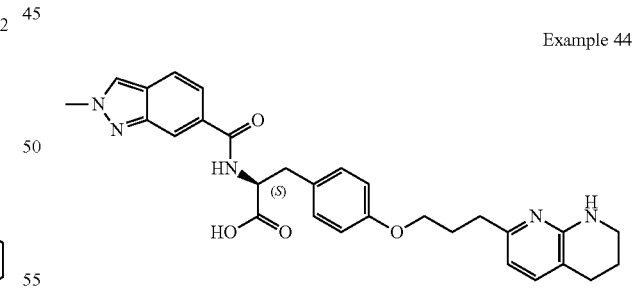

Example 44

Example 44 was prepared by the same procedure used to prepare Example 1 with the exception that benzoic acid was replaced by 2-methylindazole-6-carboxylic acid in the reaction with intermediate if-int. $^1$H NMR (500 MHz, Methanol-d$_4$) δ 8.27 (s, 1H), 8.10 (s, 1H), 7.76 (d, J=7.2 Hz, 1H), 7.53 (d, J=5.6 Hz, 1H), 7.42 (d, J=5.8 Hz, 1H), 7.24 (d, J=7.3 Hz, 2H), 6.81 (d, J=7.2 Hz, 2H), 6.61 (d, J=7.1 Hz, 1H), 4.27 (s, 3H), 4.03 (t, J=3.8 Hz, 2H), 3.48 (t, J=3.7 Hz, 2H), 3.10-3.00 (m, 1H), 2.89 (t, J=3.1 Hz, 2H), 2.77 (t, J=3.0 Hz, 2H), 2.20-2.10 (m, 2H), 2.00-1.90 (m, 2H); LCMS [M+H$^+$]: 514.

Example 45

Synthesis of (2S)-2-[(2-methylindazole-5-carbonyl)amino]-3-[4-[3-(5,6,7,8-tetrahydro-1,8-naphthyridin-2-yl)propoxy]phenyl]propanoic acid

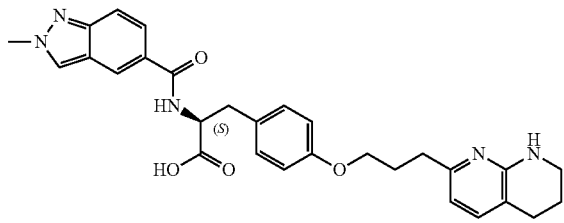

Example 45

Example 45 was prepared by the same procedure used to prepare Example 1 with the exception that benzoic acid was replaced by 2-methylindazole-5-carboxylic acid in the reaction with intermediate 1f-int. $^1$H NMR (500 MHz, Methanol-$d_4$) δ 8.38 (s, 1H), 8.23 (s, 1H), 7.71-7.57 (m, 2H), 7.51 (d, J=6.0 Hz, 1H), 7.23 (d, J=7.5 Hz, 2H), 6.80 (d, J=7.5 Hz, 2H), 6.60 (d, J=7.2 Hz, 1H), 4.26 (s, 3H), 4.02 (t, J=3.8 Hz, 2H), 3.49 (t, J=3.8 Hz, 2H), 3.15-2.98 (m, 1H), 2.89 (t, J=3.0 Hz, 2H), 2.77 (t, J=2.9 Hz, 2H), 2.22-2.05 (m, 2H), 2.02-1.86 (m, 2H); LCMS [M+H$^+$]: 514.

Example 46

Synthesis of (2S)-2-((2,6-dichlorobenzoyl)amino)-3-(4-((1-((2-pyridylamino)methyl)cyclopropyl)methoxy)phenyl)propanoic acid

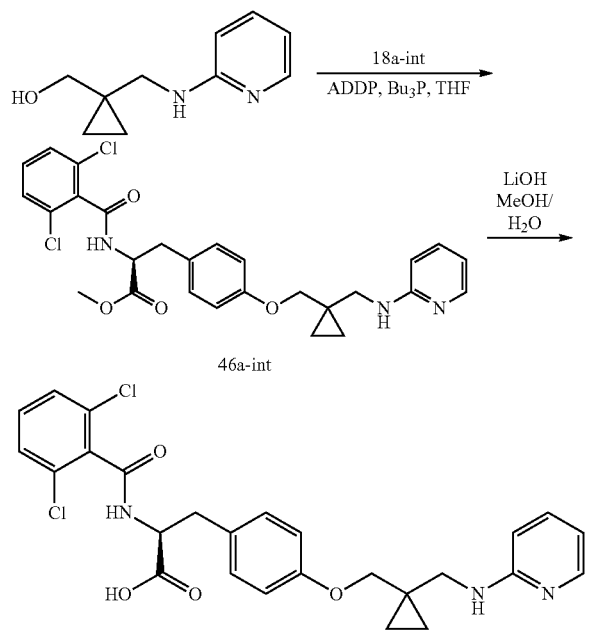

Compound 46a-int. To the mixture of 18a-int (206.59 mg, 0.56 mmol) and (1-((2-pyridylamino)methyl)cyclopropyl) methanol (100. mg, 0.56 mmol) in a mixture of DMF (0.5 mL) and THF (2.5 mL) at r.t. was added tributylphosphine (0.28 mL, 1.12 mmol) followed by ADDP (283.13 mg, 1.12 mmol) slowly. The resulting mixture was then heated at 60° C. for 2 hrs. The reaction was cooled to room temperature and diluted with EtOAc (10 mL). The mixture was then mixed with silica gel, concentrated, purified by combiflash (dry load, 0-100% EtOAc/Hexanes). Desired fractions were combined and concentrated to give 46a-int. m/z [M+H] for $C_{27}H_{27}Cl_2N_3O_4$: theoretical: 528.14 Found: 528.1.

Example 46

46a-int (42.6 mg, 0.08 mmol) (8) was dissolved in a mixture of methanol (2 mL) and water (1.6 mL) at r.t. To this stirred mixture was added lithium hydroxide (11.58 mg, 0.48 mmol). The resulting mixture was stirred for 1 hr at r.t. The reaction was then concentrated, redissolved in 50% AcOH/H$_2$O (3.0 mL), filtered and purified by reverse phase prep HPLC (C18 Gold reusable column, 30 g, 10-70% ACN/H$_2$O with 0.1% TFA). Desired fractions were combined and frozen dried to Example 46. m/z [M+H] for $C_{26}H_{25}Cl_2N_3O_4$: theoretical: 514.12, found: 514.1. $^1$H NMR (500 MHz, Methanol-$d_4$) δ 7.87-7.84 (m, 1H), 7.74-7.73 (m, 1H), 7.37-7.36 (m, 3H), 7.21-7.20 (m, 2H), 7.13-7.11 (m, 1H), 6.84-6.8 (m, 3H), 4.83-4.81 (m, 1H), 3.9 (s, 2H), 3.55-3.48 (m, 2H), 3.23-3.19 (m, 1H), 2.97-2.92 (m, 1H), 0.82-0.77 (m, 4H).

Example 47

Synthesis of (S)-2-(2,6-dichlorobenzamido)-10-((3,4,5,6-tetrahydropyrazin-2-yl)amino)decanoic acid

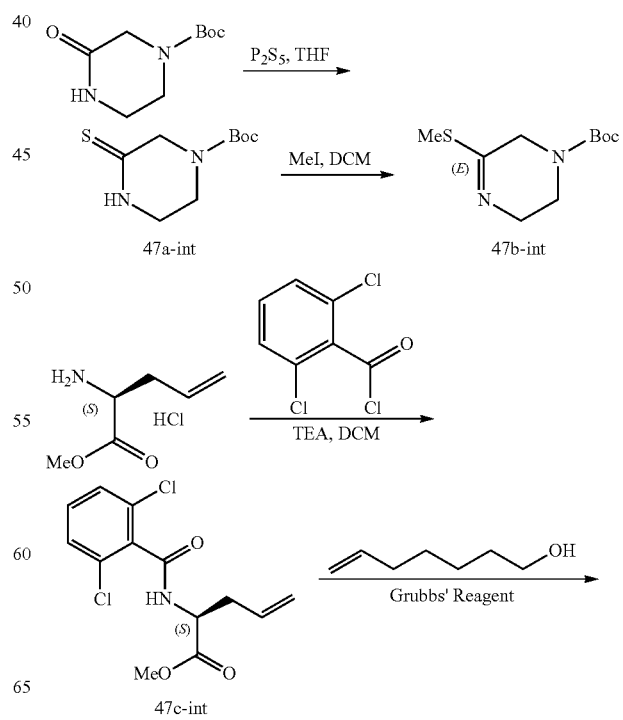

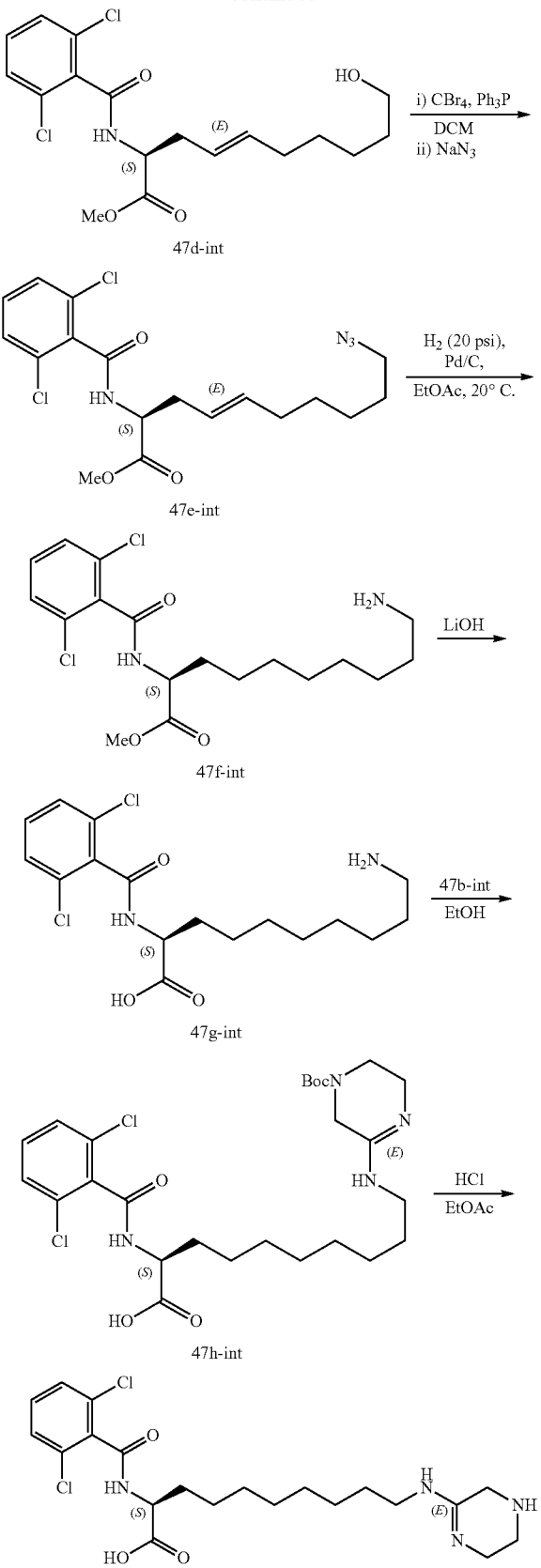

Example 47

Compound 47a-int: To a solution of tert-butyl 3-oxopiperazine-1-carboxylate (2 g, 10 mmol) in THF (50 mL) was added $P_2S_5$ (2.25 g, 10 mmol). The reaction is stirred at 60° C. for 12 hrs. TLC (PE:EA=4:1, Rf=0.6) indicated the reaction was complete. The precipitate was removed by filtration and the filtrate was concentrated in vacuum to give compound 47a-int.

Compound 47b-int: A mixture of 47a-int (2 g), methyl iodide (41.8 ml) and dichloromethane (50 ml) was stirred at 20° C. for 12 hrs. The reaction mixture was concentrated under reduced pressure and was poured into $H_2O$ (20 mL). The organic layer was separated, washed with sat. $NaHCO_3$ (20 mL), $H_2O$ (20 mL) and brine (20 mL) then dried over $Na_2SO_4$. After filtration, the solvent was removed under reduced pressure to give compound 47b-int; $^1H$ NMR (400 MHz, CHLOROFORM-d): δ ppm 4.00 (bs, 2H), 3.68-3.76 (m, 2H), 3.42 (t, J=5.2 Hz, 2H), 2.33 (s, 3H), 1.46 (s, 9H).

Compound 47c-int: Methyl (2S)-2-aminopent-4-enoate (45 g, 348.41 mmol) in DCM (500 mL) was added dropwise to TEA (88.14 g, 871.03 mmol, 120.74 mL) and 2,6-dichlorobenzoyl chloride (21 g, 100.26 mmol, 14.38 mL) in DCM at 20° C. The mixture was stirred at 20-40° C. for 12 hrs and was poured into $H_2O$ (500 mL). The organic layer was separated and washed with 1N HCl (200 mL), sat. $NaHCO_3$ (200 mL), brine (200 mL) and dried over $Na_2SO_4$. The solvent was removed by evaporation under reduced pressure and dried in vacuo to give 47c-int.

Compound 47d-int: To a mixture of compound 47c-int (13.3 g, 44.02 mmol) and hept-6-en-1-ol (5.03 g, 44.02 mmol) in DCM (1.2 L) was added the Grubbs II catalyst (5.61 g, 6.60 mmol) in one portion at 25° C. under $N_2$. The mixture was stirred at 40° C. for 24 hours. LC-MS showed 43c-int was consumed completely and one main peak with desired MS was detected. TLC (PE:EtOAc=2/1, $R_f$=0.2) indicated 47c-int was consumed completely, and one major new spot with higher polarity was detected. The reaction mixture was concentrated and purified by column chromatography ($SiO_2$, PE:EtOAc=10/1 to 2/1) to give 47d-int.

Compound 47e-int: To 47d-int (7 g, 18.03 mmol) and $PPh_3$ (4.73 g, 18.03 mmol) in DCM (70 mL) was added $CBr_4$ (5.98 g, 18.03 mmol) in one portion at 0° C. The mixture was stirred at 25° C. for 12 hrs. LC-MS showed 43d-int was consumed completely; TLC (PE:EtOAc=1/1, $R_f$=0.8) indicated 43d-int was consumed; this material was evaporated then dissolved in DMF and $NaN_3$ (3 equivalents) added. The reaction was heated at 50° C. until the starting bromide was consumed; then the reaction was diluted with water and extracted with EtOAc (3×). The combined organic extracts were washed with water (5×) dried (Na2SO4) and evaporated. This material was purified by column chromatography (SiO2, PE:EtOAc=10/1 to 6/1) to give 47e-int; $^1H$ NMR (400 MHz, CHLOROFORM-d): δ ppm 7.21-7.38 (m, 3H), 6.26-6.41 (m, 1H), 5.30-5.61 (m, 2H), 4.81-4.98 (m, 1H), 3.73-3.85 (m, 3H), 3.30-3.44 (m, 2H), 2.53-2.78 (m, 1H), 1.97-2.19 (m, 3H), 1.76-1.92 (m, 2H), 1.30-1.52 (m, 3H).

Compound 47f-int: To a solution of compound 47e-int (3.5 g, 8.47 mmol) in EtOAc (200 mL) was added Pd/C (350 mg). The suspension was degassed under vacuum and purged with $H_2$ several times. The mixture was stirred under $H_2$ (20 psi) at 25° C. for 5 hours. LC-MS showed 47e-int was consumed completely and one main peak with desired MS was detected. The reaction mixture was filtered and the filter was concentrated. The residue was purified by prep-HPLC to give compound 47f-int.

Compound 47g-int: To compound 47f-int (200 mg, 513.72 umol) in THF (5 mL) and $H_2O$ (1 mL) was added LiOH.H$_2$O (43.11 mg, 1.03 mmol). The mixture was stirred at 20° C. for 2 hours. LC-MS showed 43f-int was consumed completely and 47g-int was detected. The mixture was concentrated and adjusted to pH 6 with aq. HCl (1N). The mixture was concentrated to give compound 47g-int. The crude product was used into the next step without further purification.

Compound 47h-int: To a mixture of compound 47g-int (90 mg, 239.81 umol) and 47b-int (165.71 mg, 719.43 umol) in EtOH (10 mL) was added TEA (72.80 mg, 719.43 umol, 99.73 uL). The mixture was stirred at 80° C. for 12 hours. LC-MS showed ~5% of 47b-int remained and several new peaks on LC-MS with ~17% of 47h-int was detected. TLC (EtOAc/MeOH=10/1) indicated some 47b-int remained, and one major new spot with lower polarity was detected. The reaction mixture was concentrated and was purified by prep-TLC (SiO$_2$, EtOAc/MeOH=10/1) to give compound 47h-int.

Example 47

47h-int (70.00 mg, 125.56 umol) in HCl/EtOAc (15 mL) was stirred at 25° C. for 2 hours. LC-MS showed 47h-int was consumed completely and Example 47 was detected. The reaction mixture was concentrated and was purified by prep-HPLC to give Example 47.

HPLC purification conditions: Gilson 281 semi-preparative HPLC system; Mobile phase A: TFA/H$_2$O=0.075% v/v; B: AcN (gradient % B at T=0: 5%; at T=10 min: 35%); Column: Luna C18 100×30 5 u; Flow rate: 25 mL/min; Monitor wavelength: 220 & 254 nm.

$^1$H NMR (400 MHz, METHANOL-d$_4$): δ ppm 7.37-7.48 (m, 3H), 4.63 (dd, J=9.48, 4.63 Hz, 1H), 4.10 (br s, 2H), 3.60-3.64 (m, 2H), 3.42 (br s, 2H), 3.26 (t, J=7.17 Hz, 2H), 1.90-2.00 (m, 1H), 1.79 (ddt, J=13.75, 9.34, 6.86, 6.86 Hz, 1H), 1.63-1.71 (m, 2H), 1.50-1.58 (m, 2H), 1.40 (br s, 8H); LCMS (ESI+): m/z=457.2 (M+H)$^+$, RT: 2.1 min; HPLC purity: 79.1%, RT: 4.8 min; Chiral SFC purity: 100%, ee value: 100%, RT: 2.6 min.

Example 48

Synthesis of (S)-2-(2,6-dichlorobenzamido)-10-((4,5-dihydrooxazol-2-yl)amino)decanoic acid

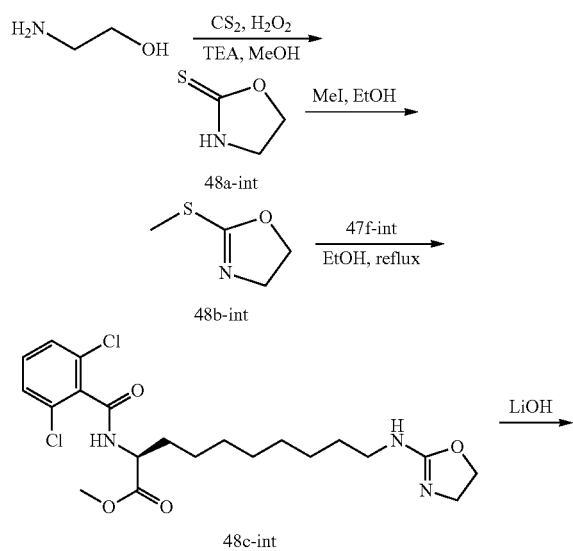

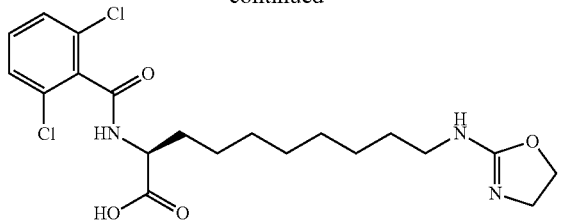

Example 48

Compound 48a-int: To a solution of 2-aminoethanol (6.1 g, 0.1 mol) in EtOH (250 mL) was added of K$_2$CO$_3$ (6.9 g, 50 mmol) and carbon disulfide (15.2 g, 0.2 mol). The mixture was heated to 40° C. and H$_2$O$_2$ (30% w/w, 15.3 mL, 150 mmol) was slowly added over 1 hr. The reaction was then allowed to cool to 20° C., and stirred for an additional 4 hrs. Sat. NH$_4$Cl (10 mL) was added and concentrated in vacuo. The mixture was extracted with EtOAc (3×150 mL). The combined organic layers were dried with Na$_2$SO$_4$, concentrated to give compound 48a-int, which was used directly for next step without any further purification.

Compound 48b-int: To a solution of 48a-int (5 g, 48 mmol) in EtOH (100 mL) was added methyl iodide (14.2 g, 0.1 mol); this was stirred at 80° C. for 12 hrs. The reaction was then allowed to cool to 20° C. and concentrated in vacuo. The mixture was poured into H$_2$O (50 mL), extracted with EtOAc (3×50 mL). The combined organic layers were dried with Na$_2$SO$_4$, then concentrated to give 48b-int, which was used directly for next step without any further purification.

Compound 48c-int: To a mixture of compound 47f-int (130 mg, 258.27 umol) and 48b-int (60.52 mg, 516.55 umol) in EtOH (5 mL) was added TEA (78.4 mg, 774.82 umol, 107.4 uL). The mixture was stirred at 80° C. for 12 hrs. LCMS showed that the reactants were consumed completely and MS for 48c-int was detected. TLC (EtOAc/MeOH=10/1) indicated the reaction was completed. The reaction mixture was concentrated and the residue was purified by prep-TLC (SiO$_2$, EtOAc/MeOH=10/1) to give compound 48c-int.

Example 48

To a mixture of compound 48c-int (100 mg, 218.16 umol) in THF (5 mL) and H$_2$O (1 mL) was added LiOH.H$_2$O (18.31 mg, 436.32 umol). The mixture was stirred at 25° C. for 2 hours. LCMS showed the major peak to be Example 48. The mixture was adjusted to pH 6 with aq. HCl (1N) then concentrated in vacuo. The residue was purified by prep-HPLC to give Example 48.

HPLC purification conditions: Gilson 281 semi-preparative HPLC system; Mobile phase A: 10 mM NH$_4$HCO$_3$ in H$_2$O; B: ACN (gradient % B at T=0: 25%; at T=12 min: 45%); Column: YMC-Actus Triart C18 150×30 5 u; Flow rate: 25 mL/min; Monitor wavelength: 220 & 254 nm.

$^1$H NMR (400 MHz, METHANOL-d$_4$): δ ppm 7.33-7.48 (m, 3H), 4.75-4.84 (m, 2H), 4.63 (dd, J=9.26, 4.63 Hz, 1H), 3.84-3.95 (m, 2H), 3.24 (t, J=7.17 Hz, 2H), 1.90-2.00 (m, 1H), 1.73-1.84 (m, 1H), 1.62 (br d, J=6.62 Hz, 2H), 1.52 (br d, J=5.73 Hz, 2H), 1.38 (br d, J=3.31 Hz, 8H); LCMS (ESI+): m/z=444.2 (M+H)$^+$, RT: 2.4 min; HPLC purity: 93.6%, RT: 4.3 min; Chiral SFC purity: 100%, ee value: 100%, RT: 2.9 min.

Example 49

Synthesis of (S)-2-(2,6-dichlorobenzamido)-10-((4,5-dihydrothiazol-2-yl)amino)decanoic acid

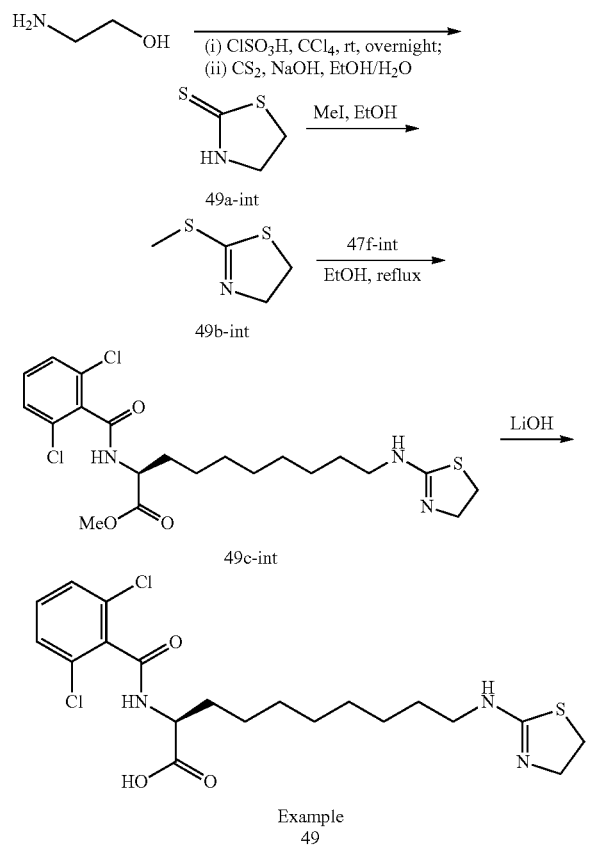

Compound 49a-int: A solution of 2-aminoethanol (6.1 g, 0.1 mol) and chlorosulfuric acid (11.7 g, 0.1 mol) in CCl$_4$ (100 mL) was stirred at 25° C. for 12 hrs. To the mixture was added CS$_2$ (7.6 g, 99.85 mmol, 6.03 mL) and NaOH (5 g) in EtOH/H$_2$O (20 mL/10 mL) in one portion at 25° C. This mixture was stirred at 40° C. for an additional 4 hrs. Saturated aqueous NH$_4$Cl (10 mL) was added and then the solution was concentrated. The mixture was extracted with EtOAc (3×150 mL). The combined organic layers were dried with Na$_2$SO$_4$, and concentrated in vacuo to give 49a-int. This was used directly for next step without any further purification.

Compound 49b-int: To a solution of 49a-int (5 g, 48 mmol) in EtOH (100 mL) was added MeI (14.2 g, 0.1 mol); this was stirred at 80° C. for 12 hrs. The reaction was allowed to cool to 20° C. and concentrated. The mixture was poured into H$_2$O (50 mL), extracted with EtOAc (3×50 mL). The combined organic layers were dried with Na$_2$SO$_4$ and concentrated to give 49b-int which was used directly for next step without any further purification.

Compound 49c-int: To a solution of compound 47f-int (70 mg, 0.16 mmol) in EtOH (1 mL) was added compound 49b-int (21 mg, 0.16 mmol). The mixture was stirred for 1 hr at 80° C. The mixture was concentrated and was purified by Prep-TLC (DCM:MeOH=10:1) to give 49c-int.

To a solution of 49c-int (35 mg, 66.74 umol) in THF (1 mL)/H$_2$O (1 mL) was added LiOH.H$_2$O (2.80 mg, 66.74 umol). The mixture was stirred for 2 h at 20° C. then was concentrated and purified by Prep-HPLC to give Example 49.

HPLC purification conditions: Gilson 281 semi-preparative HPLC system; Mobile phase A: 10 mM NH$_4$HCO$_3$ in H$_2$O; B: AcN (gradient % B at T=0: 30%; at T=12 min: 50%); Column: YMC-Actus Triart C18 150×30 5 u; Flow rate: 25 mL/min; Monitor wavelength: 220 & 254 nm.

$^1$H NMR (400 MHz, METHANOL-d$_4$): δ ppm 1.84-1.80 (m, 4H) 2.96-2.90 (m, 1H) 3.32-3.17 (m, 1H) 3.54-3.52 (m, 2H) 3.60-3.56 (m, 2H) 4.01-3.97 (m, 4H) 4.87-4.85 (m, 1H) 6.81 (d, J=8.8 Hz, 2H) 7.20 (d, J=8.8 Hz, 2H) 7.36-7.30 (m, 3H); LCMS (ESI+): m/z=460.3 (M+H)$^+$, RT: 2.4 min; HPLC purity: 95.1%, RT: 4.3 min; Chiral SFC purity: 97.5%, ee value: 95%, RT: 2.9 min.

Example 50

Synthesis of (S)-2-(2,6-dichlorobenzamido)-10-((1-methyl-5-oxo-4,5-dihydro-1H-imidazol-2-yl)amino)decanoic acid

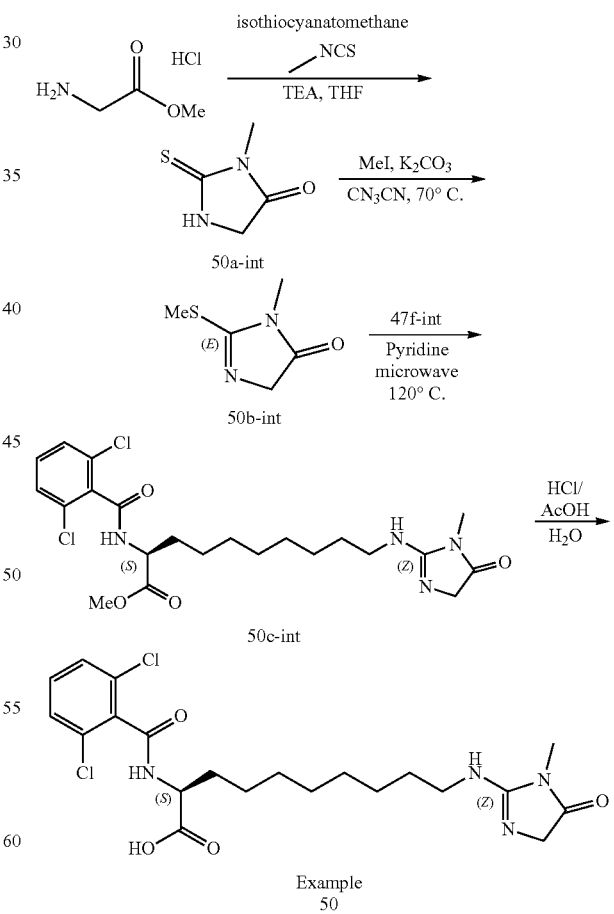

Compound 50a-int: A mixture of isothiocyanatomethane (7.3 g, 0.1 mol), methyl glycinate hydrochloride (12.5 g, 0.1 mol), and TEA (14 mL, 0.1 mol) in EtOH (100 mL) was heated to 80° C. for 14 hours. After cooling to ambient temperature, the solvent was removed under reduced pressure. The residue was crystallized from EtOH (20 mL) to give 50a-int.

Compound 50b-int: To a mixture of 50a-int (1 g, 7.68 mmol) in MeCN (10 mL) was added MeI (1.64 g, 11.52 mmol, 717.17 uL) at 25° C. The mixture was stirred at 40° C. for 12 hrs. LC-MS showed 50a-int was consumed and 50b-int was detected. TLC (PE:EtOAc=1/1, $R_f$=0.3) indicated the reaction was complete. The reaction mixture was concentrated in vacuo and the residue was purified by column chromatography (SiO$_2$, PE:EtOAc=10/1 to 3/1) to give 50b-int; $^1$H NMR (400 MHz, CHLOROFORM-d): δ ppm 4.14 (s, 2H), 3.04-3.10 (m, 3H), 2.57 (s, 3H).

Compound 50c-int: A solution of 47f-int (100 mg, 256.86 umol) and 50b-int (48.15 mg, 333.92 umol) in pyridine (3 mL) under microwave was stirred at 120° C. for 3 hr. LCMS showed that the desired product was detected. The solvent was removed in vacuum and the residue was purified by prep-TLC (DCM:MeOH=10:1, $R_f$=0.4) to give 50c-int; this product was used directly in the next step; LCMS (ESI+): m/z 485.1 (M+H)$^+$, RT: 0.71 min.

Example 50

A solution of 50c-int (60 mg, 123.61 umol), HCl (0.1 mL, 2.5N, 247.22 umol) and AcOH (7.42 mg, 123.61 umol) in H$_2$O (3 mL) was stirred at 70° C. for 10 hrs. LCMS showed that Example 50 was detected. The reaction mixture was purified by prep-HPLC to give Example 50.

HPLC purification conditions: Gilson 281 semi-preparative HPLC system; Mobile phase A: TFA/H$_2$O=0.075% v/v; B: AcN (gradient % B at T=0: 15%; at T=15 min: 45%); Column: Boston Green ODS 150×30 5 u; Flow rate: 25 mL/min; Monitor wavelength: 220 & 254 nm.

$^1$H NMR (400 MHz, METHANOL-d$_4$): δ ppm 7.35-7.46 (m, 3H), 4.64 (dd, J=9.48, 4.63 Hz, 1H), 4.21 (s, 2H), 3.38 (t, J=7.39 Hz, 2H), 3.15 (s, 3H), 1.90-2.01 (m, 1H), 1.75-1.86 (m, 1H), 1.66-1.75 (m, 2H), 1.49-1.58 (m, 2H), 1.41 (br s, 8H); LCMS (ESI+): m/z 471.0 (M+H)$^+$, RT: 2.4 min; HPLC purity: 87.1%, RT: 3.9 min; Chiral SFC purity: 96.3%, ee value: 92.6%, RT: 4.0 min.

Example 51

Synthesis of (S)-2-(2,6-dichlorobenzamido)-10-((5, 6-dihydro-4H-1,3-oxazin-2-yl)amino)decanoic acid

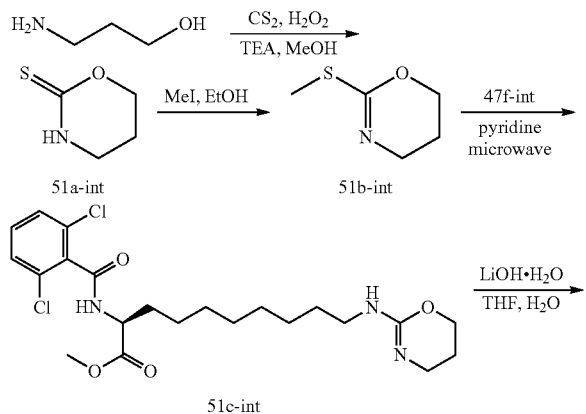

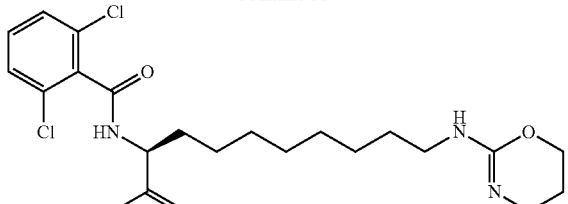

Example 51

Compound 51a-int: To a mixture of 3-aminopropan-1-ol (5 g, 66.57 mmol, 5.15 mL) and TEA (6.74 g, 66.57 mmol, 9.23 mL) in MeOH (66 mL) was added CS$_2$ (7.6 g, 99.85 mmol, 6.03 mL) in one portion at 0° C. The mixture was stirred at 20° C. for 0.5 hrs. 30% H$_2$O$_2$ (15.09 g, 133.14 mmol, 12.79 mL) was added at such a rate that the solvent was at reflux. The reaction mixture was then cooled to 20° C., filtered and concentrated under reduced pressure. NaOH solution (80 mL, 1 N) was added to free the TEA that was subsequently removed in vacuo. The mixture was neutralized with aqueous HCl (5N) and the aqueous phase was extracted with ethyl acetate (100 mL×5). The combined organic phase was dried with anhydrous Na$_2$SO$_4$, filtered and concentrated in vacuum to give 51a-int, which was used into the next step without further purification.

Compound 5 b-int: To a mixture of 51a-int (2 g, 17.07 mmol) in EtOH (6 mL) was added CH$_3$I (3.15 g, 22.19 mmol, 1.38 mL) in one portion at 20° C. The mixture was stirred at 90° C. for 1 hour. TLC (Petroleum ether I/Ethyl acetate=1/1, $R_f$=0.8) indicated the reaction was complete. The mixture was concentrated and the residue was purified by column chromatography (SiO$_2$, PE:EtOAc=10/1 to 8/1) to give compound 51b-int; $^1$H NMR (400 MHz, CHLOROFORM-d): δ ppm 3.41 (q, J=6.40 Hz, 2H), 3.20 (t, J=6.78 Hz, 2H), 2.33-2.39 (m, 3H), 2.06 (quin, J=6.68 Hz, 2H).

Compound 51c-int: To 51b-int (200 mg, 513.72 umol) and 47f-int (67.4 mg, 513.72 umol) in dioxane (6 mL) was added TEA (155.95 mg, 1.54 mmol, 213.63 uL). The mixture was stirred at 110° C. for 4 hours; LC-MS showed the reactants were consumed and the MS of 51c-int was detected. TLC (EtOAc/MeOH=10/1, $R_f$=0.4) one major new spot was detected. The reaction mixture was concentrated and the residue was purified by prep-TLC (EtOAc/MeOH=10/1) to give 51c-int.

Example 51

To 51c-int (100 mg, 211.69 umol) in THF (5 mL) and H$_2$O (2 mL) was added LiOH.H$_2$O (17.77 mg, 423.38 umol); the mixture was stirred at 25° C. for 2 hours. LCMS showed 51c-int was consumed completely and one main peak with desired MS was detected. The mixture was concentrated and adjusted to pH 6 with aq. HCl (1N) and was concentrated in vacuum. The residue was purified by prep-HPLC to give Example 51.

HPLC purification conditions: Gilson 281 semi-preparative HPLC system; Mobile phase A: 10 mM NH$_4$HCO$_3$ in H$_2$O; B: AcN (gradient % B at T=0: 25%; at T=12 min: 45%); Column: YMC-Actus Triart C18 150×30 5 u; Flow rate: 25 mL/min; Monitor wavelength: 220 & 254 nm.

$^1$H NMR (400 MHz, METHANOL-d$_4$): 6 ppm 7.33-7.47 (m, 3H), 4.56 (dd, J=8.27, 4.74 Hz, 1H), 3.21-3.30 (m, 6H), 1.86-2.00 (m, 3H), 1.71-1.84 (m, 1H), 1.45-1.58 (m, 4H), 1.26-1.42 (m, 7H), 1.25-1.26 (m, 1H); LCMS (ESI+):

m/z=458.0 (M+H)⁺, RT: 2.5 min; HPLC purity: 100%, RT: 6.5 min; Chiral SFC purity: 100%, ee value: 100%, RT: 3.0 min.

Example 52

Synthesis of (S)-2-(2,6-dichlorobenzamido)-10-((4-methyl-5-oxo-3,4,5,6-tetrahydropyrazin-2-yl)amino)decanoic acid

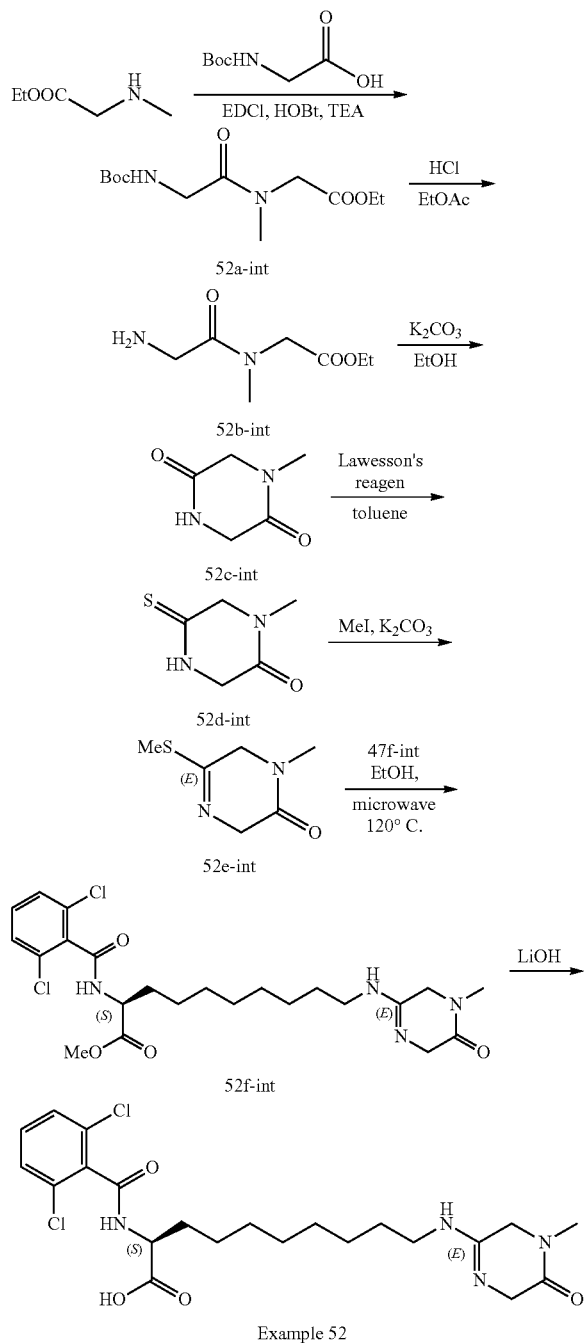

Compound 52a-int: A mixture of 2-(tert-butoxycarbonylamino)acetic acid (4.01 g, 22.92 mmol), EDCI (4.79 g, 25 mmol HOBt (3.38 g, 25 mmol) and TEA (5.27 g, 52.08 mmol) in DCM (100 mL) was stirred for 10 min, then ethyl 2-(methylamino)acetate (3.20 g, 20.83 mmol) was added, the resulting mixture was stirred at 15° C. for 12 hrs. LCMS showed the desired MS; TLC (PE:EtOAc=1:1, R$_f$=0.35) showed a new spot. The mixture was concentrated and the residue was purified by silica column chromatography (PE:EtOAc=2:1) to give 52a-int; $^1$H NMR (400 MHz, CHLOROFORM-d): δ ppm 5.46 (br s, 1H), 4.17-4.28 (m, 2H), 4.04 (d, J=4.27 Hz, 2H), 3.04 (s, 3H), 1.44-1.46 (m, 9H), 1.26-1.31 (m, 3H).

Compound 52b-int: A solution of compound 52a-int (3.9 g, 14.22 mmol) in HCl/EtOAc (60 mL) was stirred at 20° C. for 1 hr. TLC (PE:EtOAc=1:1, R$_f$=0) showed the reaction was complete; the mixture was concentrated to give the crude product compound 52b-int (3 g).

Compound 52c-int: 52b-int (1.2 g, 6.89 mmol) and K$_2$CO$_3$ (2.86 g, 20.67 mmol) in EtOH (20 mL) was heated to 80° C. for 12 hrs. LCMS showed 52c-int was present; then the mixture was filtered and the filtrate was concentrated in vacuum. The residue was dissolved in EtOAc/MeOH=10:1 (40 mL). The mixture was filtered and the filtrate was concentrated in vacuum to give 52c-int; $^1$H NMR (400 MHz, DMSO-d$_6$): δ ppm 8.10 (br s, 1H), 3.84 (s, 2H), 3.73 (s, 2H), 2.78 (s, 3H).

Compound 52d-int: 52c-int (1.90 g, 14.83 mmol) and Lawesson's Reagent (3.00 g, 7.42 mmol) in toluene (50 mL) was heated to 60° C. for 1 hr. LCMS showed product 52d-int; after cooling the mixture was filtered, the filter cake was dissolved in DCM (100 mL) then filtered and the filtrate was concentrated. This was purified by silica column chromatography (DCM:MeOH=30:1) to give 52d-int.

Compound 52e-int: A mixture of compound 52d-int (570 mg, 3.95 mmol, 1.00 eq), K$_2$CO$_3$ (1.09 g, 7.9 mmol) and CH$_3$I (1.12 g, 7.90 mmol, 491.81 uL) in CH$_3$CN (10 mL) was stirred at 20° C. for 12 hrs. LCMS showed 52e-int. The mixture was filtered and the filtrate was concentrated in vacuo; the residue was purified by prep-TLC (EtOAc) to give compound 52e-int; $^1$H NMR (400 MHz, CHLOROFORM-d): δ ppm 4.29 (t, J=2.82 Hz, 2H), 4.03 (t, J=2.89 Hz, 2H), 2.99 (s, 3H), 2.37 (s, 3H).

Compound 52f-int: 52e-int (200 mg, 513.72 umol) and 47f-int (81.28 mg, 513.72 umol) in EtOH (5 mL) was heated to 80° C. for 12 hrs. LCMS showed the desired product; the reaction mixture was concentrated and the residue was purified by prep-HPLC to give 52f-int.

Example 52

52f-int (40 mg, 80.09 umol) and LiOH.H$_2$O (10.08 mg, 240.27 umol) in THF (2 mL)/H$_2$O (500 uL) was stirred at 20° C. for 12 hrs. LCMS showed the reaction was complete. The mixture was concentrated in vacuum and the residue was purified by prep-HPLC to give Example 52.

HPLC purification conditions: Gilson 281 semi-preparative HPLC system: Mobile phase A: TFA/H$_2$O=0.075% v/v; B: AcN (gradient % B at T=0: 11%; at T=10 min: 41%); Column: Boston Green ODS 150×30 5 u; Flow rate: 25 mL/min; Monitor wavelength: 220 & 254 nm.

$^1$H NMR (400 MHz, METHANOL-d$_4$): δ ppm 7.31-7.48 (m, 3H), 4.63 (dd, J=9.48, 4.63 Hz, 1H), 4.39 (s, 2H), 4.03 (s, 2H), 3.23-3.29 (m, 2H), 3.00 (s, 3H), 1.89-2.00 (m, 1H), 1.73-1.84 (m, 1H), 1.62-1.73 (m, 1H), 1.68 (quin, J=7.06 Hz, 1H), 1.50-1.59 (m, 2H), 1.40 (br s, 8H); LCMS (ESI+): m/z=485.1 (M+H)⁺, RT: 2.0 min; HPLC purity: 95.4%, RT: 5.6 min; Chiral SFC purity: 100%, ee value: 100%, RT: 2.7 min.

Example 53

Synthesis of (S)-2-(2,6-dichlorobenzamido)-10-((4-methyl-3-oxo-3,4,5,6-tetrahydropyrazin-2-yl)amino)decanoic acid

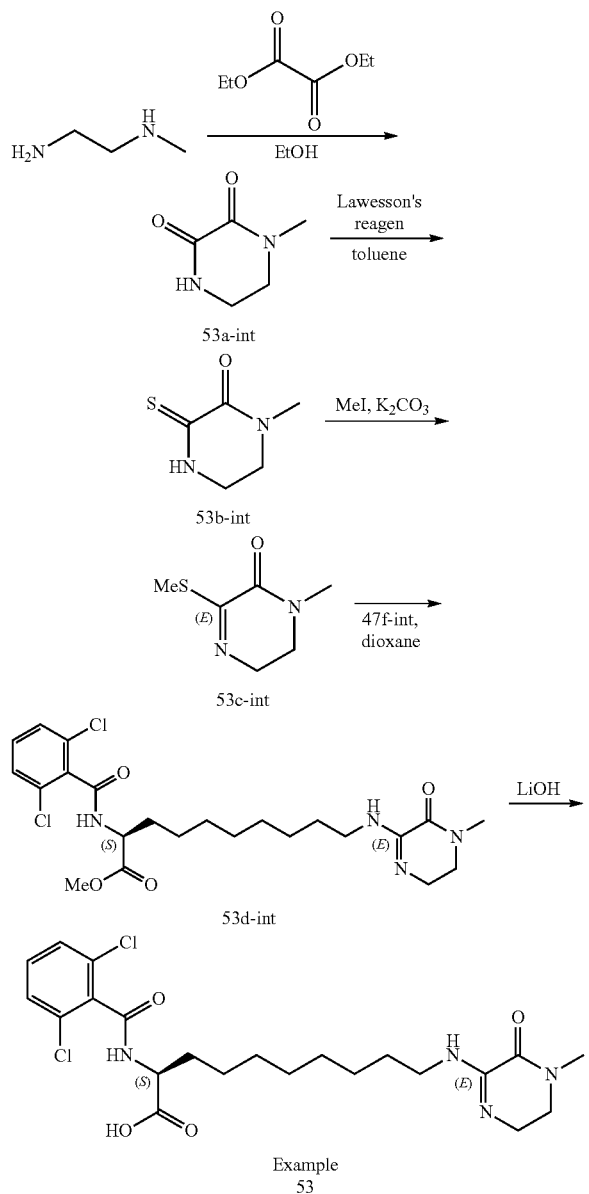

53a-int 53b-int 53c-int 53d-int

Example 53

Compound 53a-int: To N-methylethane-1,2-diamine (7.41 g, 100 mmol, 8.72 mL) in EtOH (100 mL) was added dropwise diethyl oxalate (14.61 g, 100 mmol, 13.65 mL) at 20° C. The mixture was stirred at 90° C. for 13 hrs. The solvent was removed under reduced pressure and dried under vacuum. The residue was recrystallized from EtOH (50 mL) to give compound 53a-int.

Compound 53b-int: To a mixture of Lawesson's Reagent (3.16 g, 7.81 mmol) in dry toluene (30 mL) was added compound 53a-int (2 g, 15.6 mmol) at 0° C. The mixture was heated to 45-50° C. for 1.5 hrs and stirred at 15° C. for 3 hrs. LCMS showed the desired product. After cooling, the mixture was filtered and the filtrate cake was dissolved in DCM (100 mL) then stirred for 30 min. This mixture was filtered, the filtrate was concentrated and the residue was purified column chromatography on silica gel to give 53b-int.

Compound 53c-int: 53b-int (2 g, 13.9 mmol), $CH_3I$ (2.95 g, 20.8 mmol) and $K_2CO_3$ (2.11 g, 15.3 mmol) in $CH_3CN$ (30 mL) was stirred at 15° C. for 12 hrs. LCMS showed 53c-int was present. The mixture was filtered and the filtrate was concentrated. The residue was dissolved in DCM:MeOH=10:1 (40 mL), then filtered and the filtrate was concentrated to give 53c-int; $^1H$ NMR (400 MHz, CHLOROFORM-d): δ ppm 3.77-3.81 (m, 2H), 3.39-3.43 (m, 2H), 3.03 (s, 3H), 2.23 (s, 3H).

Compound 53d-int: 53c-int (200 mg, 513.72 umol, 1.00 eq) and 47f-int (81.28 mg, 513.72 umol) in dioxane (10 mL) was heated to 110° C. for 12 hr. LCMS showed 53d-int was present; TLC (DCM:MeOH=10:1, $R_f$=0.2) showed a new spot. The mixture was concentrated and the residue was purified by prep-TLC (DCM:MeOH=10:1) to give 53d-int.

Example 53

A mixture of compound 53d-int (100 mg, 200.23 umol) and $LiOH.H_2O$ (8.40 mg, 200.23 umol) in THF (5 mL)/$H_2O$ (1 mL) was stirred at 20° C. for 1 hr. LCMS showed desired MS; the mixture was concentrated and the residue was purified by prep-HPLC (TFA) to give Example 53.

HPLC purification conditions: Gilson 281 semi-preparative HPLC system; Mobile phase A: TFA/$H_2O$=0.075% v/v; B: AcN (gradient % B at T=0: 25%; at T=12 min: 55%); Column: YMC-Actus Triart C18 150×30 5 u; Flow rate: 25 mL/min; Monitor wavelength: 220 & 254 nm.

$^1H$ NMR (400 MHz, METHANOL-$d_4$): δ ppm 7.30-7.50 (m, 3H), 4.62 (dd, J=9.26, 4.63 Hz, 1H), 3.59-3.74 (m, 4H), 3.33 (s, 2H), 3.11 (s, 3H), 1.87-2.01 (m, 1H), 1.72-1.85 (m, 1H), 1.60-1.71 (m, 2H), 1.47-1.59 (m, 2H), 1.38 (br s, 8H); LCMS (ESI+): m/z=485.2 (M+H)$^+$, RT: 2.4 min; HPLC purity: 90.6%, RT: 5.8 min; Chiral SFC purity: 100%, ee value: 100%, RT: 2.6 min.

Example 54

Synthesis of (S)-2-(2,6-dichlorobenzamido)-10-((5,6-dihydro-4H-1,3-thiazin-2-yl)amino)decanoic acid

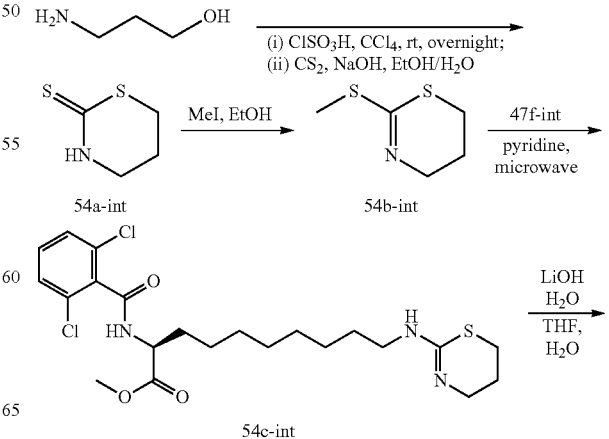

54a-int 54b-int 54c-int

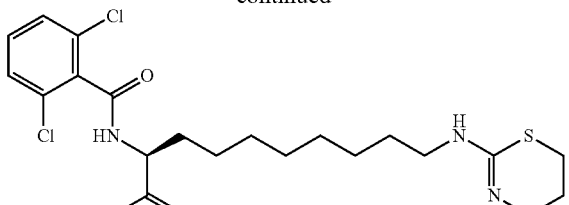

Example 54

Compound 54a-int: To a mixture of 3-aminopropan-1-ol (5 g, 66.57 mmol, 5.15 mL) in CCl$_4$ (15 mL) was added dropwise chlorosulfonic acid (7.76 g, 66.57 mmol, 4.43 mL) through an addition funnel at 0° C. under N$_2$. This was stirred at 15° C. for 12 hrs. The mixture was concentrated to give the crude product, which was suspended in MeOH (40 mL), filtered, triturated with MeOH, and dried, under high vacuum to give 3-aminopropyl hydrosulfate (as a white solid). To a suspension of the white solid (6 g, 38.6 mmol) and CS$_2$ (2.8 mL, 46.4 mmol) in 50% aqueous (v/v) EtOH (18 mL) at 0° C. was slowly added a solution of NaOH (3.4 g, 85 mmol) in 50% aqueous (v/v) EtOH (8 mL). The reaction was heated at reflux for 1 hour then cooled down to 15° C., resulting in the formation of off-white crystals. TLC (PE:EtOAc=1/1, R$_f$=0.2) indicated 3-aminopropyl hydrosulfate was consumed completely and one major new spot with lower polarity was detected. The off-white crystals were filtered, washed with ice-cold water and dried under high vacuum to yield 54a-int. The product was used in the next step without further purification.

Compound 54b-int: To 54a-int (2 g, 15.01 mmol) in EtOH (6 mL) was added CH$_3$I (4.26 g, 30.02 mmol, 1.87 mL) in one portion at 25° C.; this mixture was stirred at 90° C. for 1 hr. TLC (PE:EtOAc=1/1, RF 0.8) indicated that 54a-int was consumed completely and one major new spot with lower polarity was detected. The mixture was filtered and washed with EtOH (3 mL) to give compound 54b-int; $^1$H NMR (400 MHz, DMSO-d$_6$): δ ppm 3.61-3.70 (m, 2H), 3.26-3.35 (m, 2H), 2.62 (s, 3H), 2.04 (br d, J=4.63 Hz, 2H).

Compound 54c-int: 54b-int (200 mg, 513.72 umol) and 43f-int (90.78 mg, 616.46 umol) were taken up in pyridine (2 mL) and heated at 120° C. for 5 hours in a microwave reactor. LCMS showed 54b-int was consumed completely and 54c-int was detected. The reaction mixture was concentrated and the residue was purified by prep-HPLC to give 54c-int.

Example 54

To 54c-int (65 mg, 133.07 umol) in THF (3 mL)/H$_2$O (1 mL) was added LiOH.H$_2$O (11.17 mg, 266.14 umol). The mixture was stirred at 25° C. for 12 hours. LCMS showed 54c-int was consumed and one main peak for Example 54 was detected. The mixture was adjusted to pH 6 with aqueous HCl (1N) then concentrated and purified by prep-HPLC to give Example 54.

HPLC purification conditions: Gilson 281 semi-preparative HPLC system; Mobile phase A: 10 mM NH$_4$HCO$_3$ in H$_2$O; B: AcN (gradient % B at T=0: 30%; at T=12 min: 50%); Column: YMC-Actus Triart C18 150×30 5 u; Flow rate: 25 mL/min; Monitor wavelength: 220 & 254 nm.

$^1$H NMR (400 MHz, METHANOL-d$_4$): δ ppm 7.32-7.47 (m, 3H), 4.62 (dd, J=9.15, 4.74 Hz, 1H), 3.51 (br t, J=5.51 Hz, 2H), 3.20-3.29 (m, 4H), 2.13-2.22 (m, 2H), 1.88-2.00 (m, 1H), 1.71-1.84 (m, 1H), 1.57-1.68 (m, 2H), 1.48-1.56 (m, 1H), 1.48-1.49 (m, 1H), 1.38 (br s, 8H); LCMS (ESI+): m/z=474.0 (M+H)$^+$, RT: 2.5 min; HPLC purity: 97.6%, RT: 6.3 min; Chiral SFC purity: 99.1%, ee value: 98.2%, RT: 3.0 min.

Example 55

Synthesis of (S)-3-(4-(4-((4-acetyl-3,4,5,6-tetrahydropyrazin-2-yl)amino)butoxy)phenyl)-2-(2,6-dichlorobenzamido)propanoic acid

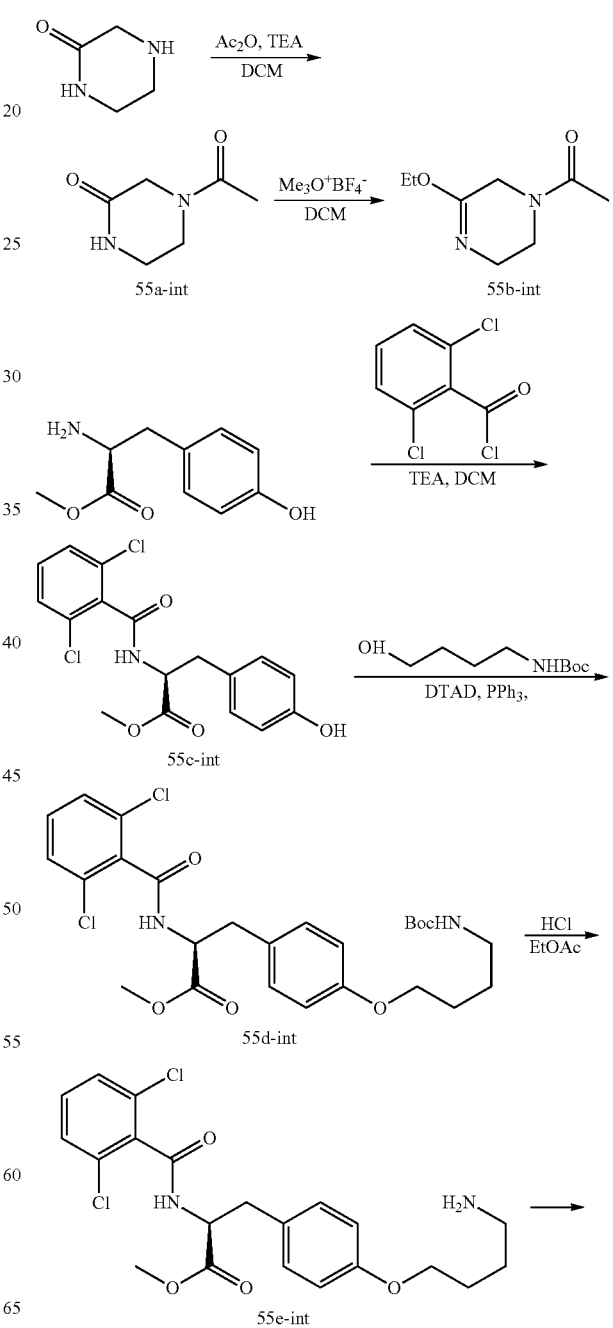

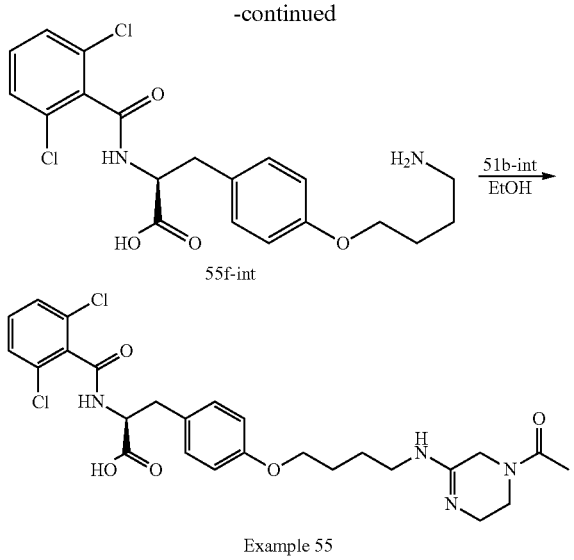

Example 55 was present then the mixture was concentrated and purified by prep-HPLC (TFA) to give Example 55.

HPLC purification conditions: Gilson 281 semi-preparative HPLC system; Mobile phase A: TFA/H$_2$O=0.075% v/v; B: AcN (gradient % B at T=0: 5%; at T=11.5 min: 35%); Column: Boston Green ODS 150×30 5 u; Flow rate: 25 mL/min; Monitor wavelength: 220 & 254 nm.

$^1$H NMR (400 MHz, METHANOL-d$_4$): δ ppm 7.28-7.43 (m, 3H), 7.24 (d, J=8.60 Hz, 2H), 6.78 (d, J=8.38 Hz, 2H), 4.70 (br t, J=5.95 Hz, 1H), 4.58 (br s, 3H), 4.48-4.52 (m, 1H), 3.99 (br s, 2H), 3.75-3.82 (m, 2H), 3.57 (br t, J=5.40 Hz, 2H), 3.49 (br d, J=5.51 Hz, 1H), 3.14-3.22 (m, 1H), 3.00-3.09 (m, 1H), 2.09-2.19 (m, 3H), 1.83 (br s, 4H); LCMS (ESI+): m/z=549.0 (M+H)$^+$, RT: 2.1 min; HPLC purity: 92.0%, RT: 3.8 min; Chiral SFC purity: 100%, ee value: 100%, RT: 2.9 min.

Example 56

Synthesis of (S)-2-(2,6-dichlorobenzamido)-3-(4-(4-((3,4,5,6-tetrahydropyrazin-2-yl)amino)butoxy)phenyl)propanoic acid

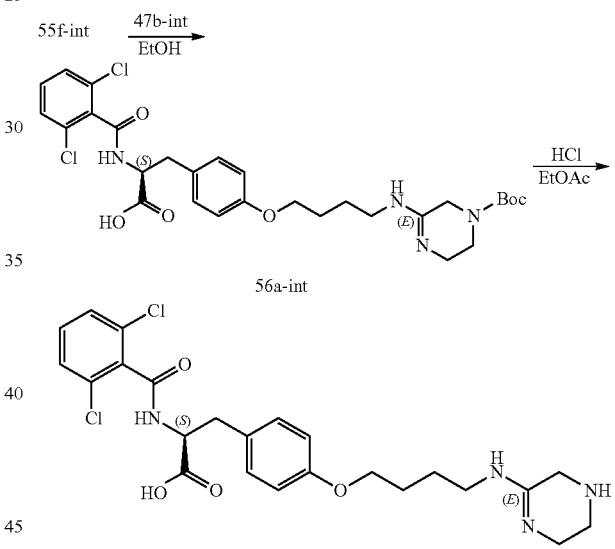

Compound 55a-int: To a solution of piperazin-2-one (500 mg, 4.99 mmol) and TEA (606.41 mg, 5.99 mmol, 830.70 uL) in DCM (10 mL) was added Ac$_2$O (509.84 mg, 4.99 mmol, 467.74 uL); this was stirred at 20° C. for 12 hrs. The mixture was concentrated to give crude 55a-int; $^1$H NMR (400 MHz, DMSO-d$_6$): δ ppm 3.98 (s, 2H), 3.54 (m, 2H), 3.22 (m, 1H), 3.20 (m, 1H), 2.01 (s, 3H).

Compound 55b-int: To 55a-int (370 mg, 2.6 mmol) in DCM (10 mL) was added trimethyloxonium tetrafluoroborate (961.42 mg, 6.50 mmol); the mixture was stirred at 20° C. for 12 hrs. TLC (PE:EtOAc=1:1, R$_f$=0.24) showed a new spot. The mixture was added to ice water (10 mL) and adjusted to pH 7 with NaHCO$_3$ solution; this was extracted with DCM (20 mL×3). The organic phases were combined, dried and concentrated to give 55b-int.

Compound 55c-int: See the procedure for 18a-int.

Compound 55d-int: To 55c-int (9 g, 24.4 mmol), tert-butyl (4-hydroxybutyl)carbamate (5.09 g, 26.9 mmol) and tributylphosphane (5.93 g, 29.3 mmol, 7.24 mL) in DCM (200 mL) was added ADDP (7.4 g, 29.3 mmol); this mixture was stirred at 15° C. for 12 hrs. TLC (PE:EtOAc=2:1, RF 0.52) showed a new spot and LCMS confirmed that 55d-int was present. The mixture was concentrated and purified by silica column chromatography (PE:EtOAc=3:1) to give 55d-int.

Compound 55e-int: A solution 55d-int (1 g, 1.85 mmol) in HCl/EtOAc (20 mL) was stirred at 20° C. for 30 min. TLC (PE:EtOAc=1:1) showed the reaction was complete; the mixture was concentrated to give 55e-int (900 mg).

Compound 55f-int: To a solution of compound 55e-int (370 mg, 2.6 mmol) in DCM (10 mL) was added trimethyloxonium tetrafluoroborate (961.42 mg, 6.5 mmol). The mixture was stirred at 20° C. for 12 hrs. TLC (PE:EtOAc=1:1, R$_f$=0.24) showed a new product. The mixture was poured into ice water (10 mL) and adjusted to pH 7 with NaHCO$_3$ solution; this was extracted with DCM (20 mL×3). The combined organic phases were dried and concentrated to give 55f-int.

Example 55

55f-int (60 mg, 141.08 umol), 51b-int (110.17 mg, 705.38 umol) and TEA (28.55 mg, 282.15 umol, 39.11 uL) in EtOH (5 mL) was heated to 80° C. for 5 hrs. LCMS showed Compound 56a-int: A mixture of compound 47b-int (30 mg, 70.54 umol), 55f-int (48.74 mg, 211.62 umol) and TEA (14.28 mg, 141.08 umol, 19.56 uL) in EtOH (5 mL) was heated to 80° C. for 12 hrs. LCMS showed desired product and the mixture was concentrated. The residue was purified by prep-HPLC to give 56a-int.

Example 56

A solution of 56a-int (27 mg, 44.44 umol) in HCl/EtOAc (5 mL) was stirred at 20° C. for 2 hr when LCMS showed the reaction was complete. The mixture was concentrated and the residue was purified by prep-HPLC (TFA) to give Example 56.

HPLC purification conditions: Gilson 281 semi-preparative HPLC system; Mobile phase A: TFA/H$_2$O=0.075% v/v; B: AcN (gradient % B at T=0: 1%: at T=11.5 min: 35%); Column: Boston Green ODS 150×30 5 u; Flow rate: 25 mL/min; Monitor wavelength: 220 & 254 nm.

¹H NMR (400 MHz, METHANOL-d₄): δ ppm 7.34-7.38 (m, 3H), 7.22 (d, J=8.77 Hz, 2H), 6.84 (d, J=8.77 Hz, 2H), 4.87-4.89 (m, 1H), 4.02 (s, 4H), 3.59 (t, J=5.70 Hz, 2H), 3.32-3.38 (m, 4H), 3.22 (dd, J=14.03, 5.26 Hz, 1H), 2.95 (dd, J=14.47, 9.21 Hz, 1H), 1.86 (br s, 4H); LCMS (ESI+): m/z=507.2 (M+H)⁺, RT: 2.1 min; HPLC purity: 98.065%, RT: 2.7 min; Chiral SFC purity: 100%, ee value: 100%, RT: 2.8 min.

Example 57

Synthesis of (S)-2-(2,6-dichlorobenzamido)-3-(4-(4-((1-methyl-5-oxo-4,5-dihydro-H-imidazol-2-yl)amino)butoxy)phenyl)propanoic acid

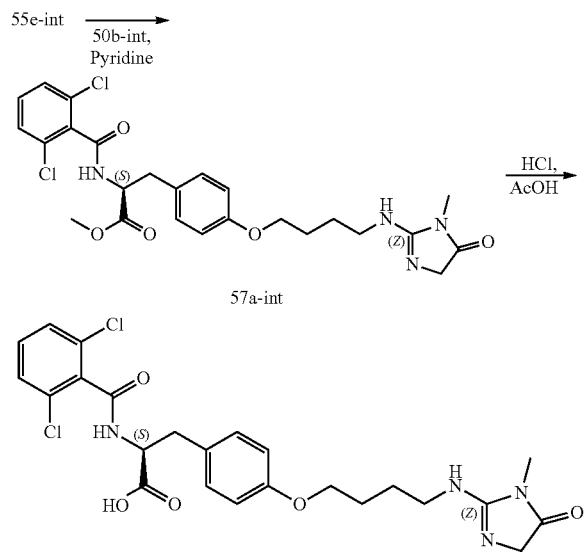

Example 57

Compound 57a-int: A solution of 55e-int (200 mg, 455.24 umol, 1.00 eq) and 50b-int (65.64 mg, 455.24 umol) in pyridine (2 mL) was stirred at 120° C. for 3 hrs in a microwave reactor. LCMS showed that the desired product was present. The solvent was removed to give 57a-int.

Example 57

To a solution of 58a-int (80 mg, 149.42 umol) in H₂O (800 uL) was added HCl (12 N, 12.45 uL) and AcOH (8.97 mg, 149.42 umol, 8.54 uL). The mixture was stirred at 70° C. for 12 hrs. LC-MS showed 57a-int was consumed completely and one main peak with desired MS for Example 57 was detected. The reaction mixture was concentrated and was purified by prep-HPLC to give Example 57.

HPLC purification conditions: Gilson 281 semi-preparative HPLC system; Mobile phase A: TFA/H₂O=0.075% v/v; B: AcN (gradient % B at T=0: 14%; at T=10.5 min: 34%); Column: Boston Green ODS 150×30 5 u; Flow rate: 25 mL/min; Monitor wavelength: 220 & 254 nm.

¹H NMR (400 MHz, METHANOL-d₄): δ ppm 7.32-7.39 (m, 3H), 7.22 (d, J=8.60 Hz, 2H), 6.82-6.85 (m, 2H), 4.87-4.89 (m, 1H), 4.22 (s, 4H), 4.00-4.05 (m, 2H), 3.47 (br t, J=6.73 Hz, 2H), 3.21 (dd, J=14.22, 5.40 Hz, 1H), 3.12-3.15 (m, 3H), 2.96 (dd, J=14.22, 9.15 Hz, 1H), 1.85-1.93 (m, 4H); LCMS (ESI+): m/z=521.0 (M+H)⁺, RT: 2.3 min; HPLC purity: 97.2%, RT: 5.5 min; Chiral SFC: purity: 100%, ee value: 100%, RT: 2.8 min.

Example 58

Synthesis of (S)-2-(2,6-dichlorobenzamido)-3-(4-(4-((4-methyl-5-oxo-3,4,5,6-tetrahydropyrazin-2-yl)amino)butoxy)phenyl)propanoic acid

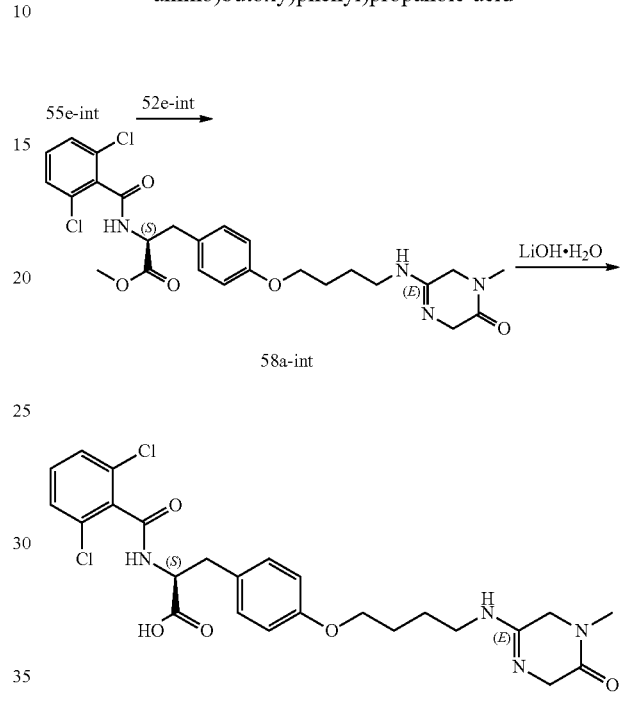

Example 58

Compound 58a-int: A mixture of 55e-int (200 mg, 455.24 umol), 52e-int (79.23 mg, 500.76 umol) and TEA (138.20 mg, 1.37 mmol, 189.31 uL) in EtOH (5 mL) was heated to 80° C. for 12 hrs. LCMS showed desired MS for 58a-int; the mixture was concentrated to give 58a-int.

Example 58

58a-int (250 mg, 455 umol) and LiOH·H₂O (38.18 mg, 910 umol) in THF (5 mL)/H₂O (1 mL) was stirred at 20° C. for 12 hrs. LCMS showed Example 58 was present; the mixture was adjusted to pH 7 with 1N HCl and concentrated. The residue was purified by prep-HPLC to give Example 58.

HPLC purification conditions: Gilson 281 semi-preparative HPLC system; Mobile phase A: TFA/H₂O=0.075% v/v; B: AcN (gradient % B at T=0: 10%; at T=12 min: 30%); Column: Luna C18 100×30 5 u; Flow rate: 20 mL/min; Monitor wavelength: 220 & 254 nm.

¹H NMR (400 MHz, METHANOL-d₄): δ ppm 7.29-7.37 (m, 3H), 7.20 (d, J=8.60 Hz, 2H), 6.80-6.84 (m, 2H), 4.87-4.89 (m, 1H), 4.36 (s, 2H), 4.03 (s, 2H), 4.00 (s, 2H), 3.33 (br d, J=7.06 Hz, 2H), 3.20 (dd, J=14.11, 5.29 Hz, 1H), 2.99 (s, 3H), 2.93 (dd, J=14.11, 9.26 Hz, 1H), 1.82-1.89 (m, 4H); LCMS (ESI+): m/z=535.0 (M+H)⁺, RT: 2.3 min; HPLC purity: 96.4%, RT: 7.3 min; Chiral SFC purity: 100%, ee value: 100%, RT: 2.9 min.

Example 59

Synthesis of (S)-2-(2,6-dichlorobenzamido)-3-(4-(4-((5,6-dihydro-4H-1,3-oxazin-2-yl)amino)butoxy)phenyl)propanoic acid

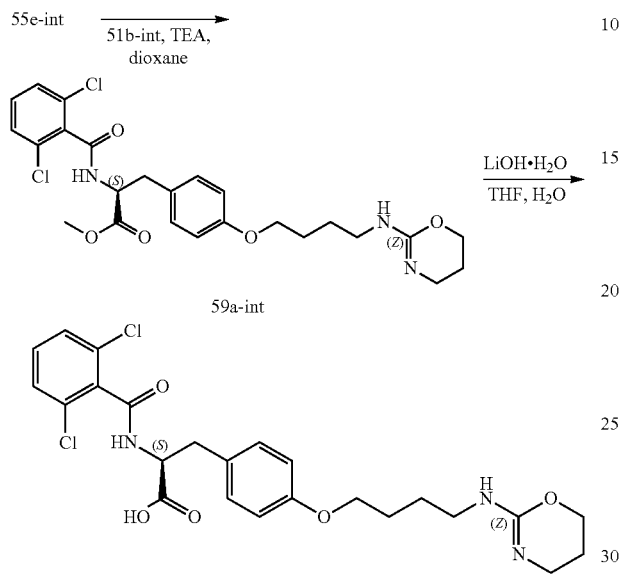

Example 59

Compound 59a-int: To 55e-int (200 mg, 420.35 umol) and 51b-int (55.15 mg, 420.35 umol) in dioxane (6 mL) was added TEA (127.61 mg, 1.26 mmol, 174.81 uL); the mixture was stirred at 110° C. for 4 hours. LC-MS showed 55e-int was consumed completely. The reaction mixture was concentrated to give then was purified by prep-HPLC to give 59a-int.

Example 59

59a-int (100 mg, 191.42 umol) in THF (5 mL) and $H_2O$ (2 mg) was added $LiOH \cdot H_2O$ (16.06 mg, 382.84 umol) in one portion at 20° C. The mixture was stirred at 20° C. for 2 hours. LCMS showed 59a-int was consumed completely and one main peak with desired MS for Example 59 was detected. The mixture was concentrated and adjusted to pH 6 with aqueous HCl (1N). The mixture was concentrated and the residue was purified by prep-HPLC to give Example 59.

HPLC purification conditions: Gilson 281 semi-preparative HPLC system; Mobile phase A: $TFA/H_2O$=0.075% v/v; B: AcN (gradient % B at T=0: 10%; at T=12 min: 70%); Column: Luna C18 100×30 5 u; Flow rate: 20 mL/min; Monitor wavelength: 220 & 254 nm.

$^1$H NMR (400 MHz, DMSO-$d_6$): δ ppm 12.69 (br s, 1H), 9.03 (br d, J=8.16 Hz, 1H), 7.35-7.46 (m, 3H), 7.18 (br d, J=8.60 Hz, 2H), 6.82 (br d, J=8.60 Hz, 2H), 6.09 (br s, 1H), 4.57-4.65 (m, 1H), 3.94 (br t, J=6.06 Hz, 2H), 3.23 (br t, J=6.84 Hz, 2H), 3.18 (br t, J=5.73 Hz, 2H), 3.01-3.11 (m, 3H), 2.86 (br dd, J=13.67, 9.48 Hz, 1H), 1.73-1.82 (m, 2H), 1.52-1.67 (m, 4H); LCMS (ESI+): m/z=508.0 (M+H)$^+$, RT: 2.7 min; HPLC purity: 100%, RT: 8.0 min; Chiral SFC: purity: 100%, ee value: 100%, RT: 3.2 min.

Example 60

Synthesis of (S)-2-(2,6-dichlorobenzamido)-3-(4-(4-((5,6-dihydro-4H-1,3-thiazin-2-yl)amino)butoxy)phenyl)propanoic acid

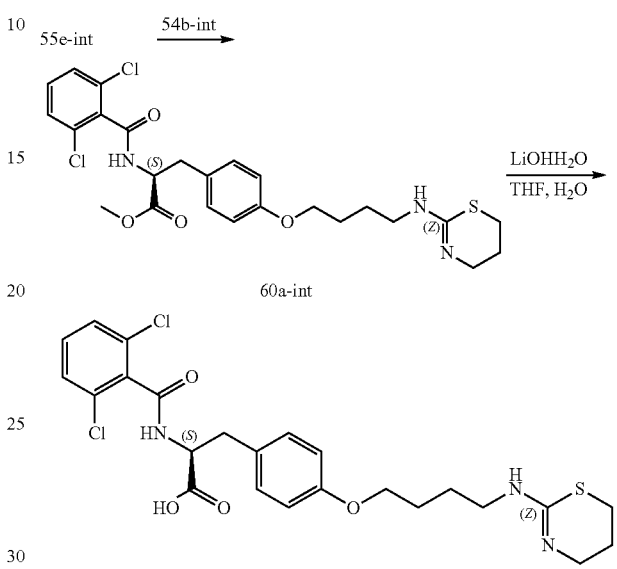

Example 60

Compound 60a-int: 55e-int (200 mg, 420.35 umol) and 54b-int (74.28 mg, 504.42 umol) were taken up in a microwave tube in pyridine (2 mL). The sealed tube was heated at 120° C. for 5 hours under microwave. LC-MS showed 55e-int was consumed completely and desired product was detected. The reaction mixture was concentrated and the residue was purified by prep-TLC (SiO$_2$, EtOAc:MeOH=10/1) to give 60a.

Example 60

To 60a-int (100 mg, 185.70 umol) in THF (5 mL) and $H_2O$ (2 mL) was added $LiOH \cdot H_2O$ (15.58 mg, 371.41 umol). The mixture was stirred at 15° C. for 2 hours. LCMS showed 60a-int was consumed completely. The mixture was concentrated and adjusted to pH 6 with aqueous HCl (1N). The mixture was concentrated and the residue was purified by prep-HPLC to give Example 60.

HPLC purification conditions: Gilson 281 semi-preparative HPLC system; Mobile phase A: $TFA/H_2O$=0.075% v/v; B: AcN (gradient % B at T=0: 19%; at T=10 min: 49%); Column: Boston Green ODS 150×30 5 u; Flow rate: 25 mL/min; Monitor wavelength: 220 & 254 nm.

$^1$H NMR (400 MHz, DMSO-$d_6$): δ ppm 7.31-7.39 (m, 3H), 7.22 (d, J=8.82 Hz, 2H), 6.82-6.86 (m, 2H), 4.89 (d, J=5.29 Hz, 1H), 3.98-4.02 (m, 2H), 3.52 (br t, J=5.40 Hz, 2H), 3.35 (br s, 2H), 3.19-3.27 (m, 3H), 2.96 (dd, J=14.11, 9.26 Hz, 1H), 2.15-2.21 (m, 2H), 1.80-1.85 (m, 3H), 1.79-1.86 (m, 1H); LCMS (ESI+): m/z=524.0 (M+H)$^+$, RT: 2.5 min; HPLC purity: 98.6%, RT: 6.1 min; Chiral SFC purity: 100%, ee value: 100%, RT: 3.2 min.

Example 61

Synthesis of (S)-2-(2,6-dichlorobenzamido)-3-(4-(4-((4,5-dihydrooxazol-2-yl)amino)butoxy)phenyl)propanoic acid

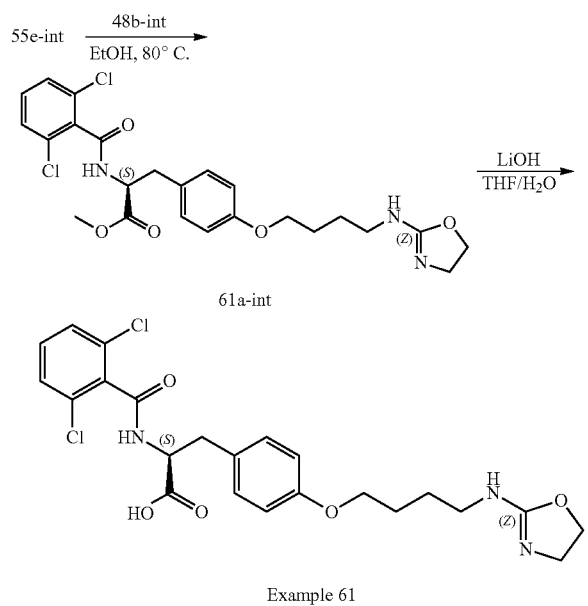

Example 61

Compound 61a-int: To 55e-int (270 mg, 0.61 mmol) in EtOH (5 mL) was added 48b-int (72 mg, 0.61 mmol). The mixture was stirred at 80° C. for 6 hrs then concentrated. The crude product was purified by Prep-TLC (DCM:MeOH=10:1) to give 61a-int.

Example 61

To 61a-int (200 mg, 393 umol) in THF (2 mL)/H$_2$O (2 mL) was added LiOH.H$_2$O (16.5 mg, 393 umol). The mixture was stirred for 2 hrs at 20° C., then was concentrated and purified by Prep-HPLC to give Example 61.

HPLC purification conditions: Gilson 281 semi-preparative HPLC system; Mobile phase A: TFA/H$_2$O=0.075% v/v; B: AcN (gradient % B at T=0: 5%; at T=10 min: 35%); Column: Luna C18 100×30 5 u; Flow rate: 25 mL/min; Monitor wavelength: 220 & 254 nm.

$^1$H NMR (400 MHz, METHANOL-d$_4$): δ ppm 1.84-1.75 (m, 4H) 3.01-2.95 (m, 1H) 3.26-3.21 (m, 1H) 3.40-3.45 (m, 4H) 4.03-3.91 (m, 4H) 4.80-4.75 (m, 1H) 6.85 (d, J=8.8 Hz, 2H) 7.24 (d, J=8.8 Hz, 2H) 7.40-7.35 (m, 3H); LCMS (ESI+): m/z=494.0 (M+H)$^+$, RT: 2.4 min; HPLC purity: 91.8%, RT: 5.8 min; Chiral SFC purity: 100%, ee value: 100%, RT: 6.0 min.

Example 62

Synthesis of (S)-2-(2,6-dichlorobenzamido)-3-(4-(4-((4,5-dihydrothiazol-2-yl)amino)butoxy)phenyl)propanoic acid

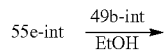

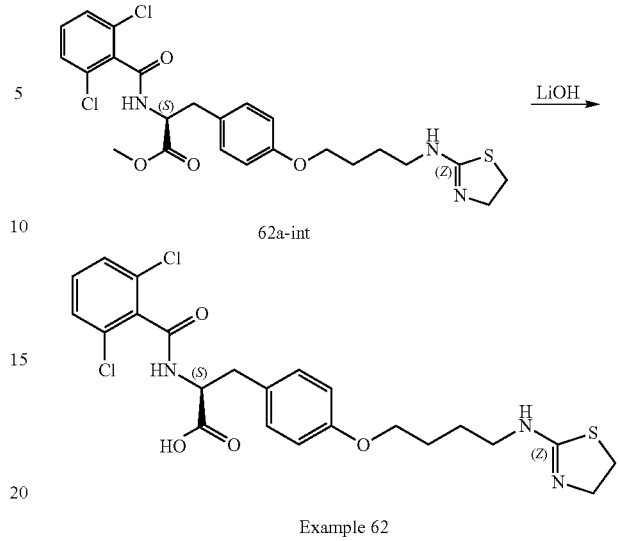

Example 62

Compound 62a-int: To 55e-int (70 mg, 0.16 mmol) in EtOH (1 mL) was added 49b-int (21 mg, 0.16 mmol). The mixture was stirred for 1 h at 80° C. then concentrated. The crude product was purified by Prep-TLC (DCM:MeOH=10:1) to give 62a-int.

Example 62

To 62a-int (35 mg, 66.74 umol) in THF (1 mL)/H$_2$O (1 mL) was added LiOH.H$_2$O (2.8 mg, 66.74 umol); the mixture was stirred for 2 h at 20° C. The reaction was concentrated and purified by Prep-HPLC to give Example 62.

HPLC purification conditions: Gilson 281 semi-preparative HPLC system; Mobile phase A: TFA/H$_2$O=0.075% v/v; B: AcN (gradient % B at T=0: 20%; at T=11.5 min: 50%); Column: Boston Green ODS 150×30 5 u; Flow rate: 25 mL/min; Monitor wavelength: 220 & 254 nm.

$^1$H NMR (400 MHz, METHANOL-d$_4$): δ ppm 7.36-7.30 (m, 3H), 7.20 (d, J=8.8 Hz, 2H), 6.81 (d, J=8.8 Hz, 2H), 4.87-4.85 (m, 1H), 4.01-3.97 (m, 4H), 3.60-3.56 (m, 2H), 3.54-3.52 (m, 2H), 3.32-3.17 (m, 1H), 2.96-2.90 (m, 1H), 1.84-1.80 (m, 4H); LCMS (ESI+): m/z=510.0 (M+H)$^+$, RT: 2.4 min; HPLC purity: 99.5%, RT: 5.9 min; Chiral SFC purity: 99.2%, ee value: 98.4%, RT: 3.3 min.

Example 63 (Compound 98a)

Synthesis of (2S)-2-(1H-indazole-6-carbonylamino)-9-(5,6,7,8-tetrahydro-1,8-naphthyridin-2-yl)nonanoic acid

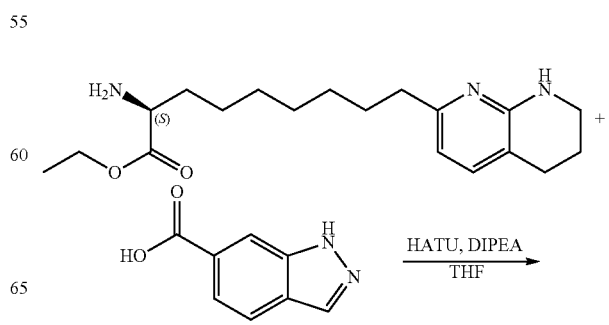

-continued

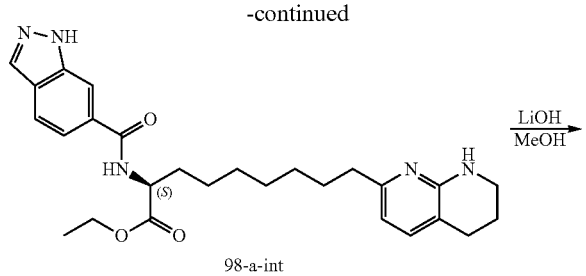

98-a-int

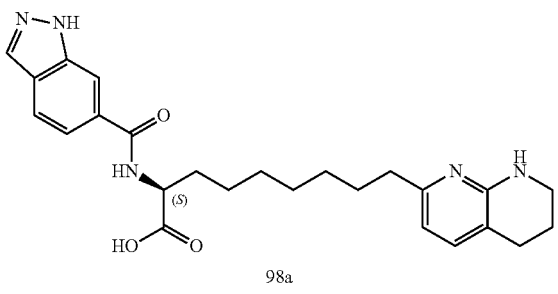

98a

Preparation of ethyl (2S)-2-(1H-indazole-6-carbonylamino)-9-(5,6,7,8-tetrahydro-1,8-naphthyridin-2-yl) nonanoate (98-a-int): Ethyl (S)-2-amino-9-(5,6,7,8-tetrahydro-1,8-naphthyridin-2-yl)nonanoate bis-HCl salt (50 mg, 0.123 mmol), 1H-indazole-6-carboxylic acid (24 mg, 0.147 mmol), HATU (70 mg, 0.184 mmol) and N,N-diisopropylethylamine (75 uL, 0.43 mmol) were stirred in THF (5 mL) at room temperature for two hours. The reaction mixture was evaporated and purified by combiflash chromatography (2.0 M $NH_3$-MeOH in DCM=0-30%) to give ethyl (2S)-2-(1H-indazole-6-carbonylamino)-9-(5,6,7,8-tetrahydro-1,8-naphthyridin-2-yl)nonanoate (35 mg, 59%). LCMS [M+H$^+$]: 478.3.

Preparation of 98a: (2S)-2-(1H-indazole-6-carbonylamino)-9-(5,6,7,8-tetrahydro-1,8-naphthyridin-2-yl) nonanoic acid: Ethyl (2S)-2-(1H-indazole-6-carbonylamino)-9-(5,6,7,8-tetrahydro-1,8-naphthyridin-2-yl) nonanoate (35 mg, 0.073 mmol) and LiOH (50 mg) were stirred in methanol (5 mL) at room temperature for two hours. The reaction mixture was evaporated and purified by reserve phase combiflash chromatography ($CH_3CN$ in water (0.1% TFA)=10-100%) to give (2S)-2-(1H-indazole-6-carbonylamino)-9-(5,6,7,8-tetrahydro-1,8-naphthyridin-2-yl) nonanoic acid (25 mg, 72%). LCMS [M+H$^+$]: 450.2; Purity: 95.7%.

Example 64 (Compound 99a)

(S)-2-benzamido-3-(4-(3-(5,6,7,8-tetrahydro-1,8-naphthyridin-2-yl)propoxy)phenyl)propanoic acid

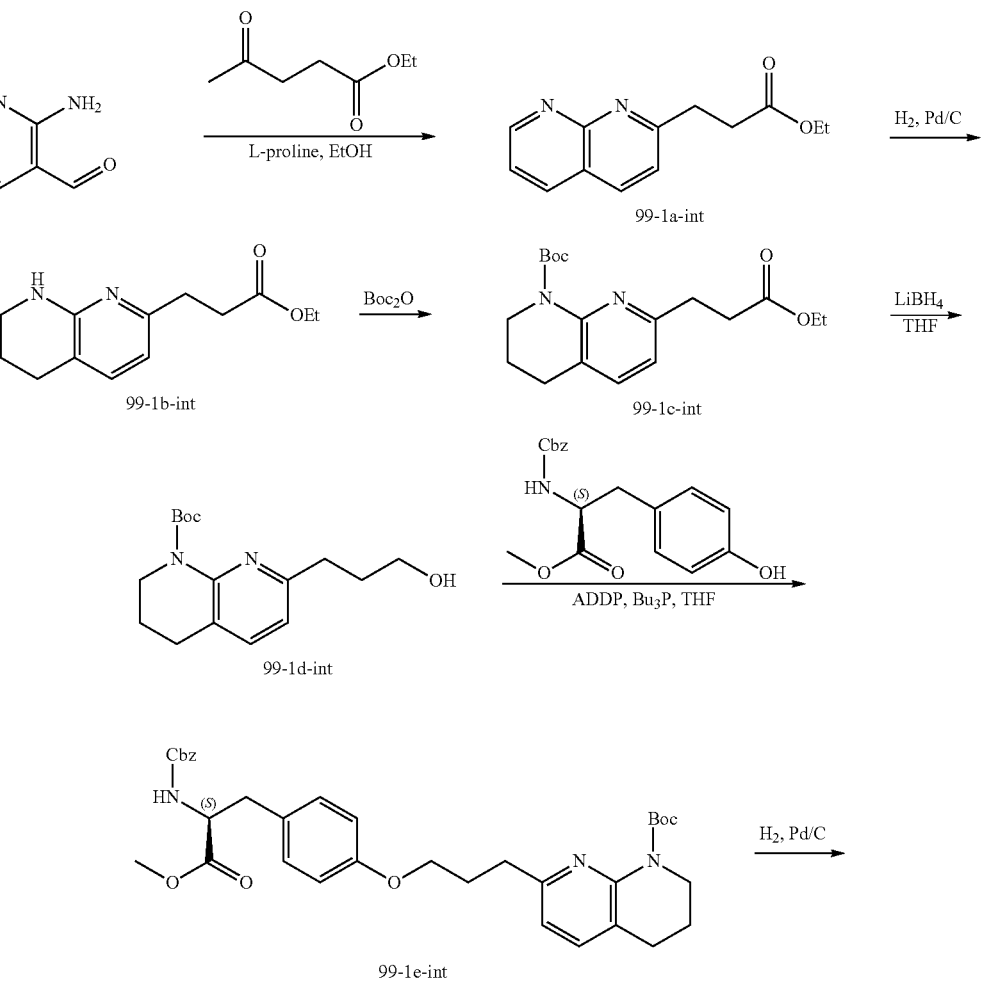

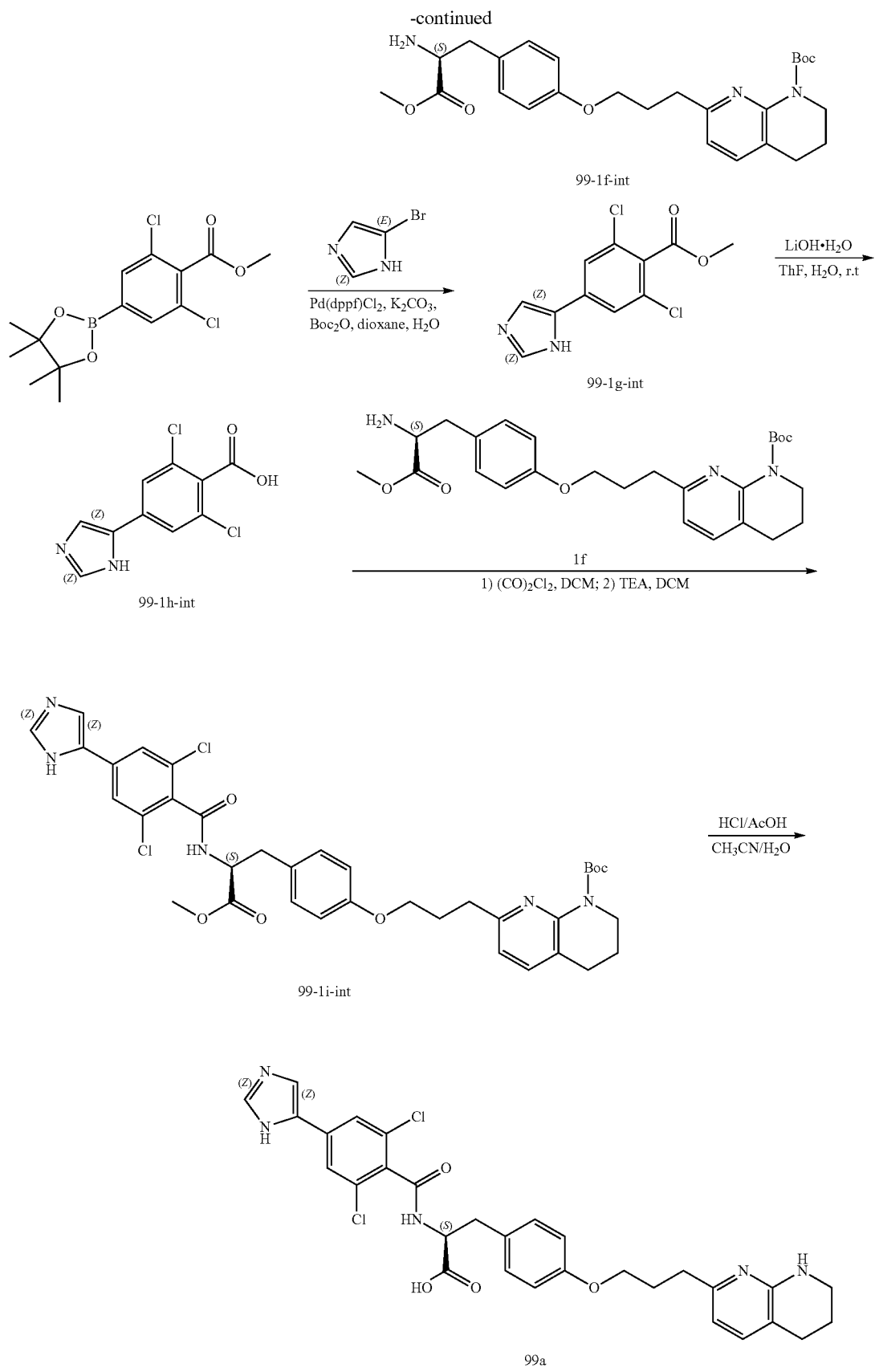

Preparation of ethyl 3-(5,6,7,8-tetrahydro-1,8-naphthyridin-2-yl)propanoate (99-1b-int)

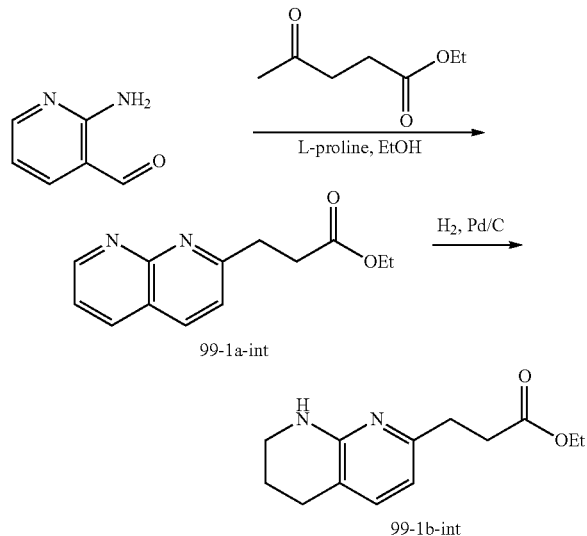

Compound 99-1a-int:

To a mixture of 2-aminonicotinaldehyde (50 g, 409.4 mmol, 1 equivalent) in EtOH (600 mL) was added ethyl 4-oxopentanoate (59.02 g, 409.4 mmol, 58.44 mL, 1 equivalent) and L-proline (23.57 g, 204.7 mmol, 0.50 equivalent). The reaction was refluxed at 80° C. for 12 hrs. TLC (petroleum ether:EtOAc=0:1, $R_f$=0.5) showed that compound 99-1a-int was formed. The reaction mixture was concentrated to give a residue. The residue was purified by column chromatography (SiO$_2$, Petroleum ether:Ethyl acetate=3:1 to 1:1) to obtain a pure product compound 99-1a-int (39.00 g, 169.37 mmol, 41.37% yield) as an off-white solid; LCMS (ESI+): m/z=231.0 (M+H)$^+$, RT=0.723 min.

Compound 99-1b-int:

To a solution of compound 99-1a-int (39 g, 169.37 mmol, 1 equivalent) in MeOH (500 mL) was added Pd/C (12 g) under N$_2$. The suspension was degassed under vacuum and purged with H$_2$ several times. The mixture was stirred under H$_2$ (50 psi) at 50° C. for 6 hrs. TLC (Ethyl acetate, $R_f$=0.6) indicated that 1a was consumed. The catalyst was removed by filtration and washed with MeOH (2×500 mL). The mixture concentrated under reduced pressure to give 99-1b-int (36 g, 153.66 mmol, 91% yield) as a white solid. This material was used in the next step without further purification.

Preparation of tert-butyl 7-(3-hydroxypropyl)-3,4-dihydro-1,8-naphthyridine-1(2H)-carboxylate (99-1d-int)

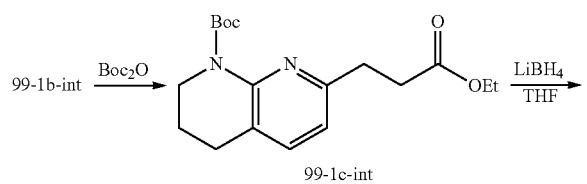

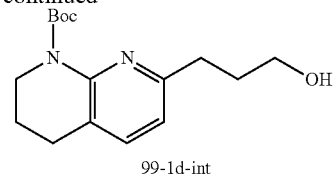

Compound 99-1c-int:

Compound 99-1b-int (36 g, 153.66 mmol, 1 equivalent) was added to Boc$_2$O (300 mL) at 25° C. The reaction mixture was stirred at 50° C. for 12 hrs; after this time, the desired product was detected by LCMS and the reaction was complete. The crude product was purified by column chromatography (SiO$_2$, Petroleum ether:Ethyl acetate=10:1 to 1:1) to give a pure 99-1c-int (47 g, 140.55 mmol, 91% yield) as colorless oil; LCMS (ESI+): m/z=335.2 (M+H)$^+$, RT=0.641 min.

Compound 99-1d-int:

To a solution of 99-1c-int (20 g, 59.81 mmol, 1 equivalent) in THF (200 mL) was added LiBH$_4$ (2.61 g, 119.62 mmol, 2 equivalents) at 0° C. The reaction was stirred at 30° C. for 30 min then at 40° C. for 5 hrs. TLC (Ethyl acetate, $R_f$=0.5) indicated that 99-1c-int was consumed. The desired product was detected by LCMS. The reaction mixture was poured into saturated NH$_4$Cl (500 mL) and was extracted with EtOAc (500 mL). The organic layer was washed with brine (200 mL), dried over solid NaSO$_4$ then was concentrated under vacuum. The residue was purified by column chromatography (SiO$_2$, Petroleum ether:Ethyl acetate=10:1 to 1:1) to give 99-1d-int (16 g, 54.73 mmol, 92% yield) as colorless oil; LCMS (ESI$^+$): m/z=335.2 (M+H)$^+$, RT=0.695 min.

$^1$H NMR (400 MHz, CHLOROFORM-d) δ: 7.34 (d, J=7.45 Hz, 1H), 6.86 (d, J=7.45 Hz, 1H), 4.25 (br s, 1H), 4.19-4.33 (m, 1H), 3.75-3.82 (m, 2H), 3.66-3.74 (m, 2H), 2.92 (t, J=6.58 Hz, 2H), 2.75 (t, J=6.58 Hz, 2H), 1.92-1.99 (m, 4H), 1.54-1.57 (m, 1H), 1.56 (s, 8H), 1.29 (t, J=7.02 Hz, 1H) ppm.

Preparation of (S)-2-benzamido-3-(4-(3-(5,6,7,8-tetrahydro-1,8-naphthyridin-2-yl)propoxy)phenyl)-propanoic acid

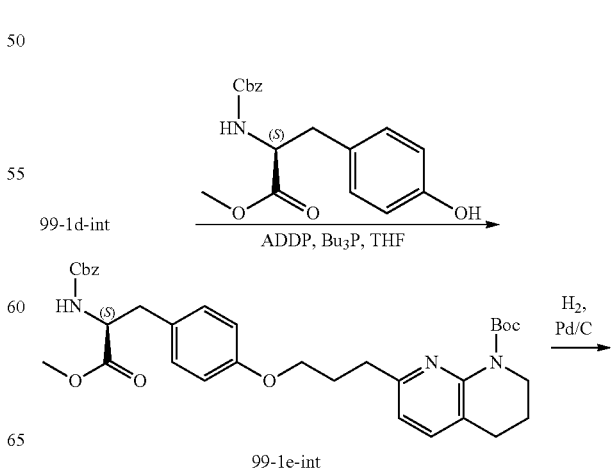

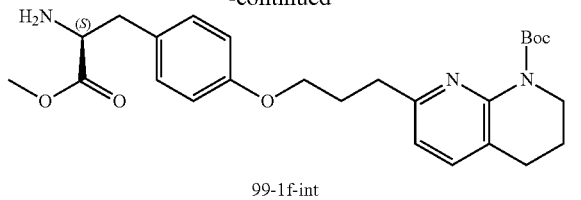

99-1f-int

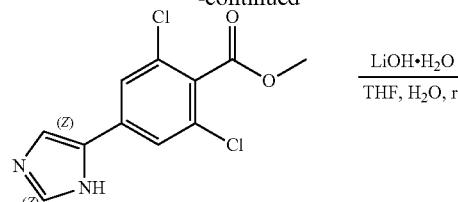

99-1g-int

Compound 99-1e-int:

To a solution of 99-1d-int (3 g, 10.26 mmol, 1 equivalent) and methyl (2S)-2-(benzyloxycarbonylamino)-3-(4-hydroxyphenyl)propanoate (4.06 g, 12.31 mmol, 1.2 equivalents) in dry THF (10 mL) was added ADDP (6.47 g, 25.65 mmol, 2.5 equivalents) at 0° C. under $N_2$. $Bu_3P$ (5.19 g, 25.65 mmol, 6.33 mL, 2.5 equivalents) was added dropwised to the reaction mixture at 0° C. Following the addition, the reaction mixture was warmed to 20° C. and stirred for 2 hours; then it was heated to 40° C. and stirred for an additional 12 hours at this temperature. TLC (Ethyl acetate: Petroleum ether=2:1, $R_f$=0.2) indicated that some 99-1d-int remained, but a new product spot was also detected. Formation of the desired product (99-1e-int) was confirmed by LCMS. The reaction mixture was concentrated to give crude 99-1e-int. Column chromatography ($SiO_2$, Petroleum ether: Ethyl acetate=10:1 to 1:1) was used to isolate 99-1e-int (3.25 g, 5.38 mmol, purity 50%); LCMS (ESI+): m/z=604.3 $(M+H)^+$; RT: 2.36 min.

Compound 99-1f-int:

To a solution of 99-1e-int (3.00 g, 4.97 mmol, 1 equivalent) in MeOH (30 mL) was added Pd/C (10%, 0.5 g). The suspension was degassed under vacuum and was purged with $H_2$ several times. The mixture was stirred under $H_2$ (15 psi) at 30° C. for 3 hrs. TLC (Ethyl acetate, $R_f$=0.3) indicated that compound 99-1e-int was consumed; the desired product (99-1f-int) was detected by LCMS. The reaction mixture was filtered and concentrated under reduced pressure. The crude product was purified by column chromatography ($SiO_2$, Petroleum ether: Ethyl acetate=1:1 to 0:1) followed by preparative scale HPLC (basic conditions) to give 99-1f-int (1.1 g, 1.76 mmol, 33.02% yield, 75% purity) as a brown oil; LCMS ($ESI^+$): m/z=470.2 $(M+H)^+$; RT=0.63 min.

Preparation of 2,6-dichloro-4-(1H-imidazol-5-yl)benzoic acid

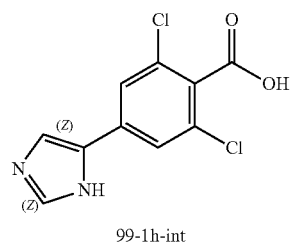

Compound 99-1g-int:

A mixture of methyl 2,6-dichloro-4-(4,4,5,5-tetramethyl-1,3,2-dioxaborolan-2-yl)benzoate (1 g, 3.02 mmol), 5-bromo-1H-imidazole (666 mg, 4.53 mmol), $Pd(dppf)Cl_2$ (44.21 mg, 60.42 μmol), $K_2CO_3$ (835.11 mg, 6.04 mmol) and $Boc_2O$ (1.32 g, 6.04 mmol, 1.39 mL) in dioxane (10 mL) and $H_2O$ (2 mL) was stirred at 90° C. for 10 hrs. After this time, the desired coupling product 99-1g-int was detected by LCMS. The reaction mixture was diluted with water (20 mL) then extracted with ethyl acetate (3×20 mL). The organic layers were combined, then were washed with brine (30 mL) and concentrated under vacuum. The crude product was purified by chromatography on silica gel (Petroleum ether: Ethyl acetate=10:1 to 1:1, $R_f$=0.3) to give compound 99-1g-int (600 mg) as an off-white solid.

Compound 99-1h-int:

A solution of 99-1g-int (600 mg, 2.21 mmol, 1 equivalent) and $LiOH.H_2O$ (185.46 mg, 4.42 mmol) in $H_2O$ (2 mL) and THF (10 mL) was stirred at 100° C. for 10 hours. After this time 99-1h-int was detected by LCMS. The reaction solution was adjusted to 5-6 pH units with citric acid; then the solution was evaporated under reduced pressure. The crude 99-1h-int was purified by preparative scale HPLC (TFA, Phenomenex Luna C18 250×50 mm×10 μm; mobile phase: [solution A: 10 mM $NH_4HCO_3$ and B: AcN]; with a gradient of B %: 0%-5% over 20 min.) to give compound 99-1h-int (50 mg, 194.5 μmol) as an off-white solid.

Preparation of Example 64 (Compound 99a): tert-butyl (S)-7-(3-(4-(2-amino-3-methoxy-3-oxopropyl) phenoxy)propyl)-3,4-dihydro-1,8-naphthyridine-1 (2H)-carboxylate

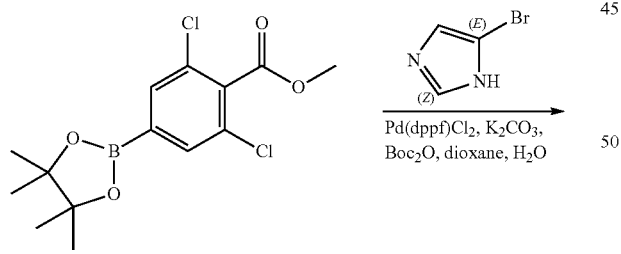

99-1h-int

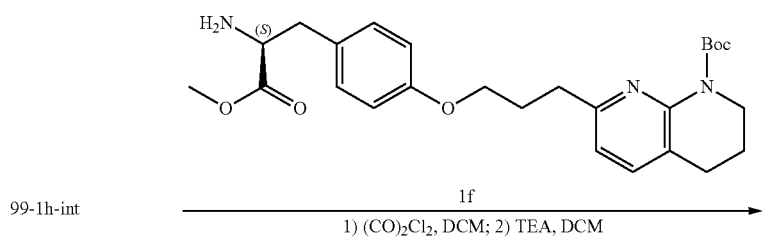

1f

1) $(CO)_2Cl_2$, DCM; 2) TEA, DCM

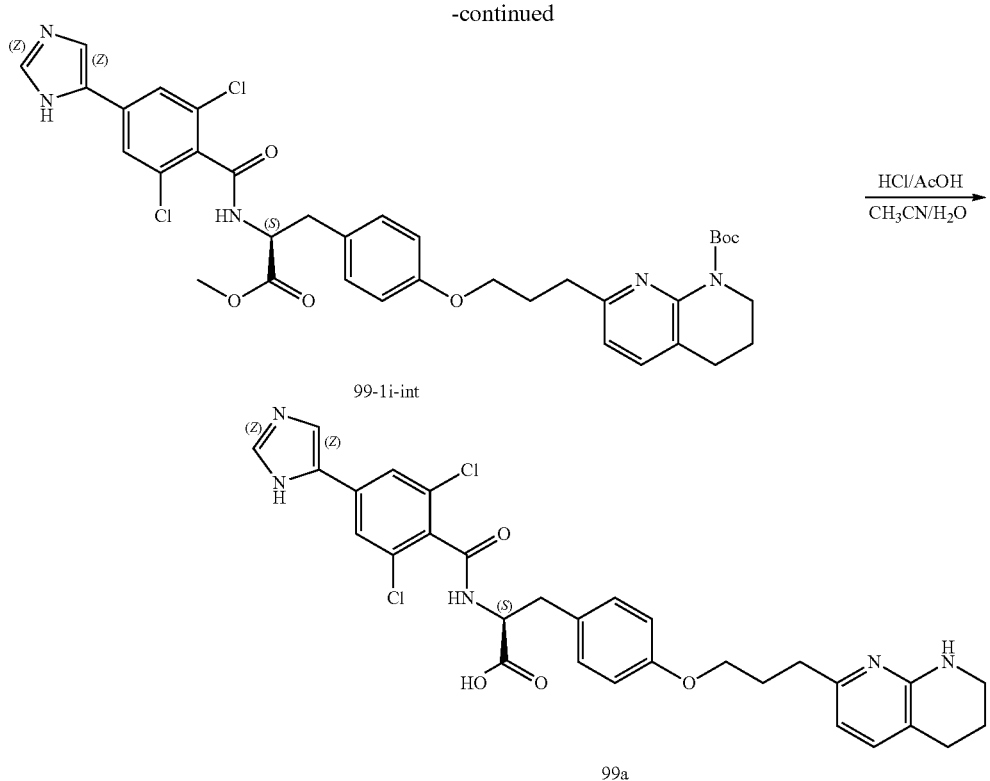

Compound 99-1i-int:

To a solution of 99-1h-int (24 mg, 93.36 μmol) and DMF (682.37 mg, 9.34 μmol) in DCM (20 mL) was added oxalyl chloride (59.25 mg, 466.80 μmol, 40.86 μL) at 0° C. under $N_2$; then this reaction was stirred at 25° C. for 1 hour. After this time, the solvent was removed under vacuum to give the acyl chloride, which was used directly in the next step.

A solution of the acyl chloride (25.72 mg, 93.35 μmol), 99-1f-int (43.83 mg, 93.35 μmol) and TEA (28.34 mg, 280.05 μmol, 38.82 μL) in THF (10 mL) was stirred at 25° C. for 10 hours. The desired coupling product, 99-1i-int, was detected by LCMS. The reaction mixture was diluted with water (10 mL) then was extracted with ethyl acetate (2×10 mL). The organic layers were combined, were washed with brine (15 mL) and evaporated under reduced pressure to give 99-1i-int (30 mg) as a yellow oil. This material was used in the next step without future purification.

Example 64 (Compound 99a), tert-butyl (S)-7-(3-(4-(2-amino-3-methoxy-3-oxopropyl)phenoxy)propyl)-3,4-dihydro-1,8-naphthyridine-1(2H)-carboxylate: A solution of 99-1i-int (30 mg, 42.34 μmol), AcOH (2.54 mg, 42.34 umol, 2.42 μL, 1 equivalent) and HCl (12 M, 10.6 μL, 3 equivalents) in $H_2O$ (5 mL) was stirred at 70° C. for 10 hrs; after this time the reaction was complete by LCMS. The solvent was removed under vacuum and the product was isolated by semi-preparative scale HPLC (TFA, Luna C18 [100×30× 5μ]; mobile phase A: water (0.1% TFA) and mobile phase B: AcN; with a gradient of B %: 15%-35% over 12 min.) to give Example 64 (Compound 99a), tert-butyl (S)-7-(3-(4-(2-amino-3-methoxy-3-oxopropyl)phenoxy)propyl)-3,4-dihydro-1,8-naphthyridine-1(2H)-carboxylate, (5.7 mg, 9.6 μmol, 23% yield) as an off-white solid; LCMS (ESI[+]): m/z=595 (M+H)[+], RT: 1.95 min.; HPLC purity (15 min.): 94.2%, RT: 3.31 min.; chiral purity [SFC]: 100%, RT: 3.35 min.

$^1$H NMR (400 MHz, METHANOL-$d_4$) δ: 8.38 (s, 1H), 7.85 (s, 1H), 7.78 (s, 1H), 7.58-7.56 (d, J=7.20 Hz, 2H), 7.23-7.21 (d, J=8.80 Hz, 2H), 6.81-6.79 (d, J=8.80 Hz, 2H), 6.64-6.62 (d, J=7.2 Hz, 1H), 4.89 (dd, J=9.48, 4.85 Hz, 1H), 4.02 (t, J=5.73 Hz, 2H), 3.47-3.51 (m, 2H), 3.20 (m, 1H), 2.97 (m, 1H), 2.90 (t, J=7.50 Hz, 2H), 2.81 (t, J=6.28 Hz, 2H), 2.16-2.17 (m, 2H) and 1.94 (m, 2H) ppm.

BIOLOGICAL EXAMPLES

Example B1—Cell Adhesion Assay

In order to determine the potency, the compounds were assessed for their ability to inhibit αvβ1 expressing CHO cells attach to TGFβ1LAP. Microplates were coated overnight with 2 ug/ml TGFβ1LAP at 4° C., and blocked with 2% BSA/PBS for 30 min before the assay. Cells were detached and washed in PBS. After that the cells were resuspended in DMEM at $1.0 \times 10^6$ cells/ml, fifty microliter of cell suspension and fifty microliter of compound solution were added into the plate. The plates were incubated for one hour at 37° C. in humidified 5% carbon dioxide. Non-adherent cells were removed by centrifugation top side down at 58g for 5 min. The attached cells were fixed and stained with 0.5% crystal violet (in 20% methanol and 1% formaldehyde) and the wells washed with PBS. Crystal violet was dissolved in 2% Triton-X in PBS. The relative number of cells in each well was evaluated by the absorbance at 595 nm in a microplate reader (Tecan). $IC_{50}$ values were determined by non-linear regression with four parameters (Graphpad Prism 7.01, Y=Bottom+(Top-Bottom)/(1+ 10^((Log IC50–X)*HillSlope)).

The IC50 values obtained for αvβ1 integrin inhibition for exemplary compounds are shown in Table B-1. The compounds tested were compound samples prepared according to procedures described in the Synthetic Examples section, with the stereochemical purity as indicated in the Examples indicated for Example or Compound No. 1-62. The compounds tested were predominantly S-configuration at the alpha carbon of the amino acid scaffold, except for compounds 123, 124, and 125 which were predominantly R-configuration at the alpha carbon of the amino acid scaffold. "Example or Compound No." in Table B-1 refers to the compound illustrated in the examples for Example or Compound Nos. 1-62 (the compounds of Examples 1-62 are labeled as Compounds 1-62 in Table 1). "Example or Compound No." in Table B-1 refers to the compound number as indicated in Table 1 or Table 2 for Example or Compound Nos. 63-126.

TABLE B-1

| Example or Compound No. | $\alpha v\beta 1$ Inhibition $IC_{50}$ (nM) - range |
|---|---|
| 1 | <50 |
| 2 | <50 |
| 3 | <50 |
| 4 | >1000 |
| 5 | <50 |
| 6 | <50 |
| 7 | <50 |
| 8 | 50-250 |
| 9 | 50-250 |
| 10 | <50 |
| 11 | 50-250 |
| 12 | <50 |
| 13 | <50 |
| 14 | <50 |
| 15 | <50 |
| 16 | <50 |
| 17 | >1000 |
| 18 | <50 |
| 19 | <50 |
| 20 | <50 |
| 21 | >1000 |
| 22 | <50 |
| 23 | <50 |
| 24 | 50-250 |
| 25 | 50-250 |
| 26 | >1000 |
| 27 | <50 |
| 28 | 250-1000 |
| 29 | <50 |
| 30 | 250-1000 |
| 31 | 50-250 |
| 32 | 50-250 |
| 33 | <50 |
| 34 | <50 |
| 34 | <50 |
| 35 | <50 |
| 36 | <50 |
| 37 | 250-1000 |
| 38 | <50 |
| 39 | >1000 |
| 40 | <50 |
| 41 | <50 |
| 42 | <50 |
| 43 | <50 |
| 44 | <50 |
| 45 | <50 |
| 46 | 50-250 |
| 47 | >1000 |
| 48 | >1000 |
| 49 | 50-250 |
| 50 | >1000 |
| 51 | >1000 |
| 52 | >1000 |
| 53 | >1000 |
| 54 | 250-1000 |
| 55 | 50-250 |
| 56 | 250-1000 |

TABLE B-1-continued

| Example or Compound No. | $\alpha v\beta 1$ Inhibition $IC_{50}$ (nM) - range |
|---|---|
| 57 | >1000 |
| 58 | >1000 |
| 59 | >1000 |
| 60 | <50 |
| 61 | 50-250 |
| 62 | <50 |
| 65 | <50 |
| 74 | 250-1000 |
| 81 | 50-250 |
| 82 | 50-250 |
| 86 | 50-250 |
| 98 (Example 63) | 50-250 |
| 99 (Example 64) | <50 |
| 100 | <50 |
| 101 | <50 |
| 102 | 50-250 |
| 103 | 50-250 |
| 104 | 50-250 |
| 105 | 250-1000 |
| 106 | 250-1000 |
| 107 | 250-1000 |
| 108 | 50-250 |
| 109 | 50-250 |
| 110 | 50-250 |
| 111 | 250-1000 |
| 112 | 50-250 |
| 113 | 50-250 |
| 114 | <50 |
| 115 | 250-1000 |
| 116 | <50 |

Example B2—Solid Phase Integrin $\alpha v\beta 1$ Binding Assay

Microplates were coated with recombinant human integrin $\alpha v\beta 1$ (2 ug/ml) in PBS (100 ul/well 4 OC, overnight). The coating solution was removed, washed with PBS. Plate was blocked with 200 ul/well of Block Buffer (2% BSA in PBS) at 37° C. for 1 h. Dilutions of testing compounds and recombinant fibronectin (2 ug/ml) in binding and washing buffer (50 mM Tris-HCl, ph 7.5; 0.1% BSA, 1 mM MnCl2; NaCl 150 mM; 0.02% Tween-20; 1 mM CaCl2; 1 mM MgCl2) were added. The plate was incubated for 2 hours at 25° C., washed, and incubated for 1 hour with Biotin-Anti-fibronectin. Bound antibody was detected by peroxidase-conjugated streptavidin. The $IC_{50}$ values for testing compounds were calculated by a four-parameter logistic regression.

The $IC_{50}$ values obtained for $\alpha v\beta 1$ integrin inhibition for exemplary compounds are shown in Table B-2. The compounds tested were compound samples prepared according to procedures described in the Synthetic Examples section, with the stereochemical purity as indicated in the Examples. The compounds tested were predominantly S-configuration at the alpha carbon of the amino acid scaffold, except for compounds 123, 124, and 125 which were predominantly R-configuration at the alpha carbon of the amino acid scaffold. "Compound No." in Table B-2 refers to the compound number as indicated in Table 1 or Table 2.

Solid Phase Assay

TABLE B-2

| Compound No. | αvβ1 Inhibition IC$_{50}$ (nM) - range |
|---|---|
| 65 | <50 |
| 75 | 250-1000 |
| 81 | <50 |
| 87 | <50 |
| 88 | <50 |
| 89 | <50 |
| 90 | <50 |
| 91 | <50 |
| 92 | <50 |
| 93 | <50 |
| 94 | <50 |
| 95 | <50 |
| 96 | <50 |
| 97 | <50 |
| 117 | <50 |
| 118 | <50 |
| 119 | <50 |
| 121 | <50 |
| 122 | <50 |
| 123 | >1000 |
| 124 | >1000 |
| 125 | >1000 |
| 126 | 50-250 |

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:
1. A compound of formula (I):

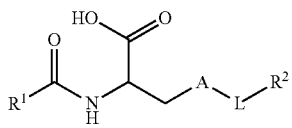

(I)

or a salt thereof, wherein:
$R^1$ is $C_6$-$C_{14}$ aryl or 5- to 10-membered heteroaryl, wherein the $C_6$-$C_{14}$ aryl and 5- to 10-membered heteroaryl of $R^1$ are independently optionally substituted by $R^{10}$;
$R^2$ is
  5- to 10-membered heteroaryl containing at least 2 ring nitrogen atoms,
  3- to 12-membered heterocyclyl containing at least 2 ring nitrogen atoms,
  —NH—$R^3$,
  —$R^3$—$R^{10}$, or
  —$R^3$—$NR^{3a}R^{3b}$,
wherein the 5- to 10-membered heteroaryl and 3- to 12-membered heterocyclyl of $R^2$ are independently optionally substituted by $R^{10}$;
$R^3$ is 5- to 10-membered heteroaryl containing at least 1 ring nitrogen atom, or 3- to 12-membered heterocyclyl containing at least 1 ring nitrogen atom, wherein the 5- to 10-membered heteroaryl and 3- to 12-membered heterocyclyl of $R^3$ are independently optionally substituted by $R^{10}$;
-A-L- is -$A^3$-;
or -A-L- is -$A^1$-$L^1$- or -$A^2$-$L^2$-, and $R^2$ is 5- to 10-membered heteroaryl, 3- to 12-membered heterocyclyl, —NH-(5- to 10-membered heteroaryl), or —NH-(3- to 12-membered heterocyclyl), wherein the 5- to 10-membered heteroaryl and 3- to 12-membered heterocyclyl of $R^2$ contain at least 2 ring nitrogen atoms and are independently optionally substituted by $R^{10}$;
$A^1$ is $C_3$-$C_8$ cycloalkylene, $C_3$-$C_8$ cycloalkenylene, $C_6$-$C_{14}$ arylene, 5- to 10-membered heteroarylene or 3- to 12-membered heterocyclylene, wherein the $C_3$-$C_8$ cycloalkylene, $C_3$-$C_8$ cycloalkenylene, $C_6$-$C_{14}$ arylene, 5- to 10-membered heteroarylene and 3- to 12-membered heterocyclylene of $A^1$ are independently optionally substituted by $R^{10}$;
$A^2$ is $C_3$-$C_8$ alkylene or $C_3$-$C_8$ alkenylene, wherein the $C_3$-$C_8$ alkylene and $C_3$-$C_8$ alkenylene of $A^2$ are independently optionally substituted by $R^9$;
$A^3$ is $C_5$-$C_{10}$ alkylene or $C_5$-$C_{10}$ alkenylene, wherein the $C_5$-$C_{10}$ alkylene and $C_5$-$C_{10}$ alkenylene of $A^3$ are independently optionally substituted by $R^9$;
$L^1$ is —O—Z—, —O—Z—$X^1$—, —O—$Y^1$—, —O—$Y^1$—$X^1$—, —O—Z—$Y^1$—, —O—Z—$Y^1$—$X^1$—, —O—Z—$X^1$—$Y^1$—, —O—Z—$X^1$—$Y^1$—$X^1$—, —Z—O—Z—, —$X^1$—Z—O—Z—, —Z—O—Z—$X^1$—, —$X^1$—Z—O—Z—$X^1$—, —Z—O—$Y^1$—, —Z—O—$Y^1$—$X^1$—, —$X^1$—Z—O—$Y^1$—, —$X^1$—Z—O—$Y^1$—$X^1$—, —N($R^4$)—Z—, —N($R^4$)—Z—$X^1$—, $X^2$, —$X^2$—$Y^1$—, $Y^2$, or —$Y^2$—$X^2$—;
$L^2$ is $C_3$-$C_6$ cycloalkylene optionally substituted by $R^{10}$;
each $X^1$ is independently $C_1$-$C_6$ alkylene or $C_2$-$C_6$ alkenylene, wherein the $C_1$-$C_6$ alkylene and $C_2$-$C_6$ alkenylene of $X^1$ are independently optionally substituted by $R^{10}$;
each $X^2$ is independently $C_1$-$C_6$ alkylene or $C_2$-$C_6$ alkenylene, wherein the $C_1$-$C_6$ alkylene and $C_2$-$C_6$ alkenylene of $X^2$ are independently optionally substituted by $R^9$;
each $Y^1$ is independently $C_3$-$C_6$ cycloalkylene optionally substituted by $R^{10}$;
each $Y^2$ is independently saturated 3- to 4-membered heterocyclylene optionally substituted by $R^{10}$;
each Z is independently —$CR^{5a}R^{5b}$—;
each $R^{3a}$, $R^{3b}$, $R^4$, $R^{5a}$ and $R^{5b}$ is independently H or $C_1$-$C_6$ alkyl;
each $R^9$ is independently $C_1$-$C_6$ alkyl, $C_2$-$C_6$ alkenyl, $C_2$-$C_6$ alkynyl, halogen, —CN, —$OR^{11}$, —$SR^{11}$, —$NR^{12}R^{13}$, —$NO_2$, —C═NH($OR^{11}$), —C(O)$R^{11}$, —OC(O)$R^{11}$, —C(O)$OR^{11}$, —C(O)$NR^{12}R^{13}$, —$NR^{11}$C(O)$R^{12}$, —$NR^{11}$C(O)$OR^{12}$, —$NR^{11}$C(O)$NR^{12}R^{13}$, —S(O)$R^{11}$, —S(O)$_2R^{11}$, —$NR^{11}$S(O)$R^{12}$, —$NR^{11}$S(O)$_2R^{12}$, —S(O)$NR^{12}R^{13}$, —S(O)$_2NR^{12}R^{13}$, —P(O)($OR^{12}$)($OR^{13}$), $C_3$-$C_8$ cycloalkyl, 3- to 12-membered heterocyclyl, 5- to 10-membered heteroaryl or $C_6$-$C_{14}$ aryl, wherein each $R^9$ is independently optionally substituted by halogen, oxo, —$OR^{14}$, —$NR^{14}R^{15}$, —C(O)$R^{14}$, —CN, —S(O)$R^{14}$, —S(O)$_2R^{14}$, —P(O)($OR^{14}$)($OR^{15}$), $C_3$-$C_8$ cycloalkyl, 3- to 12-membered heterocyclyl, 5- to 10-membered heteroaryl, $C_6$-$C_{14}$ aryl, or $C_1$-$C_6$ alkyl optionally substituted by oxo, —OH or halogen;
each $R^{10}$ is independently oxo or $R^9$;
$R^{11}$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —OR$^{16}$, —NR$^{16}$R$^{17}$, —P(O)(OR$^{16}$)(OR$^{17}$), or $C_1$-$C_6$ alkyl optionally substituted by halogen, —OH or oxo;

R$^{12}$ and R$^{13}$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —OR$^{16}$, —NR$^{16}$R$^{17}$ or $C_1$-$C_6$ alkyl optionally substituted by halogen, —OH or oxo;

or R$^{12}$ and R$^{13}$ are taken together with the atom to which they attached to form a 3- to 6-membered heterocyclyl optionally substituted by halogen, oxo, —OR$^{16}$, —NR$^{16}$R$^{17}$ or $C_1$-$C_6$ alkyl optionally substituted by halogen, oxo or —OH;

R$^{14}$ and R$^{15}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or R$^{14}$ and R$^{15}$ are taken together with the atom to which they attached to form a 3- to 6-membered heterocyclyl optionally substituted by halogen, oxo or $C_1$-$C_6$ alkyl optionally substituted by halogen or oxo; and R$^{16}$ and R$^{17}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or R$^{16}$ and R$^{17}$ are taken together with the atom to which they attached to form a 3-6 membered heterocyclyl optionally substituted by halogen, oxo or $C_1$-$C_6$ alkyl optionally substituted by oxo or halogen;

provided that the compound is other than:

L-Tyrosine, N-[(5-chloro-1,3-benzodioxol-4-yl)carbonyl]-O-[2-(5,6,7,8-tetrahydro-1,8-naphthyridin-2-yl)ethyl]- (3x);

L-Tyrosine, N-[(3-chloro-1-methyl-1H-indol-2-yl)carbonyl]-O-[2-(5,6,7,8-tetrahydro-1,8-naphthyridin-2-yl)ethyl]- (4x);

L-Tyrosine, N-[[1-cyclohexyl-2-(3-furanyl)-1H-benzimidazol-5-yl]carbonyl]-O-(1H-tetrazol-5-ylmethyl)- (5x);

L-Tyrosine, N-(2,6-dichlorobenzoyl)-O-[(5,6,7,8-tetrahydro-1,8-naphthyridin-2-yl)methyl]- (6x);

L-Tyrosine, N-(2-chloro-4-methoxybenzoyl)-O-[2-(3,4-dihydro-2H-pyrido[3,2-b]-1,4-oxazin-6-yl)ethyl]- (7x);

L-Tyrosine, N-(2-chloro-6-methylbenzoyl)-O-[2-(3,4-dihydro-2H-pyrido[3,2-b]-1,4-oxazin-6-yl)ethyl]- (8x);

L-Tyrosine, N-(2-fluoro-6-methylbenzoyl)-O-[2-(5,6,7,8-tetrahydro-1,8-naphthyridin-2-yl)ethyl]- (9x);

L-Tyrosine, N-[(2-ethyl-3-thienyl)carbonyl]-O-[2-(5,6,7,8-tetrahydro-1,8-naphthyridin-2-yl)ethyl]- (10x);

L-Tryptophan, N-benzoyl-5-[4-(1-piperazinyl)butoxyl]- (11x);

L-Tyrosine, N-(2-chlorobenzoyl)-O-[2-(5,6,7,8-tetrahydro-1,8-naphthyridin-2-yl)ethyl]- (12x);

L-Tyrosine, N-[(3-chloro-2-thienyl)carbonyl]-O-[2-(5,6,7,8-tetrahydro-1,8-naphthyridin-2-yl)ethyl]- (13x);

2-Pyridinepropanoic acid, α-[(2,6-dichlorobenzoyl)amino]-5-[2-(5,6,7,8-tetrahydro-1,8-naphthyridin-2-yl)ethoxy]-, (αS)- (14x);

L-Tyrosine, N-(2-chloro-6-fluorobenzoyl)-O-[2-(5,6,7,8-tetrahydro-1,8-naphthyridin-2-yl)ethyl]- (15x);

L-Tyrosine, N-[(3-chloro-4-pyridinyl)carbonyl]-O-[2-(3,4-dihydro-2H-pyrido[3,2-b]-1,4-oxazin-6-yl)ethyl]- (16x), L-Tyrosine, O-[2-(5,6,7,8-tetrahydro-1,8-naphthyridin-2-yl)ethyl]-N-(2,4,6-trimethylbenzoyl)- (17x);

L-Tyrosine, N-[(3,5-dichloro-4-pyridinyl)carbonyl]-O-[2-(3,4-dihydro-2H-pyrido[3,2-b]-1,4-oxazin-6-yl)ethyl]- (18x);

L-Tyrosine, N-(2,4-dichlorobenzoyl)-O-[2-(5,6,7,8-tetrahydro-1,8-naphthyridin-2-yl)ethyl]- (19x);

2-Pyridinepropanoic acid, α-[(2-chloro-4-methoxybenzoyl)amino]-5-[2(5,6,7,8-tetrahydro-1,8-naphthyridin-2-yl)ethoxy]-, (αS)- (20x);

2-Pyridinepropanoic acid, α-[(2-chlorobenzoyl)amino]-5-[2-(5,6,7,8-tetrahydro-1,8-naphthyridin-2-yl)ethoxy]-, (αS)- (21x);

L-Tyrosine, N-(2-chloro-6-fluoro-3-methylbenzoyl)-O-[2-(3,4-dihydro-2H-pyrido[3,2-b]-1,4-oxazin-6-yl)ethyl]- (22x);

3-Pyridinepropanoic acid, α-[(2-chlorobenzoyl)amino]-6-[2-(5,6,7,8-tetrahydro-1,8-naphthyridin-2-yl)ethoxy]-, (αS)- (23x);

L-Tyrosine, N-(2,6-dichlorobenzoyl)-O-[2-(5,6,7,8-tetrahydro-1,8-naphthyridin-2-yl)ethyl]- (24x);

L-Tyrosine, N-(2-chloro-6-fluorobenzoyl)-O-[2-(3,4-dihydro-2H-pyrido[3,2-b]-1,4-oxazin-6-yl)ethyl]- (25x);

L-Tyrosine, N-(2-chloro-5-fluorobenzoyl)-O-[2-(3,4-dihydro-2H-pyrido[3,2-b]-1,4-oxazin-6-yl)ethyl]- (26x);

2-Naphthalenepropanoic acid, α-(benzoylamino)-6-[2-(1-piperazinyl)ethoxy]- (27x);

L-Tyrosine, O-[2-(3,4-dihydro-2H-pyrido[3,2-b]-1,4-oxazin-6-yl)ethyl]-N-(2-ethyl-4-fluorobenzoyl)- (28x);

L-Tyrosine, N-(2,6-dichlorobenzoyl)-O-[2-(5,6,7,8-tetrahydro-5-methyl-1,8-naphthyridin-2-yl)ethyl]- (29x);

2-Pyridinepropanoic acid, α-[[(3-chloro-2-thienyl)carbonyl]amino]-5-[2-(5,6,7,8-tetrahydro-1,8-naphthyridin-2-yl)ethoxy]-, (αS)- (30x);

L-Tyrosine, N-(2,6-dichlorobenzoyl)-O-[2-(1,2,3,4-tetrahydro-1-methylpyrido[2,3-b]pyrazin-6-yl)ethyl]- (31x);

L-Tryptophan, N-benzoyl-5-[3-[4-[(1,1-dimethylethoxy)carbonyl]-1-piperazinyl]propoxy]- (32x), L-Tyrosine, N-(2,6-dimethylbenzoyl)-O-[2-(5,6,7,8-tetrahydro-1,8-naphthyridin-2-yl)ethyl]- (33x);

L-Tyrosine, O-[2-(3,4-dihydro-2H-pyrido[3,2-b]-1,4-oxazin-6-yl)ethyl]-N-[(3-methyl-4-pyridinyl)carbonyl]- (34x);

L-Tyrosine, N-(2-chloro-6-methylbenzoyl)-O-[2-(5,6,7,8-tetrahydro-1,8-naphthyridin-2-yl)ethyl]- (35x);

L-Tyrosine, N-[(3-chloro-2-thienyl)carbonyl]-O-[2-(3,4-dihydro-2H-pyrido[3,2-b]-1,4-oxazin-6-yl)ethyl]- (36x);

2-Thiophenepropanoic acid, α-[[(3,5-dichloro-4-pyridinyl)carbonyl]amino]-5-[2-(5,6,7,8-tetrahydro-1,8-naphthyridin-2-yl)ethoxy]-, (αS)- (37x);

L-Tyrosine, N-(2-chloro-3,6-difluorobenzoyl)-O-[2-(5,6,7,8-tetrahydro-1,8-naphthyridin-2-yl)ethyl]- (38x);

2-Pyridinepropanoic acid, α-[(2-fluoro-4-methylbenzoyl)amino]-5-[2-(5,6,7,8-tetrahydro-1,8-naphthyridin-2-yl)ethoxy]-, (αS)- (39x);

L-Tyrosine, N-(2,6-dichlorobenzoyl)-O-[2-(5,6,7,8-tetrahydro-4-methyl-1,8-naphthyridin-2-yl)ethyl]- (40x), 2-Pyridinepropanoic acid, α-[(2-chloro-4-fluorobenzoyl) amino]-5-[2-(5,6,7,8-tetrahydro-1,8-naphthyridin-2-yl) ethoxy]-, (αS)- (41x);

L-Tyrosine, N-(2,6-dichlorobenzoyl)-O-[2-(3,4-dihydro-2H-pyrido[3,2-b]-1,4-oxazin-6-yl)ethyl]- (42x);

3-Pyridinepropanoic acid, α-[(2-chloro-4-fluorobenzoyl) amino]-6-[2-(5,6,7,8-tetrahydro-1,8-naphthyridin-2-yl) ethoxy]-, (αS)- (43x);

L-Tyrosine, N-(2-chlorobenzoyl)-O-[2-(3,4-dihydro-2H-pyrido[3,2-b]-1,4-oxazin-6-yl)ethyl]- (44x);

L-Tyrosine, O-[2-(3,4-dihydro-2H-pyrido[3,2-b]-1,4-oxazin-6-yl)ethyl]-N-(2-ethyl-5-fluorobenzoyl)- (45x);

1-Piperazinecarboxylic acid, 4-[2-[[6-[2-(benzoylamino)-2-carboxyethyl]-2-naphthalenyl]oxy]ethyl]-, 1-(1,1-dimethylethyl) ester (46x);

L-Tyrosine, O-[2-(3,4-dihydro-2H-pyrido[3,2-b]-1,4-oxazin-6-yl)ethyl]-N-(2,4,6-trimethylbenzoyl)- (47x);

L-Tyrosine, O-[2-(3,4-dihydro-2H-pyrido[3,2-b]-1,4-oxazin-6-yl)ethyl]-N-(2,6-dimethylbenzoyl)- (48x);

3-Pyridinepropanoic acid, α-[[(3-chloro-2-thienyl)carbonyl]amino]-6-[2-(5,6,7,8-tetrahydro-1,8-naphthyridin-2-yl)ethoxy]-, (αS)- (49x);

L-Tryptophan, N-benzoyl-5-[4-[4-[(1,1-dimethylethoxy) carbonyl]-1-piperazinyl]butoxy]- (50x);

L-Tyrosine, N-(2-methylbenzoyl)-O-[2-(5,6,7,8-tetrahydro-1,8-naphthyridin-2-yl)ethyl]- (51 x);

L-Tyrosine, N-[(3,5-dichloro-4-pyridinyl)carbonyl]-O-[2-(5,6,7,8-tetrahydro-1,8-naphthyridin-2-yl)ethyl]- (52x), L-Tryptophan, N-benzoyl-5-[3-(1-piperazinyl)propoxy]- (53x);

L-Tyrosine, N-(6-chloro-2-fluoro-3-methylbenzoyl)-O-[2-(5,6,7,8-tetrahydro-1,8-naphthyridin-2-yl)ethyl]- (54x);

L-Tyrosine, N-[(4-methoxy-3-thienyl)carbonyl]-O-[2-(5,6,7,8-tetrahydro-1,8-naphthyridin-2-yl)ethyl]- (55x);

L-Tyrosine, N-(2-chloro-4-fluorobenzoyl)-O-[2-(5,6,7,8-tetrahydro-1,8-naphthyridin-2-yl)ethyl]- (56x);

L-Tyrosine, O-[2-(3,4-dihydro-2H-pyrido[3,2-b]-1,4-oxazin-6-yl)ethyl]-N-[(3,5-dimethyl-4-isoxazolyl)carbonyl]- (57x);

L-Tyrosine, N-(2-chloro-5-methylbenzoyl)-O-[2-(5,6,7,8-tetrahydro-1,8-naphthyridin-2-yl)ethyl]- (58x);

2-Pyridinepropanoic acid, α-[(2-ethyl-4-fluorobenzoyl) amino]-5-[2-(5,6,7,8-tetrahydro-1,8-naphthyridin-2-yl) ethoxy]-, αS)- (59x);

L-Tyrosine, N-(2,6-dichlorobenzoyl)-O-[2-(5,6,7,8-tetrahydro-7-methyl-1,8-naphthyridin-2-yl)ethyl]- (60x);

2-Pyridinepropanoic acid, α-[(2-chloro-6-fluorobenzoyl) amino]-5-[2-(5,6,7,8-tetrahydro-1,8-naphthyridin-2-yl) ethoxyl-, (αS)- (61x), 3-Pyridinepropanoic acid, α-(2-chloro-6-fluorobenzoyl) amino]-6-[2-(5,6,7,8-tetrahydro-1,8-naphthyridin-2-yl) ethoxy]-, (αS)- (62x);

L-Tyrosine, N-(2-chloro-4-fluorobenzoyl)-O-[2-(3,4-dihydro-2H-pyrido[3,2-b]-1,4-oxazin-6-yl)ethyl]- (63x), 3-Pyridinepropanoic acid, α-[(2,6-dichlorobenzoyl) amino]-6-[2-(5,6,7,8-tetrahydro-1,8-naphthyridin-2-yl) ethoxy]-, (αS)- (64x);

L-Tyrosine, N-(2,6-dichlorobenzoyl)-O-[2-(5,6,7,8-tetrahydro-1,8-naphthyridin-2-yl)propyl] (65x);

L-Tyrosine, N-(2,6-dichlorobenzoyl)-O-[2-methyl-2-(5,6,7,8-tetrahydro-1,8-naphthyridin-2-yl)propyl]- (66x);

L-Tyrosine, O-[3-(4-pyrimidinylamino)propyl]-N-(2,4,6-trimethylbenzoyl)- (77x);

L-Tyrosine, N-benzoyl-O-[4-[(1,4,5,6-tetrahydro-2-pyrimidinyl)amino]butyl]- (81x);

L-Tyrosine, O-[2-(2-benzothiazolylamino)ethyl]-N-(2,6-dichlorobenzoyl)- (89x);

L-Tyrosine, O-[3-[(1,4,5,6-tetrahydro-2-pyrimidinyl) amino]propyl]-N-(2,4,6-trimethylbenzol)- (93x);

L-Tyrosine, O-[3-(2-pyrimidinylamino)propyl]-N-(2,4,6-trimethylbenzoyl)- (95x);

L-Tyrosine, O-[2-(1H-benzimidazol-2-ylamino)ethyl]-N-(2,6-dichlorobenzoyl)- (96x);

L-Tyrosine, N-benzoyl-O-[4-(2-pyrimidinylamino)butyl]- (98x);

L-Tyrosine, O-[3-[(1,4,5,6-tetrahydro-2-pyrazinyl) amino]propyl]-N-(2,4,6-trimethylbenzoyl)- (109x);

L-Tyrosine, O-[3-(2-pyrazinylamino)propyl]-N-(2,4,6-trimethylbenzol)- (111 x);

2-Thiophenepropanoic acid, a-[3-(2-chloro-4-fluorobenzoyl)amino]-5-[3-(5,6,7,8-tetrahydro-1,8-naphthyridin-2-yl)propyl]-, (αS)- (126x);

2-Pyridinepropanoic acid, α-[(2-chlorobenzoyl)amino]-5-[3-(5,6,7,8-tetrahydro-1,8-naphthyridin-2-yl)propyl]-, (αS)- (127x);

3-Pyridinepropanoic acid, α-[(2-chloro-4-fluorobenzoyl) amino]-6-[3-(5,6,7,8-tetrahydro-1,8-naphthyridin-2-yl) propyl]-, (αS)- (128x);

2-Thiophenepropanoic acid, α-[[(3,5-dichloro-4-pyridinyl)carbonyl]amino]-5-[3-(5,6,7,8-tetrahydro-1,8-naphthyridin-2-yl)propyl]-, (αS)- (129x);

L-Phenylalanine, N-(2-chloro-4-fluorobenzoyl)-4-[3-(3, 4-dihydro-2H-pyrido[3,2-b]-1,4-oxazin-6-yl)propyl]- (130x);

2-Thiophenepropanoic acid, α-[(2-chloro-6-fluorobenzoyl)amino]-5-[3-(5,6,7,8-tetrahydro-1,8-naphthyridin-2-yl)propyl], (αS)- (131x);

2-Pyridinepropanoic acid, α-[(2-fluoro-6-methylbenzoyl) amino]-5-[3-(5,6,7,8-tetrahydro-1,8-naphthyridin-2-yl) propyl]-, (αS)- (132x);

3-Pyridinepropanoic acid, α-[(2-chloro-6-fluorobenzoyl) amino]-6-[3-(5,6,7,8-tetrahydro-1,8-naphthyridin-2-yl) propyl-, (αS)- (133x);

L-Phenylalanine, N-(2,6-dichlorobenzoyl)-4-[3-(3,4-dihydro-2H-pyrido[3,2-b]-1,4-oxazin-6-yl)propyl]- (134x);

2-Thiophenepropanoic acid, α-(2,6-dichlorobenzoyl) amino]-5-[3-(5,6,7,8-tetrahydro-1,8-naphthyridin-2-yl) propyl-, (αS)- (135x);

2-Pyridinepropanoic acid, α-(2-chloro-4-fluorobenzoyl) amino]-5-[3-(5,6,7,8-tetrahydro-1,8-naphthyridin-2-yl) propyl]-, (αS)- (136x);

2-Pyridinepropanoic acid, α-[[(3-chloro-2-thienyl)carbonyl]amino]-5-[3-(5,6,7,8-tetrahydro-1,8-naphthyridin-2-yl)propyl]-, (αS)- (137x);

L-Phenylalanine, N-(2-chlorobenzoyl)-4-[3-(5,6,7,8-tetrahydro-1,8-naphthyridin-2-yl)propyl]- (138x);

L-Phenylalanine, N-(2-chloro-6-fluorobenzoyl)-4-[3-(5, 6,7,8-tetrahydro-1,8-naphthyridin-2-yl)propyl]- (139x);

2-Pyridinepropanoic acid, α-[(2-chloro-6-fluorobenzoyl) amino]-5-[3-(5,6,7,8-tetrahydro-1,8-naphthyridin-2-yl) propyl]-, (αS)- (140x);

2-Pyridinepropanoic acid, α-[(2,6-dichlorobenzoyl) amino]-5-[3-(5,6,7,8-tetrahydro-1,8-naphthyridin-2-yl) propyl]-, (αS)- (141x);

L-Phenylalanine, N-(2,6-dichlorobenzoyl)-4-[3-(5,6,7,8-tetrahydro-1,8-naphthyridin-2-yl)propyl]- (142x);

3-Pyridinepropanoic acid, α-[(2,6-dichlorobenzoyl) amino]-6-[3-(5,6,7,8-tetrahydro-1,8-naphthyridin-2-yl) propyl]-, (αS)- (143x);

L-Phenylalanine, N-[(3,5-dimethyl-4-isoxazolyl)carbonyl]-4-[3-(5,6,7,8-tetrahydro-1,8-naphthyridin-2-yl)propyl]- (144x);

L-Phenylalanine, N-(2-chlorobenzoyl)-4-[3-(3,4-dihydro-2H-pyrido[3,2-b]-1,4-oxazin-6-yl)propyl]- (145x);

2-Thiophenepropanoic acid, α-[[3-[(dimethylamino)methyl]benzoyl]amino]-5-[(8-methyl-6,10-dioxo-7,9-diazaspiro[4.5]dec-7-en-9-yl)methyl]- (146x);

2-Thiophenepropanoic acid, α-[(2-chlorobenzoyl)amino]-5-[3-(5,6,7,8-tetrahydro-1,8-naphthyridin-2-yl)propyl]-, (αS)- (147x);

L-Phenylalanine, N-(2-chloro-4-fluorobenzoyl)-4-[3-(5,6,7,8-tetrahydro-1,8-naphthyridin-2-yl)propyl]- (148x);

3-Pyridinepropanoic acid, α-[(2-chlorobenzoyl)amino]-6-[3-(5,6,7,8-tetrahydro-1,8-naphthyridin-2-yl)propyl]-, (αS)- (149x);

2-Thiophenepropanoic acid, α-[[(3,5-dimethyl-4-isoxazolyl)carbonyl]amino]-5-[3-(5,6,7,8-tetrahydro-1,8-naphthyridin-2-yl)propyl]-, (αS)- (150x);

L-Phenylalanine, N-(2-chloro-6-fluorobenzoyl)-4-[3-(3,4-dihydro-2H-pyrido[3,2-b]-1,4-oxazin-6-yl)propyl]- (151x);

3-Pyridinepropanoic acid, α-[[(3-chloro-2-thienyl)carbonyl]amino]-6-[3-(5,6,7,8-tetrahydro-1,8-naphthyridin-2-yl)propyl]-, (αS)- (152x); or 1,8-Naphthyridine-2-nonanoic acid, α-(benzoylamino)-5,6,7,8-tetrahydro-, (αS)- (164x), or a salt thereof.

2. The compound of claim 1, or a salt thereof, wherein $R^1$ is a fused bicyclic $C_9$-$C_{14}$ aryl optionally substituted by $R^{10}$ or a fused bicyclic 7- to 10-membered heteroaryl optionally substituted by $R^{10}$.

3. The compound of claim 1, or a salt thereof, wherein $R^1$ is a fused bicyclic 7- to 10-membered heteroaryl optionally substituted by $R^{10}$.

4. The compound of claim 3, or a salt thereof, wherein $R^1$ is indazolyl optionally substituted by $R^{10}$, benzimidazolyl optionally substituted by $R^{10}$, or benzoxazolyl optionally substituted by $R^{10}$.

5. The compound of claim 1, or a salt thereof, wherein $R^1$ is phenyl optionally substituted by $R^{10}$.

6. The compound of claim 1, or a salt thereof, wherein $R^1$ is a monocyclic 5- or 6-membered heteroaryl optionally substituted by $R^{10}$.

7. The compound of claim 1, or a salt thereof, wherein the -A-L- moiety is -$A^1$-$L^1$-.

8. The compound of claim 7, or a salt thereof, wherein $A^1$ is $C_6$-$C_{14}$ arylene optionally substituted by $R^{10}$.

9. The compound of claim 7, or a salt thereof, wherein $A^1$ is $C_3$-$C_8$ cycloalkylene optionally substituted by $R^{10}$.

10. The compound of claim 7, or a salt thereof, wherein $A^1$ is 5- to 10-membered heteroarylene optionally substituted by $R^{10}$.

11. The compound of claim 7, or a salt thereof, wherein $A^1$ is 3- to 12-membered heterocyclylene optionally substituted by $R^{10}$.

12. The compound of claim 7, or a salt thereof, wherein $A^1$ is selected from the group consisting of 1,4-phenylene, 1,3-phenylene, 1,1-cyclopropylene, 1,2-cyclopropylene, 1,3-cyclobutylene, 1,4-cyclohexylene, 1,3-azetidinylene, 1,3-pyrrolidinylene, and 2,5-benzo[d]oxazolylene.

13. The compound of claim 7, or a salt thereof, wherein $L^1$ is —O—Z—, —O—Z—$X^1$—, —O—$Y^1$—, —O—Z—$Y^1$—, —O—Z—$X^1$—$Y^1$—, —Z—O—Z—, —$X^1$—Z—O—Z—, —O—Z—, —Z—O—Z—$X^1$—, —$X^1$—Z—O—Z—$X^1$—, —Z—O—$Y^1$—, or —$X^1$—Z—O—$Y^1$—.

14. The compound of claim 13, or a salt thereof, wherein Z is —$CR^{5a}R^{5b}$— where each of $R^{5a}$ and $R^{5b}$ is H.

15. The compound of claim 13, or a salt thereof, wherein $L^1$ is selected from the group consisting of —O—$(CH_2)_3$—, —O—$(CH_2)_4$—, —$CH_2$—O—$(CH_2)_3$—, —$CH_2$—O—$(CH_2)_2$—, —$CH(CH_3)$—O—$(CH_2)_2$—, —$CH_2$—O—$(CH_2)_3$—,

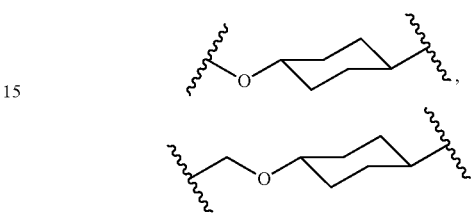

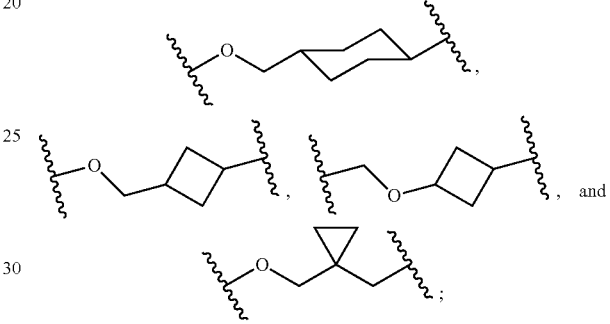

, and wherein the wavy lines denote attachment points to the parent molecule.

16. The compound of claim 7, or a salt thereof, wherein $L^1$ is —N($R^4$)—Z— or —N($R^4$)—Z—$X^1$—.

17. The compound of claim 16, or a salt thereof, wherein $R^4$ is H and Z is —$CR^{5a}R^{5b}$— where each of $R^{5a}$ and $R^{5b}$ is H.

18. The compound of claim 17, or a salt thereof, wherein $L^1$ is —NH—$C(CH_3)_2$—$(CH_2)_2$—.

19. The compound of claim 7, or a salt thereof, wherein $L^1$ is $X^2$ or —$X^2$—$Y^1$—.

20. The compound of claim 19, or a salt thereof, wherein $L^1$ is selected from the group consisting of —$(CH_2)_2$—, —$(CH_2)_4$—, —$(CH_2)_5$—, —$CF_2$—$(CH_2)_3$— and

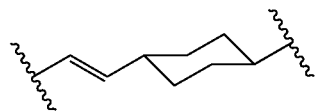

wherein the wavy lines denote attachment points to the parent molecule.

21. The compound of claim 7, or a salt thereof, wherein $L^1$ is $Y^2$ or —$Y^2$—$X^2$—.

22. The compound of claim 21, or a salt thereof, wherein $Y^2$ is saturated 4-membered heterocyclylene optionally substituted by $R^{10}$.

23. The compound of claim 21, or a salt thereof, wherein $Y^2$ is 1,3-azetidinylene.

24. The compound of claim 21, or a salt thereof, wherein $L^1$ is selected from the group consisting of

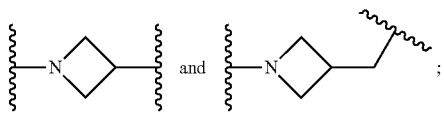 [SMILES: *C1CN(*)C1 ; *CC1CN(*)C1]

wherein the wavy lines denote attachment points to the parent molecule.

25. The compound of claim 1, or a salt thereof, wherein the -A-L- moiety is -$A^2$-$L^2$- or $A^3$.

26. The compound of claim 25, or a salt thereof, wherein $A^2$ is $C_3$-$C_8$ alkylene optionally substituted by $R^9$.

27. The compound of claim 25, or a salt thereof, wherein $A^3$ is $C_5$-$C_{10}$ alkenylene optionally substituted by $R^9$.

28. The compound of claim 25, or a salt thereof, wherein the -A-L- moiety is selected from the group consisting of —$CH_2(CH_2)_5CH_2$—, —$CH_2(CH_2)_4CH_2$—, —CH═CH—($CH_2)_3CH_2$—, and

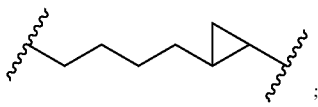 [SMILES: *CCCCC1CC1*]

wherein the wavy lines denote attachment points to the parent molecule.

29. The compound of claim 1, or a salt thereof, wherein $R^2$ is 5- to 10-membered heteroaryl containing at least 2 ring nitrogen atoms optionally substituted by $R^{10}$, or 3- to 12-membered heterocyclyl containing at least 2 ring nitrogen atoms optionally substituted by $R^{10}$.

30. The compound of claim 29, or a salt thereof, wherein $R^2$ is selected from the group consisting of 5,6,7,8-tetrahydro-1,8-naphthyridinyl, 1,2,3,4-tetrahydro-1,8-naphthyridinyl, 3,4-dihydro-2H-pyrido[3,2-b][1,4]oxazinyl, and 2,3-dihydro-1H-pyrrolo[2,3-b]pyridinyl.

31. The compound of claim 1, or a salt thereof, wherein $R^2$ is —NH—$R^3$ and -A-L- is -$A^3$-.

32. The compound of claim 31, or a salt thereof, wherein $R^3$ is 5- to 10-membered heteroaryl containing at least 1 ring nitrogen atom optionally substituted by $R^{10}$.

33. The compound of claim 32, or a salt thereof, wherein $R^3$ is selected from the group consisting of 4,5-dihydro-1H-imidazolyl, 5,6-dihydro-4H-1,3-oxazinyl, 4,5-dihydrothiazolyl, 3,4,5,6-tetrahydropyrazinyl, and 5,6-dihydro-4H-1,3-thiazinyl.

34. The compound of claim 31, or a salt thereof, wherein $R^3$ is pyridinyl optionally substituted by $R^{10}$.

35. The compound of claim 31, or a salt thereof, wherein $R^3$ is selected from the group consisting of 4,5-dihydro-1H-imidazolyl, 5,6-dihydro-4H-1,3-oxazinyl, 4,5-dihydrothiazolyl, 3,4,5,6-tetrahydropyrazinyl, and 5,6-dihydro-4H-1,3-thiazinyl.

36. The compound of claim 31, or a salt thereof, wherein $R^2$ is

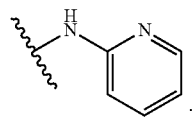

37. The compound of claim 1, or a salt thereof, wherein $R^2$ is —$R^3$—$NR^{3a}R^{3b}$ and -A-L- is -$A^3$-.

38. The compound of claim 37, or a salt thereof, wherein $R^2$ is —$R^3$—$NHR^{3a}$.

39. The compound of claim 37, or a salt thereof, wherein $R^3$ is pyridyl optionally substituted by $R^{10}$.

40. The compound of claim 1, or a salt thereof, wherein $R^2$ is

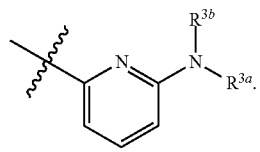

41. The compound of claim 39, or a salt thereof, wherein $R^2$ is

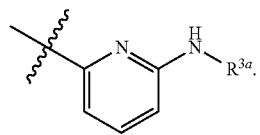

42. The compound of claim 1, wherein the compound is selected from:
2-benzamido-3-(4-(3-(5,6,7,8-tetrahydro-1,8-naphthyridin-2-yl)propoxy)phenyl)propanoic acid (1);
(S)-2-benzamido-3-(4-(3-(5,6,7,8-tetrahydro-1,8-naphthyridin-2-yl)propoxy)phenyl)propanoic acid (1a);
(R)-2-benzamido-3-(4-(3-(5,6,7,8-tetrahydro-1,8-naphthyridin-2-yl)propoxy)phenyl)propanoic acid (1b);
2-(1-methyl-1H-benzo[d]imidazole-6-carboxamido)-3-(4-(3-(5,6,7,8-tetrahydro-1,8-naphthyridin-2-yl)propoxy)phenyl)propanoic acid (2);
(S)-2-(1-methyl-1H-benzo[d]imidazole-6-carboxamido)-3-(4-(3-(5,6,7,8-tetrahydro-1,8-naphthyridin-2-yl)propoxy)phenyl)propanoic acid (2a);
(R)-2-(1-methyl-1H-benzo[d]imidazole-6-carboxamido)-3-(4-(3-(5,6,7,8-tetrahydro-1,8-naphthyridin-2-yl)propoxy)phenyl)propanoic acid (2b);
2-(5-(difluoromethyl)pyrazine-2-carboxamido)-3-(4-(3-(5,6,7,8-tetrahydro-1,8-naphthyridin-2-yl)propoxy)phenyl)propanoic acid (3);
(S)-2-(5-(difluoromethyl)pyrazine-2-carboxamido)-3-(4-(3-(5,6,7,8-tetrahydro-1,8-naphthyridin-2-yl)propoxy)phenyl)propanoic acid (3a);
(R)-2-(5-(difluoromethyl)pyrazine-2-carboxamido)-3-(4-(3-(5,6,7,8-tetrahydro-1,8-naphthyridin-2-yl)propoxy)phenyl)propanoic acid (3b);
2-(6-phenylpyrazine-2-carboxamido)-3-(4-(3-(5,6,7,8-tetrahydro-1,8-naphthyridin-2-yl)propoxy)phenyl)propanoic acid (4);
(S)-2-(6-phenylpyrazine-2-carboxamido)-3-(4-(3-(5,6,7,8-tetrahydro-1,8-naphthyridin-2-yl)propoxy)phenyl)propanoic acid (4a);
(R)-2-(6-phenylpyrazine-2-carboxamido)-3-(4-(3-(5,6,7,8-tetrahydro-1,8-naphthyridin-2-yl)propoxy)phenyl)propanoic acid (4b);
2-(2,6-dichloro-4-cyanobenzamido)-3-(4-(3-(5,6,7,8-tetrahydro-1,8-naphthyridin-2-yl)propoxy)phenyl)propanoic acid (5);
(S)-2-(2,6-dichloro-4-cyanobenzamido)-3-(4-(3-(5,6,7,8-tetrahydro-1,8-naphthyridin-2-yl)propoxy)phenyl)propanoic acid (5a);

(R)-2-(2,6-dichloro-4-cyanobenzamido)-3-(4-(3-(5,6,7,8-tetrahydro-1,8-naphthyridin-2-yl)propoxy)phenyl)propanoic acid (5b);
2-(2-fluoro-6-(trifluoromethyl)benzamido)-3-(4-(3-(5,6,7,8-tetrahydro-1,8-naphthyridin-2-yl)propoxy)phenyl) propanoic acid (6);
(S)-2-(2-fluoro-6-(trifluoromethyl)benzamido)-3-(4-(3-(5,6,7,8-tetrahydro-1,8-naphthyridin-2-yl)propoxy) phenyl)propanoic acid (6a);
(R)-2-(2-fluoro-6-(trifluoromethyl)benzamido)-3-(4-(3-(5,6,7,8-tetrahydro-1,8-naphthyridin-2-yl)propoxy) phenyl)propanoic acid (6b);
2-(2,6-difluorobenzamido)-3-(4-(3-(5,6,7,8-tetrahydro-1,8-naphthyridin-2-yl)propoxy)phenyl)propanoic acid (7);
(S)-2-(2,6-difluorobenzamido)-3-(4-(3-(5,6,7,8-tetrahydro-1,8-naphthyridin-2-yl)propoxy)phenyl)propanoic acid (7a);
(R)-2-(2,6-difluorobenzamido)-3-(4-(3-(5,6,7,8-tetrahydro-1,8-naphthyridin-2-yl)propoxy)phenyl)propanoic acid (7b);
2-(2-methylpyrimidine-4-carboxamido)-3-(4-(3-(5,6,7,8-tetrahydro-1,8-naphthyridin-2-yl)propoxy)phenyl)propanoic acid (8);
(S)-2-(2-methylpyrimidine-4-carboxamido)-3-(4-(3-(5,6,7,8-tetrahydro-1,8-naphthyridin-2-yl)propoxy)phenyl) propanoic acid (8a);
(R)-2-(2-methylpyrimidine-4-carboxamido)-3-(4-(3-(5,6,7,8-tetrahydro-1,8-naphthyridin-2-yl)propoxy)phenyl) propanoic acid (8b);
2(1-methyl-1H-benzo[d]imidazole-5-carboxamido)-3-(4-(3-(5,6,7,8-tetrahydro-1,8-naphthyridin-2-yl)propoxy) phenyl)propanoic acid (9);
(S)-2-(1-methyl-1H-benzo[d]imidazole-5-carboxamido)-3-(4-(3-(5,6,7,8-tetrahydro-1,8-naphthyridin-2-yl) propoxy)phenyl)propanoic acid (9a);
(R)-2-(1-methyl-1H-benzo[d]imidazole-5-carboxamido)-3-(4-(3-(5,6,7,8-tetrahydro-1,8-naphthyridin-2-yl) propoxy)phenyl)propanoic acid (9b);
2-(benzo[d] oxazole-5-carboxamido)-3-(4-(3-(5,6,7,8-tetrahydro-1,8-naphthyridin-2-yl)propoxy)phenyl)propanoic acid (10);
(S)- 2-(benzo[d]oxazole-5-carboxamido)-3-(4-(3-(5,6,7,8-tetrahydro-1,8-naphthyridin-2-yl)propoxy)phenyl) propanoic acid (10a);
(R)- 2-(benzo[d] oxazole-5-carboxamido)-3-(4-(3-(5,6,7,8-tetrahydro-1,8-naphthyridin-2-yl)propoxy)phenyl) propanoic acid (10b);
2-(3-amino-4-hydroxybenzamido)-3-(4-(3-(5,6,7,8-tetrahydro-1,8-naphthyridin-2-yl)propoxy)phenyl)propanoic acid (11);
(S)-2-(3-amino-4-hydroxybenzamido)-3-(4-(3-(5,6,7,8-tetrahydro-1,8-naphthyridin-2-yl)propoxy)phenyl)propanoic acid (11a);
(R)-2-(3-amino-4-hydroxybenzamido)-3-(4-(3-(5,6,7,8-tetrahydro-1,8-naphthyridin-2-yl)propoxy)phenyl)propanoic acid (11b);
2-(3-formamido-4-hydroxybenzamido)-3-(4-(3-(5,6,7,8-tetrahydro-1,8-naphthyridin-2-yl)propoxy)phenyl)propanoic acid (12);
(S)-2-(3-formamido-4-hydroxybenzamido)-3-(4-(3-(5,6,7,8-tetrahydro-1,8-naphthyridin-2-yl)propoxy)phenyl) propanoic acid (12a);
(R)-2-(3-formamido-4-hydroxybenzamido)-3-(4-(3-(5,6,7,8-tetrahydro-1,8-naphthyridin-2-yl)propoxy)phenyl) propanoic acid (12b);
2-(isonicotinamido)-3-(4-(3-(5,6,7,8-tetrahydro-1,8-naphthyridin-2-yl)propoxy)phenyl)propanoic acid (13)
(S)-2-(isonicotinamido)-3-(4-(3-(5,6,7,8-tetrahydro-1,8-naphthyridin-2-yl)propoxy)phenyl)propanoic acid (13a);
(R)-2-(isonicotinamido)-3-4((5,6,7,8-tetrahydro-1,8-naphthyridin-2-yl)propoxy)phenyl)propanoic acid (13b);
2-(nicotinamido)-3-(4-(3-(5,6,7,8-tetrahydro-1,8-naphthyridin-2-yl)propoxy)phenyl)propanoic acid (14);
(S)-2-(nicotinamido)-3-(4-(3-(5,6,7,8-tetrahydro-1,8-naphthyridin-2-yl)propoxy)phenyl)propanoic acid (14a);
(R)-2-(nicotinamido)-3-(4-(3-(5,6,7,8-tetrahydro-1,8-naphthyridin-2-yl)propoxy)phenyl)propanoic acid (14b);
2-(3,5-dichloroisonicotinamido)-3-(4-(3-(5,6,7,8-tetrahydro-1,8-naphthyridin-2-yl)propoxy)phenyl)propanoic acid (15);
(S)-2-(3,5-dichloroisonicotinamido)-3-(4-(3-(5,6,7,8-tetrahydro-1,8-naphthyridin-2-yl)propoxy)phenyl)propanoic acid (15a);
(R)-2-(3,5-dichloroisonicotinamido)-3-(4-(3-(5,6,7,8-tetrahydro-1,8-naphthyridin-2-yl)propoxy)phenyl)propanoic acid (15b);
2-(2,6-dichlorobenzamido)-3-(4-(3-(5,6,7,8-tetrahydro-1,8-naphthyridin-2-yl)propoxy)phenyl)propanoic acid (16);
(S)-2-(2,6-dichlorobenzamido)-3-(4-(3-(5,6,7,8-tetrahydro-1,8-naphthyridin-2-yl)propoxy)phenyl)propanoic acid (16a);
(R)-2-(2,6-dichlorobenzamido)-3-(4-(3-(5,6,7,8-tetrahydro-1,8-naphthyridin-2-yl)propoxy)phenyl)propanoic acid (16b);
2-(2,6-dichlorobenzamido)-3-(4-(4-((4-methyl-3-oxo-3,4,5,6-tetrahydropyrazin-2-yl)amino)butoxy)phenyl) propanoic acid (17);
(S)-2-(2,6-dichlorobenzamido)-3-(4-(4-((4-methyl-3-oxo-3,4,5,6-tetrahydropyrazin-2-yl)amino)butoxy) phenyl)propanoic acid (17a);
(R)-2-(2,6-dichlorobenzamido)-3-(4-(4-((4-methyl-3-oxo-3,4,5,6-tetrahydropyrazin-2-yl)amino)butoxy) phenyl)propanoic acid (17b);
2-(2,6-dichlorobenzamido)-3-(4-(3-(2,3-dihydro-1H-pyrrolo[2,3-b]pyridin-2-yl)propoxy)phenyl)propanoic acid (18);
(S)-2-(2,6-dichlorobenzamido)-3-(4-(3-((S)-2,3-dihydro-1H-pyrrolo[2,3-b]pyridin-2-yl)propoxy)phenyl)propanoic acid (18a);
(R)-2-(2,6-dichlorobenzamido)-3-(4-(3-(R)-2,3-dihydro-1H-pyrrolo[2,3-b]pyridin-2-yl)propoxy)phenyl)propanoic acid (18b);
(S)-2-(2,6-dichlorobenzamido)-3-(4-(3-(R)-2,3-dihydro-1H-pyrrolo[2,3-b]pyridin-2-yl)propoxy)phenyl)propanoic acid (18c);
(R)-2-(2,6-dichlorobenzamido)-3-(4-(3-((S)-2,3-dihydro-1H-pyrrolo[2,3-b]pyridin-2-yl)propoxy)phenyl)propanoic acid (18d);
2-(2,6-dichlorobenzamido)-9-(5,6,7,8-tetrahydro-1,8-naphthyridin-2-yl)nonanoic acid (19);
(S)-2-(2,6-dichlorobenzamido)-9-(5,6,7,8-tetrahydro-1,8-naphthyridin-2-yl)nonanoic acid (19a);
(R)-2-(2,6-dichlorobenzamido)-9-(5,6,7,8-tetrahydro-1,8-naphthyridin-2-yl)nonanoic acid (19b);
(E)-2-(2,6-dichlorobenzamido)-9-(5,6,7,8-tetrahydro-1,8-naphthyridin-2-yl)non-4-enoic acid (20);

(S,E)-2-(2,6-dichlorobenzamido)-9-(5,6,7,8-tetrahydro-1,8-naphthyridin-2-yl)non-4-enoic acid (20a);

(R,E)-2-(2,6-dichlorobenzamido)-9-(5,6,7,8-tetrahydro-1,8-naphthyridin-2-yl)non-4-enoic acid (20b);

2-(2,6-dichlorobenzamido)-3-(4-(3-((5,6,7,8-tetrahydro-1,8-naphthyridin-2-yl)methyl)azetidin-1-yl)phenyl)propanoic acid (21);

(S)-2-(2,6-dichlorobenzamido)-3-(4-(3-((5,6,7,8-tetrahydro-1,8-naphthyridin-2-yl)methyl)azetidin-1-yl)phenyl)propanoic acid (21a);

(R)-2-(2,6-dichlorobenzamido)-3-(4-(3-((5,6,7,8-tetrahydro-1,8-naphthyridin-2-yl)methyl)azetidin-1-yl)phenyl)propanoic acid (21 b);

2-(2,6-dichlorobenzamido)-3-(4-(3-(5,6,7,8-tetrahydro-1,8-naphthyridin-2-yl)azetidin-1-yl)phenyl)propanoic acid (22);

(S)-2- 2,6-dichlorobenzamido)-3-(4-(3-(5,6,7,8-tetrahydro-1,8-naphthyridin-2-yl)azetidin-1-yl)phenyl)propanoic acid (22a);

(R)-2-(2,6-dichlorobenzamido)-3-(4-(3-(5,6,7,8-tetrahydro-1,8-naphthyridin-2-yl)azetidin-1-yl)phenyl)propanoic acid (22b);

2-(2,6-dichlorobenzamido)-3-(4-(3-(1,2,3,4-tetrahydro-1,8-naphthyridin-2-yl)propoxy)phenyl)propanoic acid (27);

(2S)-2-(2,6-dichlorobenzamido)-3-(4-(3-(1,2,3,4-tetrahydro-1,8-naphthyridin-2-yl)propoxy)phenyl)propanoic acid (27a);

(2R)-2-(2,6-dichlorobenzamido)-3-(4-(3-(1,2,3,4-tetrahydro-1,8-naphthyridin-2-yl)propoxy)phenyl)propanoic acid (27b);

(+/−) 26-dichlorobenzamido)-3-(3-(3-(5,6,7,8-tetrahydro-1,8-naphthyridin-2-yl)propoxy)azetidin-1-yl)propanoic acid (28);

(S)-2-(2,6-dichlorobenzamido)-3-(3-(3-(5,6,7,8-tetrahydro-1,8-naphthyridin-2-yl)propoxy)azetidin-1-yl)propanoic acid (28a);

(R)-2-(2,6-dichlorobenzamido)-3-(3-(3-(5,6,7,8-tetrahydro-1,8-naphthyridin-2-yl)propoxy)azetidin-1-yl)propanoic acid (28b);

2-(2,6-dichlorobenzamido)-3-(4-((2-(5,6,7,8-tetrahydro-1,8-naphthyridin-2-yl)ethoxy)methyl)phenyl)propanoic acid (29);

(S)-2-(2,6-dichlorobenzamido)-3-(4-(2-(5,6,7,8-tetrahydro-1,8-naphthyridin-2-yl)ethoxy)methyl)phenyl)propanoic acid (29a);

(R)-2-(2,6-dichlorobenzamido)-3-(4-((2-(5,6,7,8-tetrahydro-1,8-naphthyridin-2-yl)ethoxy)methyl)phenyl)propanoic acid (29b);

2-(2,6-dichlorobenzamido)-3-(4-(1-(2-(5,6,7,8-tetrahydro-1,8-naphthyridin-2-yl)ethoxy)ethyl)phenyl)propanoic acid (33);

(2S)-2-(2,6-dichlorobenzamido)-3-(4-(1-(2-(5,6,7,8-tetrahydro-1,8-naphthyridin-2-yl)ethoxy)ethyl)phenyl)propanoic acid (33a);

(2R)-2-(2,6-dichlorobenzamido)-3-(4-(1-(2-(5,6,7,8-tetrahydro-1,8-naphthyridin-2-yl)ethoxy)ethyl)phenyl)propanoic acid (33b);

2-(4-cyclopropylbenzamido)-3-(4-(3-(5,6,7,8-tetrahydro-1,8-naphthyridin-2-yl)propoxy)phenyl)propanoic acid (34);

(2S)-2-(4-cyclopropylbenzamido)-3-(4-(3-(5,6,7,8-tetrahydro-1,8-naphthyridin-2-yl)propoxy)phenyl)propanoic acid (3 4a);

(2R)-2-(4-cyclopropylbenzamido)-3-(4-(3-(5,6,7,8-tetrahydro-1,8-naphthyridin-2-yl)propoxy)phenyl)propanoic acid (34b);

2-(3,5-dichlorobenzamido)-3-(4-(3-(5,6,7,8-tetrahydro-1,8-naphthyridin-2-yl)propoxy)phenyl)propanoic acid (35);

(2S)-2-(3,5-dichlorobenzamido)-3-(4-(3-(5,6,7,8-tetrahydro-1,8-naphthyridin-2-yl)propoxy)phenyl)propanoic acid (35a);

(2R)-2-(3,5-dichlorobenzamido)-3-(4-(3-(5,6,7,8-tetrahydro-1,8-naphthyridin-2-yl)propoxy)phenyl)propanoic acid (35b);

2-(2-chloro-5-fluorobenzamido)-3-(4-(3-(5,6,7,8-tetrahydro-1,8-naphthyridin-2-yl)propoxy)phenyl)propanoic acid (36);

(2S)-2-(2-chloro-5-fluorobenzamido)-3-(4-(3-(5,6,7,8-tetrahydro-1,8-naphthyridin-2-yl)propoxy)phenyl)propanoic acid (3 6a);

(2R)-2-(2-chloro-5-fluorobenzamido)-3-(4-(3-(5,6,7,8-tetrahydro-1,8-naphthyridin-2-yl)propoxy)phenyl)propanoic acid (36b);

2-(2,6-dichlorobenzamido)-3-(3-(3-(5,6,7,8-tetrahydro-1,8-naphthyridin-2-yl)propoxy)phenyl)propanoic acid (37);

(2S)-2-(2,6-dichlorobenzamido)-3-(3-(3-(5,6,7,8-tetrahydro-1,8-naphthyridin-2-yl)propoxy)phenyl)propanoic acid (3 7a);

(2R)-2-(2,6-dichlorobenzamido)-3-(3-(3-(5,6,7,8-tetrahydro-1,8-naphthyridin-2-yl)propoxy)phenyl)propanoic acid (37b);

2(1H-indazole-6-carboxamido)-3-(4-(3-(5,6,7,8-tetrahydro-1,8-naphthyridin-2-yl)propoxyl)phenyl)propanoic acid (40);

(2S)-2-(1H-indazole-6-carboxamido)-3-(4-(3-(5,6,7,8-tetrahydro-1,8-naphthyridin-2-yl)propoxy)phenyl)propanoic acid (40a);

(2R')-2-(1H-indazole-6-carboxamido)-3-(4-(3-(5,6,7,8-tetrahydro-1,8-naphthyridin-2-yl)propoxy)phenyl)propanoic acid (40b);

2-(1-methyl-1H-indazole-6-carboxamido)-3-(4-(3-(5,6,7,8-tetrahydro-1,8-naphthyridin-2-yl)propoxy)phenyl)propanoic acid (41);

(2S)-2-(1-methyl-1H-indazole-6-carboxamido)-3-(4-(3-(5,6,7,8-tetrahydro-1,8-naphthyridin-2-yl)propoxy)phenyl)propanoic acid (41a);

(2R)-2-(1-methyl-1H-indazole-6-carboxamido)-3-(4-(3-(5,6,7,8-tetrahydro-1,8-naphthyridin-2-yl)propoxy)phenyl)propanoic acid (41 b);

2(1H-indazole-5-carboxamido)-3-(4-(3-(5,6,7,8-tetrahydro-1,8-naphthyridin-2-yl)propoxy)phenyl)propanoic acid (42);

(2S)-2-(1H-indazole-5-carboxamido)-3-(4-(3-(5,6,7,8-tetrahydro-1,8-naphthyridin-2-yl)propoxy)phenyl)propanoic acid (42a);

(2R)-2-(1H-indazole-5-carboxamido)-3-(4-(3-(5,6,7,8-tetrahydro-1,8-naphthyridin-2-yl)propoxy)phenyl)propanoic acid (42b);

2(1-methyl-1H-indazole-5-carboxamido)-3-(4-(3-(5,6,7,8-tetrahydro-1,8-naphthyridin-2-yl)propoxy)phenyl)propanoic acid (43);

(2S)-2-(1-methyl-1H-indazole-5-carboxamido)-3-(4-(3-(5,6,7,8-tetrahydro-1,8-naphthyridin-2-yl)propoxy)phenyl)propanoic acid (43a);

(2R)-2-(1-methyl-1H-indazole-5-carboxamido)-3-(4-(3-(5,6,7,8-tetrahydro-1,8-naphthyridin-2-yl)propoxy)phenyl)propanoic acid (43b);

2-(2-methyl-2H-indazole-6-carboxamido)-3-(4-(3-(5,6,7,8-tetrahydro-1,8-naphthyridin-2-yl)propoxy)phenyl)propanoic acid (44);

(2S)-2-(2-methyl-2H-indazole-6-carboxamido)-3-(4-(3-(5,6,7,8-tetrahydro-1,8-naphthyridin-2-yl)propoxy)phenyl)propanoic acid (44a);

(2R)-2-(2-methyl-2H-indazole-6-carboxamido)-3-(4-(3-(5,6,7,8-tetrahydro-1,8-naphthyridin-2-yl)propoxy)phenyl)propanoic acid (44b);

2-(2-methyl-2H-indazole-5-carboxamido)-3-(4-(3-(5,6,7,8-tetrahydro-1,8-naphthyridin-2-yl)propoxy)phenyl)propanoic acid (45);

(2S)-2-(2-methyl-2H-indazole-5-carboxamido)-3-(4-(3-(5,6,7,8-tetrahydro-1,8-naphthyridin-2-yl)propoxy)phenyl)propanoic acid (45a);

(2R)-2-(2-methyl-2H-indazole-5-carboxamido)-3-(4-(3-(5,6,7,8-tetrahydro-1,8-naphthyridin-2-yl)propoxy)phenyl)propanoic acid (45b);

2-(2,6-dichlorobenzamido)- 10-((3,4,5,6-tetrahydropyrazin-2-yl)amino)decanoic acid (47);

(S)-2-(2,6-dichlorobenzamido)- 10-((3,4,5,6-tetrahydropyrazin-2-yl)amino)decanoic acid (47a);

(R)-2-(2,6-dichlorobenzamido)- 10-((3,4,5 6-tetrahydropyrazin-2-yl)amino)decanoic acid (47b);

2-(2,6-dichlorobenzamido)- 10-((4,5-dihydrooxazol-2-yl)amino)decanoic acid (48);

(S)-2-(2,6-dichlorobenzamido)- 10-((4,5-dihydrooxazol-2-yl)amino)decanoic acid (48a);

(R)-2-(2,6-dichlorobenzamido)-10-(4,5-dihydrooxazol-2-yl)amino)decanoic acid (48b);

2-(2,6-dichlorobenzamido)- 10-((4,5-dihydrothiazol-2-yl)amino)decanoic acid (49);

(S)-2-(2,6-dichlorobenzamido)- 10-((4,5-dihydrothiazol-2-yl)amino)decanoic acid (49a);

(R)-2-(2,6-dichlorobenzamido)- 10-((4,5-dihydrothiazol-2-yl)amino)decanoic acid (49b);

2(2,6-dichlorobenzamido)- 10-((1-methyl-5-oxo-4,5-dihydro-1H-imidazol-2-yl)amino)decanoic acid (50);

(S)-2-(2,6-dichlorobenzamido)- 10-((1-methyl-5-oxo-4,5-dihydro-1H-imidazol-2-yl)amino)decanoic acid (50a);

(R)-2-(2,6-dichlorobenzamido)- 10-((1-methyl-5-oxo-4,5-dihydro-1H-imidazol-2-yl)amino)decanoic acid (50b);

2-(2,6-dichlorobenzamido)- 10- ((5,6-dihydro-4H-1,3-oxazin-2-yl)amino)decanoic acid (51);

(S)-2-(2,6-dichlorobenzamido)- 10-((5,6-dihydro-4H-1,3-oxazin-2-yl)amino)decanoic acid (51a);

(R)-2-(2,6-dichlorobenzamido)- 10-((5,6-dihydro-4H-1,3-oxazin-2-yl)amino)decanoic acid (5 1b);

2-(2,6-dichlorobenzamido)- 10-((4-methyl-5-oxo-3,4,5 6-tetrahydropyrazin-2-yl)amino)decanoic acid (52);

(S)-2-(2,6-dichlorobenzamido)- 10-((4-methyl-5-oxo-3,4,5,6-tetrahydropyrazin-2-yl)amino)decanoic acid (52a);

(R)-2-(2,6-dichlorobenzamido)- 10-((4-methyl-5-oxo-3,4,5,6-tetrahydropyrazin-2-yl)amino)decanoic acid (52b);

2-(2,6-dichlorobenzamido)- 10-((4-methyl-3-oxo-3,4,5,6-tetrahydropyrazin-2-yl)amino)decanoic acid (53);

(S)-2-(2,6-dichlorobenzamido)- 10-((4-methyl-3-oxo-3,4,5 6-tetrahydropyrazin-2-yl)amino)decanoic acid (53a);

(R)-2-(2,6-dichlorobenzamido)- 10-((4-methyl-3-oxo-3,4,5,6-tetrahydropyrazin-2-yl)amino)decanoic acid (53b);

2-(2,6-dichlorobenzamido)- 10-((5,6-dihydro-4H-1,3-thiazin-2-yl)amino)decanoic acid (54);

(S)-2-(2,6-dichlorobenzamido)- 10-((5,6-dihydro-4H-1,3-thiazin-2-yl)amino)decanoic acid (54a);

(R)-2-(2,6-dichlorobenzamido)- 10-((5,6-dihydro-4H-1,3-thiazin-2-yl)amino)decanoic acid (54b);

3-(4-(4-((4-acetyl-3,4,5,6-tetrahydropyrazin-2-yl)amino)butoxy)phenyl)-2-(2,6-dichlorobenzamido)propanoic acid (55);

(S)-3-(4-(4-((4-acetyl-3,4,5,6-tetrahydropyrazin-2-yl)amino)butoxy)phenyl)-2-(2,6-dichlorobenzamido)propanoic acid (55a);

(R)-3-(4-(4-((4-acetyl-3,4,5,6-tetrahydropyrazin-2-yl)amino)butoxy)phenyl)-2-(2,6-dichlorobenzamido)propanoic acid (55b);

2-(2,6-dichlorobenzamido)-3-(4-(4-((3,4,5,6-tetrahydropyrazin-2-yl)amino)butoxy)phenyl)propanoic acid (56);

(S)-2-(2,6-dichlorobenzamido)-3-(4-(4-((3,4,5,6-tetrahydropyrazin-2-yl)amino)butoxy)phenyl)propanoic acid (5 6a);

(R)-2-(2,6-dichlorobenzamido)-3-(4-(4-((3,4,5,6-tetrahydropyrazin-2-yl)amino)butoxy)phenyl)propanoic acid (56b);

2-(2,6-dichlorobenzamido)-3-(4-(4-((1-methyl-5-oxo-4,5-dihydro-1H-imidazol-2-yl)amino)butoxy)phenyl)propanoic acid (57);

(S)-2-(2,6-dichlorobenzamido)-3-(4-(4-((1-methyl-5-oxo-4,5-dihydro-1H-imidazol-2-yl)amino)butoxy)phenyl)propanoic acid (5 7a);

(R)-2-(2,6-dichlorobenzamido)-3-(4-(4-((1-methyl-5-oxo-4,5-dihydro-1H-imidazol-2-yl)amino)butoxy)phenyl)propanoic acid (57b);

2-(2,6-dichlorobenzamido)-3-(4-(4-((4-methyl-5-oxo-3,4,5,6-tetrahydropyrazin-2-yl)amino)butoxy)phenyl)propanoic acid (58);

(S)-2-(2,6-dichlorobenzamido)-3-(4-(4-((4-methyl-5-oxo-3,4,5,6-tetrahydropyrazin-2-yl)amino)butoxyl)phenyl)propanoic acid (5 8a);

(R)-2-(2,6-dichlorobenzamido)-3-(4-(4-((4-methyl-5-oxo-3,4,5,6-tetrahydropyrazin-2-yl)amino)butoxy)phenyl)propanoic acid (58b);

2-(2,6-dichlorobenzamido)-3-(4-(3-(3,4-dihydro-2H-pyrido[3,2-b][1,4] oxazin-3-yl)propoxyl)phenyl)propanoic acid (63);

(2S)-2-(2,6-dichlorobenzamido)-3-(4-(3-(3,4-dihydro-2H-pyrido[3,2-b][1,4]oxazin-3-yl)propoxy)phenyl)propanoic acid (63a);

(2R)-2-(2,6-dichlorobenzamido)-3-(4-(3-(3,4-dihydro-2H-pyrido[3,2-b][1,4] oxazin-3-yl)propoxyl)phenyl)propanoic acid (63b);

2-(2,6-dichlorobenzamido)-9-(3,4-dihydro-2H-pyrido[3,2-b][1,4]oxazin-3-yl)nonanoic acid (66);

(2S)-2-(2,6-dichlorobenzamido)-9-(3,4-dihydro-2H-pyrido[3,2-b][1,4]oxazin-3-yl)nonanoic acid (66a);

(2R)-2,6-dichlorobenzamido)-9-(3,4-dihydro-2H-pyrido[3,2-b][1,4] oxazin-3-yl)nonanoic acid (66b);

2-(2,6-dichlorobenzamido)-7-(2-(5,6,7,8-tetrahydro-1,8-naphthyridin-2-yl)cyclopropyl)heptanoic acid (67);

(2S)-2-(2,6-dichlorobenzamido)-7-(2-(5,6,7,8-tetrahydro-1,8-naphthyridin-2-yl)cyclopropyl)heptanoic acid (67a);

(2R)-2-(2,6-dichlorobenzamido)-7-(2-(5,6,7,8-tetrahydro-1,8-naphthyridin-2-yl)cyclopropyl)heptanoic acid (67b);

2-(2,6-dichlorobenzamido)-3-(2-(4-(5,6,7,8-tetrahydro-1,8-naphthyridin-2-yl)butyl)cyclopropyl)propanoic acid (68);

(2S)-2-(2,6-dichlorobenzamido)-3-(2-(4-(5,6,7,8-tetrahydro-1,8-naphthyridin-2-yl)butyl)cyclopropyl)propanoic acid (68a);

(2R)-2-(2,6-dichlorobenzamido)-3-(2-(4-(5,6,7,8-tetrahydro-1,8-naphthyridin-2-yl)butyl)cyclopropyl)propanoic acid (68b);

2-(2,6-dichlorobenzamido)-3-(1-(5-(5,6,7,8-tetrahydro-1,8-naphthyridin-2-yl)pentyl)cyclopropyl)propanoic acid (69);

(S)-2-(2,6-dichlorobenzamido)-3-(1-(5-(5,6,7,8-tetrahydro-1,8-naphthyridin-2-yl)pentyl)cyclopropyl)propanoic acid (69a);

(R)-2-(2,6-dichlorobenzamido)-3-(1-(5-(5,6,7,8-tetrahydro-1,8-naphthyridin-2-yl)pentyl)cyclopropyl)propanoic acid (69b);

2-(2,6-dichlorobenzamido)-3-(3-(3-(5,6,7,8-tetrahydro-1,8-naphthyridin-2-yl)propoxy)cyclobutyl)propanoic acid (70);

(S)-2-(2,6-dichlorobenzamido)-3-(3-(3-(5,6,7,8-tetrahydro-1,8-naphthyridin-2-yl)propoxy)cyclobutyl)propanoic acid (70a);

(R)-2-(2,6-dichlorobenzamido)-3-(3-(3-(5,6,7,8-tetrahydro-1,8-naphthyridin-2-yl)propoxy)cyclobutyl)propanoic acid (70b);

2-(2,6-dichlorobenzamido)-3-(3-((3-(5,6,7,8-tetrahydro-1,8-naphthyridin-2-yl)propoxy)methyl)cyclobutyl)propanoic acid (71);

(S)-2-(2,6-dichlorobenzamido)-3-(3-((3-(5,6,7,8-tetrahydro-1,8-naphthyridin-2-yl)propoxy)methyl)cyclobutyl)propanoic acid (71a);

(R)-2-(2,6-dichlorobenzamido)-3-(3-(3-(5,6,7,8-tetrahydro-1,8-naphthyridin-2-yl)propoxy)methyl)cyclobutyl)propanoic acid (71 b);

2-(2,6-dichlorobenzamido)-3-(4-(3-(5,6,7,8-tetrahydro-1,8-naphthyridin-2-yl)propoxy)cyclohexyl)propanoic acid (72);

(S)-2-(2,6-dichlorobenzamido)-3-(4-(3-(5,6,7,8-tetrahydro-1,8-naphthyridin-2-yl)propoxy)cyclohexyl)propanoic acid (72a);

(R)-2-(2,6-dichlorobenzamido)-3-(4-(3-(5,6,7,8-tetrahydro-1,8-naphthyridin-2-yl)propoxy)cyclohexyl)propanoic acid (72b);

2-(2,6-dichlorobenzamido)-3-(3-((3-(5,6,7,8-tetrahydro-1,8-naphthyridin-2-yl)propoxy)methyl)azetidin-1-yl)propanoic acid (73);

(S)-2-(2,6-dichlorobenzamido)-3-(3-((3-(5,6,7,8-tetrahydro-1,8-naphthyridin-2-yl)propoxy)methyl)azetidin-1-yl)propanoic acid (73a);

(R)-2-(2,6-dichlorobenzamido)-3-(3-((3-(5,6,7,8-tetrahydro-1,8-naphthyridin-2-yl)propoxy)methyl)azetidin-1-yl)propanoic acid (73b);

2-(2,6-dichlorobenzamido)-3-(3-(3-(5,6,7,8-tetrahydro-1,8-naphthyridin-2-yl)propoxy)pyrrolidin-1-yl)propanoic acid (75);

(2S)-2-(2,6-dichlorobenzamido)-3-(3-(3-(5,6,7,8-tetrahydro-1,8-naphthyridin-2-yl)propoxy)pyrrolidin- 1-yl)propanoic acid (75a);

(2R)-2-(2,6-dichlorobenzamido)-3-(3-(3-(5,6,7,8-tetrahydro-1,8-naphthyridin-2-yl)propoxy)pyrrolidin- 1-yl)propanoic acid (75b);

2-(2,6-dichlorobenzamido)-3-(2-(2-(5, 6,7,8-tetrahydro-1,8-naphthyridin-2-yl)ethyl)benzo[d] oxazol-5-yl)propanoic acid (76);

(S)-2-(2,6-dichlorobenzamido)-3-(2-(2-(5,6,7,8-tetrahydro-1,8-naphthyridin-2-yl)ethyl)benzo[d]oxazol-5-yl)propanoic acid (76a);

(R)-2-(2,6-dichlorobenzamido)-3-(2-(2-(5,6,7,8-tetrahydro-1,8-naphthyridin-2-yl)ethyl)benzo[d]oxazol-5-yl)propanoic acid (76b);

2-(2,6-dichlorobenzamido)-3-(4-(1,1-difluoro-4-(5,6,7,8-tetrahydro-1,8-naphthyridin-2-yl)butyl)phenyl)propanoic acid (77);

(S)- 2-(2,6-dichlorobenzamido)-3-(4-(1,1-difluoro-4-(5,6,7,8-tetrahydro-1,8-naphthyridin-2-yl)butyl)phenyl) propanoic acid (77a);

(R)-2-(2,6-dichlorobenzamido)-3-(4-(1,1-difluoro-4-(5,6,7,8-tetrahydro-1,8-naphthyridin-2-yl)butyl)phenyl) propanoic acid (77b);

9-(3,4-dihydro-2H-pyrido[3,2-b][1,4]oxazin-3-yl)-2-(1-methyl-1H-indazole-5-carboxamido)nonanoic acid (78);

(2S)-9-(3,4-dihydro-2H-pyrido[3,2-b] [1,4] oxazin-3-yl)-2-(1-methyl-1H-indazole-5-carboxamido)nonanoic acid (78a);

(2R)-9-(3,4-dihydro-2H-pyrido[3,2-b][1,4]oxazin-3-yl)-2-(1-methyl-1H-indazole-5-carboxamido)nonanoic acid (78b);

2-(1-methyl-1H-indazole-5-carboxamido)-9-(1,2,3,4-tetrahydro-1,8-naphthyridin-2-yl)nonanoic acid (79);

(2S)-2-(1-methyl-1H-indazole-5-carboxamido)-9-(1,2,3,4-tetrahydro-1,8-naphthyridin-2-yl)nonanoic acid (79a);

(2R)-2-(1-methyl-1H-indazole-5-carboxamido)-(1,2,3,4-tetrahydro-1,8-naphthyridin-2-yl)nonanoic acid (79b);

9-(3,4-dihydro-2H-pyrido[3,2-b][1,4]oxazin-3-yl)-2-(1-methyl-1H-indazole-6-carboxamido)nonanoic acid (80);

(2S)-9-(3,4-dihydro-2H-pyrido[3,2-b] [1,4] oxazin-3-yl)-2-(1-methyl-1H-indazole-6-carboxamido)nonanoic acid (80a);

(2R)-9-(3,4-dihydro-2H-pyrido[3,2-b][1,4]oxazin-3-yl)-2-(1-methyl-1H-indazole-6-carboxamido)nonanoic acid (80b);

2-(1-methyl-1H-indazole-6-carboxamido)-9-(5,6,7,8-tetrahydro-1,8-naphthyridin-2-yl)nonanoic acid (81);

(S)-2-(1-methyl-1H-indazole-6-carboxamido)-9-(5,6,7,8-tetrahydro-1,8-naphthyridin-2-yl)nonanoic acid (81a);

(R)-2-(1-methyl-1H-indazole-6-carboxamido)-9-(5,6,7,8-tetrahydro-1,8-naphthyridin-2-yl)nonanoic acid (81b);

2-(1-methyl-1H-indazole-5-carboxamido)-9-(5,6,7,8-tetrahydro-1,8-naphthyridin-2-yl)nonanoic acid (82);

(S)-2-(1-methyl-1H-indazole-5-carboxamido)-9-(5,6,7,8-tetrahydro-1,8-naphthyridin-2-yl)nonanoic acid (82a);

(R)-2-(1-methyl-1H-indazole-5-carboxamido)-9-(5,6,7,8-tetrahydro-1,8-naphthyridin-2-yl)nonanoic acid (82b);

2-(1-(tert-butyl)-1H-indazole-6-carboxamido)-9-(5,6,7,8-tetrahydro-1,8-naphthyridin-2-yl)nonanoic acid (83);

(S)-2-(1-tert-butyl)-1H-indazole-6-carboxamido)-9-(5,6,7,8-tetrahydro-1,8-naphthyridin-2-yl)nonanoic acid (83a);

(R)-2-(1-(tert-butyl)-1H-indazole-6-carboxamido)-9-(5,6,7,8-tetrahydro-1,8-naphthyridin-2-yl)nonanoic acid (83b);

2-(1-(cyclopropylmethyl)-1H-indazole-6-carboxamido)-9-(5,6,7,8-tetrahydro-1,8-naphthyridin-2-yl)nonanoic acid (84);

(S)-2-(1-(cyclopropylmethyl)-1H-indazole-6-carboxamido)-9-(5,6,7,8-tetrahydro-1,8-naphthyridin-2-yl)nonanoic acid (84a);

(R)-2-(1-(cyclopropylmethyl)-1H-indazole-6-carboxamido)-9-(5,6,7,8-tetrahydro-1,8-naphthyridin-2-yl) nonanoic acid (84b);

2-(2-methyl-2H-indazole-5-carboxamido)-9-(1,2,3 4-tetrahydro-1,8-naphthyridin-2-yl)nonanoic acid (85);

(2S)-2-(2-methyl-2H-indazole-5-carboxamido)-(1,2,3,4-tetrahydro-1,8-naphthyridin-2-yl)nonanoic acid (85a);
(2R)-2-(2-methyl-2H-indazole-5-carboxamido)-9-(1,2,3 4-tetrahydro-1,8-naphthyridin-2-yl)nonanoic acid (85b);
2-(2-methyl-2H-indazole-5-carboxamido)-9-(5,6,7,8-tetrahydro-1,8-naphthyridin-2-yl)nonanoic acid (86);
(S)-2-(2-methyl-2H-indazole-5-carboxamido)-9-(5,6,7,8-tetrahydro-1,8-naphthyridin-2-yl)nonanoic acid (86a);
(R)-2-(2-methyl-2H-indazole-5-carboxamido)-9-(5,6,7,8-tetrahydro-1,8-naphthyridin-2-yl)nonanoic acid (86b);
2-(4-chlorobenzamido)-9-(5,6,7,8-tetrahydro-1,8-naphthyridin-2-yl)nonanoic acid (87);
2-(4-fluorobenzamido)-9-(5,6,7,8-tetrahydro-1,8-naphthyridin-2-yl)nonanoic acid (88);
2-(4-methoxybenzamido)-9-(5,6,7,8-tetrahydro-1,8-naphthyridin-2-yl)nonanoic acid (89);
2-(4-cyanobenzamido)-(5,6,7,8-tetrahydro-1,8-naphthyridin-2-yl)nonanoic acid (90);
2-(3-chlorobenzamido)-9-(5,6,7,8-tetrahydro-1,8-naphthyridin-2-yl)nonanoic acid (91);
2-(3-fluorobenzamido)-9-(5,6,7,8-tetrahydro-1,8-naphthyridin-2-yl)nonanoic acid (92);
2-(3-methoxybenzamido)-9-(5,6,7,8-tetrahydro-1,8-naphthyridin-2-yl)nonanoic acid (93);
2-(3-cyanobenzamido)-9-(5,6,7,8-tetrahydro-1,8-naphthyridin-2-yl)nonanoic acid (94);
2-(2-fluorobenzamido)-9-(5,6,7,8-tetrahydro-1,8-naphthyridin-2-yl)nonanoic acid (95);
2-(2-chlorobenzamido)-9-(5,6,7,8-tetrahydro-1,8-naphthyridin-2-yl)nonanoic acid (96);
9-(5,6,7,8-tetrahydro-1,8-naphthyridin-2-yl)-2-(3-(trifluoromethyl)-5,6,7,8-tetrahydro-[1,2,4]triazolo[4,3-a]pyrazine-7-carboxamido)nonanoic acid (97);
2-(1H-indazole-6-carboxamido)-9-(5,6,7,8-tetrahydro-1,8-naphthyridin-2-yl)nonanoic acid (98);
2-(2,6-dichloro-4-(1H-imidazol-5-yl)benzamido)-3-(4-(3-(5,6,7,8-tetrahydro-1,8-naphthyridin-2-yl)propoxy)phenyl)propanoic acid (99);
(S)-2-(2-chloro-5-cyanobenzamido)-9-(5,6,7,8-tetrahydro-1,8-naphthyridin-2-yl)nonanoic acid (100);
(S)-2-(4-cyano-2-fluorobenzamido)-9-(5,6,7,8-tetrahydro-1,8-naphthyridin-2-yl)nonanoic acid (101);
(S)-2-(1H-indazole-5-carboxamido)-9-(5,6,7,8-tetrahydro-1,8-naphthyridin-2-yl)nonanoic acid (103);
(S)-2-(1-(difluoromethyl)-1H-indazole-6-carboxamido)-9-(5, 6,7,8-tetrahydro-1,8-naphthyridin-2-yl)nonanoic acid (105);
(S)-2- 2-(difluoromethyl)-2H-indazole-5-carboxamido)-9-(5,6,7,8-tetrahydro-1,8-naphthyridin-2-yl)nonanoic acid (106);
(S)-2-(1-(difluoromethyl)-1H-indazole-5-carboxamido)-9-(5,6,7,8-tetrahydro-1,8-naphthyridin-2-yl)nonanoic acid (107);
(S)-2- 2-(difluoromethyl)-2H-indazole-6-carboxamido)-9-(5,6,7,8-tetrahydro-1,8-naphthyridin-2-yl)nonanoic acid (108);
(S)-2-(5-phenyl- 1H-pyrazole-4-carboxamido)-9-(5,6,7,8-tetrahydro-1,8-naphthyridin-2-yl)nonanoic acid (110);
(S)-2- 4-(pyridin-3-yl)benzamido)-9-(5,6,7,8-tetrahydro-1,8-naphthyridin-2-yl)nonanoic acid (111);
(S)-2-(4-(pyridin-4-yl)benzamido)-9-(5,6,7,8-tetrahydro-1,8-naphthyridin-2-yl)nonanoic acid (112);
(S)-2-(4-(1-methyl-1H-pyrazol-4-yl)benzamido)-9-(5,6,7,8-tetrahydro-1,8-naphthyridin-2-yl)nonanoic acid (113);
(S)-2-(1-methyl-1H-indazole-7-carboxamido)-9-(5,6,7,8-tetrahydro-1,8-naphthyridin-2-yl)nonanoic acid (114);
(S)-2-(1-methyl-1H-indazole-4-carboxamido)-9-(5,6,7,8-tetrahydro-1,8-naphthyridin-2-yl)nonanoic acid (115);
(S)-2-(1H-indazole-4-carboxamido)-9-(5,6,7,8-tetrahydro-1,8-naphthyridin-2-yl)nonanoic acid (116);
(S)-2-(2-chloro-4-isopropoxybenzamido)-9-(5,6,7,8-tetrahydro-1,8-naphthyridin-2-yl)nonanoic acid (117);
(S)-2-(2-chloro-5-(trifluoromethoxy)benzamido)-9-(5,6,7,8-tetrahydro-1,8-naphthyridin-2-yl)nonanoic acid (118);
(S)-2-(3-(3,5-dimethyl-1H-pyrazol-1-yl)benzamido)-9-(5,6,7,8-tetrahydro-1,8-naphthyridin-2-yl)nonanoic acid (119);
(S)-2-benzamido-9-(5,6,7,8-tetrahydro-1,8-naphthyridin-2-yl)nonanoic acid (120);
(S)-2-(2-chloro-3-fluorobenzamido)-9-(5,6,7,8-tetrahydro-1,8-naphthyridin-2-yl)nonanoic acid (121);
(S)-2-(3-fluoro-5-(trifluoromethyl)benzamido)-9-(5,6,7,8-tetrahydro-1,8-naphthyridin-2-yl)nonanoic acid (122);
(R)-2-(3-(1-methyl-1H-pyrazol-4-yl)benzamido)-9-(5,6,7,8-tetrahydro-1,8-naphthyridin-2-yl)nonanoic acid (123);
(R)-9-(5,6,7,8-tetrahydro-1,8-naphthyridin-2-yl)-2-(3-(thiazol-5-yl)benzamido)nonanoic acid (124);
(R)-2-(3-fluoro-5-(trifluoromethyl)benzamido)-9-(5,6,7,8-tetrahydro-1,8-naphthyridin-2-yl)nonanoic acid (125); and
(S)-9-(5,6,7,8-tetrahydro-1,8-naphthyridin-2-yl)-2-(3-(thiazol-5-yl)benzamido)nonanoic acid (126),
or a salt thereof.

43. A pharmaceutical composition comprising a compound of claim 1, or a salt thereof, and a pharmaceutically acceptable carrier or excipient.

44. A kit comprising a compound of claim 1, or a pharmaceutically acceptable salt thereof.

45. The kit of claim 44, further comprising instructions for the treatment of a fibrotic disease.

46. The kit of claim 45, wherein the fibrotic disease is pulmonary fibrosis, liver fibrosis, skin fibrosis, cardiac fibrosis, kidney fibrosis, or gastrointestinal fibrosis.

47. The kit of claim 45, wherein the fibrotic disease is liver fibrosis associated with nonalcoholic fatty liver disease (NAFLD), nonalcoholic steatohepatitis (NASH), alcoholic steatosis, or infection.

48. A method of treating a fibrotic disease in an individual in need thereof comprising administering to the individual a therapeutically effective amount of a compound of claim 1 or a pharmaceutically acceptable salt thereof.

49. The method of claim 48, wherein the fibrotic disease is pulmonary fibrosis, liver fibrosis, skin fibrosis, cardiac fibrosis, kidney fibrosis, or gastrointestinal fibrosis.

50. The method of claim 48, wherein the fibrotic disease is liver fibrosis associated with nonalcoholic fatty liver disease (NAFLD), nonalcoholic steatohepatitis (NASH), alcoholic steatosis, or infection.

51. A method of inhibiting αvβ1 integrin in an individual comprising administering a compound of claim 1 previously presented or a pharmaceutically acceptable salt thereof.

52. A method of inhibiting TGFβ activation in a cell comprising administering to the cell a compound of claim 1 or a pharmaceutically acceptable salt thereof.

* * * * *

UNITED STATES PATENT AND TRADEMARK OFFICE
CERTIFICATE OF CORRECTION

PATENT NO. : 10,604,520 B2
APPLICATION NO. : 15/698435
DATED : March 31, 2020
INVENTOR(S) : Lan Jiang et al.

Page 1 of 1

It is certified that error appears in the above-identified patent and that said Letters Patent is hereby corrected as shown below:

In the Claims

At Column 280, Claim number 51, Line number 62, delete "previously"

At Column 280, Claim number 51, Line number 63, delete "presented"

Signed and Sealed this
Second Day of June, 2020

Andrei Iancu
*Director of the United States Patent and Trademark Office*